(12) United States Patent
Roy et al.

(10) Patent No.: US 7,491,508 B2
(45) Date of Patent: *Feb. 17, 2009

(54) METHODS OF GENERATING CHIMERIC ADENOVIRUSES AND USES FOR SUCH CHIMERIC ADENOVIRUSES

(75) Inventors: Soumitra Roy, Wayne, PA (US); James M. Wilson, Gladwyne, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 324 days.

This patent is subject to a terminal disclaimer.

(21) Appl. No.: 10/561,201

(22) PCT Filed: Jun. 15, 2004

(86) PCT No.: PCT/US2004/016614

§ 371 (c)(1),
(2), (4) Date: Dec. 19, 2005

(87) PCT Pub. No.: WO2005/001103

PCT Pub. Date: Jan. 6, 2005

(65) Prior Publication Data

US 2006/0211115 A1    Sep. 21, 2006

Related U.S. Application Data

(63) Continuation of application No. 10/465,302, filed on Jun. 20, 2003, now Pat. No. 7,291,498.

(60) Provisional application No. 60/575,429, filed on May 28, 2004, provisional application No. 60/566,212, filed on Apr. 28, 2004.

(51) Int. Cl.
| | |
|---|---|
| C12N 15/63 | (2006.01) |
| C12N 15/64 | (2006.01) |
| C12N 15/861 | (2006.01) |
| C12N 5/10 | (2006.01) |
| A61K 48/00 | (2006.01) |
| C12P 21/00 | (2006.01) |
| C07H 21/04 | (2006.01) |
| C12Q 1/68 | (2006.01) |
| C12Q 1/70 | (2006.01) |

(52) U.S. Cl. .................. 435/69.1; 435/320.1; 435/455; 435/456; 435/325; 435/366; 424/93.1; 424/93.2; 424/93.6

(58) Field of Classification Search .................. None
See application file for complete search history.

(56) References Cited

U.S. PATENT DOCUMENTS

| | | | |
|---|---|---|---|
| 5,712,136 A | 1/1998 | Wickham et al. | |
| 5,846,782 A | 12/1998 | Wickham et al. | |
| 5,856,152 A | 1/1999 | Wilson et al. | |
| 5,871,982 A | 2/1999 | Wilson et al. | |
| 5,922,315 A | 7/1999 | Roy | |
| 5,965,541 A | 10/1999 | Wickman et al. | |
| 6,001,557 A | 12/1999 | Wilson et al. | |
| 6,057,155 A | 5/2000 | Wickham et al. | |
| 6,083,716 A | 7/2000 | Wilson et al. | |
| 6,127,525 A | 10/2000 | Crystal et al. | |
| 6,153,435 A | 11/2000 | Crystal et al. | |
| 6,203,975 B1 | 3/2001 | Wilson et al. | |
| 6,251,677 B1 | 6/2001 | Wilson et al. | |
| 6,329,190 B1 | 12/2001 | Wickham et al. | |
| 6,387,368 B1 | 5/2002 | Wilson et al. | |
| 6,465,253 B1 | 10/2002 | Wickham et al. | |
| 6,576,456 B2 | 6/2003 | Wickham et al. | |
| 6,649,407 B2 | 11/2003 | Wickham et al. | |
| 7,247,472 B2 | 7/2007 | Wilson | |
| 7,291,498 B2 | 11/2007 | Roy | |
| 2004/0171807 A1 | 9/2004 | Gao et al. | |
| 2004/0241181 A1 | 12/2004 | Ertl et al. | |
| 2005/0069866 A1 | 3/2005 | Wilson et al. | |

FOREIGN PATENT DOCUMENTS

WO    WO 96/13598 A2    5/1996

(Continued)

OTHER PUBLICATIONS

Wu et al., "Construction and characterization of adenovirus serotype 5 packaged by serotype 3 hexon", J Virol., Dec. 2002;76(24):12775-82.

(Continued)

*Primary Examiner*—David Guzo
(74) *Attorney, Agent, or Firm*—Howson & Howson LLP

(57) ABSTRACT

A method for providing an adenovirus from a serotype which does not grow efficiently in a desired cell line with the ability to grow in that cell line is described. The method involves replacing the left and right termini of the adenovirus with the corresponding termini from an adenovirus which grow efficiently in the desired cell line. At a minimum, the left terminus spans the (5') inverted terminal repeat, the left terminus spans the E4 region and the (3') inverted terminal repeat. The resulting chimeric adenovirus contains the internal regions spanning the genes encoding the penton, hexon and fiber from the serotype which does not grow efficiently in the desired cell. Also provided are vectors constructed from novel simian adenovirus sequences and proteins, host cells containing same, and uses thereof.

20 Claims, 2 Drawing Sheets

FOREIGN PATENT DOCUMENTS

| WO | WO 00/03029 | 1/2000 |
|----|----|----|
| WO | WO 03/000283 A1 | 1/2003 |
| WO | WO 03/000851 | 1/2003 |
| WO | WO 03/046124 A2 | 6/2003 |

OTHER PUBLICATIONS

Roy et al., "Circumvention of immunity to the adenovirus major coat protein hexon", J Virol., Aug. 1998;72(8):6875-9.

Gall et al., "Construction and characterization of hexon-chimeric adenoviruses: specification of adenovirus serotype", J Virol., Dec. 1998;72(12):10260-4.

Gall et al., "Adenovirus type 5 and 7 capsid chimera: fiber replacement alters receptor tropism without affecting primary immune neutralization epitopes", J Virol., Apr. 1996;70(4):2116-23.

Wohlfart, C., "Neutralization of adenoviruses: kinetics, stoichiometry, and mechanisms", J Virol., Jul. 1988;62(7):2321-8.

Youil et al., "Hexon gene switch strategy for the generation of chimeric recombinant adenovirus", Hum Gene Ther., Jan. 20, 2002;13(2):311-20.

Farina et al., "Replication-defective vector based on a chimpanzee adenovirus", J Virol., Dec. 2001;75(23):11603-13.

Stevens, D., "SA18 (Simian adenovirus 18) ATCC VR-943", American Type Culture Collection Catalogue of Strains II: Viruses and Antisera, 1983, p. 227: paragraph 1.

Roy et al., "Characterization of a family chimpanzee adenoviruses and development of molecular clones for gene transfer vectors", Hum Gene Ther., May 2004;15(5):519-30.

International Search Report for PCT/US2004/016614 (WO 2005/001103 A2).

Written Opinion for PCT/US2004/016614 (WO 2005/001103 A2).

Roy et al., "Novel Chimeric Adenovirus Vaccine Vectors", 7th Annual Meeting of the American Society of Gene Therapy [Jun. 2-6, 2004], Abstract 1016.

Roy et al., "Use of Chimeric Adenoviral Vectors to Assess Capsid Neutralization Determinants", 7th Annual Meeting of the American Society of Gene Therapy [Jun. 2-6, 2004], Abstract 128.

Horwitz, "Adenoviridae and Their Replication", Virology, 2d ed., 1990, pp. 1679-1721.

Roy et al., "Use of chimeric adenoviral vectors to assess capsid neutralization determinants", Virology, Mar. 15, 2005;333(2):207-14.

Freimuth et al, Codon Insertion Mutants of the Adenovirus Terminal Protein, Proc. Nat'l Acad. Sci. USA, vol. 83, pp. 7816-7820, (Oct. 1986).

Simian Adenovirus
34302 bp

Ad H5S25H5eGFP
31518 bp

METHODS OF GENERATING CHIMERIC ADENOVIRUSES AND USES FOR SUCH CHIMERIC ADENOVIRUSES

BACKGROUND OF THE INVENTION

The presence of humoral immunity (circulating antibodies) to adenovirus capsid proteins is a barrier to the use of adenovirus vectors for gene therapy. The prototype adenovirus vectors that have been developed for gene therapy are based on subgroup C adenoviruses such as that of serotype 5. The prevalence of neutralizing antibodies against subgroup C adenoviruses is generally high in human populations as a result of frequent exposure to these pathogens. This fact is likely to greatly limit the effectiveness of gene therapy vectors based on serotypes such as Ad5.

Analysis of the nature of the protective antibodies against adenoviruses has indicated that the most important target is the major capsid protein, hexon [Wolfhart (1988) J. Virol 62, 2321; Gall et al. (1996) J. Virol. 70, 2116]. Several efforts have been made to engineer the hexon so as to evade the anti-hexon antibodies by making chimeric adenoviruses harboring hexons from other serotypes [Roy et al. (1998) J. Virol. 72, 6875; U.S. Pat. No. 5,922,315; Gall et al. (1998) J. Virol. 72, 10260; Youil et al. (2002) Hum. Gene Ther. 13, 311; Wu et al. (2002) J. Virol. 76, 12775]. However, this has been largely unsuccessful when exchanges among distant serotypes are attempted.

Alternatively, investigators have proposed using adenovirus vectors that rarely cause human infections or using adenoviruses from non-human sources. However, the lack of a practical manner in which to produce large numbers of such vectors has proved to be a hindrance to developing such vectors.

SUMMARY OF THE INVENTION

The present invention provides a method of modifying adenoviruses having capsids, and particularly, including hexons, from serotypes which are not well adapted for growth in cells useful for adenoviral virion production. The method is useful for production of scalable amounts of adenoviruses. The resulting chimeric adenovirus genomes are useful for a variety of purposes which are described herein.

The invention further provides novel, isolated, adenovirus SA18 nucleic acid and amino acid sequences, vectors containing same, cell lines containing such SA18 sequences and/or vectors, and uses thereof.

Other aspects and advantages of the present invention will be readily apparent from the following detailed description of the invention.

DETAILED DESCRIPTION OF THE INVENTION

Figure 1:
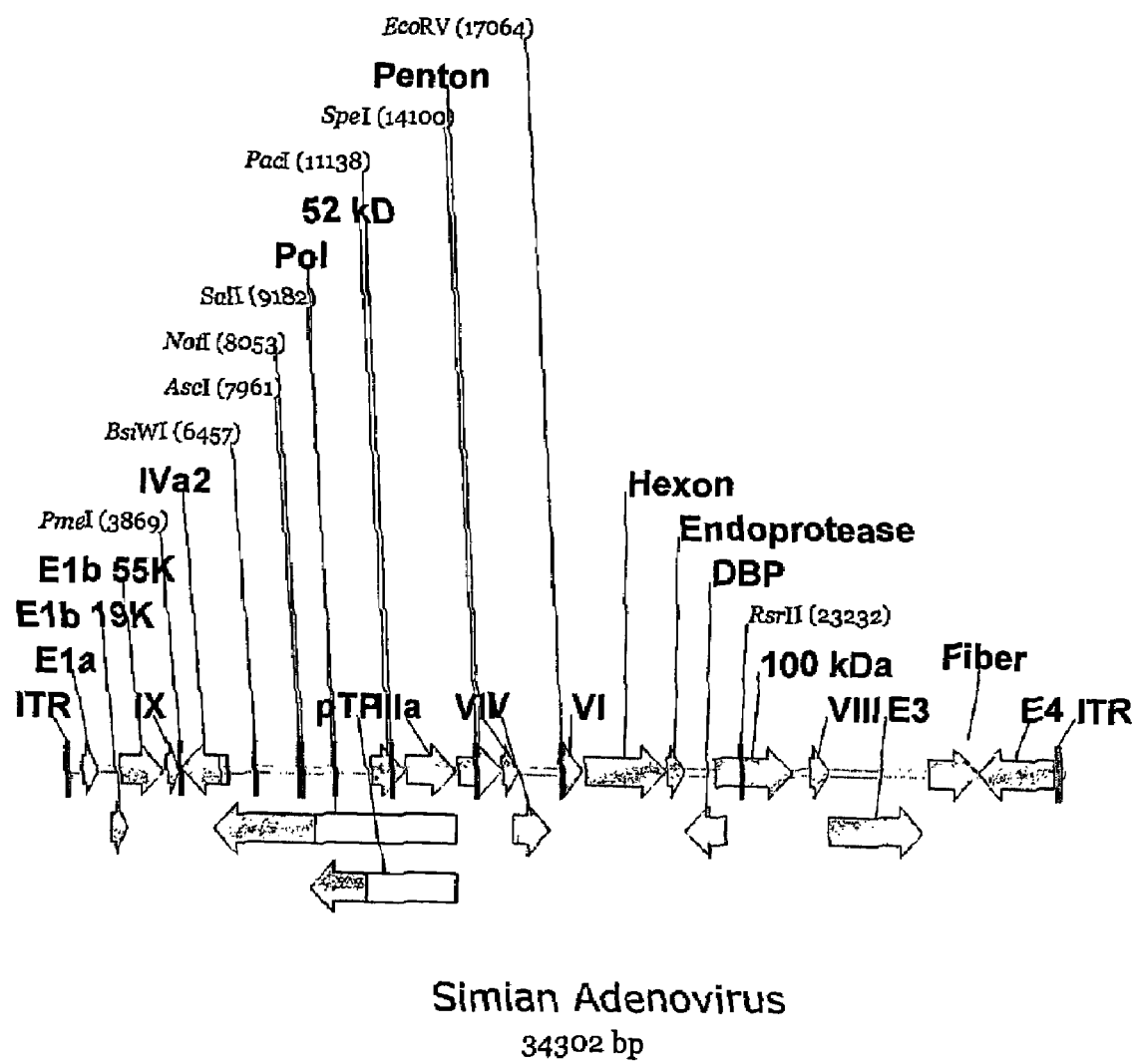
FIG. 1 provides the map of the genome of the simian adenovirus generated by shotgun cloning as described in the examples below.

The present invention provides chimeric adenovirus genomes composed of the left terminal end and right terminal end of an adenovirus which can be cultured in the selected host cell, and the internal regions encoding, at a minimum, the capsid proteins of another adenovirus serotype. This invention is particularly advantageous for generating adenoviruses having serotypes which are difficult to culture in a desired cell type. The invention thus permits generation of chimeric adenoviruses vectors of varying serotypes.

In the embodiments illustrated herein, chimeric adenoviruses have been constructed where most structural proteins, and not merely the hexon or fiber, are derived from an adenovirus of an unrelated serotype, thereby preserving the majority of the protein-protein interactions that are involved in capsid assembly. Most of the early genes such as those encoded by the adenovirus E1 and E4 regions that are responsible for transcription regulation and regulation of the host cell cycle, are retained from a different serotype that is known to result in high titer virus generation in the commonly used cell types, such as HEK 293 which supplies the Ad5 E1 proteins in trans.

In another embodiment, the invention provides novel nucleic acid and amino acid sequences from Ad SA18, which was originally isolated from vervet monkey [ATCC VR-943]. The present invention further provides novel adenovirus vectors and packaging cell lines to produce those vectors for use in the in vitro production of recombinant proteins or fragments or other reagents. The invention further provides compositions for use in delivering a heterologous molecule for therapeutic or vaccine purposes. Such therapeutic or vaccine compositions contain the adenoviral vectors carrying an inserted heterologous molecule. In addition, novel sequences of the invention are useful in providing the essential helper functions required for production of recombinant adeno-associated viral (AAV) vectors. Thus, the invention provides helper constructs, methods and cell lines which use these sequences in such production methods.

The term "substantial homology" or "substantial similarity," when referring to a nucleic acid or fragment thereof, indicates that, when optimally aligned with appropriate nucleotide insertions or deletions with another nucleic acid (or its complementary strand), there is nucleotide sequence identity in at least about 95 to 99% of the aligned sequences.

The term "substantial homology" or "substantial similarity," when referring to amino acids or fragments thereof, indicates that, when optimally aligned with appropriate amino acid insertions or deletions with another amino acid (or its complementary strand), there is amino acid sequence identity in at least about 95 to 99% of the aligned sequences. Preferably, the homology is over full-length sequence, or a protein thereof, or a fragment thereof which is at least 8 amino acids, or more desirably, at least 15 amino acids in length. Examples of suitable fragments are described herein.

The term "percent sequence identity" or "identical" in the context of nucleic acid sequences refers to the residues in the two sequences that are the same when aligned for maximum correspondence. The length of sequence identity comparison may be over the full-length of the genome (e.g., about 36 kbp), the full-length of an open reading frame of a gene, protein, subunit, or enzyme [see, e.g., the tables providing the adenoviral coding regions], or a fragment of at least about 500 to 5000 nucleotides, is desired. However, identity among smaller fragments, e.g., of at least about nine nucleotides, usually at least about 20 to 24 nucleotides, at least about 28 to 32 nucleotides, at least about 36 or more nucleotides, may also be desired. Similarly, "percent sequence identity" may be readily determined for amino acid sequences, over the full-length of a protein, or a fragment thereof. Suitably, a fragment is at least about 8 amino acids in length, and may be up to about 700 amino acids. Examples of suitable fragments are described herein.

Identity is readily determined using such algorithms and computer programs as are defined herein at default settings. Preferably, such identity is over the full length of the protein, enzyme, subunit, or over a fragment of at least about 8 amino acids in length. However, identity may be based upon shorter regions, where suited to the use to which the identical gene product is being put.

As described herein, alignments are performed using any of a variety of publicly or commercially available Multiple Sequence Alignment Programs, such as "Clustal W", accessible through Web Servers on the internet. Alternatively, Vector NTI utilities are also used. There are also a number of algorithms known in the art that can be used to measure nucleotide sequence identity, including those contained in the programs described above. As another example, polynucleotide sequences can be compared using Fasta, a program in GCG Version 6.1. Fasta provides alignments and percent sequence identity of the regions of the best overlap between the query and search sequences. For instance, percent sequence identity between nucleic acid sequences can be determined using Fasta with its default parameters (a word size of 6 and the NOPAM factor for the scoring matrix) as provided in GCG Version 6.1, herein incorporated by reference. Similarly programs are available for performing amino acid alignments. Generally, these programs are used at default settings, although one of skill in the art can alter these settings as needed. Alternatively, one of skill in the art can utilize another algorithm or computer program that provides at least the level of identity or alignment as that provided by the referenced algorithms and programs.

As used throughout this specification and the claims, the term "comprise" and its variants including, "comprises", "comprising", among other variants, is inclusive of other components, elements, integers, steps and the like. The term "consists of" or "consisting of" are exclusive of other components, elements, integers, steps and the like.

Except where otherwise specified, the term "vector" includes any genetic element known in the art which will deliver a target molecule to a cell, including, naked DNA, a plasmid, phage, transposon, cosmids, episomes, viruses, etc.

By "minigene" is meant the combination of a selected heterologous gene and the other regulatory elements necessary to drive translation, transcription and/or expression of the gene product in a host cell.

As used herein, the term "transcomplement" refers to when a gene (gene product) of one adenovirus serotype supplies an adenovirus serotype lacking this gene (gene product) from another serotype with the missing function. For example, human adenovirus serotype 5 E1a and E1b functions are known to transcomplement E1-deleted chimpanzee adenovirus Pan 9. Similarly, the inventors have found that human Ad5 E1 transcomplements E1-deleted chimpanzee adenovirus serotypes Pan5, Pan6, Pan7, and simian adenovirus serotypes SV1, SV25 and SV39. Other examples of transcomplementing serotypes include human Ad5 and human Ad2, Ad3, Ad4, Ad5, Ad7, and Ad12.

The term "functionally deleted" or "functional deletion" means that a sufficient amount of the gene region is removed or otherwise damaged, e.g., by mutation or modification, so that the gene region is no longer capable of producing functional products of gene expression. If desired, the entire gene region may be removed. Other suitable sites for gene disruption or deletion are discussed elsewhere in the application.

The term "functional" refers to a product (e.g., a protein or peptide) which performs its native function, although not necessarily at the same level as the native product. The term "functional" may also refer to a gene which encodes and from which a desired product can be expressed.

I. Chimeric Adenoviral Vectors

The compositions of this invention include chimeric adenoviral vectors that deliver a heterologous molecule to cells. For delivery of such a heterologous molecule, the vector can be a plasmid or, preferably, a chimeric adenovirus. The chimeric adenoviruses of the invention include adenovirus DNA from at least two source serotypes, a "donating serotype" and a "parental adenovirus" as described in more detail herein, and a minigene.

Because the adenoviral genome contains open reading frames on both strands, in many instances reference is made herein to 5' and 3' ends of the various regions to avoid confusion between specific open reading frames and gene regions. Thus, when reference is made herein to the "left" and "right" end of the adenoviral genome, this reference is to the ends of the approximately 36 kb adenoviral genome when depicted in schematic form as is conventional in the art [see, e.g., Horwitz, "Adenoviridae and Their Replication", in VIROLOGY, 2d ed., pp. 1679-1721 (1990)]. Thus, as used herein, the "left terminal end" of the adenoviral genome refers to portion of the adenoviral genome which, when the genome is depicted schematically in linear form, is located at the extreme left end of the schematic. Typically, the left end refers to be portion of the genome beginning at map unit 0 and extending to the right to include at least the 5' inverted terminal repeats (ITRs), and excludes the internal regions of the genome encoding the structural genes. As used herein, the "right terminal end" of the adenoviral genome refers to portion of the adenoviral genome which, when the genome is depicted schematically in linear form, is located at the extreme right end of the schematic. Typically, the right end of the adenoviral genome refers to be portion of the genome ending at map unit 36 and extending to the left to include at least the 3' ITRs, and excludes the internal regions of the genome encoding the structural genes.

A. Adenovirus Regulatory Sequences

1. Serotype

The selection of the adenovirus serotype donating its left terminal end and right terminal end can be readily made by one of skill in the art from among serotypes which can readily be cultured in the desired cell line. Among other factors which may be considered in selecting the serotype of the donating serotype is compatibility with the adenovirus serotype which will be supplying the internal regions at the location at which their sequences are hybridized.

Suitable adenoviruses for donating their left and right termini are available from the American Type Culture Collection, Manassas, Va., US (ATCC), a variety of academic and commercial sources, or the desired regions of the donating adenoviruses may be synthesized using known techniques with reference to sequences published in the literature or available from databases (e.g., GenBank, etc.). Examples of suitable donating adenoviruses include, without limitation, human adenovirus serotypes 2, 3, 4, 5, 7, and 12, and further including any of the presently identified human types [see, e.g., Horwitz, "Adenoviridae and Their Replication", in VIROLOGY, 2d ed., pp. 1679-1721 (1990)] which can be cultured in the desired cell. Similarly adenoviruses known to infect non-human primates (e.g., chimpanzees, rhesus, macaque, and other simian species) or other non-human mammals and which grow in the desired cell can be employed in the vector constructs of this invention. Such serotypes include, without limitation, chimpanzee adenoviruses Pan 5 [VR-591], Pan6 [VR-592], Pan7 [VR-593], and C68 (Pan9), described in U.S. Pat. No. 6,083,716; and simian adenoviruses including, without limitation SV1 [VR-195]; SV25 [SV-201]; SV35; SV15; SV-34; SV-36; SV-37, and baboon adenovirus [VR-275], among others. The sequences of Pan 5 (also termed C5), Pan 6 (also termed C6), Pan 7 (also termed C7), SV1, SV25, and SV39 have been described [WO 03/046124, published 5 Jun. 2003; and in U.S. patent application Ser. No. 10/739,096, filed Dec. 19, 2003)], which are incorporated by reference. In the following examples, the human 293 cells and adenovirus type 5 (Ad5), Pan9, and Ad40 are used for convenience. However, one of skill in the art will understand that other cell lines and/or comparable regions derived from other adenoviral strains may be readily selected and used in the present invention in the place of (or in combination with) these serotypes.

2. Sequences

The minimum sequences which must be supplied by the adenovirus donating its left terminal end and its right terminal end include the 5' cis-elements and the 3' cis-elements necessary for replication and packaging. Typically, the 5' cis-elements necessary for packaging and replication include the 5' inverted terminal repeat (ITR) sequences (which functions as origins of replication) and the native 5' packaging enhancer domains (that contain sequences necessary for packaging linear Ad genomes and enhancer elements for the E1 promoter). The right end of the adenoviral genome includes the 3' cis-elements (including the ITRs) necessary for packaging and encapsidation. Desirably, the adenovirus serotype donating its left and right termini and/or an adenovirus serotype which transcomplements the serotype of the donating adenovirus, further provides the functions of the necessary adenovirus early genes, including E1 (E1a and E1b), E2 (E2a and E2b), and E4 (including at least the ORF6 region). E3 is not essential and may be deleted as desired, e.g., for insertion of a transgene in this region or to provide space for a transgene inserted in another region (typically for packaging it is desirable for the total adenoviral genome to be under 36 kb).

In certain embodiments, the necessary adenovirus early genes are contained in the chimeric construct of the invention. In other embodiment, one or more of the necessary adenovirus early genes can be provided by the packaging host cell or in trans.

In general, the chimeric adenovirus of the invention contains regulatory sequences from the donating adenovirus serotype, or a transcomplementing serotype, to provide the chimeric adenovirus with compatible regulatory proteins. Optionally, one or more of the necessary adenoviral structural genes is provided by the adenovirus donating its left terminal and its right terminal end.

In certain embodiments, the chimeric adenovirus further contains one or more functional adenovirus genes, including, the Endoprotease open reading frame, DNA binding protein, 100 kDa scaffolding protein, 33 kDa protein, protein VIII, pTP, 52/55 kDa protein, protein VII, Mu and/or protein VI from the adenovirus serotype donating its left and right termini. Where all of these genes are derived from the adenovirus serotype donating the 5' and 3' ITRs, a "pseudotyped" virus is formed. In one embodiment, the chimeric adenovirus contains the left end of the adenovirus genome from the donating serotype, from the 5' ITR through the end of the pol gene (or the pTP). In another embodiment, the chimeric adenovirus contains the left end of the donating adenovirus serotype, from the 5' ITR through the penton. In yet another embodiment, the chimeric adenovirus contains the left end of the donating adenovirus serotype, e.g., through the end of pTP, but contains an ITR from an adenovirus serotype heterologous to the donating adenovirus serotype. Still other embodiments will be readily apparent from the present disclosure.

Optionally, one or more of the genes can be hybrids formed from the fusion of the donating adenovirus serotype and the parental adenovirus serotype providing the capsid proteins (e.g., without limitation, polymerase, terminal protein, IIIa protein). Suitably, these genes express functional proteins which permit packaging of the adenovirus genes into the capsid. Alternatively, one or more of these proteins (whether hybrid or non-hybrid) can be functionally deleted in the chimeric adenovirus. Where desired, any necessary proteins functionally deleted in the chimeric adenovirus can be expressed in trans in the packaging cell.

B. Parental Adenovirus Structural Proteins

1. Serotypes

This invention is particularly well adapted for use in generating chimeric adenoviruses in which the capsid proteins are from a parental adenovirus which does not efficiently grow in a desirable host cell. The selection of the parental adenovirus serotype providing the internal regions can be readily made by one of skill in the art based on the information provided herein.

A variety of suitable adenoviruses can serve as a parental adenovirus supplying the regions encoding the structural (i.e., capsid proteins). Many of such adenoviruses can be obtained from the same sources as described above for the donating adenovirus serotypes. Examples of suitable parental adenovirus serotypes includes, without limitation, human adenovirus serotype 40, among others [see, e.g., Horwitz, "Adenoviridae and Their Replication", in VIROLOGY, 2d ed., pp. 1679-1721 (1990)], and adenoviruses known to infect non-human primates (e.g., chimpanzees, rhesus, macaque, and other simian species) or other non-human mammals, including, without limitation, chimpanzee adenovirus C1, described in U.S. Pat. No. 6,083,716, which is incorporated by reference; simian adenoviruses, and baboon adenoviruses, among others. In addition, the parental adenovirus supplying the internal regions may be from a non-naturally occurring adenovirus serotype, such as may be generated using a variety of techniques known to those of skill in the art.

In one embodiment illustrated herein, a chimeric virus that was constructed was that between the chimpanzee adenoviruses Pan-5 and C1 exhibited a higher titer in human 293 cells than the wild-type parental virus. However, the invention is not limited to the use of these chimpanzee adenoviruses, or to the combination of simian-simian, human-human, or simian-human chimeric adenoviruses. For example, it may be desirable to utilize bovine or canine adenoviruses, or other non-human mammalian adenoviruses which do not naturally infect and/or replicate in human cells.

In the following examples, the human adenovirus type 40 (Ad40) and the chimpanzee adenovirus C1, simian Pan 5 and Ad40, and Pan 5 and simian adenovirus SA18, are used. However, one of skill in the art will understand that other adenoviral serotypes may be readily selected and used in the present invention in the place of (or in combination with) these serotypes.

2. Sequences

The parental adenovirus provides to the chimeric construct of the invention its internal regions which includes structural proteins necessary for generating a capsid having the desired characteristics of the parental adenovirus. These desired characteristics include, but are not limited to, the ability to infect target cells and delivery a heterologous transgene, the ability to elude neutralizing antibodies directed to another adenovirus serotype (i.e., avoiding clearance due to cross-reactivity), and/or the ability to infect cells in the absence of an immune response to the chimeric adenovirus. The advantages of such characteristics may be most readily apparent in a regimen which involves repeat delivery of adenoviral vectors. The left and right termini of the parent adenovirus, including at least the 5' ITRs, the E1 region, the E4 region and the 3' ITRs are non-functional and, preferably, completely absent. Optionally, all adenovirus regulatory proteins from this parental adenovirus are non-functional and only the structural proteins (or selected structural proteins) are retained.

At a minimum, the parental adenovirus provides the adenoviral late region encoding the hexon protein. Suitably, the parental adenovirus further provides the late regions encoding the penton and the fiber. In certain embodiments, all of the functional adenoviral late regions, including L1 (encoding 52/55 Da, IIIa proteins), L2 (encoding penton, VII, V, Mu proteins), L3 (encoding VI, hexon, Endoprotease), L4 (encoding 100 kD, 33 kD, VIII proteins) and L5 (encoding fiber protein) are supplied by the parental adenovirus. Optionally, one or more of these late gene functions, with the exception of those encoding the hexon, penton and fiber proteins, can be functionally deleted. Any necessary structural proteins may be supplied in trans.

Thus, in certain embodiments, the chimeric adenovirus further contains one or more functional adenovirus genes, including, the Endoprotease open reading frame, DNA binding protein, 100 kDa scaffolding protein, 33 kDa protein, protein VIII, pTP, 52/55 kDa protein, protein VII, Mu and/or protein VI from the parental adenovirus donating its internal regions. Optionally, one or more of the genes can be hybrids formed from the fusion of the donating adenovirus serotype and the parental adenovirus serotype providing the capsid proteins, as described above.

C. The "Minigene"

Typically, an adenoviral vector of the invention is designed to contain a minigene which may be inserted into the site of a partially deleted, fully deleted (absent), or disrupted adenoviral gene. For example, the minigene may be located in the site of such a functional E1 deletion or functional E3 deletion, or another suitable site.

The methods employed for the selection of the transgene, the cloning and construction of the "minigene" and its insertion into the viral vector are within the skill in the art given the teachings provided herein.

1. The transgene

The transgene is a nucleic acid sequence, heterologous to the vector sequences flanking the transgene, which encodes a polypeptide, protein, or other product, of interest. The nucleic acid coding sequence is operatively linked to regulatory components in a manner which permits transgene transcription, translation, and/or expression in a host cell.

The composition of the transgene sequence will depend upon the use to which the adenoviral vector will be put. For example, the adenoviral vector may be used as a helper virus in production of recombinant adeno-associated viruses or in production of recombinant adenoviruses deleted of essential adenoviral gene functions which are supplied by the adenoviral vector, or for a variety of production uses. Alternatively, the adenoviral vector may be used for diagnostic purposes.

One type of transgene sequence includes a reporter sequence, which upon expression produces a detectable signal. Such reporter sequences include, without limitation, DNA sequences encoding β-lactamase, β-galactosidase (LacZ), alkaline phosphatase, thymidine kinase, green fluorescent protein (GFP), chloramphenicol acetyltransferase (CAT), luciferase, membrane bound proteins including, for example, CD2, CD4, CD8, the influenza hemagglutinin protein, and others well known in the art, to which high affinity antibodies directed thereto exist or can be produced by conventional means, and fusion proteins comprising a membrane bound protein appropriately fused to an antigen tag domain from, among others, hemagglutinin or Myc. These coding sequences, when associated with regulatory elements which drive their expression, provide signals detectable by conventional means, including enzymatic, radiographic, colorimetric, fluorescence or other spectrographic assays, fluorescent activating cell sorting assays and immunological assays, including enzyme linked immunosorbent assay (ELISA), radioimmunoassay (RIA) and immunohistochemistry. For example, where the marker sequence is the LacZ gene, the presence of the vector carrying the signal is detected by assays for beta-galactosidase activity. Where the transgene is GFP or luciferase, the vector carrying the signal may be measured visually by color or light production in a luminometer.

However, desirably, the transgene is a non-marker sequence encoding a product which is useful in biology and medicine, such as proteins, peptides, RNA, enzymes, or catalytic RNAs. Desirable RNA molecules include tRNA, dsRNA, ribosomal RNA, si RNAs, small hairpin RNAs, trans-splicing RNAs, catalytic RNAs, and antisense RNAs. One example of a useful RNA sequence is a sequence which extinguishes expression of a targeted nucleic acid sequence in the treated animal.

The transgene may be used for treatment, e.g., of genetic deficiencies, as a cancer therapeutic or vaccine, for induction of an immune response, and/or for prophylactic vaccine purposes. As used herein, induction of an immune response refers to the ability of a molecule (e.g., a gene product) to induce a T cell and/or a humoral immune response to the molecule. The invention further includes using multiple transgenes, e.g., to correct or ameliorate a condition caused by a multi-subunit protein. In certain situations, a different transgene may be used to encode each subunit of a protein, or to encode different peptides or proteins. This is desirable when the size of the DNA encoding the protein subunit is large, e.g., for an immunoglobulin, the platelet-derived growth factor, or a dystrophin protein. In order for the cell to produce the multi-subunit protein, a cell is infected with the recombinant virus containing each of the different subunits. Alternatively, different subunits of a protein may be encoded by the same transgene. In this case, a single transgene includes the DNA encoding each of the subunits, with the DNA for each subunit separated by an internal ribozyme entry site (IRES). This is desirable when the size of the DNA encoding each of the subunits is small, e.g., the total size of the DNA encoding the subunits and the IRES is less than five kilobases. As an alternative to an IRES, the DNA may be separated by sequences encoding a 2A peptide, which self-cleaves in a post-translational event. See, e.g., M. L. Donnelly, et al, *J. Gen. Virol.*, 78(Pt 1):13-21 (January 1997); Furler, S., et al, *Gene Ther.*, 8(11):864-873 2001); Klump H., et al., *Gene Ther.*, 8(10):811-817 (May 2001). This 2A peptide is significantly smaller than an IRES, making it well suited for use when space is a limiting factor. However, the selected transgene may encode any biologically active product or other product, e.g., a product desirable for study.

Suitable transgenes may be readily selected by one of skill in the art. The selection of the transgene is not considered to be a limitation of this invention.

2. Vector and Transgene Regulatory Elements

In addition to the major elements identified above for the minigene, the adenoviral vector also includes conventional control elements which are operably linked to the transgene in a manner that permits its transcription, translation and/or expression in a cell transfected with the plasmid vector or infected with the virus produced by the invention. As used herein, "operably linked" sequences include both expression control sequences that are contiguous with the gene of interest and expression control sequences that act in trans or at a distance to control the gene of interest.

Expression control sequences include appropriate transcription initiation, termination, promoter and enhancer sequences; efficient RNA processing signals such as splicing and polyadenylation (polyA) signals; sequences that stabilize cytoplasmic mRNA; sequences that enhance translation efficiency (i.e., Kozak consensus sequence); sequences that enhance protein stability; and when desired, sequences that enhance secretion of the encoded product. A great number of expression control sequences, including promoters which are native, constitutive, inducible and/or tissue-specific, are known in the art and may be utilized.

Examples of constitutive promoters include, without limitation, the retroviral Rous sarcoma virus (RSV) LTR promoter (optionally with the RSV enhancer), the cytomegalovirus (CMV) promoter (optionally with the CMV enhancer) [see, e.g., Boshart et al, *Cell,* 41:521-530 (1985)], the SV40 promoter, the dihydrofolate reductase promoter, the β-actin promoter, the phosphoglycerol kinase (PGK) promoter, and the EF1α promoter [Invitrogen].

Inducible promoters allow regulation of gene expression and can be regulated by exogenously supplied compounds, environmental factors such as temperature, or the presence of a specific physiological state, e.g., acute phase, a particular differentiation state of the cell, or in replicating cells only. Inducible promoters and inducible systems are available from a variety of commercial sources, including, without limitation, Invitrogen, Clontech and Ariad. Many other systems have been described and can be readily selected by one of skill in the art. For example, inducible promoters include the zinc-inducible sheep metallothionine (MT) promoter and the dexamethasone (Dex)-inducible mouse mammary tumor virus (MMTV) promoter. Other inducible systems include the T7 polymerase promoter system [WO 98/10088]; the ecdysone insect promoter [No et al, *Proc. Natl. Acad. Sci. USA,* 93:3346-3351 (1996)], the tetracycline-repressible system [Gossen et al, *Proc. Natl. Acad. Sci. USA,* 89:5547-5551 (1992)], the tetracycline-inducible system [Gossen et al, *Science,* 268:1766-1769 (1995), see also Harvey et al, *Curr. Opin. Chem. Biol.,* 2:512-518 (1998)]. Other systems include the FK506 dimer, VP16 or p65 using castradiol, diphenol murislerone, the RU486-inducible system [Wang et al, *Nat. Biotech.,* 15:239-243 (1997) and Wang et al, *Gene Ther.,* 4:432-441 (1997)] and the rapamycin-inducible system [Magari et al, *J. Clin. Invest.,* 100:2865-2872 (1997)]. The effectiveness of some inducible promoters increases over time. In such cases one can enhance the effectiveness of such systems by inserting multiple repressors in tandem, e.g., TetR linked to a TetR by an IRES. Alternatively, one can wait at least 3 days before screening for the desired function. One can enhance expression of desired proteins by known means to enhance the effectiveness of this system. For example, using the Woodchuck Hepatitis Virus Posttranscriptional Regulatory Element (WPRE).

In another embodiment, the native promoter for the transgene will be used. The native promoter may be preferred when it is desired that expression of the transgene should mimic the native expression. The native promoter may be used when expression of the transgene must be regulated temporally or developmentally, or in a tissue-specific manner, or in response to specific transcriptional stimuli. In a further embodiment, other native expression control elements, such as enhancer elements, polyadenylation sites or Kozak consensus sequences may also be used to mimic the native expression.

Another embodiment of the transgene includes a transgene operably linked to a tissue-specific promoter. For instance, if expression in skeletal muscle is desired, a promoter active in muscle should be used. These include the promoters from genes encoding skeletal β-actin, myosin light chain 2A, dystrophin, muscle creatine kinase, as well as synthetic muscle promoters with activities higher than naturally occurring promoters (see L1 et al., Nat. Biotech., 17:241-245 (1999)). Examples of promoters that are tissue-specific are known for liver (albumin, Miyatake et al., *J. Virol.,* 71:5124-32 (1997); hepatitis B virus core promoter, Sandig et al., *Gene Ther.,* 3:1002-9 (1996); alpha-fetoprotein (AFP), Arbuthnot et al., *Hum. Gene Ther.,* 7:1503-14 (1996)), bone osteocalcin (Stein et al., *Mol. Biol. Rep.,* 24:185-96 (1997)); bone sialoprotein (Chen et al., *J. Bone Miner. Res.,* 11:654-64 (1996)), lymphocytes (CD2, Hansal et al., *J. Immunol.,* 161:1063-8 (1998); immunoglobulin heavy chain; T cell receptor chain), neuronal such as neuron-specific enolase (NSE) promoter (Andersen et al., *Cell. Mol. Neurobiol.,* 13:503-15 (1993)), neurofilament light-chain gene (Piccioli et al., *Proc. Natl. Acad. Sci. USA,* 88:5611-5 (1991)), and the neuron-specific vgf gene (Piccioli et al., *Neuron,* 15:373-84 (1995)), among others.

Optionally, vectors carrying transgenes encoding therapeutically useful or immunogenic products may also include selectable markers or reporter genes may include sequences encoding geneticin, hygromicin or purimycin resistance, among others. Such selectable reporters or marker genes (preferably located outside the viral genome to be packaged into a viral particle) can be used to signal the presence of the plasmids in bacterial cells, such as ampicillin resistance. Other components of the vector may include an origin of replication. Selection of these and other promoters and vector elements are conventional and many such sequences are available [see, e.g., Sambrook et al, and references cited therein].

These vectors are generated using the techniques and sequences provided herein, in conjunction with techniques known to those of skill in the art. Such techniques include conventional cloning techniques of cDNA such as those described in texts [Sambrook et al, Molecular Cloning: A Laboratory Manual, Cold Spring Harbor Press, Cold Spring Harbor, N.Y.], use of overlapping oligonucleotide sequences of the adenovirus genomes, polymerase chain reaction, and any suitable method which provides the desired nucleotide sequence.

II. Production of the Recombinant Viral Particle

In one embodiment, the invention provides a method of generating recombinant chimeric adenoviral particles in which the capsid of the chimeric adenovirus is of a serotype incapable of efficient growth in the selected host cell. A vector suitable for production of recombinant chimeric adenoviral particles can be generated by direct cloning. Alternatively, such particles can be generated by homologous recombination between a first vector containing the left end of the chimeric adenoviral genome and a second vector containing the right end of the chimeric adenoviral genome. However, any suitable methodology known to those of skill in the art can be readily utilized to generate a vector suitable to generate a production vector, preferably which contains the entire chimeric adenoviral genome, including a minigene. This production vector is then introduced into a host cell in which the adenoviral capsid protein is assembled and the chimeric adenoviral particle assembled as described.

The chimeric adenoviruses of the invention include those in which one or more adenoviral genes are absent, or otherwise rendered non-functional. If any of the missing gene functions are essential to the replication and infectivity of the adenoviral particle, these functions are supplied by a complementation (or transcomplementing) cell line or a helper vector expressing these functions during production of the chimeric adenoviral particle.

Examples of chimeric adenoviruses containing such missing adenoviral gene functions include those which are partially or completely deleted in the E1a and/or E1b gene. In such a case, the E1 gene functions can be supplied by the packaging host cell, permitting the chimeric construct to be deleted of E1 gene functions and, if desired, for a transgene to be inserted in this region. Optionally, the E1 gene can be of a serotype which transcomplements the serotype providing the other adenovirus sequences in order to further reduce the possibility of recombination and improve safety. In other embodiments, it is desirable to retain an intact E1a and/or E1b region in the recombinant adenoviruses. Such an intact E1 region may be located in its native location in the adenoviral genome or placed in the site of a deletion in the native adenoviral genome (e.g., in the E3 region).

In another example, all or a portion of the adenovirus delayed early gene E3 may be eliminated from the chimeric adenovirus. The function of adenovirus E3 is believed to be irrelevant to the function and production of the recombinant virus particle. Chimeric adenovirus vectors may also be constructed having a deletion of at least the ORF6 region of the E4 gene, and more desirably because of the redundancy in the function of this region, the entire E4 region. Still another vector of this invention contains a deletion in the delayed early gene E2a. Similarly, deletions in the intermediate genes IX and IVa$_2$ may be useful for some purposes. Optionally, deletions may also be made in selected portions of the late genes L1 through L5, as described above.

Other deletions may be made in the other structural or non-structural adenovirus genes. The above-discussed deletions may be used individually, i.e., an adenovirus sequence for use in the present invention may contain deletions in only a single region. Alternatively, deletions of entire genes or portions thereof effective to destroy their biological activity may be used in any combination. For example, in one exemplary vector, the adenovirus sequence may have deletions of the E1 genes and the E4 gene, or of the E1, E2a and E3 genes, or of the E1 and E3 genes, or of E1, E2a and E4 genes, with or without deletion of E3, and so on. As discussed above, such deletions may be used in combination with other mutations, such as temperature-sensitive mutations, to achieve a desired result.

Examples of suitable transcomplementing serotypes are provided above. The use of transcomplementing serotypes can be particularly advantageous where there is diversity between the Ad sequences in the vector of the invention and the human AdE1 sequences found in currently available packaging cells. In such cases, the use of the current human E1-containing cells prevents the generation of replication-competent adenoviruses during the replication and production process. However, in certain circumstances, it will be desirable to utilize a cell line which expresses the E1 gene products can be utilized for production of an E1-deleted simian adenovirus. Such cell lines have been described. See, e.g., U.S. Pat. No. 6,083,716.

A. Packaging Host Cells

Suitably, the packaging host cell is selected from among cells in which the adenovirus serotype donating the left and right terminal ends of the chimeric genome are capable of efficient growth. The host cells are preferably of mammalian origin, and most preferably are of non-human primate or human origin.

Particularly desirable host cells are selected from among any mammalian species, including, without limitation, cells such as A549 [ATCC Accession No. CCL 185], 911 cells, WEHI, 3T3, 10T1/2, HEK 293 cells or PERC6 (both of which express functional adenoviral E1) [Fallaux, F J et al, (1998), Hum Gene Ther, 9:1909-1917], Saos, C2C12, L cells, HT1080, HepG2, HeLa [ATCC Accession No. CCL 2], KB [CCL 17], Detroit [e.g., Detroit 510, CCL 72] and WI-38 [CCL 75] cells, and primary fibroblast, hepatocyte and myoblast cells derived from mammals including human, monkey, mouse, rat, rabbit, and hamster. These cell lines are all available from the American Type Culture Collection, 10801 University Boulevard, Manassas, Va. 20110-2209. Other suitable cell lines may be obtained from other sources. The selection of the mammalian species providing the cells is not a limitation of this invention; nor is the type of mammalian cell, i.e., fibroblast, hepatocyte, tumor cell, etc.

As described above, a chimeric adenovirus of the invention can lack one or more functional adenoviral regulatory and/or structural genes which are supplied either by the host cell or in trans to effect packaging of the chimeric adenovirus into the viral capsid to generate the viral particle. Thus, the ability of a selected host cell to supply transcomplementing adenoviral sequences may be taken into consideration in selecting a desired host cell.

In one example, the cells are from a stable cell line which expresses adenovirus E1a and E1b functions from a cell line which transcomplements the adenovirus serotype which donates the left and right termini to the chimera of the invention, permitting the chimera to be E1-deleted. Alternatively, where the cell line does not transcomplement the adenovirus donating the termini, E1 functions may be provided by the chimera, or in trans.

If desired, one may utilize the sequences provided herein to generate a packaging cell or cell line that expresses, at a minimum, the adenovirus E1 gene from the adenovirus serotype donating the 5' ITR under the transcriptional control of a promoter for expression, or a transcomplementing serotype, in a selected parent cell line. Inducible or constitutive promoters may be employed for this purpose. Examples of such promoters are described in detail elsewhere in this specification. A parent cell is selected for the generation of a novel cell line expressing any desired adenovirus or adenovirus gene, including, e.g., a human Ad5, AdPan5, Pan6, Pan7, SV1, SV25 or SV39 gene. Without limitation, such a parent cell line may be HeLa [ATCC Accession No. CCL 2), A549 [ATCC Accession No. CCL 185], HEK 293, KB [CCL 17], Detroit [e.g., Detroit 510, CCL 72] and WI-38 [CCL 75] cells, among others. Many of these cell lines are all available from the ATCC. Other suitable parent cell lines may be obtained from other sources.

Such E1-expressing cell lines are useful in the generation of chimeric adenovirus E1 deleted vectors. Additionally, or alternatively, the invention provides cell lines that express one or more simian adenoviral gene products, e.g., E1a, E1b, E2a, and/or E4 ORF6, can be constructed using essentially the same procedures for use in the generation of chimeric viral vectors. Such cell lines can be utilized to transcomplement adenovirus vectors deleted in the essential genes that encode those products, or to provide helper functions necessary for packaging of a helper-dependent virus (e.g., adeno-associated virus). The preparation of a host cell according to this invention involves techniques such as assembly of selected DNA sequences. This assembly may be accomplished utilizing conventional techniques. Such techniques include cDNA and genomic cloning, which are well known and are described in Sambrook et al., cited above, use of overlapping oligonucleotide sequences of the adenovirus genomes, combined with polymerase chain reaction, synthetic methods, and any other suitable methods which provide the desired nucleotide sequence.

In still another alternative, the essential adenoviral gene products are provided in trans by the adenoviral vector and/or helper virus. In such an instance, a suitable host cell can be selected from any biological organism, including prokaryotic (e.g., bacterial) cells, and eukaryotic cells, including, insect cells, yeast cells and mammalian cells. Particularly desirable host cells are selected from among any mammalian species, including, without limitation, cells such as A549, WEHI, 3T3, 1 OT1/2, HEK 293 cells or PERC6 (both of which express functional adenoviral E1) [Fallaux, F J et al, (1998), *Hum Gene Ther,* 9:1909-1917], Saos, C2C12, L cells, HT1080, HepG2 and primary fibroblast, hepatocyte and myoblast cells derived from mammals including human, monkey, mouse, rat, rabbit, and hamster. The selection of the mammalian species providing the cells is not a limitation of this invention; nor is the type of mammalian cell, i.e., fibroblast, hepatocyte, tumor cell, etc.

B. Helper Vectors

Thus, depending upon the adenovirus gene content of the adenoviral vectors and any adenoviral gene functions expressed from the host cell, a helper vector may be necessary to provide sufficient adenovirus gene sequences necessary to produce an infective recombinant viral particle containing the minigene. See, for example, the techniques described for preparation of a "minimal" human Ad vector in International Patent Application WO96/13597, published May 9, 1996, and incorporated herein by reference. Suitably, these helper vectors may be non-replicating genetic elements, a plasmid, or a virus.

Useful helper vectors contain selected adenovirus gene sequences not present in the adenovirus vector construct and/or not expressed by the packaging cell line in which the vector is transfected. In one embodiment, the helper virus is replication-defective and contains a variety of adenovirus genes in addition to the sequences described above. Such a helper vector is desirably used in combination with an E1-expressing cell line.

Helper vectors may be formed into poly-cation conjugates as described in Wu et al, *J. Biol. Chem.,* 264:16985-16987 (1989); K. J. Fisher and J. M. Wilson, *Biochem. J.,* 299:49 (Apr. 1, 1994). A helper vector may optionally contain a second reporter minigene. A number of such reporter genes are known to the art. The presence of a reporter gene on the helper virus which is different from the transgene on the adenovirus vector allows both the Ad vector and the helper vector to be independently monitored. This second reporter is used to enable separation between the resulting recombinant virus and the helper virus upon purification.

C. Assembly of Viral Particle and Transfection of a Cell Line

Generally, when delivering the vector comprising the minigene by transfection, the vector is delivered in an amount from about 5 µg to about 100 µg DNA, and preferably about 10 to about 50 µg DNA to about $1 \times 10^4$ cells to about $1 \times 10^{13}$ cells, and preferably about $10^5$ cells. However, the relative amounts of vector DNA to host cells may be adjusted, taking into consideration such factors as the selected vector, the delivery method and the host cells selected.

Introduction into the host cell of the vector may be achieved by any means known in the art or as disclosed above, including transfection, and infection. One or more of the adenoviral genes may be stably integrated into the genome of the host cell, stably expressed as episomes, or expressed transiently. The gene products may all be expressed transiently, on an episome or stably integrated, or some of the gene products may be expressed stably while others are expressed transiently.

Furthermore, the promoters for each of the adenoviral genes may be selected independently from a constitutive promoter, an inducible promoter or a native adenoviral promoter. The promoters may be regulated by a specific physiological state of the organism or cell (i.e., by the differentiation state or in replicating or quiescent cells) or by exogenously added factors, for example.

Introduction of the molecules (as plasmids or viruses) into the host cell may also be accomplished using techniques known to the skilled artisan and as discussed throughout the specification. In preferred embodiment, standard transfection techniques are used, e.g., $CaPO_4$ transfection or electroporation.

Assembly of the selected DNA sequences of the adenovirus (as well as the transgene and other vector elements) into various intermediate plasmids, and the use of the plasmids and vectors to produce a recombinant viral particle are all achieved using conventional techniques. Such techniques include direct cloning as described [G. Gao et al, *Gene Ther.* 2003 October; 10(22):1926-1930; US Patent Publication No. 2003-0092161-A, published May 15, 2003; International Patent Application No. PCT/US03/12405]. Other cloning techniques of cDNA such as those described in texts [Sambrook et al, cited above], use of overlapping oligonucleotide sequences of the adenovirus genomes, polymerase chain reaction, and any suitable method which provides the desired nucleotide sequence can be utilized. Standard transfection and co-transfection techniques are employed, e.g., $CaPO_4$ precipitation techniques. Other conventional methods employed include homologous recombination of the viral genomes, plaquing of viruses in agar overlay, methods of measuring signal generation, and the like.

For example, following the construction and assembly of the desired minigene-containing viral vector, the vector is transfected in vitro in the presence of an optional helper vector into the packaging cell line. The functions expressed from the plasmid, packaging cell line and helper virus, if any, permits the adenovirus-transgene sequences in the vector to be replicated and packaged into virion capsids, resulting in the chimeric viral particles. The current method for producing such virus particles is transfection-based. However, the invention is not limited to such methods. The resulting chimeric adenoviruses are useful in transferring a selected transgene to a selected cell.

III. Use of the Chimeric Adenovirus Vectors

The chimeric adenovirus vectors of the invention are useful for gene transfer to a human or veterinary subject (including, non-human primates, non-simian primates, and other mammals) in vitro, ex vivo, and in vivo.

The recombinant adenovirus vectors described herein can be used as expression vectors for the production of the products encoded by the heterologous genes in vitro. For example, the recombinant adenoviruses containing a gene inserted into the location of an E1 deletion may be transfected into an E1-expressing cell line as described above. Alternatively, replication-competent adenoviruses may be used in another selected cell line. The transfected cells are then cultured in the conventional manner, allowing the recombinant adenovirus to express the gene product from the promoter. The gene product may then be recovered from the culture medium by known conventional methods of protein isolation and recovery from culture.

A chimeric adenoviral vector of the invention provides an efficient gene transfer vehicle that can deliver a selected transgene to a selected host cell in vivo or ex vivo even where the organism has neutralizing antibodies to one or more AAV serotypes. In one embodiment, the rAd and the cells are mixed ex vivo; the infected cells are cultured using conventional methodologies; and the transduced cells are re-infused into the patient. These compositions are particularly well suited to gene delivery for therapeutic purposes and for immunization, including inducing protective immunity.

More commonly, the chimeric adenoviral vectors of the invention will be utilized for delivery of therapeutic or immunogenic molecules, as described below. It will be readily understood for both applications that the recombinant adenoviral vectors of the invention are particularly well suited for use in regimens involving repeat delivery of recombinant adenoviral vectors. Such regimens typically involve delivery of a series of viral vectors in which the viral capsids are alternated. The viral capsids may be changed for each subsequent administration, or after a pre-selected number of administrations of a particular serotype capsid (e.g., one, two, three, four or more). Thus, a regimen may involve delivery of a rAd with a first capsid, delivery with a rAd with a second capsid, and delivery with a third capsid. A variety of other regimens which use the Ad capsids of the invention alone, in combination with one another, or in combination with other Ad serotypes will be apparent to those of skill in the art. Optionally, such a regimen may involve administration of rAd with capsids of non-human primate adenoviruses, human adenoviruses, or artificial (e.g., chimeric) serotypes such as are described herein. Each phase of the regimen may involve administration of a series of injections (or other delivery routes) with a single Ad serotype capsid followed by a series with another Ad serotype capsid. Alternatively, the recombinant Ad vectors of the invention may be utilized in regimens involving other non-adenoviral-mediated delivery systems, including other viral systems, non-viral delivery systems, protein, peptides, and other biologically active molecules.

The following sections will focus on exemplary molecules which may be delivered via the adenoviral vectors of the invention.

A. Ad-Mediated Delivery of Therapeutic Molecules

In one embodiment, the Ad vectors described herein are administered to humans according to published methods for gene therapy. A viral vector of the invention bearing the selected transgene may be administered to a patient, preferably suspended in a biologically compatible solution or pharmaceutically acceptable delivery vehicle. A suitable vehicle includes sterile saline. Other aqueous and non-aqueous isotonic sterile injection solutions and aqueous and non-aqueous sterile suspensions known to be pharmaceutically acceptable carriers and well known to those of skill in the art may be employed for this purpose.

The adenoviral vectors are administered in sufficient amounts to transduce the target cells and to provide sufficient levels of gene transfer and expression to provide a therapeutic benefit without undue adverse or with medically acceptable physiological effects, which can be determined by those skilled in the medical arts. Conventional and pharmaceutically acceptable routes of administration include, but are not limited to, direct delivery to the retina and other intraocular delivery methods, direct delivery to the liver, inhalation, intranasal, intravenous, intramuscular, intratracheal, subcutaneous, intradermal, rectal, oral and other parenteral routes of administration. Routes of administration may be combined, if desired, or adjusted depending upon the transgene or the condition. The route of administration primarily will depend on the nature of the condition being treated.

Dosages of the viral vector will depend primarily on factors such as the condition being treated, the age, weight and health of the patient, and may thus vary among patients. For example, a therapeutically effective adult human or veterinary dosage of the viral vector is generally in the range of from about 100 μL to about 100 mL of a carrier containing concentrations of from about $1 \times 10^6$ to about $1 \times 10^{15}$ particles, about $1 \times 10^{11}$ to $1 \times 10^{13}$ particles, or about $1 \times 10^9$ to $1 \times 10^{12}$ particles. Dosages will range depending upon the size of the animal and the route of administration. For example, a suitable human or veterinary dosage (for about an 80 kg animal) for intramuscular injection is in the range of about $1 \times 10^9$ to about $5 \times 10^{12}$ particles per mL, for a single site. Optionally, multiple sites of administration may be delivered. In another example, a suitable human or veterinary dosage may be in the range of about $1 \times 10^{11}$ to about $1 \times 10^{15}$ particles for an oral formulation. One of skill in the art may adjust these doses, depending the route of administration, and the therapeutic or vaccinal application for which the recombinant vector is employed. The levels of expression of the transgene, or for an immunogen, the level of circulating antibody, can be monitored to determine the frequency of dosage administration. Yet other methods for determining the timing of frequency of administration will be readily apparent to one of skill in the art.

An optional method step involves the co-administration to the patient, either concurrently with, or before or after administration of the viral vector, of a suitable amount of a short acting immune modulator. The selected immune modulator is defined herein as an agent capable of inhibiting the formation of neutralizing antibodies directed against the recombinant vector of this invention or capable of inhibiting cytolytic T lymphocyte (CTL) elimination of the vector. The immune modulator may interfere with the interactions between the T helper subsets ($T_{H1}$ or $T_{H2}$) and B cells to inhibit neutralizing antibody formation. Alternatively, the immune modulator may inhibit the interaction between $T_{H1}$ cells and CTLs to reduce the occurrence of CTL elimination of the vector. A variety of useful immune modulators and dosages for use of same are disclosed, for example, in Yang et al., *J. Virol.*, 70(9) (Sept 1996); International Patent Application No. WO96/12406, published May 2, 1996; and International Patent Application No. PCT/US96/03035, all incorporated herein by reference. Typically, such immune modulators would be selected when the transgene is a therapeutic which requires repeat delivery.

1. Therapeutic Transgenes

Useful therapeutic products encoded by the transgene include hormones and growth and differentiation factors including, without limitation, insulin, glucagon, growth hormone (GH), parathyroid hormone (PTH), growth hormone releasing factor (GRF), follicle stimulating hormone (FSH), luteinizing hormone (LH), human chorionic gonadotropin (hCG), vascular endothelial growth factor (VEGF), angiopoietins, angiostatin, granulocyte colony stimulating factor (GCSF), erythropoietin (EPO), connective tissue growth factor (CTGF), basic fibroblast growth factor (bFGF), acidic fibroblast growth factor (aFGF), epidermal growth factor (EGF), transforming growth factor α (TGF α), platelet-derived growth factor (PDGF), insulin growth factors I and II (IGF-I and IGF-II), any one of the transforming growth factor superfamily, including TGF, activins, inhibins, or any of the bone morphogenic proteins (BMP) BMPs 1-15, any one of the heregluin/neuregulin/ARIA/neu differentiation factor (NDF) family of growth factors, nerve growth factor (NGF), brain-derived neurotrophic factor (BDNF), neurotrophins NT-3 and NT4/5, ciliary neurotrophic factor (CNTF), glial cell line derived neurotrophic factor (GDNF), neurturin, agrin, any one of the family of semaphorins/collapsins, netrin-1 and netrin-2, hepatocyte growth factor (HGF), ephrins, noggin, sonic hedgehog and tyrosine hydroxylase.

Other useful transgene products include proteins that regulate the immune system including, without limitation, cytokines and lymphokines such as thrombopoietin (TPO), interleukins (IL) IL-1 through IL-25 (including, e.g., IL-2, IL-4, IL-12 and IL-18), monocyte chemoattractant protein, leukemia inhibitory factor, granulocyte-macrophage colony stimulating factor, Fas ligand, tumor necrosis factors and, interferons, and, stem cell factor, flk-2/flt3 ligand. Gene products produced by the immune system are also useful in the invention. These include, without limitation, immunoglobulins IgG, IgM, IgA, IgD and IgE, chimeric immunoglobulins, humanized antibodies, single chain antibodies, T cell receptors, chimeric T cell receptors, single chain T cell receptors, class I and class II MHC molecules, as well as engineered immunoglobulins and MHC molecules. Useful gene products also include complement regulatory proteins such as complement regulatory proteins, membrane cofactor protein (MCP), decay accelerating factor (DAF), CR1, CF2 and CD59.

Still other useful gene products include any one of the receptors for the hormones, growth factors, cytokines, lymphokines, regulatory proteins and immune system proteins. The invention encompasses receptors for cholesterol regulation, including the low density lipoprotein (LDL) receptor, high density lipoprotein (HDL) receptor, the very low density lipoprotein (VLDL) receptor, proteins useful in the regulation of lipids, including, e.g., apolipoprotein (apo) A and its isoforms (e.g., ApoAI), apoE and its isoforms including E2, E3 and E4), SRB1, ABC1, and the scavenger receptor. The invention also encompasses gene products such as members of the steroid hormone receptor superfamily including glucocorticoid receptors and estrogen receptors, Vitamin D receptors and other nuclear receptors. In addition, useful gene products include transcription factors such as jun, fos, max, mad, serum response factor (SRF), AP-1, AP2, myb, MyoD and myogenin, ETS-box containing proteins, TFE3, E2F, ATF1, ATF2, ATF3, ATF4, ZF5, NFAT, CREB, HNF-4, C/EBP, SPI, CCAAT-box binding proteins, interferon regulation factor (IRF-1), Wilms tumor protein, ETS-binding protein, STAT, GATA-box binding proteins, e.g., GATA-3, and the forkhead family of winged helix proteins.

Other useful gene products include, carbamoyl synthetase I, ornithine transcarbamylase, arginosuccinate synthetase, arginosuccinate lyase, arginase, fumarylacetacetate hydrolase, phenylalanine hydroxylase, alpha-1 antitrypsin, glucose-6-phosphatase, porphobilinogen deaminase, cystathione beta-synthase, branched chain ketoacid decarboxylase, albumin, isovaleryl-coA dehydrogenase, propionyl CoA carboxylase, methyl malonyl CoA mutase, glutaryl CoA dehydrogenase, insulin, beta-glucosidase, pyruvate carboxylate, hepatic phosphorylase, phosphorylase kinase, glycine decarboxylase, H-protein, T-protein, a cystic fibrosis transmembrane regulator (CFTR) sequence, and a dystrophin cDNA sequence. Other useful gene products include those useful for treatment of hemophilia A (e.g., Factor VIII and its variants, including the light chain and heavy chain of the heterodimer, optionally operably linked by a junction), and the B-domain deleted Factor VIII, see U.S. Pat. Nos. 6,200,560 and 6,221,349], and useful for treatment of hemophilia B (e.g, Factor IX).

Still other useful gene products include non-naturally occurring polypeptides, such as chimeric or hybrid polypeptides having a non-naturally occurring amino acid sequence containing insertions, deletions or amino acid substitutions. For example, single-chain engineered immunoglobulins could be useful in certain immunocompromised patients. Other types of non-naturally occurring gene sequences include antisense molecules and catalytic nucleic acids, such as ribozymes, which could be used to reduce overexpression of a target.

Reduction and/or modulation of expression of a gene are particularly desirable for treatment of hyperproliferative conditions characterized by hyperproliferating cells, as are cancers and psoriasis. Target polypeptides include those polypeptides which are produced exclusively or at higher levels in hyperproliferative cells as compared to normal cells. Target antigens include polypeptides encoded by oncogenes such as myb, myc, fyn, and the translocation gene bcr/abl, ras, src, P53, neu, trk and EGRF. In addition to oncogene products as target antigens, target polypeptides for anti-cancer treatments and protective regimens include variable regions of antibodies made by B cell lymphomas and variable regions of T cell receptors of T cell lymphomas which, in some embodiments, are also used as target antigens for autoimmune disease. Other tumor-associated polypeptides can be used as target polypeptides such as polypeptides which are found at higher levels in tumor cells including the polypeptide recognized by monoclonal antibody 17-1A and folate binding polypeptides.

Other suitable therapeutic polypeptides and proteins include those which may be useful for treating individuals suffering from autoimmune diseases and disorders by conferring a broad based protective immune response against targets that are associated with autoimmunity including cell receptors and cells which produce self-directed antibodies. T-cell mediated autoimmune diseases include rheumatoid arthritis (RA), multiple sclerosis (MS), Sjögren's syndrome, sarcoidosis, insulin dependent diabetes mellitus (DDM), autoimmune thyroiditis, reactive arthritis, ankylosing spondylitis, scleroderma, polymyositis, dermatomyositis, psoriasis, vasculitis, Wegener's granulomatosis, Crohn's disease and ulcerative colitis. Each of these diseases is characterized by T cell receptors (TCRs) that bind to endogenous antigens and initiate the inflammatory cascade associated with autoimmune diseases.

The chimeric adenoviral vectors of the invention are particularly well suited for therapeutic regimens in which multiple adenoviral-mediated deliveries of transgenes is desired, e.g., in regimens involving redelivery of the same transgene or in combination regimens involving delivery of other transgenes. Such regimens may involve administration of a chimeric adenoviral vector, followed by re-administration with a vector from the same serotype adenovirus. Particularly desirable regimens involve administration of a chimeric adenoviral vector of the invention, in which the serotype of the viral vector delivered in the first administration differs from the serotype of the viral vector utilized in one or more of the subsequent administrations. For example, a therapeutic regimen involves administration of a chimeric vector and repeat administration with one or more adenoviral vectors of the same or different serotypes. In another example, a therapeutic regimen involves administration of an adenoviral vector followed by repeat administration with a chimeric vector of the invention which differs from the serotype of the first delivered adenoviral vector, and optionally further administration with another vector which is the same or, preferably, differs from the serotype of the vector in the prior administration steps. These regimens are not limited to delivery of adenoviral vectors constructed using the chimeric serotypes of the invention. Rather, these regimens can readily utilize chimeric or non-chimeric vectors of other adenoviral serotypes, which may be of artificial, human or non-human primate, or other mammalian sources, in combination with one or more of the chimeric vectors of the invention. Examples of such serotypes are discussed elsewhere in this document. Further, these therapeutic regimens may involve either simultaneous or sequential delivery of chimeric adenoviral vectors of the invention in combination with non-adenoviral vectors, non-viral vectors, and/or a variety of other therapeutically useful compounds or molecules. The present invention is not limited to these therapeutic regimens, a variety of which will be readily apparent to one of skill in the art.

B. Ad-Mediated Delivery of Immunogenic Transgenes

The adenoviruses of the invention may also be employed as immunogenic compositions. As used herein, an immunogenic composition is a composition to which a humoral (e.g., antibody) or cellular (e.g., a cytotoxic T cell) response is mounted to a transgene product delivered by the immunogenic composition following delivery to a mammal, and preferably a primate. The present invention provides an Ad that can contain in any of its adenovirus sequence deletions a gene encoding a desired immunogen. Chimeric adenoviruses based on simian or other non-human mammalian primate serotypes are likely to be better suited for use as a live recombinant virus vaccine in different animal species compared to an adenovirus of human origin, but is not limited to such a use. The recombinant adenoviruses can be used as prophylactic or therapeutic vaccines against any pathogen for which the antigen(s) crucial for induction of an immune response and able to limit the spread of the pathogen has been identified and for which the cDNA is available.

Such vaccinal (or other immunogenic) compositions are formulated in a suitable delivery vehicle, as described above. Generally, doses for the immunogenic compositions are in the range defined above for therapeutic compositions. The levels of immunity of the selected gene can be monitored to determine the need, if any, for boosters. Following an assessment of antibody titers in the serum, optional booster immunizations may be desired.

Optionally, a vaccinal composition of the invention may be formulated to contain other components, including, e.g. adjuvants, stabilizers, pH adjusters, preservatives and the like. Such components are well known to those of skill in the vaccine art. Examples of suitable adjuvants include, without limitation, liposomes, alum, monophosphoryl lipid A, and any biologically active factor, such as cytokine, an interleukin, a chemokine, a ligands, and optimally combinations thereof. Certain of these biologically active factors can be expressed in vivo, e.g., via a plasmid or viral vector. For example, such an adjuvant can be administered with a priming DNA vaccine encoding an antigen to enhance the antigen-specific immune response compared with the immune response generated upon priming with a DNA vaccine encoding the antigen only.

The adenoviruses are administered in "an immunogenic amount", that is, an amount of adenovirus that is effective in a route of administration to transfect the desired cells and provide sufficient levels of expression of the selected gene to induce an immune response. Where protective immunity is provided, the recombinant adenoviruses are considered to be vaccine compositions useful in preventing infection and/or recurrent disease.

Alternatively, or in addition, the vectors of the invention may contain a transgene encoding a peptide, polypeptide or protein which induces an immune response to a selected immunogen. The recombinant adenoviruses of this invention are expected to be highly efficacious at inducing cytolytic T cells and antibodies to the inserted heterologous antigenic protein expressed by the vector.

For example, immunogens may be selected from a variety of viral families. Example of desirable viral families against which an immune response would be desirable include, the picornavirus family, which includes the genera rhinoviruses, which are responsible for about 50% of cases of the common cold; the genera enteroviruses, which include polioviruses, coxsackieviruses, echoviruses, and human enteroviruses such as hepatitis A virus; and the genera apthoviruses, which are responsible for foot and mouth diseases, primarily in non-human animals. Within the picornavirus family of viruses, target antigens include the VP1, VP2, VP3, VP4, and VPG. Another viral family includes the calcivirus family, which encompasses the Norwalk group of viruses, which are an important causative agent of epidemic gastroenteritis. Still another viral family desirable for use in targeting antigens for inducing immune responses in humans and non-human animals is the togavirus family, which includes the genera alphavirus, which include Sindbis viruses, RossRiver virus, and Venezuelan, Eastern & Western Equine encephalitis, and rubivirus, including Rubella virus. The flaviviridae family includes dengue, yellow fever, Japanese encephalitis, St. Louis encephalitis and tick borne encephalitis viruses. Other target antigens may be generated from the Hepatitis C or the coronavirus family, which includes a number of non-human viruses such as infectious bronchitis virus (poultry), porcine transmissible gastroenteric virus (pig), porcine hemagglutinatin encephalomyelitis virus (pig), feline infectious peritonitis virus (cats), feline enteric coronavirus (cat), canine coronavirus (dog), and human respiratory coronaviruses, which may cause the common cold and/or non-A, B or C hepatitis. In addition, the human coronaviruses include the putative causative agent of sudden acute respiratory syndrome (SARS). Within the coronavirus family, target antigens include the E1 (also called M or matrix protein), E2 (also called S or Spike protein), E3 (also called HE or hemagglutin-elterose) glycoprotein (not present in all coronaviruses), or N (nucleocapsid). Still other antigens may be targeted against the rhabdovirus family, which includes the genera vesiculovirus (e.g., Vesicular Stomatitis Virus), and the general lyssavirus (e.g., rabies). Within the rhabdovirus family, suitable antigens may be derived from the G protein or the N protein. The family filoviridae, which includes hemorrhagic fever viruses such as Marburg and Ebola virus, may be a suitable source of antigens. The paramyxovirus family includes parainfluenza Virus Type 1, parainfluenza Virus Type 3, bovine parainfluenza Virus Type 3, rubulavirus (mumps virus), parainfluenza Virus Type 2, parainfluenza virus Type 4, Newcastle disease virus (chickens), rinderpest, morbillivirus, which includes measles and canine distemper, and pneumovirus, which includes respiratory syncytial virus. The influenza virus is classified within the family orthomyxovirus and is a suitable source of antigen (e.g., the HA protein, the N1 protein). The bunyavirus family includes the genera bunyavirus (California encephalitis, La Crosse), phlebovirus (Rift Valley Fever), hantavirus (puremala is a hemahagin fever virus), nairovirus (Nairobi sheep disease) and various unassigned bungaviruses. The arenavirus family provides a source of antigens against LCM and Lassa fever virus. The reovirus family includes the genera reovirus, rotavirus (which causes acute gastroenteritis in children), orbiviruses, and cultivirus (Colorado Tick fever), Lebombo (humans), equine encephalosis, blue tongue.

The retrovirus family includes the sub-family oncorivirinal which encompasses such human and veterinary diseases as feline leukemia virus, HTLVI and HTLVII, lentivirinal (which includes human immunodeficiency virus (HIV), simian immunodeficiency virus (SIV), feline immunodeficiency virus (FIV), equine infectious anemia virus, and spumavirinal). Among the lentiviruses, many suitable antigens have been described and can readily be selected. Examples of suitable HIV and SIV antigens include, without limitation the gag, pol, Vif, Vpx, VPR, Env, Tat, Nef, and Rev proteins, as well as various fragments thereof. For example, suitable fragments of the Env protein may include any of its subunits such as the gp120, gp160, gp41, or smaller fragments thereof, e.g., of at least about 8 amino acids in length. Similarly, fragments of the tat protein may be selected. [See, U.S. Pat. No. 5,891,994 and U.S. Pat. No. 6,193,981.] See, also, the HIV and SIV proteins described in D. H. Barouch et al, *J. Virol.,* 75(5): 2462-2467 (March 2001), and R. R. Amara, et al, *Science,* 292:69-74 (6 Apr. 2001). In another example, the HIV and/or SIV immunogenic proteins or peptides may be used to form fusion proteins or other immunogenic molecules. See, e.g., the HIV-1 Tat and/or Nef fusion proteins and immunization regimens described in WO 01/54719, published Aug. 2, 2001, and WO 99/16884, published Apr. 8, 1999. The invention is not limited to the HIV and/or SIV immunogenic proteins or peptides described herein. In addition, a variety of modifications to these proteins have been described or could readily be made by one of skill in the art. See, e.g., the modified gag protein that is described in U.S. Pat. No. 5,972,596. Further, any desired HIV and/or SIV immunogens may be delivered alone or in combination. Such combinations may include expression from a single vector or from multiple vectors. Optionally, another combination may involve delivery of one or more expressed immunogens with delivery of one or more of the immunogens in protein form. Such combinations are discussed in more detail below.

The papovavirus family includes the sub-family polyomaviruses (BKU and JCU viruses) and the sub-family papillomavirus (associated with cancers or malignant progression of papilloma). The adenovirus family includes viruses (EX, AD7, ARD, O.B.) which cause respiratory disease and/or enteritis. The parvovirus includes family feline parvovirus (feline enteritis), feline panleucopeniavirus, canine parvovirus, and porcine parvovirus. The herpesvirus family includes the sub-family alphaherpesvirinae, which encompasses the genera simplexvirus (HSVI, HSVII), varicellovirus (pseudorabies, varicella zoster) and the sub-family betaherpesvirinae, which includes the genera cytomegalovirus (HCMV, muromegalovirus) and the sub-family gammaherpesvirinae, which includes the genera lymphocryptovirus, EBV (Burkitts lymphoma), infectious rhinotracheitis, Marek's disease virus, and rhadinovirus. The poxvirus family includes the sub-family chordopoxyirinae, which encompasses the genera orthopoxvirus (Variola (Smallpox) and Vaccinia (Cowpox)), parapoxvirus, avipoxvirus, capripoxvirus, leporipoxvirus, suipoxvirus, and the sub-family entomopoxyirinae. The hepadnavirus family includes the Hepatitis B virus. One unclassified virus which may be suitable source of antigens is the Hepatitis delta virus. Still other viral sources may include avian infectious bursal disease virus and porcine respiratory and reproductive syndrome virus. The alphavirus family includes equine arteritis virus and various Encephalitis viruses.

The viruses of the present invention may also carry immunogens which are useful to immunize a human or non-human animal against other pathogens including bacteria, fungi, parasitic microorganisms or multicellular parasites which infect human and non-human vertebrates, or from a cancer cell or tumor cell. Examples of bacterial pathogens include pathogenic gram-positive cocci include pneumococci; staphylococci; and streptococci. Pathogenic gram-negative cocci include meningococcus; gonococcus. Pathogenic enteric gram-negative bacilli include enterobacteriaceae; *pseudomonas,* acinetobacteria and eikenella; melioidosis; salmonella; shigella; haemophilus; moraxella; *H. ducreyi* (which causes chancroid); brucella; *Franisella tularensis* (which causes tularemia); *yersinia* (pasteurella); streptobacillus moniliformis and spirillum; Gram-positive bacilli include listeria monocytogenes; erysipelothrix rhusiopathiae; *Corynebacterium diphtheria* (diphtheria); cholera; *B. anthracis* (anthrax); donovanosis (granuloma inguinale); and bartonellosis. Diseases caused by pathogenic anaerobic bacteria include tetanus; botulism; other clostridia; tuberculosis; leprosy; and other mycobacteria. Pathogenic spirochetal diseases include syphilis; treponematoses: yaws, pinta and endemic syphilis; and leptospirosis. Other infections caused by higher pathogen bacteria and pathogenic fungi include actinomycosis; nocardiosis; cryptococcosis, blastomycosis, histoplasmosis and coccidioidomycosis; candidiasis, aspergillosis, and mucormycosis; sporotrichosis; paracoccidiodomycosis, petriellidiosis, torulopsosis, mycetoma and chromomycosis; and dermatophytosis. Rickettsial infections include Typhus fever, Rocky Mountain spotted fever, Q fever, and Rickettsialpox. Examples of mycoplasma and chlamydial infections include: mycoplasma pneumoniae; lymphogranuloma venereum; psittacosis; and perinatal chlamydial infections. Pathogenic eukaryotes encompass pathogenic protozoans and helminths and infections produced thereby include: amebiasis; malaria; leishmaniasis; trypanosomiasis; toxoplasmosis; *Pneumocystis carinii*; Trichans; *Toxoplasma gondii*; babesiosis; giardiasis; trichinosis; filariasis; schistosomiasis; nematodes; trematodes or flukes; and cestode (tapeworm) infections.

Many of these organisms and/or toxins produced thereby have been identified by the Centers for Disease Control [(CDC), Department of Heath and Human Services, USA), as agents which have potential for use in biological attacks. For example, some of these biological agents, include, *Bacillus anthracis* (anthrax), *Clostridium botulinum* and its toxin (botulism), *Yersinia pestis* (plague), variola major (smallpox), *Francisella tularensis* (tularemia), and viral hemorrhagic fevers [filoviruses (e.g., Ebola, Marburg], and arenaviruses [e.g., Lassa, Machupo]), all of which are currently classified as Category A agents; *Coxiella burnetti* (Q fever); *Brucella* species (brucellosis), *Burkholderia mallei* (glanders), *Burkholderia pseudomallei* (meloidosis), *Ricinus communis* and its toxin (ricin toxin), *Clostridium perfringens* and its toxin (epsilon toxin), *Staphylococcus* species and their toxins (enterotoxin B), *Chlamydia psittaci* (psittacosis), water safety threats (e.g., *Vibrio cholerae, Crytosporidium parvum*), Typhus fever (*Richettsia powazekii*), and viral encephalitis (alphaviruses, e.g., Venezuelan equine encephalitis; eastern equine encephalitis; western equine encephalitis); all of which are currently classified as Category B agents; and Nipan virus and hantaviruses, which are currently classified as Category C agents. In addition, other organisms, which are so classified or differently classified, may be identified and/or used for such a purpose in the future. It will be readily understood that the viral vectors and other constructs described herein are useful to deliver antigens from these organisms, viruses, their toxins or other by-products, which will prevent and/or treat infection or other adverse reactions with these biological agents.

Administration of the vectors of the invention to deliver immunogens against the variable region of the T cells elicit an immune response including CTLs to eliminate those T cells. In RA, several specific variable regions of TCRs which are involved in the disease have been characterized. These TCRs include V-3, V-14, V-17 and Vα-17. Thus, delivery of a nucleic acid sequence that encodes at least one of these polypeptides will elicit an immune response that will target T cells involved in RA. In MS, several specific variable regions of TCRs which are involved in the disease have been characterized. These TCRs include V-7 and Vα-10. Thus, delivery of a nucleic acid sequence that encodes at least one of these polypeptides will elicit an immune response that will target T cells involved in MS. In scleroderma, several specific variable regions of TCRs which are involved in the disease have been characterized. These TCRs include V-6, V-8, V-14 and Vα-16, Vα-3C, Vα-7, Vα-14, Vα-15, Vα-16, Vα-28 and Vα-12. Thus, delivery of a chimeric adenovirus that encodes at least one of these polypeptides will elicit an immune response that will target T cells involved in scleroderma.

C. Ad-Mediated Delivery Methods

The therapeutic levels, or levels of immunity, of the selected gene can be monitored to determine the need, if any, for boosters. Following an assessment of CD8+ T cell response, or optionally, antibody titers, in the serum, optional booster immunizations may be desired. Optionally, the adenoviral vectors of the invention may be delivered in a single administration or in various combination regimens, e.g., in combination with a regimen or course of treatment involving other active ingredients or in a prime-boost regimen. A variety of such regimens have been described in the art and may be readily selected.

For example, prime-boost regimens may involve the administration of a DNA (e.g., plasmid) based vector to prime the immune system to a second or further, booster, administration with a traditional antigen, such as a protein or a recombinant virus carrying the sequences encoding such an antigen. See, e.g., WO 00/11140, published Mar. 2, 2000, incorporated by reference. Alternatively, an immunization regimen may involve the administration of a chimeric adenoviral vector of the invention to boost the immune response to a vector (either viral or DNA-based) carrying an antigen, or a protein. In still another alternative, an immunization regimen involves administration of a protein followed by booster with a vector encoding the antigen.

In one embodiment, the invention provides a method of priming and boosting an immune response to a selected antigen by delivering a plasmid DNA vector carrying said antigen, followed by boosting with an adenoviral vector of the invention. In one embodiment, the prime-boost regimen involves the expression of multiproteins from the prime and/or the boost vehicle. See, e.g., R. R. Amara, *Science*, 292:69-74 (6 Apr. 2001) which describes a multiprotein regimen for expression of protein subunits useful for generating an immune response against HIV and SIV. For example, a DNA prime may deliver the Gag, Pol, Vif, VPX and Vpr and Env, Tat, and Rev from a single transcript. Alternatively, the SIV Gag, Pol and HIV-1 Env is delivered in a recombinant adenovirus construct of the invention. Still other regimens are described in WO 99/16884 and WO 01/54719.

However, the prime-boost regimens are not limited to immunization for HIV or to delivery of these antigens. For example, priming may involve delivering with a first vector of the invention followed by boosting with a second vector, or with a composition containing the antigen itself in protein form. In one example, the prime-boost regimen can provide a protective immune response to the virus, bacteria or other organism from which the antigen is derived. In another desired embodiment, the prime-boost regimen provides a therapeutic effect that can be measured using convention assays for detection of the presence of the condition for which therapy is being administered.

The priming composition may be administered at various sites in the body in a dose dependent manner, which depends on the antigen to which the desired immune response is being targeted. The invention is not limited to the amount or situs of injection(s) or to the pharmaceutical carrier. Rather, the regimen may involve a priming and/or boosting step, each of which may include a single dose or dosage that is administered hourly, daily, weekly or monthly, or yearly. As an example, the mammals may receive one or two doses containing between about 10 µg to about 50 µg of plasmid in carrier. A desirable amount of a DNA composition ranges between about 1 µg to about 10,000 µg of the DNA vector. Dosages may vary from about 1 µg to 1000 µg DNA per kg of subject body weight. The amount or site of delivery is desirably selected based upon the identity and condition of the mammal. The dosage unit of the vector suitable for delivery of the antigen to the mammal is described herein. The vector is prepared for administration by being suspended or dissolved in a pharmaceutically or physiologically acceptable carrier such as isotonic saline; isotonic salts solution or other formulations that will be apparent to those skilled in such administration. The appropriate carrier will be evident to those skilled in the art and will depend in large part upon the route of administration. The compositions of the invention may be administered to a mammal according to the routes described above, in a sustained release formulation using a biodegradable biocompatible polymer, or by on-site delivery using micelles, gels and liposomes. Optionally, the priming step of this invention also includes administering with the priming composition, a suitable amount of an adjuvant, such as are defined herein.

Preferably, a boosting composition is administered about 2 to about 27 weeks after administering the priming composition to the mammalian subject. The administration of the boosting composition is accomplished using an effective amount of a boosting composition containing or capable of delivering the same antigen as administered by the priming DNA vaccine. The boosting composition may be composed of a recombinant viral vector derived from the same viral source (e.g., adenoviral sequences of the invention) or from another source. Alternatively, the "boosting composition" can be a composition containing the same antigen as encoded in the priming DNA vaccine, but in the form of a protein or peptide, which composition induces an immune response in the host. In another embodiment, the boosting composition contains a DNA sequence encoding the antigen under the control of a regulatory sequence directing its expression in a mammalian cell, e.g., vectors such as well-known bacterial or viral vectors. The primary requirements of the boosting composition are that the antigen of the composition is the same antigen, or a cross-reactive antigen, as that encoded by the priming composition.

In another embodiment, the adenoviral vectors of the invention are also well suited for use in a variety of other immunization and therapeutic regimens. Such regimens may involve delivery of adenoviral vectors of the invention simultaneously or sequentially with Ad vectors of different serotype capsids, regimens in which adenoviral vectors of the invention are delivered simultaneously or sequentially with non-Ad vectors, regimens in which the adenoviral vectors of the invention are delivered simultaneously or sequentially with proteins, peptides, and/or other biologically useful therapeutic or immunogenic compounds. Such uses will be readily apparent to one of skill in the art.

IV. Simian Adenovirus 18 Sequences

The invention provides nucleic acid sequences and amino acid sequences of Ad SA18, which are isolated from the other viral material with which they are associated in nature. These sequences are useful in preparing heterologous molecules containing the nucleic acid sequences and amino acid sequences, and regions or fragments thereof as are described herein, viral vectors which are useful for a variety of purposes, including the constructs and compositions, and such methods as are described herein for the chimeric adenoviruses, including, e.g., in host cells for production of viruses requiring adenoviral helper functions, as delivery vehicles for heterologous molecules such as those described herein. These sequences are also useful in generating the chimeric adenoviruses of the invention.

A. Nucleic Acid Sequences

The SA18 nucleic acid sequences of the invention include nucleotides SEQ D NO: 12, nt 1 to 31967. See, Sequence Listing, which is incorporated by reference herein. The nucleic acid sequences of the invention further encompass the strand which is complementary to the sequences of SEQ ID NO: 12, as well as the RNA and cDNA sequences corresponding to the sequences of these sequences figures and their complementary strands. Further included in this invention are nucleic acid sequences which are greater than 95 to 98%, and more preferably about 99 to 99.9% homologous or identical to the Sequence Listing. Also included in the nucleic acid sequences of the invention are natural variants and engineered modifications of the sequences provided in SEQ ID NO: 12 and their complementary strands. Such modifications include, for example, labels that are known in the art, methylation, and substitution of one or more of the naturally occurring nucleotides with a degenerate nucleotide.

The invention further encompasses fragments of the sequences of SA18, their complementary strand, cDNA and RNA complementary thereto. Suitable fragments are at least 15 nucleotides in length, and encompass functional fragments, i.e., fragments which are of biological interest. For example, a functional fragment can express a desired adenoviral product or may be useful in production of recombinant viral vectors. Such fragments include the gene sequences and fragments listed in the tables below.

The following tables provide the transcript regions and open reading frames in the simian adenovirus sequences of the invention. For certain genes, the transcripts and open reading frames (ORFs) are located on the strand complementary to that presented in SEQ ID NO: 12. See, e.g., E2b, E4 and E2a. The calculated molecular weights of the encoded proteins are also shown.

| Adenovirus Gene Region | Protein | Ad SA18, SEQ ID NO: 12 | | |
|---|---|---|---|---|
| | | start | End | M.W. |
| ITR | | 1 | 180 | |
| E1a | 13S | 916 | 1765 | 27264 |
| | 12S | 916 | 1765 | 24081 |
| E1b | Small T | 1874 | 2380 | 19423 |
| | LargeT | 2179 | 3609 | 52741 |
| | IX | 3678 | 4079 | 13701 |
| E2b | IVa2 | 5478 | 4126 | 51295 |
| | Polymerase | 13745 | 5229 | 128392 |
| | PTP | 13745 | 8597 | 75358 |
| | Agnoprotein | 8007 | 8705 | 23610 |
| L1 | 52/55 kD | 10788 | 11945 | 43416 |
| | IIIa | 11966 | 13699 | 63999 |
| L2 | Penton | 13796 | 15322 | 57166 |
| | VII | 15328 | 15873 | 20352 |
| | V | 15920 | 17050 | 42020 |
| L3 | VI | 17348 | 18154 | 29222 |
| | Hexon | 18257 | 21010 | 102912 |
| | Endoprotease | 21029 | 21640 | 23015 |
| 2a | DBP | 23147 | 21711 | 53626 |
| L4 | 100 kD | 23175 | 25541 | 87538 |
| | 22 kD homolog | 25204 | 25797 | 22206 |
| | 33 kD homolog | 25204 | 26025 | 24263 |
| | VIII | 26107 | 26817 | 25490 |
| E3 | Orf#1 | 26817 | 27125 | 11814 |
| L5 | Fiber | 27192 | 29015 | 65455 |
| E4 | Orf 6/7 | 30169 | 29067 | 13768 |
| | Orf 6 | 30169 | 29303 | 33832 |
| | Orf 4 | 30464 | 30099 | 14154 |
| | Orf 3 | 30816 | 30466 | 13493 |
| | Orf 2 | 31205 | 30813 | 14698 |
| | Orf 1 | 31608 | 31231 | 14054 |
| ITR | | 31788 | 31967 | |

The SA18 adenoviral nucleic acid sequences are useful as therapeutic and immunogenic agents and in construction of a variety of vector systems and host cells. Such vectors are useful for any of the purposes described above for the chimeric adenovirus. Additionally, these SA18 sequences and products may be used alone or in combination with other adenoviral sequences or fragments, or in combination with elements from other adenoviral or non-adenoviral sequences. The adenoviral sequences of the invention are also useful as antisense delivery vectors, gene therapy vectors, or vaccine vectors, and in methods of using same. Thus, the invention further provides nucleic acid molecules, gene delivery vectors, and host cells which contain the Ad sequences of the invention.

For example, the invention encompasses a nucleic acid molecule containing simian Ad ITR sequences of the invention. In another example, the invention provides a nucleic acid molecule containing simian Ad sequences of the invention encoding a desired Ad gene product. Still other nucleic acid molecule constructed using the sequences of the invention will be readily apparent to one of skill in the art, in view of the information provided herein.

In one embodiment, the simian Ad gene regions identified herein may be used in a variety of vectors for delivery of a heterologous molecule to a cell. Examples of such molecules and methods of delivery are provided in Section III herein. For example, vectors are generated for expression of an adenoviral capsid protein (or fragment thereof) for purposes of generating a viral vector in a packaging host cell. Such vectors may be designed for expression in trans. Alternatively, such vectors are designed to provide cells which stably contain sequences which express desired adenoviral functions, e.g., one or more of E1a, E1b, the terminal repeat sequences, E2a, E2b, E4, E40RF6 region.

In addition, the adenoviral gene sequences and fragments thereof are useful for providing the helper functions necessary for production of helper-dependent viruses (e.g., adenoviral vectors deleted of essential functions or adeno-associated viruses (AAV)). For such production methods, the simian adenoviral sequences of the invention are utilized in such a method in a manner similar to those described for the human Ad. However, due to the differences in sequences between the simian adenoviral sequences of the invention and those of human Ad, the use of the sequences of the invention essentially eliminate the possibility of homologous recombination with helper functions in a host cell carrying human Ad E1 functions, e.g., 293 cells, which may produce infectious adenoviral contaminants during rAAV production.

Methods of producing rAAV using adenoviral helper functions have been described at length in the literature with human adenoviral serotypes. See, e.g., U.S. Pat. No. 6,258,595 and the references cited therein. See, also, U.S. Pat. No. 5,871,982; WO 99/14354; WO 99/15685; WO 99/47691. These methods may also be used in production of non-human serotype AAV, including non-human primate AAV serotypes. The simian adenoviral gene sequences of the invention which provide the necessary helper functions (e.g., E1a, E1b, E2a and/or E4 ORF6) can be particularly useful in providing the necessary adenoviral function while minimizing or eliminating the possibility of recombination with any other adenoviruses present in the rAAV-packaging cell which are typically of human origin. Thus, selected genes or open reading frames of the adenoviral sequences of the invention may be utilized in these rAAV production methods.

Alternatively, recombinant adenoviral simian vectors of the invention may be utilized in these methods. Such recombinant adenoviral simian vectors may include, e.g., a hybrid simian Ad/AAV in which simian Ad sequences flank a rAAV expression cassette composed of, e.g., AAV 3' and/or 5' ITRs and a transgene under the control of regulatory sequences which control its expression. One of skill in the art will recognize that still other simian adenoviral vectors and/or gene sequences of the invention will be useful for production of rAAV and other viruses dependent upon adenoviral helper.

In still another embodiment, nucleic acid molecules are designed for delivery and expression of selected adenoviral gene products in a host cell to achieve a desired physiologic effect. For example, a nucleic acid molecule containing sequences encoding an adenovirus E1a protein of the invention may be delivered to a subject for use as a cancer therapeutic. Optionally, such a molecule is formulated in a lipid-based carrier and preferentially targets cancer cells. Such a formulation may be combined with other cancer therapeutics (e.g., cisplatin, taxol, or the like). Still other uses for the adenoviral sequences provided herein will be readily apparent to one of skill in the art.

In addition, one of skill in the art will readily understand that the Ad sequences of the invention can be readily adapted for use for a variety of viral and non-viral vector systems for in vitro, ex vivo or in vivo delivery of therapeutic and immunogenic molecules, including any of those identified as being deliverable via the chimeric adenoviruses of the invention. For example, the simian Ad genome of the invention can be utilized in a variety of rAd and non-rAd vector systems. Such vectors systems may include, e.g., plasmids, lentiviruses, retroviruses, poxviruses, vaccinia viruses, and adeno-associated viral systems, among others. Selection of these vector systems is not a limitation of the present invention.

The invention further provides molecules useful for production of the simian and simian-derived proteins of the invention. Such molecules which carry polynucleotides including the simian Ad DNA sequences of the invention can be in the form of a vector.

B. Simian Adenoviral Proteins of the Invention

The invention further provides gene products of the above adenoviruses, such as proteins, enzymes, and fragments thereof, which are encoded by the adenoviral nucleic acids of the invention. The invention further encompasses SA18 proteins, enzymes, and fragments thereof, having the amino acid sequences encoded by these nucleic acid sequences which are generated by other methods. Such proteins include those encoded by the open reading frames identified in the tables above, and fragments thereof.

Thus, in one aspect, the invention provides unique simian adenoviral proteins which are substantially pure, i.e., are free of other viral and proteinaceous proteins. Preferably, these proteins are at least 10% homogeneous, more preferably 60% homogeneous, and most preferably 95% homogeneous.

In one embodiment, the invention provides unique simian-derived capsid proteins. As used herein, a simian-derived capsid protein includes any adenoviral capsid protein that contains a SA18 capsid protein or a fragment thereof, as defined above, including, without limitation, chimeric capsid proteins, fusion proteins, artificial capsid proteins, synthetic capsid proteins, and recombinantly capsid proteins, without limitation to means of generating these proteins.

Suitably, these simian-derived capsid proteins contain one or more SA18 regions or fragments thereof (e.g., a hexon, penton, fiber or fragment thereof) in combination with capsid regions or fragments thereof of different adenoviral serotypes, or modified simian capsid proteins or fragments, as described herein. A "modification of a capsid protein associated with altered tropism" as used herein includes an altered capsid protein, i.e, a penton, hexon or fiber protein region, or fragment thereof, such as the knob domain of the fiber region, or a polynucleotide encoding same, such that specificity is altered. The simian-derived capsid may be constructed with one or more of the simian Ad of the invention or another Ad serotypes which may be of human or non-human origin. Such Ad may be obtained from a variety of sources including the ATCC, commercial and academic sources, or the sequences of the Ad may be obtained from GenBank or other suitable sources.

The amino acid sequences of the simian adenoviruses penton proteins of the invention are provided herein. The AdSA18 penton protein is provided in SEQ ID NO: 13. Suitably, any of these penton proteins, or unique fragments thereof, may be utilized for a variety of purposes. Examples of suitable fragments include the penton having N-terminal and/or C-terminal truncations of about 50, 100, 150, or 200 amino acids, based upon the amino acid numbering provided above. Other suitable fragments include shorter internal, C-terminal, or N-terminal fragments, Further, the penton protein may be modified for a variety of purposes known to those of skill in the art.

The invention further provides the amino acid sequences of the hexon protein of SA18, SEQ ID NO:14. Suitably, this hexon protein, or unique fragments thereof, may be utilized for a variety of purposes. Examples of suitable fragments include the hexon having N-terminal and/or C-terminal truncations of about 50, 100, 150, 200, 300, 400, or 500 amino acids, based upon the amino acid numbering provided above and in SEQ ID NO: 14. Other suitable fragments include shorter internal, C-terminal, or N-terminal fragments. For example, one suitable fragment the loop region (domain) of the hexon protein, designated DE1 and FG1, or a hypervariable region thereof. Such fragments include the regions spanning amino acid residues about 125 to 443; about 138 to 441, or smaller fragments, such as those spanning about residue 138 to residue 163; about 170 to about 176; about 195 to about 203; about 233 to about 246; about 253 to about 264; about 287 to about 297; about 404 to about 430, about 430 to 550, about 545 to 650; of the simian hexon proteins, with reference to SEQ ID NO: 14. Other suitable fragments may be readily identified by one of skill in the art. Further, the hexon protein may be modified for a variety of purposes known to those of skill in the art. Because the hexon protein is the determinant for serotype of an adenovirus, such artificial hexon proteins would result in adenoviruses having artificial serotypes. Other artificial capsid proteins can also be constructed using the chimp Ad penton sequences and/or fiber sequences of the invention and/or fragments thereof.

In one example, it may be desirable to generate an adenovirus having an altered hexon protein utilizing the sequences of a hexon protein of the invention. One suitable method for altering hexon proteins is described in U.S. Pat. No. 5,922,315, which is incorporated by reference. In this method, at least one loop region of the adenovirus hexon is changed with at least one loop region of another adenovirus serotype. Thus, at least one loop region of such an altered adenovirus hexon protein is a simian Ad hexon loop region of the invention. In one embodiment, a loop region of the SA18 hexon protein is replaced by a loop region from another adenovirus serotype. In another embodiment, the loop region of the SA18 hexon is used to replace a loop region from another adenovirus serotype. Suitable adenovirus serotypes may be readily selected from among human and non-human serotypes, as described herein. SA18 is selected for purposes of illustration only; the other simian Ad hexon proteins of the invention may be similarly altered, or used to alter another Ad hexon. The selection of a suitable serotype is not a limitation of the present invention. Still other uses for the hexon protein sequences of the invention will be readily apparent to those of skill in the art.

The invention further encompasses the fiber proteins of the simian adenoviruses of the invention. The fiber protein of AdSA18 has the amino acid sequence of SEQ ID NO: 15. Suitably, this fiber protein, or unique fragments thereof, may be utilized for a variety of purposes. One suitable fragment is the fiber knob, which spans about amino acids 247 to 425 of SEQ ID NO: 15. Examples of other suitable fragments include the fiber having N-terminal and/or C-terminal truncations of about 50, 100, 150, or 200 amino acids, based upon the amino acid numbering provided above and in SEQ ID NO: 15. Still other suitable fragments include internal fragments. Further, the fiber protein may be modified using a variety of techniques known to those of skill in the art.

The invention further encompasses unique fragments of the proteins of the invention which are at least 8 amino acids in length. However, fragments of other desired lengths can be readily utilized. In addition, the invention encompasses such modifications as may be introduced to enhance yield and/or expression of an SA18 gene product, e.g., construction of a fusion molecule in which all or a fragment of the SA18 gene product is fused (either directly or via a linker) with a fusion partner to enhance. Other suitable modifications include, without limitation, truncation of a coding region (e.g., a protein or enzyme) to eliminate a pre- or pro-protein ordinarily cleaved and to provide the mature protein or enzyme and/or mutation of a coding region to provide a secretable gene product. Still other modifications will be readily apparent to one of skill in the art. The invention further encompasses proteins having at least about 95% to 99% identity to the SA18 proteins provided herein.

As described herein, vectors of the invention containing the adenoviral capsid proteins of the invention are particularly well suited for use in applications in which the neutralizing antibodies diminish the effectiveness of other Ad serotype based vectors, as well as other viral vectors. The rAd vectors of the invention are particularly advantageous in readministration for repeat gene therapy or for boosting immune response (vaccine titers). Examples of such regimens are provided herein.

Under certain circumstances, it may be desirable to use one or more of the SA18 gene products (e.g., a capsid protein or a fragment thereof) to generate an antibody. The term "an antibody," as used herein, refers to an immunoglobulin molecule which is able to specifically bind to an epitope. Thus, the antibodies of the invention bind, preferably specifically and without cross-reactivity, to a SA18 epitope. The antibodies in the present invention exist in a variety of forms including, for example, high affinity polyclonal antibodies, monoclonal antibodies, synthetic antibodies, chimeric antibodies, recombinant antibodies and humanized antibodies. Such antibodies originate from immunoglobulin classes IgG, IgM, IgA, IgD and IgE.

Such antibodies may be generated using any of a number of methods know in the art. Suitable antibodies may be generated by well-known conventional techniques, e.g. Kohler and Milstein and the many known modifications thereof. Similarly desirable high titer antibodies are generated by applying known recombinant techniques to the monoclonal or polyclonal antibodies developed to these antigens [see, e.g., PCT Patent Application No. PCT/GB85/00392; British Patent Application Publication No. GB2188638A; Amit et al., 1986 *Science*, 233:747-753; Queen et al., 1989 *Proc. Natl. Acad. Sci. USA*, 86:10029-10033; PCT Patent Application No. PCT/WO9007861; and Riechmann et al., *Nature*, 332:323-327 (1988); Huse et al, 1988a *Science*, 246:1275-1281]. Alternatively, antibodies can be produced by manipulating the complementarity determining regions of animal or human antibodies to the antigen of this invention. See, e.g., E. Mark and Padlin, "Humanization of Monoclonal Antibodies", Chapter 4, The Handbook of Experimental Pharmacology, Vol. 113, The Pharmacology of Monoclonal Antibodies, Springer-Verlag (June, 1994); Harlow et al., 1999, Using Antibodies: A Laboratory Manual, Cold Spring Harbor Laboratory Press, NY; Harlow et al., 1989, Antibodies: A Laboratory Manual, Cold Spring Harbor, N.Y.; Houston et al., 1988, *Proc. Natl. Acad. Sci. USA* 85:5879-5883; and Bird et al., 1988, *Science* 242:423-426. Further provided by the present invention are anti-idiotype antibodies (Ab2) and anti-anti-idiotype antibodies (Ab3). See, e.g., M. Wettendorff et al., "Modulation of anti-tumor immunity by anti-idiotypic antibodies." In Idiotypic Network and Diseases, ed. by J. Cerny and J. Hiernaux, 1990 *J. Am. Soc. Microbiol., Washington D.C.: pp.* 203-229]. These anti-idiotype and anti-anti-idiotype antibodies are produced using techniques well known to those of skill in the art. These antibodies may be used for a variety of purposes, including diagnostic and clinical methods and kits.

Under certain circumstances, it may be desirable to introduce a detectable label or a tag onto a SA18 gene product, antibody or other construct of the invention. As used herein, a detectable label is a molecule which is capable, alone or upon interaction with another molecule, of providing a detectable signal. Most desirably, the label is detectable visually, e.g. by fluorescence, for ready use in immunohistochemical analyses or immunofluorescent microscopy. For example, suitable labels include fluorescein isothiocyanate (FITC), phycoerythrin (PE), allophycocyanin (APC), coriphosphine-O (CPO) or tandem dyes, PE-cyanin-5 (PC5), and PE-Texas Red (ECD). All of these fluorescent dyes are commercially available, and their uses known to the art. Other useful labels include a colloidal gold label. Still other useful labels include radioactive compounds or elements. Additionally, labels include a variety of enzyme systems that operate to reveal a colorimetric signal in an assay, e.g., glucose oxidase (which uses glucose as a substrate) releases peroxide as a product which in the presence of peroxidase and a hydrogen donor such as tetramethyl benzidine (TMB) produces an oxidized TMB that is seen as a blue color. Other examples include horseradish peroxidase (HRP) or alkaline phosphatase (AP), and hexokinase in conjunction with glucose-6-phosphate dehydrogenase which reacts with ATP, glucose, and NAD+ to yield, among other products, NADH that is detected as increased absorbance at 340 nm wavelength.

Other label systems that are utilized in the methods of this invention are detectable by other means, e.g., colored latex microparticles [Bangs Laboratories, Indiana] in which a dye is embedded are used in place of enzymes to form conjugates with the target sequences provide a visual signal indicative of the presence of the resulting complex in applicable assays.

Methods for coupling or associating the label with a desired molecule re similarly conventional and known to those of skill in the art. Known methods of label attachment are described [see, for example, Handbook of Fluorescent probes and Research Chemicals, 6th Ed., R. P. M. Haugland, Molecular Probes, Inc., Eugene, Oreg., 1996; Pierce Catalog and Handbook, Life Science and Analytical Research Products, Pierce Chemical Company, Rockford, Ill., 1994/1995]. Thus, selection of the label and coupling methods do not limit this invention.

The sequences, proteins, and fragments of the invention may be produced by any suitable means, including recombinant production, chemical synthesis, or other synthetic means. Suitable production techniques are well known to those of skill in the art. See, e.g., Sambrook et al, Molecular Cloning: A Laboratory Manual, Cold Spring Harbor Press (Cold Spring Harbor, N.Y.). Alternatively, peptides can also be synthesized by the well known solid phase peptide synthesis methods (Merrifield, *J. Am. Chem. Soc.,* 85:2149 (1962); Stewart and Young, Solid Phase Peptide Synthesis (Freeman, San Francisco, 1969) pp. 27-62). These and other suitable production methods are within the knowledge of those of skill in the art and are not a limitation of the present invention.

In addition, one of skill in the art will readily understand that the Ad sequences of the invention can be readily adapted for use for a variety of viral and non-viral vector systems for in vitro, ex vivo or in vivo delivery of therapeutic and immunogenic molecules. For example, in one embodiment, the simian Ad capsid proteins and other simian adenovirus proteins described herein are used for non-viral, protein-based delivery of genes, proteins, and other desirable diagnostic, therapeutic and immunogenic molecules. In one such embodiment, a protein of the invention is linked, directly or indirectly, to a molecule for targeting to cells with a receptor for adenoviruses. Preferably, a capsid protein such as a hexon, penton, fiber or a fragment thereof having a ligand for a cell surface receptor is selected for such targeting. Suitable molecules for delivery are selected from among the therapeutic molecules described herein and their gene products. A variety of linkers including, lipids, polyLys, and the like may be utilized as linkers. For example, the simian penton protein may be readily utilized for such a purpose by production of a fusion protein using the simian penton sequences in a manner analogous to that described in Medina-Kauwe L K, et al, *Gene Ther.* 2001 May; 8(10):795-803 and Medina-Kauwe L K, et al, *Gene Ther.* 2001 December; 8(23): 1753-1761. Alternatively, the amino acid sequences of simian Ad protein IX may be utilized for targeting vectors to a cell surface receptor, as described in US Patent Appln 20010047081. Suitable ligands include a CD40 antigen, an RGD-containing or polylysine-containing sequence, and the like. Still other simian Ad proteins, including, e.g., the hexon protein and/or the fiber protein, may be used for used for these and similar purposes.

Still other adenoviral proteins of the invention may be used as alone, or in combination with other adenoviral protein, for a variety of purposes which will be readily apparent to one of skill in the art. In addition, still other uses for the adenoviral proteins of the invention will be readily apparent to one of skill in the art.

The compositions of this invention include vectors that deliver a heterologous molecule to cells, either for therapeutic or vaccine purposes. Such vectors, containing simian adenovirus DNA of SA18 and a minigene, can be constructed using techniques such as those described herein for the chimeric adenoviruses and such techniques as are known in the art. Alternatively, SA19 may be a source for sequences of the chimeric adenoviruses are described herein.

The following examples illustrate construction and use of several chimeric viruses, including Pan5/C1, hu5/Pan7 and hu5/SV25, and Pan6/Pan7. However, these chimera are illustrative only and are not intended to limit the invention to those illustrated embodiments.

EXAMPLE 1

Construction of Pan5/C1 Chimeric Simian Viruses

Five different adenoviruses initially isolated from the chimpanzee, AdC68 [U.S. Pat. No. 6,083,716], AdPan5, AdPan7, AdPan6 and AdC1 [U.S. Pat. No. 6,083,716] have been sequenced. See, International Application No. PCT/US02/33645, filed November 2002 for the sequences of Pan5 [SEQ ID NO: 1], Pan7 [SEQ ID NO:3], and Pan6 [SEQ ID NO:2]. This application also provides sequences for SV1, SV25 and SV39 [SEQ ID No. 4, 5, 6, respectively]. Sequence comparison of the capsid protein sequences predicted that AdC1 clearly belonged to a different serological subgroup than the other four chimpanzee derived adenoviruses.

However, attempts to cultivate AdC1 in HEK293 cells revealed it to be fastidious in its growth characteristics (data not shown) and therefore possibly unsuitable for use as a vector using the currently available E1 complementing cell lines. However, because of the obvious sequence dissimilarity of AdC1 capsid protein sequence from the other chimpanzee derived adenoviruses (as well as the huAd5), chimeric adenovirus vectors were generated with the capsid characteristics of AdC1. In view of the above-mentioned drawbacks associated with only making hexon changes, more extensive replacements were made in the chimera described herein, i.e., construction of chimeras where the replacement went beyond just the hexon, to achieve two goals. The first was to determine whether making extended replacements would allow for the rescue of viruses containing hexons of unrelated serotypes that may not otherwise be amenable to rescue. The second goal was to test whether the growth characteristics of adenovirus vectors such as AdPan5, that have been found in our laboratory to be able to be grown to high titer for the purpose of manufacture, would also be present in the chimeric virus, particularly when the hexon (and other capsid proteins) are derived from a virus such as AdC1 that are difficult to grow to a high yield in cell lines such as HEK293.

An added bonus of extending the replacement to include the fiber protein would be to further increase the antigenic dissimilarity to beyond that afforded by a hexon change alone.

As an alternative to obtaining purified virus as source for adenoviral DNA to sequence, we have resorted to cloning restriction fragments of viral DNA obtained from infected cells ("Hirt prep"). The first adenovirus we have sequenced in this way is Simian Adenovirus. EcoRI digestion of the Simian Adenovirus yielded 7 fragments. Shotgun cloning yielded clones of the 5 internal fragments, which were cloned and sequenced. Completion of the sequencing was carried out by walking towards each of the ends of the genome. The map of the genome is shown in FIG. 1.

A. Construction of Two Pan5/C1 Chimeric Plasmids

The overall approach towards constructing chimeric viruses was to first assemble the complete E1 deleted virus DNA into a single plasmid flanked by recognition sites for the restriction enzyme SwaI, digest the plasmid DNA with SwaI to release the virus DNA ends, and transfect the DNA into HEK293 cells to determine whether viable chimeric adenovirus could be rescued. Two chimeric virus plasmids were constructed, p5C1short and p5C1long.

The plasmid p5C1short harbors an E1 deleted Pan5 virus where an internal 15226 bp segment (18332-33557) has been replaced by a functionally analogous 14127 bp (18531-32657) from AdC1. This results in the replacement of the Pan5 proteins hexon, endoprotease, DNA binding protein, 100 kD scaffolding protein, 33 kD protein, protein VIII, and fiber, as well as the entire E3 region, with the homologous segment from AdC1. The ClaI site at the left end of the AdC1 fragment is at the beginning of the hexon gene and the resulting protein is identical to the C1 hexon. The EcoRI site which constitutes the right end of the AdC1 fragment is within the E4 orf 7 part of the AdC1. The right end was ligated to a PCR generated right end fragment from AdPan5 such that the regenerated orf 7-translation product is chimeric between AdPan5 and AdC1.

The plasmid p5C1 long harbors an E1 deleted Pan5 virus where an internal 25603 bp segment (7955-33557) has been replaced by a functionally analogous 24712 bp (7946-32657) from AdC1. This results in the replacement of the AdPan5 pre-terminal protein, 52/55 kD protein, penton base protein, protein VII, Mu, and protein VI with those from AdC1 in addition to those replaced in p5C1 short. The AscI site at the left end of the AdC1 fragment is at the beginning of the DNA polymerase gene and results in a chimeric protein where the first 165 amino acids of the AdPan5 DNA polymerase has been replaced by a 167 amino acid segment from AdC1 DNA polymerase. In this N-terminal region, the homology between the AdPan5 and AdC1 DNA polymerase proteins is 81% (72% identity).

The plasmid pDVP5Mlu which contains the left end of AdPan5 was used as the starting plasmid for the chimeric vector construction.

The plasmid pDVP5Mlu was made as follows. A synthetic DNA fragment harboring recognition sites for the restriction enzymes SmaI, MluI, EcoRI and EcoRV respectively was ligated into pBR322 digested with EcoRI and NdeI so as to retain the origin of replication and the beta-lactamase gene. The left end of Pan5 extending to the MluI site (15135 bp) was cloned into this plasmid between the SmaI and MluI sites. The E1 gene was functionally deleted and replaced by a DNA fragment harboring recognition sites for the extremely rare cutter restriction enzyme sites I-CeuI and PI-SceI). The 2904 base pairs of the right end of Pan-5 was PCR amplified using the primers P5L [GCG CAC GCG TCT CTA TCG ATG AAT TCC ATT GGT GAT GGA CAT GC, SEQ ID NO:7] and P51TR [GCG CAT TTA AAT CAT CAT CAA TAA TAT ACC TCA AAC, SEQ ID NO:8] using Tgo polymerase (Roche). The PCR product was cut with MluI and SwaI, and cloned between MluI and EcoRV of pDVP5Mlu to yield pPan5Mlu+RE. A 3193 bp fragment extending from the MluI site (15135) to the ClaI (18328) site of Pan5 was then inserted between the same sites of pPan5Mlu+RE to yield pPan5Cla+RE. The 3671 bp ClaI (18531) to EcoRI (22202) fragment of the adenovirus C1 was cloned into pPan5Cla+RE between ClaI (16111) and EcoRI (16116) to yield pPan5C1delRI. The 10452 bp internal EcoRI fragment of the adenovirus C1 (22202-32653) was cloned into the EcoRI site of pPan5C1delRI to yield p5C1short. To construct pSC1long, the AdC1 replacement was further extended by replacing the AscI-ClaI 10379 bp fragment of AdPan5 in p5C1short with the AdC1 AscI-ClaI 10591 bp fragment. Finally a green fluorescent protein (GFP) expression cassette was inserted into both p5C1short and p5C1long between the I-CeuI and PI-SceI sites to yield p5C1shortGFP and p5C1longGFP respectively.

B. Rescue of Chimeric Pan5/C1 Recombinant Vector Adenoviruses

The plasmids p5C1shortGFP and p5C1longGFP were digested with the restriction enzyme SwaI and transfected into HEK 293 cells. A typical adenovirus induced cytopathic effect was observed. The rescue of recombinant chimeric adenovirus from the p5C1longGFP transfection was confirmed by collecting the supernatant from the transfection and re-infecting fresh cells which were found to be transduced as determined by GFP expression. Viral DNA prepared from the chimeric recombinant virus was digested with several restriction enzymes and found to have the expected pattern on electrophoresis (data not shown).

The chimeric adenoviral construct with the shorter replacement p5C1short encodes the C1 proteins hexon and fiber as well as the intervening open reading frames for endoprotease, DNA binding protein, 100 kDa scaffolding protein, 33 kDa protein, and protein VIII. (The E3 region is also included within this region but is unlikely to impact on the viability of the chimeric virus). When the replacement was extended to include the additional AdC1 proteins pTP (pre-terminal protein), 52/55 kDa protein, penton base, protein VII, Mu, and protein VI, there was no difficulty in rescuing viable chimeric virus. In this experiment, the chimeric adenovirus construction strategy utilized the presence of AscI and ClaI restriction enzyme sites present on the genes for DNA polymerase and hexon respectively on both AdPan5 and AdC1.

The reasons for the relatively higher yield of the chimeric virus compared to the wild-type AdC1 virus are not clear. In the growth of the 5C1 chimeric virus in 293 cells, the adenoviral early region gene products of E1 and E4 are derived from Ad5 and AdPan5 respectively. The E1 and E4 gene products bind, regulate and de-repress several cellular transcription complexes and coordinate their activity towards viral multiplication. Thus it is possible that the E1 gene products supplied in trans from the 293 cells and the E4 gene products from AdPan5 are more optimal in the human 293 cell background than are the equivalent AdC1 gene products. This may also apply to the activity of the major late promoter whose activity is responsible for the transcription of the capsid protein genes. In the chimeric virus, the major late promoter, and the protein IVa2 which transactivates it, are derived from AdPan5. However the E2 gene products required for adenoviral DNA replication pTP and single-stranded DNA—binding protein are derived from AdC1. The adenoviral DNA polymerase, which complexes with pTP, is chimeric in Ad5C1 but mostly AdPan5 derived.

EXAMPLE 2

Construction of Ad5 Chimeric Simian Viruses

Plasmids have been constructed where the structural proteins derive from the chimpanzee adenovirus Pan 7 and the flanking sequences are derived from human Ad5 (the commonly used vector strain). The Adhu5-Pan7 chimeric adenovirus has been rescued, demonstrating that the chimeric virus construction method used to derive the chimeric virus is broadly applicable.

A. Construction of the Ad5-Pan 7 Chimeric Adenovirus

A plasmid was constructed which harbors the complete (E1 deleted) chimeric genome in order to establish that the chimeric adenovirus is viable, and then transfected the plasmid into the E1 complementing cell line HEK 293. It was found that the recombinant virus could be rescued. The chimeric adenovirus genome that was constructed is composed of a left end segment derived from Ad5 that contributes the ITR, the E1 deletion region containing the transgene expression cassette, the pIX and IVa2 genes and 954 C-terminal amino acids of the polymerase gene (which is transcribed in the right to left direction from the bottom strand). Ad5 also contributes the right end of the chimeric genome containing the E4 genes and the right ITR. All the other genes present in the central part of the chimeric construct are derived from the chimpanzee adenovirus Pan 7 including the N-terminal 235 amino acids of a chimeric DNA polymerase.

In order to construct the plasmid which harbors the complete (E1 deleted) chimeric genome, the starting plasmid was pBRAd5lere which is comprised of three parts; the bacterial origin of replication and ampicillin resistance gene derived from the plasmid pBR322, the left end of an Ad5 derived E1 deleted vector extending from the left ITR to the StuI site located at base pair number 5782 of the wild-type Ad5 genome (the E1 deletion extends from base pair 342 to 3533 of the wild-type Ad5 genome), and the right end of Ad5 extending from the StuI site at base pair number 31954 of the wild-type Ad5 genome to the right end of the right ITR. The PacI sites located adjacent to the two ITRs are used to release the Ad5 genome from the bacterial plasmid backbone. The fragment containing I-CeuI and the PI-SceI sites which is located in place of the E1 deletion is used to insert transgene cassettes.

A synthetic DNA oligomer was inserted at the StuI site containing sites for AscI, XbaI and EcoRI, which allowed the creation of the plasmid pAd5endsAscRI where using PCR, the Ad5 polymerase gene was extended to base pair #8068 of the wild-type Ad5 genome and incorporating a newly created AscI site at this location by silent mutagenesis of the polymerase gene (translated from the bottom strand) as depicted below.

```
Original sequence
GCG ACG GGC CGA CGC TGC CCG GCT     [SEQ ID NO:16]
Arg Arg Ala Ser                      [SEQ ID NO:17]

Mutated sequence (The AscI recognition site is
underlined)
GCG GCG CGC CGA CGC TGC CCG GCT     [SEQ ID NO:18]
Arg Arg Ala Ser                      [SEQ ID NO:17]
```

The Pan 7 fiber containing region was amplified by PCR (mutating the fiber stop codon from TGA to TAA to provide a polyadenylation signal similar to that in Ad5) and inserted into the EcoRI site to yield pAd5endsP7fib. Several cloning steps led to the construction of pH5C$_7$H$_5$ where the complete chimeric adenoviral genome has been assembled A transgene cassette expressing GFP (green fluorescent protein) was inserted between the I-CeuI and PI-SceI sites of pHSC7H5. The final construct was digested with PacI to separate the adenoviral genome from the plasmid backbone and transfected into HEK 293 cells. The cell lysate was harvested 2 weeks later, and the chimeric adenovirus was amplified and purified by standard methods.

B. Construction of the Ad5-Simian Virus 25 (SV-25) Chimeric Adenovirus

[N. B. Simian virus 25 (ATCC catalog number VR-201) is distinct from the chimpanzee adenovirus Simian adenovirus 25 ATCC catalog number VR-594]

The construction of the Ad5 based chimeric adenovirus where the left and right end segments are derived from Ad5 and the central portion was derived from the monkey adenovirus SV-25 was carried out in a manner completely analogous to that described above for the chimeric adenovirus described above that is chimeric between Ad5 and the chimpanzee adenovirus Pan 7. Thus, the chimeric adenovirus genome that was constructed is composed of a left end segment derived from Ad5 that contributes the ITR, the E1 deletion region containing the transgene expression cassette, the pIX and IVa2 genes and 956 C-terminal amino acids of the polymerase gene. Ad5 also contributes the right end of the chimeric genome containing the E4 genes and the right ITR. [Additionally, the left end of the Ad5 genome was extended beyond that present in pH5C$_7$H$_5$ so that 454 base pairs of the Ad5 left end was present. Although not absolutely essential, this was done in order to improve packaging efficiency.] All the genes present in the central part of the chimeric construct are derived from the monkey adenovirus SV-25 including the N-terminal 230 amino acids of a chimeric DNA polymerase. The starting plasmid for the construction of the chimeric genome was pAd5endsAscRI which contains both the left and right ends of Ad5 as well as the created (by silent mutation) AscI site in the polymerase gene where Ad5-SV25 chimeric fusion was made (as was done for the Ad5-Pan 7 chimeric adenovirus). In the final construct pH5S25H5, the SV25 genome segment has been incorporated by sequential cloning steps, including creation of an AscI site at the ligation junction within the polymerase coding sequence. A transgene cassette expressing GFP (green fluorescent protein) was inserted between the I-CeuI and PI-SceI sites of pH5S25H5. The final construct was digested with PacI to separate the adenoviral genome from the plasmid backbone and transfected into HEK 293 cells. The cell lysate was harvested 2 weeks later, and the chimeric adenovirus was amplified and purified by standard methods.

Figure 2:
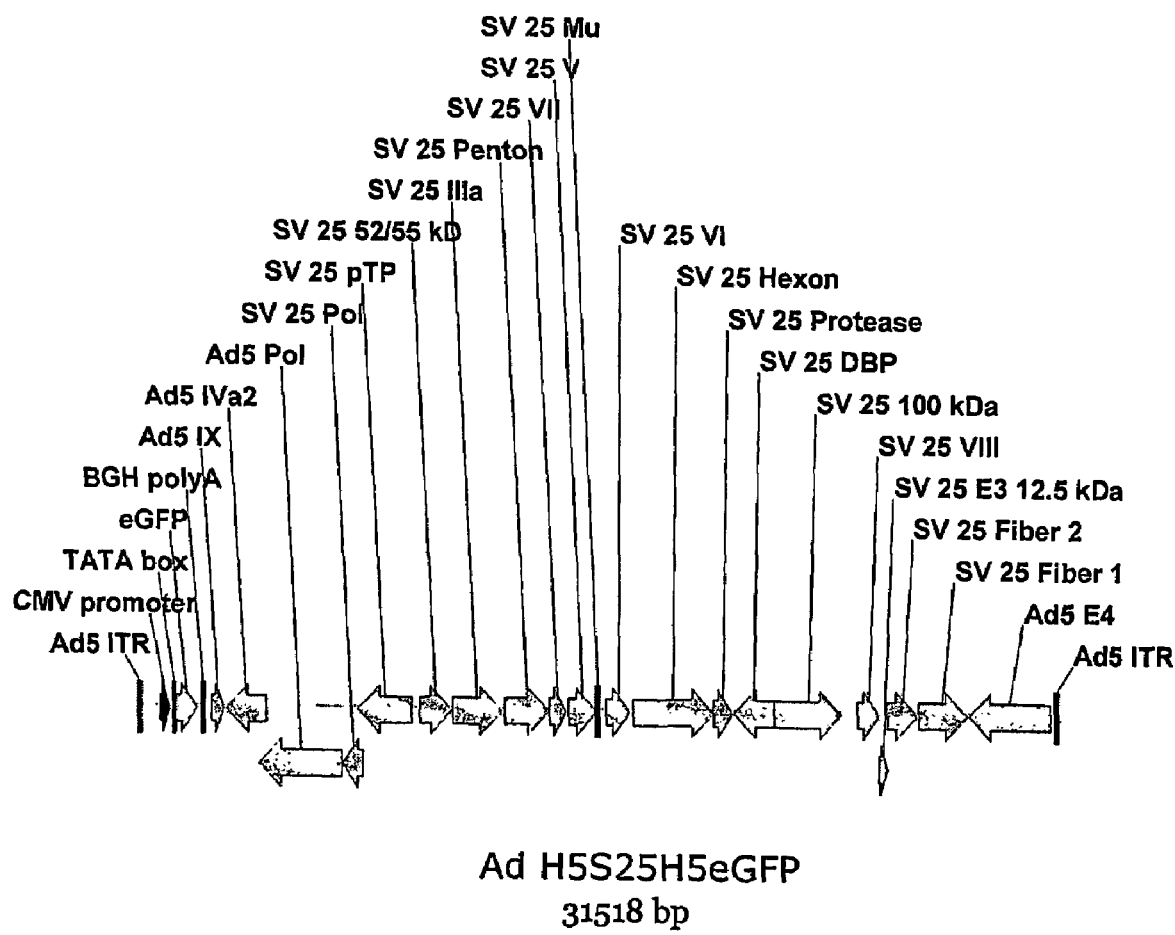
FIG. 2 provides the map of the recombinant Adhu5-SV25 chimeric virus, termed H5S25H5.

FIG. 2 provides the map of the recombinant Adhu5-SV25 chimeric virus. The portion of the genome replaced by DNA from Pan7 is indicated.

EXAMPLE 3

Pan5—C1 Chimeric Vector of Invention as a Delivery Vehicle for Immunogenic Compositions A Pan 5 (Simian adenovirus 22, a subgroup E adenovirus, also termed C5) —C1 (Simian adenovirus 21, a subgroup B adenovirus) chimeric expressing the Ebola virus (Zaire) glycoprotein (C5C1C5-CMVGP) was constructed as a model antigen in order to test the efficacy of the vector C5C1C5-CMVGP as a vaccine; this vector has been compared it to the Adhu5 based vector (H5-CMVGP). Compared to H5-CM- VGP, the C5C1-CMVGP vector yielded only a slightly decreased level of GP expression in transduced A549 cells.

Thereafter, GP-specific T cell and B cell responses elicited in B10BR mice vaccinated intramuscularly with either $5\times10^{10}$ H5-CMVGP or C5C1-CMVGP vectors were compared.

The C5C1C5-CMVGP vector appeared to induce lower frequencies of gamma interferon producing CD8+ T cells with kinetics slower than the H5-CMVGP vector as determined by intracellular cytokine staining using a H-2k restricted GP-specific peptide as stimulant. The total IgG response to GP, measured by ELISA, was equivalent in serum from mice vaccinated with the C5C1C5-CMVGP or the H5-CMVGP vectors. However, the C5C1C5-CMVGP vector induced a more potent Th1 type response while the H5-CMVGP vector stimulated a more balanced Th1/Th2 type response. In a survival study, mice were vaccinated as above and challenged 28 days later with 200 LD/50 mouse-adapted Ebola Zaire virus. 100% survival was seen for both groups.

EXAMPLE 4

Generation of Chimeric Pan6/Pan7 Vectors

A panel of GFP expressing vectors were generated. This panel includes vectors that are chimeric between Pan 6 and Pan 7 where (a) the hexon protein of Pan 7 was replaced by that of Pan 6 (termed C767), (b), the fiber protein of Pan7 was replaced by that of Pan 6 (termed C776), (c) both the hexon and fiber proteins of the Pan 7 vector have been replaced by those from Pan 6 (termed C766).

The chimeric virus termed C767 was constructed essentially as described above for the C5C1C5 virus in Example 1. However, due to substantial homology between the Pan6 and Pan7 sequences 5' to the hexon sequence, it was not necessary to substitute the 5' end of the genome between the penton and the pol gene.

The chimeric vector C767 was compared to the C776, C766, the parent C6, and the parent C7, each expressing GFP.

Balb/C mice (25 per group) were immunized intramuscularly with either Pan 6 or Pan 7 ($10^{10}$ particles). Re-administration ($10^{11}$ particles i.v., by tail vein injection) was attempted 3 weeks later using each of the five GFP expressing vectors (C6-GFP, C7-GFP, and the three chimeric vectors). Three days later the level of liver transduction was estimated qualitatively by examining liver sections for the presence of GFP expression and quantitatively by estimating copies of GFP DNA by Taqman analysis. Administration of either one of the two chimpanzee adenovirus vectors does not affect the transduction efficiency of the other vector, while re-administration of the same vector is severly compromised. The data showed that antibodies to both hexon and fiber are important in preventing re-administration of adenoviral vectors.

All publications cited in this specification are incorporated herein by reference, as are the priority documents, U.S. Patent Application 60/575,429, filed Mar. 28, 2004; U.S. Patent Application No. 60/566,212, filed Apr. 28, 2004, and U.S. patent application Ser. No. 10/465,302, filed Jun. 20, 2003. While the invention has been described with reference to a particularly preferred embodiment, it will be appreciated that modifications can be made without departing from the spirit of the invention. Such modifications are intended to fall within the scope of the appended claims.

What is claimed is:

1. A chimeric adenovirus comprising a hexon protein of an adenovirus serotype which is incapable of efficient growth in a selected host cell selected from the group consisting of C1, Pan6, and Ad40, said chimeric adenovirus comprising:
   (a) adenovirus sequences of the left terminal end of the genome of a first adenovirus which grows in a selected host cell type, said left end region comprising the E1a, E1b and 5' inverted terminal repeat (ITRs);
   (b) adenovirus sequences of the internal region of the genome of the selected adenovirus serotype which is incapable of efficient growth in the selected host cell, said internal region comprising the genes encoding the penton, hexon and fiber of the selected adenovirus;
   (c) adenovirus sequences of the right terminal end of the genome of the first adenovirus, said right end region comprising the necessary E4 gene functions and the 3' inverted terminal repeats (ITRs),
   wherein the resulting chimeric adenovirus comprises adenoviral structural and regulatory proteins necessary for infection and replication.

2. The chimeric adenovirus according to claim 1, wherein the chimeric adenovirus further comprises the IIIa, 52/55 kDa and terminal protein (pTP) of the selected adenovirus serotype.

3. The chimeric adenovirus according to claim 1, wherein chimeric adenovirus comprises the polymerase of the first adenovirus.

4. The chimeric adenovirus according to claim 1, wherein the chimeric adenovirus expresses a functional chimeric protein formed from the first adenovirus and the selected adenovirus, said chimeric protein is selected from the group consisting of polymerase, terminal protein, 52/55 kDa protein, and IIIa.

5. The chimeric adenovirus according to claim 1, wherein the chimeric adenovirus comprises the terminal protein, 52/55 kDa, and/or IIIa of the selected adenovirus.

6. An isolated host cell comprising a chimeric adenovirus according to claim 1.

7. A composition comprising a virus according to claim 1 in a pharmaceutically acceptable carrier.

8. A method for delivering a heterologous gene to a mammalian cell comprising introducing into said cell an effective amount of the virus according to claim 1.

9. An isolated host cell according to claim 6, wherein said isolated host cell is a human cell.

10. A chimeric adenovirus comprising a hexon protein of a C1 adenovirus, said chimeric adenovirus comprising:
  (a) adenovirus sequences of the left terminal end of the genome of a first adenovirus which grows in a selected host cell type, said left end region comprising the E1a, E1b and 5' inverted terminal repeat (ITRs);
  (b) adenovirus sequences of the internal region of the genome of the C1 adenovirus, said internal region comprising the genes encoding the penton, hexon and fiber of the C1 adenovirus;
  (c) adenovirus sequences of the right terminal end of the genome of the first adenovirus, said right end region comprising the necessary E4 gene functions and the 3' inverted terminal repeat (ITRs),
    wherein the resulting chimeric adenovirus comprises adenoviral structural and regulatory proteins necessary for infection and replication.

11. A method for producing a selected gene product comprising infecting a mammalian cell with the virus according to claim 10, culturing said cell under suitable conditions and recovering from said cell culture the expressed gene product.

12. The chimeric adenovirus according to claim 10, wherein the chimeric adenovirus further comprises the IIIa, 52/55 kDa and terminal protein (pTP) of the C1 adenovirus serotype.

13. The chimeric adenovirus according to claim 10, wherein the chimeric adenovirus comprises the polymerase of the first adenovirus.

14. The chimeric adenovirus according to claim 10, wherein the chimeric adenovirus expresses a functional chimeric protein formed from the first adenovirus and the C1 adenovirus, said chimeric protein is selected from the group consisting of polymerase, terminal protein, 52/55 kDa protein, and IIIa.

15. The chimeric adenovirus according to claim 10, wherein the chimeric adenovirus comprises the terminal protein, 52/55 kDa, and/or IIIa of the C1 adenovirus.

16. An isolated host cell comprising a chimeric adenovirus according to claim 10.

17. The chimeric adenovirus according to claim 10, wherein the first adenovirus is selected from the group consisting of human adenovirus type 5 and Pan5.

18. A composition comprising a virus according to claim 10 in a pharmaceutically acceptable carrier.

19. A method for delivering a heterologous gene to a mammalian cell comprising introducing into said cell an effective amount of the virus according to claim 10, wherein said virus comprises the heterologous gene under the control of sequences which direct expression thereof in the cell.

20. An isolated host cell according to claim 16, wherein said isolated host cell is a human cell in culture.

* * * * *

SEQUENCE LISTING

```
<160> NUMBER OF SEQ ID NOS: 18

<210> SEQ ID NO 1
<211> LENGTH: 36462
<212> TYPE: DNA
<213> ORGANISM: chimpanzee adenovirus serotype Pan5

<400> SEQUENCE: 1
catcatcaat aatatacctc aaacttttgg tgcgcgttaa tatgcaaatg aggtatttga     60
atttggggat gcggggcggt gattggctgc gggagcggcg accgttaggg gcggggcggg    120
tgacgttttg atgacgtggc cgtgaggcgg agccggtttg caagttctcg tgggaaaagt    180
gacgtcaaac gaggtgtggt ttgaacacgg aaatactcaa ttttcccgcg ctctctgaca    240
ggaaatgagg tgtttctggg cggatgcaag tgaaaacggg ccattttcgc gcgaaaactg    300
aatgaggaag tgaaaatctg agtaattccg cgtttatggc agggaggagt atttgccgag    360
ggccgagtag actttgaccg attacgtggg ggtttcgatt accgtatttt tcacctaaat    420
ttccgcgtac ggtgtcaaag tccggtgttt ttacgtaggt gtcagctgat cgccagggta    480
tttaaacctg cgctctctag tcaagaggcc actcttgagt gccagcgagt agagttttct    540
cctccgcgcc gcgagtcaga tctacacttt gaaagatgag gcacctgaga gacctgcccg    600
gtaatgtttt cctggctact gggaacgaga ttctggaact ggtggtggac gccatgatgg    660
gtgacgaccc tccggagccc cctaccccat ttgaagcgcc ttcgctgtac gatttgtatg    720
atctggaggt ggatgtgccc gagaacgacc ccaacgagga ggcggtgaat gatttgttta    780
```

```
gcgatgccgc gctgctggct gccgagcagg ctaatacgga ctctggctca gacagcgatt    840
cctctctcca taccccgaga cccggcagag gtgagaaaaa gatccccgag cttaaagggg    900
aagagctcga cctgcgctgc tatgaggaat gcttgcctcc gagcgatgat gaggaggacg    960
aggaggcgat tcgagctgca gcgaaccagg gagtgaaaac agcgagcgag ggctttagcc   1020
tggactgtcc tactctgccc ggacacggct gtaagtcttg tgaatttcat cgcatgaata   1080
ctggagataa gaatgtgatg tgtgccctgt gctatatgag agcttacaac cattgtgttt   1140
acagtaagtg tgattaactt tagctgggga ggcagagggt gactgggtgc tgactggttt   1200
atttatgtat atgtttttta tgtgtaggtc ccgtctctga cgtagatgag acccccacta   1260
cagagtgcat ttcatcaccc ccagaaattg gcgaggaacc gcccgaagat attattcata   1320
gaccagttgc agtgagagtc accgggcgta gagcagctgt ggagagtttg gatgacttgc   1380
tacagggtgg ggatgaacct ttggacttgt gtacccggaa acgccccagg cactaagtgc   1440
cacacatgtg tgtttactta aggtgatgtc agtatttata gggtgtggag tgcaataaaa   1500
tccgtgttga ctttaagtgc gtggtttatg actcaggggt ggggactgtg ggtatataag   1560
caggtgcaga cctgtgtggt cagttcagag caggactcat ggagatctgg acagtcttgg   1620
aagactttca ccagactaga cagctgctag agaactcatc ggagggagtc tcttacctgt   1680
ggagattctg cttcggtggg cctctagcta agctagtcta tagggccaag caggattata   1740
aggatcaatt tgaggatatt tgagagagt gtcctggtat ttttgactct ctcaacttgg    1800
gccatcagtc tcactttaac cagagtattc tgagagccct tgactttct actcctggca    1860 gaactaccgc cgcggtagcc tttttttgcct ttatccttga caaatggagt caagaaaccc   1920
atttcagcag ggattaccgt ctggactgct tagcagtagc tttgtggaga acatggaggt   1980
gccagcgcct gaatgcaatc tccggctact tgccagtaca gccggtagac acgctgagga   2040
tcctgagtct ccagtcaccc caggaacacc aacgccgcca gcagccgcag caggagcagc   2100
agcaagagga ggaccgagaa gagaacctga gagccggtct ggaccctccg gtggcggagg   2160
aggaggagta gctgacttgt ttcccgagct gcgccgggtg ctgactaggt cttccagtgg   2220
acgggagagg gggattaagc gggagaggca tgaggagact agccacagaa ctgaactgac   2280
tgtcagtctg atgagtcgca ggcgcccaga atcggtgtgg tggcatgagg tgcagtcgca   2340
ggggatagat gaggtctcag tgatgcatga gaaatattcc ctagaacaag tcaagacttg   2400
ttggttggag cccgaggatg attgggaggt agccatcagg aattatgcca agctggctct   2460
gaggccagac aagaagtaca agattaccaa actgattaat atcagaaatt cctgctacat   2520
ttcagggaat ggggccgagg tggagatcag tacccaggag agggtggcct tcagatgctg   2580
catgatgaat atgtacccgg gggtggtggg catggaggga gtcacccttta tgaacgcgag   2640 gttcaggggt gatgggtata atgggtggt ctttatggcc aacaccaagc tgacagtgca    2700
cggatgctcc ttctttggct tcaataacat gtgcattgag gctgggcca gtgtttcagt    2760 gaggggatgc agttttttcag ccaactggat ggggtcgtg ggcagaacca agagcatggt    2820
gtcagtgaag aaatgcctgt tcgagaggtg ccacctgggg gtgatgagcg agggcgaagc   2880
caaagtcaaa cactgcgcct ctaccgagac gggctgcttt gtactgatca agggcaatgc   2940
caaagtcaag cataatatga tctgtggggc ctcggatgag cgcggctacc agatgctgac   3000
ctgcgccggt gggaacagcc atatgctagc caccgtgcat gtggcctcgc acccccgcaa   3060
gacatggccc gagttcgagc acaacgtcat gacccgctgc aatgtgcacc tggggtcccg   3120
ccgaggcatg ttcatgccct accagtgcaa catgcaattt gtgaaggtgc tgctggagcc   3180
```

```
cgatgccatg tccagagtga gcctgacggg ggtgtttgac atgaatgtgg agctgtggaa      3240
aattctgaga tatgatgaat ccaagaccag gtgccgggcc tgcgaatgcg gaggcaagca      3300
cgccaggctt cagcccgtgt gtgtggaggt gacggaggac ctgcgacccg atcatttggt      3360
gttgtcctgc aacgggacgg agttcggctc cagcggggaa gaatctgact agagtgagta      3420
gtgtttggga ctgggtggga gcctgcatga tgggcagaat gactaaaatc tgtgtttttc      3480
tgcgcagcag catgagcgga agcgcctcct ttgagggagg ggtattcagc ccttatctga      3540
cggggcgtct cccctcctgg gcgggagtgc gtcagaatgt gatgggatcc acggtggacg      3600
gccggcccgt gcagcccgcg aactcttcaa ccctgaccta cgcgaccctg agctcctcgt      3660
ccgtggacgc agctgccgcc gcagctgctg cttccgccgc cagcgccgtg cgcggaatgg      3720
ccctgggcgc cggctactac agctctctgg tggccaactc gagttccacc aataatcccg      3780
ccagcctgaa cgaggagaag ctgctgctgc tgatggccca gctcgaggcc ctgacccagc      3840
gcctgggcga gctgacccag caggtggctc agctgcaggc ggagacgcgg gccgcggttg      3900
ccacggtgaa aaccaaataa aaatgaatc aataaataaa cggagacggt tgttgatttt      3960
aacacagagt cttgaatctt tatttgattt ttcgcgcgcg gtaggccctg gaccaccggt      4020
ctcgatcatt gagcacccgg tggatctttt ccaggacccg gtagaggtgg gcttggatgt      4080
tgaggtacat gggcatgagc ccgtcccggg ggtggaggta gctccattgc agggcctcgt      4140
gctcggggt ggtgttgtaa atcacccagt catagcaggg gcgcagggcg tggtgctgca      4200
cgatgtcctt gaggaggaga ctgatggcca cgggcagccc cttggtgtag gtgttgacga      4260
acctgttgag ctgggaggga tgcatgcggg gggagatgag atgcatcttg gcctggatct      4320
tgagattggc gatgttcccg cccagatccc gccgggggtt catgttgtgc aggaccacca      4380
gcacggtgta tccggtgcac ttggggaatt tgtcatgcaa cttggaaggg aaggcgtgaa      4440
agaatttgga gacgcccttg tgaccgccca ggttttccat gcactcatcc atgatgatgg      4500
cgatgggccc gtgggcggcg gcttgggcaa agacgtttcg ggggtcggac acatcgtagt      4560
tgtggtcctg ggtgagctcg tcataggcca ttttaatgaa tttggggcgg agggtgcccg      4620
actgggggac gaaggtgccc tcgatcccgg gggcgtagtt gccctcgcag atctgcatct      4680
cccaggcctt gagctcggag gggggatca tgtccacctg cggggcgatg aaaaaaacgg      4740
tttccggggc gggggagatg agctgggccg aaagcaggtt ccggagcagc tgggacttgc      4800
cgcagccggt ggggccgtag atgacccccga tgaccggctg caggtggtag ttgagggaga      4860
gacagctgcc gtcctcgcgg aggaggggg ccacctcgtt catcatctcg cgcacatgca      4920
tgttctcgcg cacgagttcc gccaggaggc gctcgccccc aagcgagagg agctcttgca      4980
gcgaggcgaa gttttcagc ggcttgagcc cgtcggccat gggcattttg gagagggtct      5040
gttgcaagag ttccagacgg tcccagagct cggtgatgtg ctctagggca tctcgatcca      5100
gcagacctcc tcgtttcgcg ggttggggcg actgcgggag tagggcacca ggcgatgggc      5160
gtccagcgag gccagggtcc ggtccttcca ggggcgcagg gtccgcgtca gcgtggtctc      5220
cgtcacggtg aaggggtgcg cgccgggctg ggcgcttgcg agggtgcgct tcaggctcat      5280
ccggctggtc gagaaccgct cccgtcggc gccctgcgcg tcggccaggt agcaattgag      5340
catgagttcg tagttgagcg cctcggccgc gtggcccttg gcgcggagct tacctttgga      5400
agtgtgtccg cagacgggac agaggaggga cttgagggcg tagagcttgg ggcgaggaa      5460
gacggactcg ggggcgtagg cgtccgcgcc gcagctggcg cagacggtct cgcactccac      5520
```

```
gagccaggtg aggtctggcc ggtcggggtc aaaaacgagg tttcctccgt gcttttgat    5580 gcgtttctta cctctggtct ccatgagctc gtgtccccgc tgggtgacaa agaggctgtc    5640
cgtgtccccg tagaccgact ttatgggccg gtcctcgagc ggggtgccgc ggtcctcgtc    5700
gtagaggaac cccgcccact ccgagacgaa ggcccgggtc caggccagca cgaaggaggc    5760
cacgtgggag gggtagcggt cgttgtccac cagcgggtcc accttctcca gggtatgcaa    5820
gcacatgtcc ccctcgtcca catccaggaa ggtgattggc ttgtaagtgt aggccacgtg    5880
accgggggtc ccggccgggg gggtataaaa gggggcgggc cctgctcgt cctcactgtc     5940 ttccggatcg ctgtccagga gcgccagctg ttggggtagg tattccctct cgaaggcggg    6000
catgacctcg gcactcaggt tgtcagtttc tagaaacgag gaggatttga tattgacggt    6060
gccgttggag acgcctttca tgagcccctc gtccatctgg tcagaaaaga cgatcttttt    6120
gttgtcgagc ttggtggcga aggagccgta gagggcgttg gagagcagct ggcgatgga     6180 gcgcatggtc tggttctttt ccttgtcggc gcgctccttg gcggcgatgt tgagctgcac    6240
gtactcgcgc gccacgcact tccattcggg gaagacggtg gtgagcttgt cgggcacgat    6300
tctgacccgc cagccgcggt tgtgcagggt gatgaggtcc acgctggtgg ccacctcgcc    6360
gcgcaggggc tcgttggtcc agcagaggcg cccgcccttg cgcgagcaga agggggcag    6420 cgggtccagc atgagctcgt cggggggtc ggcgtccacg tgaagatgc cgggcaggag     6480 ctcggggtcg aagtagctga tgcaggtgcc cagatcgtcc agcgccgctt gccagtcgcg    6540 cacgccagc gcgcgctcgt aggggctgag gggcgtgccc cagggcatgg ggtgcgtgag     6600
cgcggaggcg tacatgccgc agatgtcgta gacgtagagg ggctcctcga ggacgccgat    6660
gtaggtgggg tagcagcgcc ccccgcggat gctggcgcgc acgtagtcgt acagctcgtg    6720
cgagggcgcg aggagcccgg tgccgaggtt ggagcgctgc ggcttttcgg cgcggtagac    6780
gatctggcgg aagatggcgt gggagttgga ggagatggtg ggcctctgga agatgttgaa    6840
gtgggcgtgg ggcagtccga ccgagtccct gatgaagtgg gcgtaggagt cctgcagctt    6900
ggcgacgagc tcggcggtga cgaggacgtc cagggcgcag tagtcgaggg tctcttggat    6960
gatgtcgtac ttgagctggc ccttctgctt ccacagctcg cggttgagaa ggaactcttc    7020
gcggtccttc cagtactctt cgagggggaa cccgtcctga tcggcacggt aagagcccac    7080
catgtagaac tggttgacgg ccttgtaggc gcagcagccc ttctccacgg ggagggcgta    7140
agcttgcgcg gccttgcgca gggaggtgtg ggtgagggcg aaggtgtcgc gcaccatgac    7200
cttgaggaac tggtgcttga agtcgaggtc gtcgcagccg ccctgctccc agagctggaa    7260
gtccgtgcgc ttcttgtagg cggggttggg caaagcgaaa gtaacatcgt tgaagaggat    7320
cttgcccgcg cggggcatga agttgcgagt gatgcgaaa ggctggggca cctcggcccg     7380
gttgttgatg acctgggcgg cgaggacgat ctcgtcgaag ccgttgatgt tgtgcccgac    7440
gatgtagagt tccacgaatc gcgggcggcc cttgacgtgg ggcagcttct tgagctcgtc    7500
gtaggtgagc tcggcggggt cgctgaggcc gtgctgctcg agggcccagt cggcgaggtg    7560
ggggttggcg ccgaggaagg aagtccagag atccacggcc agggcggtct gcaagcggtc    7620
ccggtactga cggaactgct ggcccacggc cattttttcg ggggtgacgc agtagaaggt    7680
gcgggggtcg ccgtgccagc ggtcccactt gagctggagg gcgaggtcgt gggcgagctc    7740
gacgagcggc gggtccccgg agagtttcat gaccagcatg aaggggacga gctgcttgcc    7800
gaaggacccc atccaggtgt aggtttccac gtcgtaggtg aggaagagcc tttcggtgcg    7860
aggatgcgag ccgatgggga agaactggat ctcctgccac cagttggagg aatggctgtt    7920
```

-continued

```
gatgtgatgg aagtagaaat gccgacggcg cgccgagcac tcgtgcttgt gtttatacaa    7980
gcgtccgcag tgctcgcaac gctgcacggg atgcacgtgc tgcacgagct gtacctgggt    8040
tcctttgacg aggaatttca gtgggcagtg gagcgctggc ggctgcatct ggtgctgtac    8100
tacgtcctgg ccatcggcgt ggccatcgtc tgcctcgatg gtggtcatgc tgacgaggcc    8160
gcgcgggagg caggtccaga cctcggctcg gacgggtcgg agagcgagga cgagggcgcg    8220
caggccggag ctgtccaggg tcctgagacg ctgcggagtc aggtcagtgg gcagcggcgg    8280
cgcgcggttg acttgcagga gcttttccag ggcgcgcggg aggtccagat ggtacttgat    8340
ctccacggcg ccgttggtgg cgacgtccac ggcttgcagg gtcccgtgcc cctggggcgc    8400
caccaccgtg ccccgtttct tcttgggtgc tggcggcggc ggctccatgc ttagaagcgg    8460
cggcgaggac gcgcgccggg cggcaggggc ggctcggggc ccggaggcag gggcggcagg    8520
ggcacgtcgg cgccgcgcgc gggcaggttc tggtactgcg cccggagaag actggcgtga    8580
gcgacgacgc gacggttgac gtcctggatc tgacgcctct gggtgaaggc cacgggaccc    8640
gtgagtttga acctgaaaga gagttcgaca gaatcaatct cggtatcgtt gacggcggcc    8700
tgccgcagga tctcttgcac gtcgcccgag ttgtcctggt aggcgatctc ggtcatgaac    8760
tgctcgatct cctcctcctg aaggtctccg cgaccggcgc gctcgacggt ggccgcgagg    8820
tcgttggaga tgcggcccat gagctgcgag aaggcgttca tgccgcctc gttccagacg    8880 cggctgtaga ccacggctcc gtcgggtcg cgcgcgcgca tgaccacctg ggcgaggttg    8940
agctcgacgt ggcgcgtgaa gaccgcgtag ttgcagaggc gctggtagag gtagttgagc    9000
gtggtggcga tgtgctcggt gacgaagaag tacatgatcc agcggcggag cggcatctcg    9060
ctgacgtcgc ccagggcttc caagcgctcc atggcctcgt agaagtccac ggcgaagttg    9120
aaaaactggg agttgcgcgc cgagacggtc aactcctcct ccagaagacg gatgagctcg    9180
gcgatggtgg cgcgcacctc gcgctcgaag gccccggggg gctcctcttc ttccatctcc    9240
tcctcctctt ccatctcctc cactaacatc tcttctactt cctcctcagg aggcggcggc    9300
gggggagggg ccctgcgtcg ccggcggcgc acgggcagac ggtcgatgaa gcgctcgatg    9360
gtctccccgc gccggcgacg catggtctcg gtgacggcgc gcccgtcctc gcggggccgc    9420
agcgtgaaga cgccgccgcg catctccagg tggccgccgg ggggtctcc gttgggcagg    9480 gagagggcgc tgacgatgca tcttatcaat tggcccgtag ggactccgcg caaggacctg    9540
agcgtctcga gatccacggg atccgaaaac cgctgaacga aggcttcgag ccagtcgcag    9600
tcgcaaggta ggctgagccc ggtttcttgt tcttcgggta tttggtcggg aggcgggcgg    9660
gcgatgctgc tggtgatgaa gttgaagtag gcggtcctga gacggcggat ggtggcgagg    9720
agcaccaggt ccttgggccc ggcttgctgg atgcgcagac ggtcggccat gccccaggcg    9780
tggtcctgac acctggcgag gtccttgtag tagtcctgca tgagccgctc cacgggcacc    9840
tcctcctcgc ccgcgcggcc gtgcatgcgc gtgagcccga acccgcgctg cggctggacg    9900
agcgccaggt cggcgacgac gcgctcggcg aggatggcct gctggatctg ggtgagggtg    9960
gtctggaagt cgtcgaagtc gacgaagcgg tggtaggctc cggtgttgat ggtgtaggag    10020
cagttggcca tgacggacca gttgacggtc tggtggccgg ggcgcacgag ctcgtggtac    10080
ttgaggcgcg agtaggcgcg cgtgtcgaag atgtagtcgt tgcaggtgcg cacgaggtac    10140
tggtatccga cgaggaagtg cggcggcggc tggcggtaga gcggccatcg ctcggtggcc    10200
ggggcgccgg gcgcgaggtc ctcgagcatg aggcggtggt agccgtagat gtacctggac    10260
```

```
atccaggtga tgccggcggc ggtggtggag gcgcgcggga actcgcggac gcggttccag    10320
atgttgcgca gcggcaggaa gtagttcatg gtggccgcgg tctggcccgt gaggcgcgcg    10380
cagtcgtgga tgctctagac atacgggcaa aaacgaaagc ggtcagcggc tcgactccgt    10440
ggcctggagg ctaagcgaac gggttgggct gcgcgtgtac cccggttcga gtccctgctc    10500
gaatcaggct ggagccgcag ctaacgtggt actggcactc ccgtctcgac ccaagcctgc    10560
taacgaaacc tccaggatac ggaggcgggt cgttttggcc attttcgtca ggccggaaat    10620
gaaactagta agcgcggaaa gcggccgtcc gcgatggctc gctgccgtag tctggagaaa    10680
gaatcgccag ggttgcgttg cggtgtgccc cggttcgagc ctcagcgctc ggcgccggcc    10740
ggattccgcg gctaacgtgg gcgtggctgc cccgtcgttt ccaagacccc ttagccagcc    10800
gacttctcca gttacggagc gagccctct ttttcttgtg tttttgccag atgcatcccg    10860
tactgcggca gatgcgcccc caccctccac cacaaccgcc cctaccgcag cagcagcaac    10920
agccggcgct tctgccccg ccccagcagc agcagccagc cactaccgcg gcggccgccg    10980
tgagcggagc cggcgttcag tatgacctgg ccttggaaga gggcgagggg ctggcgcggc    11040
tgggggcgtc gtcgccggag cggcaccgc gcgtgcagat gaaaagggac gctcgcgagg    11100
cctacgtgcc caagcagaac ctgttcagag acaggagcgg cgaggagccc gaggagatgc    11160
gcgcctcccg cttccacgcg gggcgggagc tgcggcgcgg cctggaccga agcgggtgc    11220 tgagggacga ggatttcgag gcggacgagc tgacggggat cagccccgcg cgcgcgcacg    11280
tggccgcggc caacctggtc acggcgtacg agcagaccgt gaaggaggag agcaacttcc    11340
aaaaatcctt caacaaccac gtgcgcacgc tgatcgcgcg cgaggaggtg accctgggcc    11400
tgatgcacct gtgggacctg ctggaggcca tcgtgcagaa ccccacgagc aagccgctga    11460
cggcgcagct gtttctggtg gtgcagcaca gtcgggacaa cgagacgttc agggaggcgc    11520
tgctgaatat caccgagccc gagggccgct ggctcctgga cctggtgaac attctgcaga    11580
gcatcgtggt gcaggagcgc gggctgccgc tgtccgagaa gctggcggcc atcaacttct    11640
cggtgctgag cctgggcaag tactacgcta ggaagatcta caagacccg tacgtgccca    11700 tagacaagga ggtgaagatc gacgggtttt acatgcgcat gaccctgaaa gtgctgaccc    11760
tgagcgacga tctgggggtg taccgcaacg acaggatgca ccgcgcggtg agcgccagcc    11820
gccggcgcga gctgagcgac caggagctga tgcacagcct gcagcgggcc ctgaccgggg    11880 ccggaccga gggggagagc tactttgaca tgggcgcgga cctgcgctgg cagcctagcc    11940
gccgggcctt ggaagctgcc ggcggttccc cctacgtgga ggaggtggac gatgaggagg    12000
aggagggcga gtacctggaa gactgatggc gcgaccgtat ttttgctaga tgcagcaaca    12060
gccaccgccg cctcctgatc ccgcgatgcg ggcggcgctg cagagccagc cgtccggcat    12120
taactcctcg gacgattgga cccaggccat gcaacgcatc atggcgctga cgacccgcaa    12180
tcccgaagcc tttagacagc agcctcaggc caaccgactc tcggccatcc tggaggccgt    12240
ggtgccctcg cgctcgaacc ccacgcacga aaggtgctg gccatcgtga acgcgctggt    12300
ggagaacaag gccatccgcg gcgacgaggc cgggctggta tacaacgcgc tgctggagcg    12360
cgtggcccgc tacaacagca ccaacgtgca gacgaacctg gaccgcatgg tgaccgacgt    12420
gcgcgaggcg gtgtcgcagc gcgagcggtt ccaccgcgag tcgaacctgg ctccatggt    12480 ggcgctgaac gccttcctga gcacgcagcc cgccaacgtg ccccggggcc aggaggacta    12540
caccaacttc atcagcgcgc tgcggctgat ggtggccgag gtgccccaga gcgaggtgta    12600
ccagtcgggg ccggactact tcttccagac cagtcgccag ggcttgcaga ccgtgaacct    12660
```

-continued

```
gagccaggct ttcaagaact tgcagggact gtggggcgtg caggcccgg tcggggaccg    12720
cgcgacggtg tcgagcctgc tgacgccgaa ctcgcgcctg ctgctgctgc tggtggcgcc    12780
cttcacggac agcggcagcg tgagccgcga ctcgtacctg gctacctgc ttaacctgta    12840
ccgcgaggcc atcgggcagg cgcacgtgga cgagcagacc taccaggaga tcacccacgt    12900
gagccgcgcg ctgggccagg aggacccggg caacctggag gccaccctga acttcctgct    12960
gaccaaccgg tcgcagaaga tcccgcccca gtacgcgctg agcaccgagg aggagcgcat    13020
cctgcgctac gtgcagcaga gcgtgggggct gttcctgatg caggaggggg ccacgcccag    13080
cgccgcgctc gacatgaccg cgcgcaacat ggagcccagc atgtacgccc gcaaccgccc    13140
gttcatcaat aagctgatgg actacttgca tcgggcggcc gccatgaact cggactactt    13200
taccaacgcc atcttgaacc cgcactggct cccgccgccc gggttctaca cgggcgagta    13260
cgacatgccc gaccccaacg acgggttcct gtgggacgac gtggacagca gcgtgttctc    13320
gccgcgcccc accaccacca ccgtgtggaa gaaagagggc ggggaccggc ggccgtcctc    13380
ggcgctgtcc ggtcgcgcgg gtgctgccgc ggcggtgccc gaggccgcca gcccttccc    13440
gagcctgccc ttttcgctga acagcgtgcg cagcagcgag ctgggtcggc tgacgcggcc    13500
gcgcctgctg ggcgaggagg agtacctgaa cgactccttg cttcggcccg agcgcgagaa    13560
gaacttcccc aataacggga tagagagcct ggtggacaag atgagccgct ggaagacgta    13620
cgcgcacgag cacagggacg agccccgagc tagcagcagc accggcgcca cccgtagacg    13680
ccagcggcac gacaggcagc ggggtctggt gtgggacgat gaggattccg ccgacgacag    13740
cagcgtgttg gacttgggtg ggagtggtgg tggtaacccg ttcgctcacc tgcgcccccg    13800
tatcgggcgc ctgatgtaag aatctgaaaa aataaaagac ggtactcacc aaggccatgg    13860
cgaccagcgt gcgttcttct ctgttgtttg tagtagtatg atgaggcgcg tgtacccgga    13920
gggtcctcct ccctcgtacg agagcgtgat gcagcaggcg gtggcggcgg cgatgcagcc    13980
cccgctggag gcgccttacg tgccccgcg gtacctggcg cctacggagg ggcggaacag    14040
cattcgttac tcggagctgg cacccttgta cgataccacc cggttgtacc tggtggacaa    14100
caagtcggcg gacatcgcct cgctgaacta ccagaacgac cacagcaact tcctgaccac    14160
cgtggtgcag aacaacgatt tcacccccac ggaggccagc acccagacca tcaactttga    14220
cgagcgctcg cggtggggcg gccagctgaa aaccatcatg cacaccaaca tgcccaacgt    14280
gaacgagttc atgtacagca acaagttcaa ggcgcgggtg atggtctcgc gcaagacccc    14340
caacggggtc acagtaacag atggtagtca ggacgagctg acctacgagt gggtggagtt    14400
tgagctgccc gagggcaact tctcggtgac catgaccatc gatctgatga caacgccat    14460
catcgacaac tacttggcgg tggggcggca gaacggggtg ctggagagcg acatcggcgt    14520
gaagttcgac acgcgcaact tccggctggg ctgggacccc gtgaccgagc tggtgatgcc    14580
gggcgtgtac accaacgagg ccttccaccc cgacatcgtc ctgctgcccg gctgcggcgt    14640
ggacttcacc gagagccgcc tcagcaacct gctgggcatc cgcaagcggc agcccttcca    14700
ggagggcttc cagatcctgt acgaggacct ggaggggggc aacatccccg cgctgctgga    14760
cgtggacgcc tacgagaaaa gcaaggagga tagcgccgcc gcgcgaccg cagccgtggc    14820
caccgcctct accgaggtgc ggggcgataa ttttgctagc gccgcgacac tggcagcggc    14880
cgaggcggct gaaaccgaaa gtaagatagt gatccagccg gtggagaagg acagcaagga    14940
gaggagctac aacgtgctcg cggacaagaa aaacaccgcc taccgcagct ggtacctggc    15000
```

```
ctacaactac ggcgaccccg agaagggcgt gcgctcctgg acgctgctca ccacctcgga   15060
cgtcacctgc ggcgtggagc aagtctactg gtcgctgccc gacatgatgc aagacccggt   15120
caccttccgc tccacgcgtc aagttagcaa ctacccggtg gtgggcgccg agctcctgcc   15180
cgtctactcc aagagcttct tcaacgagca ggccgtctac tcgcagcagc tgcgcgcctt   15240
cacctcgctc acgcacgtct tcaaccgctt ccccgagaac cagatcctcg ttcgcccgcc   15300
cgcgcccacc attaccaccg tcagtgaaaa cgttcctgct ctcacagatc acgggaccct   15360
gccgctgcgc agcagtatcc ggggagtcca gcgcgtgacc gtcactgacg ccagacgccg   15420
cacctgcccc tacgtctaca aggccctggg cgtagtcgcg ccgcgcgtcc tctcgagccg   15480
caccttctaa aaaatgtcca ttctcatctc gcccagtaat aacaccggtt ggggcctgcg   15540
cgcgcccagc aagatgtacg gaggcgctcg ccaacgctcc acgcaacacc ccgtgcgcgt   15600
gcgcgggcac ttccgcgctc cctggggcgc cctcaagggc gcgtgcgct cgcgcaccac   15660
cgtcgacgac gtgatcgacc aggtggtggc cgacgcgcgc aactacacgc ccgccgccgc   15720
gcccgtctcc accgtggacg ccgtcatcga cagcgtggtg gccgacgcgc gccggtacgc   15780
ccgcgccaag agccggcggc ggcgcatcgc ccggcggcac cggagcaccc ccgccatgcg   15840
cgcggcgcga gccttgctgc gcagggccag gcgcacggga cgcagggcca tgctcagggc   15900
ggccagacgc gcggcctccg gcagcagcag cgccggcagg accgcagac gcgcggccac   15960
ggcggcggcg gcggccatcg ccagcatgtc ccgcccgcgg cgcggcaacg tgtactgggt   16020
gcgcgacgcc gccaccggtg tgcgcgtgcc cgtgcgcacc cgccccctc gcacttgaag   16080
atgctgactt cgcgatgttg atgtgtccca gcggcgagga ggatgtccaa gcgcaaattc   16140
aaggaagaga tgctccaggt catcgcgcct gagatctacg gccggcggc ggtgaaggag   16200
gaaagaaagc cccgcaaact gaagcgggtc aaaaaggaca aaaaggagga ggaagatgtg   16260
gacggactgg tggagtttgt gcgcgagttc gccccccggc ggcgcgtgca gtggcgcggg   16320
cggaaagtga accggtgct gcgacccggc accacggtgg tcttcacgcc cggcgagcgt   16380
tccggctccg cctccaagcg ctcctacgac gaggtgtacg gggacgagga catcctcgag   16440
caggcggccg aacgtctggg cgagtttgct tacggcaagc gcagccgccc cgcgcccttg   16500
aaagaggagg cggtgtccat cccgctggac cacggcaacc ccacgccgag cctgaagccg   16560
gtgaccctgc agcaggtgct gcctggtgcg gcgccgcgcc ggggcttcaa gcgcgagggc   16620
ggcgaggatc tgtacccgac catgcagctg atggtgccca gcgccagaa gctggaggac   16680
gtgctggagc acatgaaggt ggaccccgag gtgcagcccg aggtcaaggt gcggcccatc   16740
aagcaggtgg ccccgggcct gggcgtgcag accgtggaca tcaagatccc cacggagccc   16800
atggaaacgc agaccgagcc cgtgaagccc agcaccagca ccatggaggt gcagacggat   16860
ccctggatgc cggcaccggc ttccaccacc cgccgaagac gcaagtacgg cgcggccagc   16920
ctgctgatgc ccaactacgc gctgcatcct tccatcatcc ccacgccggg ctaccgcggc   16980
acgcgcttct accgcggcta caccagcagc cgccgccgca agaccaccac ccgccgccgc   17040
cgtcgtcgca cccgccgcag cagcaccgcg acttccgccg ccgccctggt gcggagagtg   17100
taccgcagcg ggcgcgagcc tctgaccctg ccgcgcgcgc gctaccaccc gagcatcgcc   17160
atttaactac cgcctcctac ttgcagatat ggccctcaca tgccgcctcc gcgtccccat   17220
tacgggctac cgaggaagaa agccgcgccg tagaaggctg acggggaacg ggctgcgtcg   17280
ccatcaccac cggcggcggc gcgccatcag caagcggttg gggggaggct tcctgcccgc   17340
gctgatgccc atcatcgccg cggcgatcgg ggcgatcccc ggcatagctt ccgtggcggt   17400
```

```
gcaggcctct cagcgccact gagacacagc ttggaaaatt tgtaataaaa aatggactga  17460
cgctcctggt cctgtgatgt gtgtttttag atggaagaca tcaatttttc gtccctggca  17520
ccgcgacacg gcacgcggcc gtttatgggc acctggagcg acatcggcaa cagccaactg  17580
aacgggggcg ccttcaattg gagcagtctc tggagcgggc ttaagaattt cgggtccacg  17640
ctcaaaacct atggcaacaa ggcgtggaac agcagcacag ggcaggcgct gagggaaaag  17700
ctgaaagagc agaacttcca gcagaaggtg gtcgatggcc tggcctcggg catcaacggg  17760
gtggtggacc tggccaacca ggccgtgcag aaacagatca acagccgcct ggacgcggtc  17820
ccgcccgcgg ggtccgtgga gatgccccag gtggaggagg agctgcctcc cctggacaag  17880
cgcggcgaca agcgaccgcg tcccgacgcg gaggagacgc tgctgacgca cacggacgag  17940
ccgcccccgt acgaggaggc ggtgaaactg ggtctgccca ccacgcggcc cgtggcgcct  18000
ctggccaccg gggtgctgaa acccagcagc agcagcagcc agcccgcgac cctggacttg  18060
cctccgcctg cttcccgccc ctccacagtg gctaagcccc tgccgccggt ggccgtcgcg  18120
tcgcgcgccc cccgaggccg ccccccaggcg aactggcaga gcactctgaa cagcatcgtg  18180
ggtctgggag tgcagagtgt gaagcgccgc cgctgctatt aaaagacact gtagcgctta  18240
acttgcttgt ctgtgtgtat atgtatgtcc gccgaccaga aggaggagga agaggcgcgt  18300
cgccgagttg caagatggcc accccatcga tgctgcccca gtgggcgtac atgcacatcg  18360
ccggacagga cgcttcggag tacctgagtc cgggtctggt gcagttcgcc cgcgccacag  18420
acacctactt cagtctgggg aacaagttta ggaaccccac ggtggcgccc acgcacgatg  18480
tgaccaccga ccgcagccag cggctgacgc tgcgcttcgt gcccgtggac cgcgaggaca  18540
acacctactc gtacaaagtg cgctacacgc tggccgtggg cgacaaccgc gtgctggaca  18600
tggccagcac ctactttgac atccgcggcg tgctggatcg gggccctagc ttcaaaccct  18660
actccggcac gcttacaac agcctggctc ccaagggagc gcccaacact gccagtggaa  18720
catataaagc tgatggtgat actggtacag aaaaaaccta tacatatgga aatgcgcctg  18780
tgcaaggcat tagtattaca aaagatggta ttcaacttgg aactgacact gatgatcagc  18840
ccatttatgc agataaaact tatcaaccag agcctcaagt gggtgatgct gaatggcatg  18900
acatcactgg tactgatgaa aaatatggag gcagagctct caagcctgac accaaaatga  18960
agccctgcta tggttctttt gccaagccta ccaataaaga aggaggtcag gcaaatgtga  19020
aaaccgaaac aggcggtacc aaagaatatg acattgacat ggcattcttc gataatcgaa  19080
gtgcagctgc ggctggcctg gccccagaaa ttgttttgta tactgagaat gtggatctgg  19140
aaactccaga tactcatatt gtatacaagg cgggcacaga tgacagcagc tcttctatca  19200
atttgggtca gcagtccatg cccaacagac ccaactacat tggctttaga gacaacttta  19260
tcgggctcat gtactacaac agcactggca acatgggcgt gctggctggt caggcctccc  19320
agctgaatgc tgtggtggac ttgcaggaca gaaacactga actgtcctac cagctcttgc  19380
ttgactctct gggcgacaga accaggtatt tcagtatgtg gaatcaggcg gtggacagct  19440
atgaccccga tgtgcgcatt attgaaaatc acggtgtgga ggatgaactc cctaactatt  19500
gcttcccct ggatgctgtg ggtagaactg atacttacca gggaattaag gccaatggtg  19560
ctgatcaaac cacctggacc aaagatgata ctgttaatga tgctaatgaa ttgggcaagg  19620
gcaatccttt cgccatggag atcaacatcc aggccaacct gtggcggaac ttcctctacg  19680
cgaacgtggc gctgtacctg cccgactcct acaagtacac gccggccaac atcacgctgc  19740
```

```
cgaccaacac caacacctac gattacatga acggccgcgt ggtggcgccc tcgctggtgg   19800
acgcctacat caacatcggg gcgcgctggt cgctggaccc catggacaac gtcaacccct   19860
tcaaccacca ccgcaacgcg ggcctgcgct accgctccat gctcctgggc aacgggcgct   19920
acgtgccctt ccacatccag gtgccccaaa agttcttcgc catcaagagc ctcctgctcc   19980
tgcccgggtc ctacacctac gagtggaact ccgcaagga cgtcaacatg atcctgcaga   20040
gctccctcgg caacgacctg cgcacggacg gggcctccat cgccttcacc agcatcaacc   20100
tctacgccac cttcttcccc atggcgcaca acaccgcctc cacgctcgag gccatgctgc   20160
gcaacgacac caacgaccag tccttcaacg actacctctc ggcggccaac atgctctacc   20220
ccatcccggc caacgccacc aacgtgccca tctccatccc ctcgcgcaac tgggccgcct   20280
tccgcggatg gtccttcacg cgcctcaaga cccgcgagac gccctcgctc ggctccgggt   20340
tcgaccccta cttcgtctac tcgggctcca tccctacct cgacggcacc ttctacctca   20400
accacacctt caagaaggtc tccatcacct tcgactcctc cgtcagctgg cccggcaacg   20460
accgcctcct gacgcccaac gagttcgaaa tcaagcgcac cgtcgacgga gaggggtaca   20520
acgtggccca gtgcaacatg accaaggact ggttcctggt ccagatgctg gcccactaca   20580
acatcggcta ccagggcttc tacgtgcccg agggctacaa ggaccgcatg tactccttct   20640
tccgcaactt ccagcccatg agccgccagg tcgtggacga ggtcaactac aaggactacc   20700
aggccgtcac cctggcctac cagcacaaca actcgggctt cgtcggctac ctcgcgccca   20760
ccatgcgcca gggacagccc taccccgcca actaccccta cccgctcatc ggcaagagcg   20820
ccgtcgccag cgtcacccag aaaaagttcc tctgcgaccg ggtcatgtgg cgcatcccct   20880
tctccagcaa cttcatgtcc atgggcgcgc tcaccgacct cggccagaac atgctctacg   20940
ccaactccgc ccacgcgcta gacatgaatt tcgaagtcga ccccatggat gagtccaccc   21000
ttctctatgt tgtcttcgaa gtcttcgacg tcgtccgagt gcaccagccc caccgcggcg   21060
tcatcgaggc cgtctacctg cgcacgccct tctcggccgg caacgccacc acctaagccc   21120
cgctcttgct tcttgcaaga tgacggcctg tgcgggctcc ggcgagcagg agctcagggc   21180
catcctccgc gacctgggct gcgggccctg cttcctgggc accttcgaca agccgcttcc   21240
gggattcatg gccccgcaca agctggcctg cgccatcgtc aacacggccg gccgcgagac   21300 cggggcgag cactggctgg ccttcgcctg gaacccgcgc tcccacacct gctacctctt   21360 cgacccctc gggttctcgg acgagcgcct caagcagatc taccagttcg agtacgaggg   21420
cctgctgcgc cgcagcgccc tggccaccga ggaccgctgc gtcaccctgg aaaagtccac   21480
ccagaccgtg cagggtccgc gctcggccgc ctgcgggctc ttctgctgca tgttcctgca   21540
cgccttcgtg cactggcccg accgcccat ggacaagaac cccaccatga acttgctgac   21600 ggggggtgccc aacggcatgc tccagtcgcc ccaggtggaa cccacccctgc gccgcaacca   21660 ggaggcgctc taccgcttcc tcaacgccca ctccgcctac tttcgctccc accgcgcgcg   21720
catcgagaag gccaccgcct tcgaccgcat gaatcaagac atgtaaaccg tgtgtgtatg   21780
tgaatgcttt attcataata aacagcacat gtttatgcca ccttttctga ggctctgact   21840
ttatttagaa atcgaagggg ttctgccggc tctcggcgtg cccgcgggc agggatacgt   21900 tgcggaactg gtacttgggc agccacttga actcggggat cagcagcttc ggcacgggga   21960
ggtcggggaa cgagtcgctc cacagcttgc gcgtgagttg cagggcgccc agcaggtcgg   22020
gcgcggagat cttgaaatcg cagttgggac ccgcgttctg cgcgcgggag ttgcggtaca   22080
cggggttgca gcactggaac accatcaggg ccgggtgctt cacgctcgcc agcaccgtcg   22140
```

```
cgtcggtgat gccctccacg tccagatcct cggcgttggc catcccgaag ggggtcatct    22200
tgcaggtctg ccgccccatg ctgggcacgc agccgggctt gtggttgcaa tcgcagtgca    22260
gggggatcag catcatctgg gcctgctcgg agctcatgcc cgggtacatg gccttcatga    22320
aagcctccag ctggcggaag gcctgctgcg ccttgccgcc ctcggtgaag aagaccccgc    22380
aggacttgct agagaactgg ttggtggcgc agccggcgtc gtgcacgcag cagcgcgcgt    22440
cgttgttggc cagctgcacc acgctgcgcc cccagcggtt ctgggtgatc ttggcccggt    22500
cggggttctc cttcagcgcg cgctgcccgt tctcgctcgc cacatccatc tcgatcgtgt    22560
gctccttctg gatcatcacg gtcccgtgca ggcatcgcag cttgccctcg gcctcggtgc    22620
acccgtgcag ccacagcgcg cagccggtgc actcccagtt cttgtgggcg atctgggagt    22680
gcgagtgcac gaagccctgc aggaagcggc ccatcatcgt ggtcagggtc ttgttgctgg    22740
tgaaggtcag cgggatgccg cggtgctcct cgttcacata caggtggcag atgcggcggt    22800
acacctcgcc ctgctcgggc atcagctgga aggcggactt caggtcgctc tccacgcggt    22860
accggtccat cagcagcgtc atgacttcca tgcccttctc ccaggccgag acgatcggca    22920
ggctcagggg gttcttcacc gccgttgtca tcttagtcgc cgccgctgag gtcagggggt    22980
cgttctcgtc cagggtctca aacactcgct tgccgtcctt ctcggtgatg cgcacggggg    23040
gaaagctgaa gcccacggcc gccagctcct cctcggcctg cctttcgtcc tcgctgtcct    23100
ggctgatgtc ttgcaaaggc acatgcttgg tcttgcgggg tttcttttg ggcggcagag    23160
gcggcggcgg agacgtgctg ggcgagcgcg agttctcgct caccacgact atttcttctt    23220
cttggccgtc gtccgagacc acgcggcggt aggcatgcct cttctggggc agaggcggag    23280
gcgacgggct ctcgcggttc ggcgggcggc tggcagagcc ccttccgcgt tcgggggtgc    23340
gctcctggcg gcgctgctct gactgacttc ctccgcggcc ggccattgtg ttctcctagg    23400
gagcaacaag catggagact cagccatcgt cgccaacatc gccatctgcc cccgccgccg    23460
ccgacgagaa ccagcagcag aatgaaagct taaccgcccc gccgcccagc cccacctccg    23520
acgccgccgc ggccccagac atgcaagaga tggaggaatc catcgagatt gacctgggct    23580
acgtgacgcc cgcggagcac gaggaggagc tggcagcgcg cttttcagcc ccggaagaga    23640
accaccaaga gcagccagag caggaagcag agagcgagca gcagcaggct gggctcgagc    23700
atggcgacta cctgagcggg gcagaggacg tgctcatcaa gcatctggcc cgccaatgca    23760
tcatcgtcaa ggacgcgctg ctcgaccgcg ccgaggtgcc cctcagcgtg gcggagctca    23820
gccgcgccta cgagcgcaac ctcttctcgc cgcgcgtgcc cccaagcgc cagcccaacg    23880
gcacctgcga gcccaacccg cgcctcaact tctacccggt cttcgcggtg cccgaggccc    23940
tggccaccta ccacctcttt ttcaagaacc aaaggatccc cgtctcctgc cgcgccaacc    24000
gcacccgcgc cgacgccctg ctcaacctgg gtcccggcgc ccgcctacct gatatcgcct    24060
ccttggaaga ggttcccaag atcttcgagg gtctgggcag cgacgagact cgggccgcga    24120
acgctctgca aggaagcgga gaggagcatg agcaccacag cgccctggtg gagttggaag    24180
gcgacaacgc gcgcctggcg gtgctcaagc gcacggtcga gctgacccac ttcgcctacc    24240
cggcgctcaa cctgccccc aaggtcatga gcgccgtcat ggaccaggtg ctcatcaagc    24300
gcgcctcgcc cctctcggat gaggacatgc aggacccga gagctcggac gagggcaagc    24360
ccgtggtcag cgacgagcag ctggcgcgct ggctgggagc gagtagcacc ccccagagct    24420
tggaagagcg gcgcaagctc atgatggccg tggtcctggt gaccgtggag ctggagtgtc    24480
```

```
tgcgccgctt cttcgccgac gcagagaccc tgcgcaaggt cgaggagaac ctgcactacc   24540
tcttcaggca cgggtttgtg cgccaggcct gcaagatctc caacgtggag ctgaccaacc   24600
tggtctccta catgggcatc ctgcacgaga accgctgggg gcagaacgtg ctgcacacca   24660
ccctgcgcgg ggaggcccgc cgcgactaca tccgcgactg cgtctacctg tacctctgcc   24720
acacctggca gacgggcatg ggcgtgtggc agcagtgcct ggaggagcag aacctgaaag   24780
agctctgcaa gctcctgcag aagaacctga aggccctgtg gaccgggttc gacgagcgca   24840
ccaccgcctc ggacctggcc gacctcatct tccccgagcg cctgcggctg acgctgcgca   24900
acggactgcc cgactttatg agtcaaagca tgttgcaaaa ctttcgctct ttcatcctcg   24960
aacgctccgg gatcctgccc gccacctgct ccgcgctgcc ctcggacttc gtgccgctga   25020
ccttccgcga gtgccccccg ccgctctgga gccactgcta cctgctgcgc ctggccaact   25080
acctggccta ccactcggac gtgatcgagg acgtcagcgg cgagggtctg ctcgagtgcc   25140
actgccgctg caacctctgc acgccgcacc gctccctggc ctgcaacccc cagctgctga   25200
gcgagaccca gatcatcggc accttcgagt tgcaaggccc cggcgagggc aaggggggtc   25260
tgaaactcac cccgggggctg tggacctcgg cctacttgcg caagttcgtg cccgaggact   25320 accatcccttt cgagatcagg ttctacgagg accaatccca gccgcccaag gccgaactgt   25380
cggcctgcgt catcacccag ggggccatcc tggcccaatt gcaagccatc cagaaatccc   25440
gccaagaatt tctgctgaaa aagggccacg gggtctacct ggaccccccag accggagagg   25500 agctcaaccc cagcttcccc caggatgccc gaggaagca gcaagaagct gaaagtggag   25560
ctgccgccgc cggaggattt ggaggaagac tgggagagca gtcaggcaga ggaggaggag   25620
atggaagact gggacagcac tcaggcagag gaggacagcc tgcaagacag tctggaagac   25680
gaggtggagg aggaggcaga ggaagaagca gccgccgcca gaccgtcgtc ctcggcggag   25740
aaagcaagca gcacggatac catctccgct ccgggtcggg gtcgcggcga ccgggccccac   25800 agtaggtggg acgagaccgg gcgcttcccg aaccccacca cccagaccgg taagaaggag   25860
cggcagggat acaagtcctg gcgggggcac aaaaacgcca tcgtctcctg cttgcaagcc   25920 tgcggggggca acatctcctt cacccgccgc tacctgctct ccaccgcgg ggtgaacttc   25980 ccccgcaaca tcttgcatta ctaccgtcac ctccacagcc cctactactg tttccaagaa   26040
gaggcagaaa cccagcagca gcagaaaacc agcggcagca gcagctagaa aatccacagc   26100
ggcggcaggt ggactgagga tcgcagcgaa cgagccggcg cagacccggg agctgaggaa   26160 ccggatctttt cccaccctct atgccatctt ccagcagagt cggggggcagg agcaggaact   26220 gaaagtcaag aaccgttctc tgcgctcgct caccccgcagt tgtctgtatc acaagagcga   26280
agaccaactt cagcgcactc tcgaggacgc cgaggctctc ttcaacaagt actgcgcgct   26340
cactcttaaa gagtagcccg cgcccgccca cacacggaaa aaggcgggaa ttacgtcacc   26400
acctgcgccc ttcgcccgac catcatcatg agcaaagaga ttcccacgcc ttacatgtgg   26460
agctaccagc cccagatggg cctggccgcc ggcgccgccc aggactactc cacccgcatg   26520
aactggctca gcgccgggcc cgcgatgatc tcacgggtga atgacatccg cgcccgccga   26580
aaccagatac tcctagaaca gtcagcgatc accgccacgc cccgccatca ccttaatccg   26640
cgtaattggc ccgccgccct ggtgtaccag gaaattcccc agcccacgac cgtactactt   26700
ccgcgagacg cccaggccga agtccagctg actaactcag gtgtccagct ggccggcggc   26760
gccgccctgt gtcgtcaccg ccccgctcag ggtataaagc ggctggtgat ccgaggcaga   26820
ggcacacagc tcaacgacga ggtggtgagc tcttcgctgg gtctgcgacc tgacggagtc   26880
```

```
ttccaactcg ccggatcggg gagatcttcc ttcacgcctc gtcaggccgt cctgactttg   26940
gagagttcgt cctcgcagcc ccgctcgggt ggcatcggca ctctccagtt cgtggaggag   27000
ttcactccct cggtctactt caaccccttc tccggctccc ccggccacta cccggacgag   27060
ttcatcccga acttcgacgc catcagcgag tcggtggacg gctacgattg aatgtcccat   27120
ggtggcgcag ctgacctagc tcggcttcga cacctggacc actgccgccg cttccgctgc   27180
ttcgctcggg atctcgccga gtttgcctac tttgagctgc ccgaggagca ccctcagggc   27240
ccggcccacg gagtgcggat catcgtcgaa ggggcctcg actcccacct gcttcggatc   27300
ttcagccagc gaccgatcct ggtcgagcgc gagcaaggac agacccttct gaccctgtac   27360
tgcatctgca accaccccgg cctgcatgaa agtctttgtt gtctgctgtg tactgagtat   27420
aataaaagct gagatcagcg actactccgg actcgattgt ggtgttcctg ctatcaaccg   27480
gtccctgttc ttcaccggga acgagaccga gctccagctt cagtgtaagc cccacaagaa   27540
gtacctcacc tggctgttcc agggctcccc gatcgccgtt gtcaaccact gcgacaacga   27600
cggagtcctg ctgagcggcc ccgccaacct tacttttttcc acccgcagaa gcaagctcca   27660
gctcttccaa cccttcctcc ccgggaccta tcagtgcgtc tcgggaccct gccatcacac   27720
cttccacctg atcccgaata ccacagcgcc gctccccgct actaacaacc aaactaccca   27780
ccatcgccac cgtcgcgacc tttctgaatc taacactacc cccacaccg gaggtgagct   27840 ccgaggtcga ccaacctctg ggatttacta cggcccctgg gaggtggtgg ggttaatagc   27900
gctaggccta gttgtgggtg ggcttttggc tctctgctac ctatacctcc cttgctgttc   27960
gtacttagtg gtgctgtgtt gctggtttaa gaaatgggga agatcaccct agtgagctgc   28020
ggtgcgctgg tggcggtggt ggtgttttcg attgtggac tgggcggcgc ggctgtagtg   28080
aaggagaagg ccgatccctg cttgcatttc aatcccgaca attgccagct gagttttcag   28140
cccgatggca atcggtgcgc ggtgctgatc aagtgcggat gggaatgcga gaacgtgaga   28200
atcgagtaca ataacaagac tcggaacaat actctcgcgt ccgtgtggca gcccggggac   28260
cccgagtggt acaccgtctc tgtccccggt gctgacggct cccgcgcac cgtgaacaat   28320 actttcattt ttgcgcacat gtgcgacacg gtcatgtgga tgagcaagca gtacgatatg   28380
tggcccccca cgaaggagaa catcgtggtc ttctccatcg cttacagcgc gtgcacggcg   28440
ctaatcaccg ctatcgtgtg cctgagcatt cacatgctca tcgctattcg ccccagaaat   28500
aatgccgaaa aagagaaaca gccataacac gttttttcac acaccttttt cagaccatgg   28560
cctctgttaa attttgctt ttatttgcca gtctcattac tgttataagt aatgagaaac   28620
tcactattta cattggcact aaccacactt tagacggaat tccaaaatcc tcatggtatt   28680
gctattttga tcaagatcca gacttaacta tagaactgtg tggtaacaag ggaaaaaata   28740
caagcattca tttaattaac tttaattgcg gagacaattt gaaattaatt aatatcacta   28800
aagagtatgg aggtatgtat tactatgttg cagaaaataa caacatgcag ttttatgaag   28860
ttactgtaac taatcccacc acacctagaa caacaacaac caccaccaca aaaactacac   28920
ctgttaccac tatgcagctc actaccaata acatttttgc catgcgtcaa atggtcaaca   28980
atagcactca accccacccca cccagtgagg aaattcccaa atccatgatt ggcattattg   29040
ttgctgtagt ggtgtgcatg ttgatcatcg ccttgtgcat ggtgtactat gccttctgct   29100
acagaaagca cagactgaac gacaagctgg aacacttact aagtgttgaa ttttaatttt   29160
ttagaaccat gaagatccta ggccttttaa tttttttctat cattacctct gctctatgca   29220
```

```
attctgacaa tgaggacgtt actgtcgttg tcggaaccaa ttatacactg aaaggtccag   29280
cgaagggtat gctttcgtgg tattgctggt ttggaactga cgagcaacag acagagctct   29340
gcaatgctca aaaaggcaaa acctcaaatt ctaaaatctc taattatcaa tgcaatggca   29400
ctgacttagt actgctcaat gtcacgaaag catatgctgg cagctacacc tgccctggag   29460
atgatactga aacatgcatt ttttacaaag tggaagtggt tgatcccact actccacctc   29520
cacccaccac aactactcac accacacaca cagaacaaac cacagcagag gaggcagcaa   29580
agttagcctt gcaggtccaa gacagttcat ttgttggcat tacccctaca cctgatcagc   29640
ggtgtccggg gctgctcgtc agcggcattg tcggtgtgct ttcgggatta gcagtcataa   29700
tcatctgcat gttcattttt gcttgctgct atagaaggct ttaccgacaa aaatcagacc   29760
cactgctgaa cctctatgtt taattttttc cagagccatg aaggcagtta gcactctagt   29820
tttttgttct ttgattggca ctgttttag tgttagcttt ttgaaacaaa tcaatgttac   29880
tgagggggaa aatgtgacac tggtaggcgt agagggtgct caaaatacca cctggacaaa   29940
attccatcta gatgggtgga aagaaatttg cacctggaat gtcagtactt atacatgtga   30000
aggagttaat cttaccattg tcaatgtcag ccaaattcaa aagggttgga ttaaagggca   30060
atctgttagt gttagcaata gtgggtacta tacccagcat actcttatct atgacattat   30120
agttatacca ctgcctacac ctagcccacc tagcactacc acacagacaa cccacactac   30180
acaaacaacc acatacagta catcaaaatca gcctaccacc actacaacag cagaggttgc   30240
cagctcgtct ggggtccgag tggcatttt gatgttggcc ccatctagca gtcccactgc   30300
tagtaccaat gagcagacta ctgaattttt gtccactgtc gagagccaca ccacagctac   30360
ctcgagtgcc ttctctagca ccgccaatct atcctcgctt tcctacacac caatcagtcc   30420
cgctactact cctaccccccg ctattctccc cactcccctg aagcaaacag acggcgacat   30480
gcaatggcag atcaccctgc tcattgtgat cgggttggtc atcctggccg tgttgctcta   30540
ctacatcttc tgccgccgca ttcccaacgc gcaccgcaag ccggcctaca gcccatcgt   30600
tgtcgggcag ccggagccgc ttcaggtgga agggggtcta aggaatcttc tcttctcttt   30660
tacagtatgg tgattgaatt atgattccta gacaaatctt gatcactatt cttatctgcc   30720
tcctccaagt ctgtgccacc ctcgctctgg tggccaacgc cagtccagac tgtattgggc   30780
ccttcgcctc ctacgtgctc tttgccttca tcacctgcat ctgctgctgt agcatagtct   30840
gcctgcttat caccttcttc cagttcattg actggatctt tgtgcgcatc gcctacctgc   30900
gccaccaccc ccagtaccgc gaccagcgag tggcgcggct gctcaggatc ctctgataag   30960
catgcgggct ctgctacttc tcgcgcttct gctgttagtg ctccccgtc ccgtcgaccc   31020
ccggaccccc acccagtccc ccgaggaggt ccgcaaatgc aaattccaag aaccctggaa   31080
attcctcaaa tgctaccgcc aaaaatcaga catgcatccc agctggatca tgatcattgg   31140
gatcgtgaac attctggcct gcaccctcat ctcctttgtg atttacccct gctttgactt   31200
tggttggaac tcgccagagg cgctctatct cccgcctgaa cctgacacac caccacagca   31260
acctcaggca cacgcactac caccaccacc acagcctagg ccacaataca tgcccatatt   31320
agactatgag gccgagccac agcgacccat gctccccgct attagttact tcaatctaac   31380
cggcggagat gactgaccca ctggccaaca caacgtcaa cgaccttctc ctggacatgg   31440
acggccgcgc ctcggagcag cgactcgccc aacttcgcat tcgccagcag caggagagag   31500
ccgtcaagga gctgcaggac ggcatagcca tccaccagtg caagaaaggc atcttctgcc   31560
tggtgaaaca ggccaagatc tcctacgagg tcacccagac cgaccatcgc ctctcctacg   31620
```

```
agctcctgca gcagcgccag aagttcacct gcctggtcgg agtcaacccc atcgtcatca    31680
cccagcagtc gggcgatacc aagggtgca tccactgctc ctgcgactcc cccgactgcg     31740
tccacactct gatcaagacc ctctgcggcc tccgcgacct cctccccatg aactaatcac    31800 cccctta tcc agtgaaataa agatcatatt gatgatttga gtttaataaa ataaagaat    31860 cacttacttg aaatctgata ccaggtctct gtccatgttt tctgccaaca ccacttcact    31920
cccctcttcc cagctctggt actgcaggcc ccggcgggct gcaaacttcc tccacaccct    31980 gaagggatg tcaaattcct cctgtccctc aatcttcatt ttatcttcta tcagatgtcc    32040 aaaagcgcg tccgggtgga tgatgacttc gaccccgtct accccctacga tgcagacaac    32100 gcaccgaccg tgcccttcat caaccccccc ttcgtctctt cagatggatt ccaagagaag    32160
cccctggggg tgctgtccct gcgtctggcc gatcccgtca ccaccaagaa cggggaaatc    32220
accctcaagc tgggagatgg ggtggacctc gactcctcgg gaaaactcat ctccaacacg    32280
gccaccaagg ccgccgcccc tctcagtttt tccaacaaca ccatttccct taacatggat    32340
accccttttt acaacaacaa tggaaagtta ggcatgaaag tcactgctcc actgaagata    32400
ctagacacag acttgctaaa aacacttgtt gtagcttatg acaaggtttt aggaacaaac    32460
accactggtg cccttgttgc ccaactagca tccccacttg cttttgatag caatagcaaa    32520 attgcccttca atttaggcaa tggaccattg aaagtggatg caaatagact gaacatcaat    32580
tgcaatagag gactctatgt tactaccaca aaagatgcac tggaagccaa tataagttgg    32640
gctaatgcta tgacatttat aggaaatgcc atgggtgtca atattgatac acaaaaaggc    32700 ttgcaattg gcaccactag taccgtcgca gatgttaaaa acgcttaccc catacaaatc    32760
aaacttggag ctggtctcac atttgacagc acaggtgcaa ttgttgcatg aacaaagat    32820 gatgacaagc ttacactatg gaccacagcc gacccctctc caaattgtca catatattct    32880
gaaaaggatg ctaagcttac actttgcttg acaaagtgtg gcagtcagat tctgggcact    32940
gtttccctca tagctgttga tactggcagt ttaaatccca taacaggaac agtaaccact    33000
gctcttgtct cacttaaatt cgatgcaaat ggagttttgc aaagcagctc aacactagac    33060
tcagactatt ggaatttcag acagggagat gttacacctg ctgaagccta tactaatgct    33120
ataggtttca tgcccaatct aaaagcatac cctaaaaaca caagtggagc tgcaaaaagt    33180
cacattgttg ggaaagtgta cctacatggg gatacaggca accactggaa cctcattatt    33240
actttcaatg aaacaagtga tgaatcttgc acttactgta ttaactttca atggcagtgg    33300
ggggctgatc aatataaaaa tgaaacactt gccgtcagtt cattcacctt tcctatatt    33360 gctaaagaat aaaccccact ctgtacccca tctctgtcta tggaaaaaac tctgaaacac    33420
aaaataaaat aaagttcaag tgttttattg attcaacagt tttacaggat tcgagcagtt    33480 attttcctc caccctccca ggacatggaa tacaccaccc tctcccccg cacagccttg     33540 aacatctgaa tgccattggt gatggacatg cttttggtct ccacgttcca cacagtttca    33600
gagcgagcca gtctcgggtc ggtcaggag atgaaaccct ccgggcactc ccgcatctgc    33660
acctcacagc tcaacagctg aggattgtcc tcggtggtcg ggatcacggt tatctggaag    33720
aagcagaaga gcggcggtgg gaatcatagt ccgcgaacgg gatcggccgg tggtgtcgca    33780
tcaggccccg cagcagtcgc tgtcgccgcc gctccgtcaa gctgctgctc aggggtccg    33840 ggtccaggga ctccctcagc atgatgccca cggccctcag catcagtcgt ctggtgcggc    33900
gggcgcagca gcgcatgcgg atctcgctca ggtcgctgca gtacgtgcaa cacaggacca    33960
```

```
ccaggttgtt caacagtcca tagttcaaca cgctccagcc gaaactcatc gcgggaagga   34020
tgctacccac gtggccgtcg taccagatcc tcaggtaaat caagtggcgc ccctccaga    34080 acacgctgcc catgtacatg atctccttgg gcatgtggcg gttcaccacc tcccggtacc   34140
acatcaccct ctggttgaac atgcagcccc ggatgatcct gcggaaccac agggccagca   34200
ccgccccgcc cgccatgcag cgaagagacc ccgggtcccg acaatggcaa tggaggaccc   34260
accgctcgta cccgtggatc atctgggagc tgaacaagtc tatgttggca cagcacaggc   34320
atatgctcat gcatctcttc agcactctca gctcctcggg ggtcaaaacc atatcccagg   34380 gcacgggaa ctcttgcagg acagcgaacc ccgcagaaca gggcaatcct cgcacataac     34440
ttacattgtg catggacagg gtatcgcaat caggcagcac cgggtgatcc tccaccagag   34500
aagcgcgggt ctcggtctcc tcacagcgtg gtaaggggc cggccgatac gggtgatggc    34560
gggacgcggc tgatcgtgtt cgcgaccgtg ttatgatgca gttgctttcg acattttcg    34620 tacttgctgt agcagaacct ggtccggcg ctgcacaccg atcgccggcg cggtcccgg     34680 cgcttggaac gctcggtgtt gaagttgtaa acagccact ctctcagacc gtgcagcaga    34740
tctagggcct caggagtgat gaagatccca tcatgcctga tggctctaat cacatcgacc   34800
accgtggaat gggccagacc cagccagatg atgcaatttt gttgggtttc ggtgacggcg   34860
ggggagggaa gaacaggaag aaccatgatt aacttttaat ccaaacggtc tcggagcact   34920
tcaaaatgaa gatcgcggag atggcacctc tcgcccccgc tgtgttggtg gaaaataaca   34980
gccaggtcaa aggtgatacg gttctcgaga tgttccacgg tggcttccag caaagcctcc   35040
acgcgcacat ccagaaacaa gacaatagcg aaagcgggag ggttctctaa ttcctcaatc   35100
atcatgttac actcctgcac catccccaga taattttcat ttttccagcc ttgaatgatt   35160
cgaactagtt cctgaggtaa atccaagcca gccatgataa agagctcgcg cagagcgccc   35220
tccaccggca ttcttaagca caccctcata attccaagat attctgctcc tggttcacct   35280
gcagcagatt gacaagcgga atatcaaaat ctctgccgcg atccctaagc tcctccctca   35340
gcaataactg taagtactct ttcatatcct ctccgaaatt tttagccata ggaccaccag   35400
gaataagatt agggcaagcc acagtacaga taaaccgaag tcctcccag tgagcattgc     35460 caaatgcaag actgctataa gcatgctggc tagacccggt gatatcttcc agataactgg   35520
acagaaaatc gcccaggcaa tttttaagaa aatcaacaaa agaaaatcc tccaggtgca     35580 cgtttagagc ctcgggaaca acgatggagt aaatgcaagc ggtgcgttcc agcatggtta   35640
gttagctgat ctgtagaaaa aaacaaaaat gaacattaaa ccatgctagc ctggcgaaca   35700
ggtgggtaaa tcgttctctc cagcaccagg caggccacgg gtctccggc acgaccctcg    35760 taaaaattgt cgctatgatt gaaaccatc acagagagac gttcccggtg gccggcgtga    35820
atgattcgac aagatgaata cacccccgga acattggcgt ccgcgagtga aaaaagcgc    35880 ccaaggaagc aataaggcac tacaatgctc agtctcaagt ccagcaaagc gatgccatgc   35940
ggatgaagca caaattctc aggtgcgtac aaaatgtaat tactcccctc ctgcacaggc     36000
agcaaagccc ccgatccctc caggtacaca tacaaagcct cagcgtccat agcttaccga   36060
gcagcagcac acaacaggcg caagagtcag agaaaggctg agctctaacc tgtccacccg   36120
ctctctgctc aatatatagc ccagatctac actgacgtaa aggccaaagt ctaaaaatac   36180
ccgccaaata atcacacacg cccagcacac gcccagaaac cggtgacaca ctcaaaaaaa   36240
tacgcgcact tcctcaaacg cccaaactgc cgtcatttcc gggttcccac gctacgtcat   36300
caaaattcga cttcaaatt ccgtcgaccg ttaaaaacgt cgcccgcccc gcccctaacg     36360
```

```
gtcgccgctc ccgcagccaa tcaccgcccc gcatccccaa attcaaatac ctcatttgca    36420
tattaacgcg caccaaaagt ttgaggtata ttattgatga tg                        36462

<210> SEQ ID NO 2
<211> LENGTH: 36604
<212> TYPE: DNA
<213> ORGANISM: chimpanzee adenovirus serotype Pan6

<400> SEQUENCE: 2
catcatcaat aatatacctc aaacttttgg tgcgcgttaa tatgcaaatg agctgtttga      60
atttggggag ggaggaaggt gattggctgc gggagcggcg accgttaggg gcggggcggg     120
tgacgttttg atgacgtggc tatgaggcgg agccggtttg caagttctcg tgggaaaagt     180
gacgtcaaac gaggtgtggt ttgaacacgg aaatactcaa ttttcccgcg ctctctgaca     240
ggaaatgagg tgtttctggg cggatgcaag tgaaaacggg ccattttcgc gcgaaaactg     300
aatgaggaag tgaaaatctg agtaatttcg cgtttatggc agggaggagt atttgccgag     360
ggccgagtag actttgaccg attacgtggg gtttcgatt accgtatttt tcacctaaat      420
ttccgcgtac ggtgtcaaag tccggtgttt ttacgtaggc gtcagctgat cgccagggta     480
tttaaacctg cgctctctag tcaagaggcc actcttgagt gccagcgagt agagttttct     540
cctccgcgcc gcgagtcaga tctacacttt gaaagatgag gcacctgaga gacctgcccg     600
gtaatgtttt cctggctact gggaacgaga ttctggaatt ggtggtggac gccatgatgg     660
gtgacgaccc tccagagccc cctaccccat ttgaggcgcc ttcgctgtac gatttgtatg     720
atctggaggt ggatgtgccc gagagcgacc taacgaggga ggcggtgaat gatttgttta     780
gcgatgccgc gctgctggct gccgagcagg ctaatacgga ctctggctca gacagcgatt     840
cctctctcca tacccgagaa cccggcagag tgagaaaaaa gatccccgag cttaaagggg     900
aagagctcga cctgcgctgc tatgaggaat gcttgcctcc gagcgatgat gaggaggacg     960
aggaggcgat tcgagctgcg gtgaaccagg gagtgaaaac tgcgggcgag agctttagcc    1020
tggactgtcc tactctgccc ggacacggct gtaagtcttg tgaatttcat cgcatgaata    1080
ctggagataa gaatgtgatg tgtgccctgt gctatatgag agcttacaac cattgtgttt    1140
acagtaagtg tgattaactt tagttgggaa ggcagagggt gactgggtgc tgactggttt    1200
atttatgtat atgtttttttt atgtgtaggt cccgtctctg acgtagatga acccccact    1260 tcagagtgca tttcatcacc cccagaaatt ggcgaggaac cgcccgaaga tattattcat    1320
agaccagttg cagtgagagt caccgggcgg agagcagctg tggagagttt ggatgacttg    1380
ctacagggtg gggatgaacc tttggacttg tgtacccgga aacgcccag gcactaagtg     1440 ccacacatgt gtgtttactt aaggtgatgt cagtatttat agggtgtgga gtgcaataaa    1500
atccgtgttg actttaagtg cgtgttttat gactcagggg tggggactgt gggtatataa    1560
gcaggtgcag acctgtgtgg tcagttcaga gcaggactca tggagatctg gactgtcttg    1620
gaagactttc accagactag acagttgcta gagaactcat cggagggagt ctcttacctg    1680
tggagattct gcttcggtgg gcctctagct aagctagtct ataggccaa acaggattat      1740 aaggaacaat ttgaggatat tttgagagag tgtcctggta ttttttgactc tctcaacttg    1800 ggccatcagt ctcactttaa ccagagtatt ctgagagccc ttgacttttc tactcctggc    1860
agaactaccg ccgcggtagc cttttttgcc tttattcttg acaaatggag tcaagaaacc    1920
catttcagca gggattaccg tctggactgc ttagcagtag ctttgtggag aacatggagg    1980
```

```
tgccagcgcc tgaatgcaat ctccggctac ttgccagtac agccggtaga cacgctgagg    2040
atcctgagtc tccagtcacc ccaggaacac caacgccgcc agcagccgca gcaggagcag    2100
cagcaagagg aggaccgaga agagaaaccg agagccggtc tggaccctcc ggtggcggag    2160
gaggaggagt agctgacttg tttcccgagc tgcgccgggt gctgactagg tcttccagtg    2220
gacgggagag ggggattaag cgggagaggc atgaggagac tagccacaga actgaactga    2280
ctgtcagtct gatgagccgc aggcgcccag aatcggtgtg gtggcatgag gtgcagtcgc    2340
aggggataga tgaggtctcg gtgatgcatg agaaatattc cctagaacaa gtcaagactt    2400
gttggttgga gcccgaggat gattggggag tagccatcag gaattatgcc aagctggctc    2460
tgaagccaga caagaagtac aagattacca aactgattaa tatcagaaat tcctgctaca    2520
tttcagggaa tggggccgag gtggagatca gtacccagga gagggtggcc ttcagatgtt    2580
gtatgatgaa tatgtacccg ggggtggtgg gcatggaggg agtcaccttt atgaacacga    2640
ggttcagggg tgatgggtat aatggggtgg tctttatggc caacaccaag ctgacagtgc    2700
acggatgctc cttctttggc ttcaataaca tgtgcatcga ggcctggggc agtgtttcag    2760
tgaggggatg cagcttttca gccaactgga tggggtcgt gggcagaacc aagagcaagg    2820
tgtcagtgaa gaaatgcctg ttcgagaggt gccacctggg ggtgatgagc gagggcgaag    2880
ccaaagtcaa acactgcgcc tctaccgaga cgggctgctt tgtgctgatc aagggcaatg    2940
cccaagtcaa gcataacatg atctgtgggg cctcggatga gcgcggctac cagatgctga    3000
cctgcgccgg tgggaacagc catatgctgg ccaccgtgca tgtggcctcg cacccccgca    3060
agacatggcc cgagttcgag cacaacgtca tgacccgctg caatgtgcac ctgggctccc    3120
gccgaggcat gttcatgccc taccagtgca acatgcaatt tgtgaaggtg ctgctggagc    3180
ccgatgccat gtccagagtg agcctgacgg gggtgtttga catgaatgtg gagctgtgga    3240
aaattctgag atatgatgaa tccaagacca ggtgccgggc ctgcgaatgc ggaggcaagc    3300
acgccaggct tcagcccgtg tgtgtggagg tgacggagga cctgcgaccc gatcatttgg    3360
tgttgtcctg caacgggacg gagttcggct ccagcgggga agaatctgac tagagtgagt    3420
agtgtttggg gctgggtgtg agcctgcatg aggggcagaa tgactaaaat ctgtggtttt    3480
ctgtgtgttg cagcagcatg agcggaagcg cctcctttga gggaggggta ttcagccctt    3540
atctgacggg gcgtctcccc tcctgggcgg gagtgcgtca gaatgtgatg ggatccacgg    3600
tggacggccg gcccgtgcag cccgcgaact cttcaaccct gacctacgcg accctgagct    3660
cctcgtccgt ggacgcagct gccgccgcag ctgctgcttc cgccgccagc gccgtgcgcg    3720
gaatggccct gggcgccggc tactacagct ctctggtggc caactcgagt tccaccaata    3780
atcccgccag cctgaacgag gagaagctgc tgctgctgat ggcccagctc gaggccctga    3840
cccagcgcct gggcgagctg acccagcagg tggctcagct gcaggcggag acgcgggccg    3900
cggttgccac ggtgaaaaac aaataaaaaa tgaatcaata aataaacgga gacggttgtt    3960
gattttaaca cagagtcttg aatctttatt tgattttcg cgcgcggtag gccctggacc    4020
accggtctcg atcattgagc acccggtgga tcttttccag gacccggtag aggtgggctt    4080
ggatgttgag gtacatgggc atgagcccgt cccggggtg gaggtagctc cattgcaggg    4140
cctcgtgctc gggatggtg ttgtaaatca cccagtcata gcaggggcgc agggcgtggt    4200
gctgcacgat gtccttgagg aggagactga tggccacggg cagccccttg gtgtaggtgt    4260
tgacgaacct gttgagctgg gagggatgca tgcgggggga gatgagatgc atcttggcct    4320
ggatcttgag attggcgatg ttcccgccca gatcccgccg ggggttcatg ttgtgcagga    4380
```

```
ccaccagcac ggtgtatccg gtgcacttgg ggaatttgtc atgcaacttg gaagggaagg    4440
cgtgaaagaa tttggagacg cccttgtgac cgcccaggtt ttccatgcac tcatccatga    4500
tgatggcgat gggcccgtgg gcggcggcct gggcaaagac gtttcggggg tcggacacat    4560
cgtagttgtg gtcctgggtg agctcgtcat aggccatttt aatgaatttg gggcggaggg    4620
tgcccgactg ggggacgaag gtgccctcga tcccgggggc gtagttgccc tcgcagatct    4680
gcatctccca ggccttgagc tcggaggggg ggatcatgtc cacctgcggg gcgatgaaaa    4740
aaacggtttc cggggcgggg gagatgagct gggccgaaag caggttccgg agcagctggg    4800
acttgccgca accggtgggg ccgtagatga ccccgatgac cggctgcagg tggtagttga    4860
gggagagaca gctgccgtcc tcgcggagga gggggccac ctcgttcatc atctcgcgca     4920
catgcatgtt ctcgcgcacg agttccgcca ggaggcgctc gccccccagc gagaggagct    4980
cttgcagcga ggcgaagttt ttcagcggct tgagtccgtc ggccatgggc attttggaga    5040
gggtctgttg caagagttcc agacggtccc agagctcggt gatgtgctct agggcatctc    5100
gatccagcag acctcctcgt ttcgcgggtt ggggcgactg cgggagtagg caccaggcg     5160 atgggcgtcc agcgaggcca gggtccggtc cttccagggc cgcagggtcc gcgtcagcgt    5220
ggtctccgtc acggtgaagg ggtgcgcgcc gggctgggcg cttgcgaggg tgcgcttcag    5280
gctcatccgg ctggtcgaga accgctcccg gtcggcgccc tgcgcgtcgg ccaggtagca    5340
attgagcatg agttcgtagt tgagcgcctc ggccgcgtgg cccttggcgc ggagcttacc    5400 tttgaagtg tgtccgcaga cgggacagag gagggacttg agggcgtaga gcttgggggc     5460
gaggaagacg gactcggggg cgtaggcgtc cgccgcgcag ctggcgcaga cggtctcgca    5520
ctccacgagc caggtgaggt cggggcggtt ggggtcaaaa acgaggtttc ctccgtgctt    5580
tttgatgcgt ttcttacctc tggtctccat gagctcgtgt ccccgctggg tgacaaagag    5640
gctgtccgtg tccccgtaga ccgactttat gggccggtcc tcgagcgggg tgccgcggtc    5700
ctcgtcgtag aggaaccccg cccactccga gacgaaggcc cgggtccagg ccagcacgaa    5760
ggaggccacg tgggagggt agcggtcgtt gtccaccagc gggtccacct tctccagggt     5820
atgcaagcac atgtcccct cgtccacatc caggaaggtg attggcttgt aagtgtaggc      5880
cacgtgaccg ggggtcccgg ccggggggt ataaagggg gcgggcccct gctcgtcctc      5940
actgtcttcc ggatcgctgt ccaggagcgc cagctgttgg ggtaggtatt ccctctcgaa    6000
ggcgggcatg acctcggcac tcaggttgtc agtttctaga aacgaggagg atttgatatt    6060
gacggtgccg ttggagacgc cttttcatgag cccctcgtcc atttggtcag aaaagacgat    6120 cttttttgttg tcgagcttgg tggcgaagga gccgtagagg gcgttggaga gcagcttggc    6180
gatggagcgc atggtctggt tcttttcctt gtcggcgcgc tccttggcgg cgatgttgag    6240
ctgcacgtac tcgcgcgcca cgcacttcca ttcggggaag acggtggtga gctcgtcggg    6300
cacgattctg acccgccagc cgcggttgtg cagggtgatg aggtccacgc tggtggccac    6360
ctcgccgcgc aggggctcgt tggtccagca gaggcgcccg cccttgcgcg agcagaaggg    6420
gggcagcggg tccagcatga gctcgtcggg ggggtcggcg tccacggtga agatgccggg    6480
caggagctcg gggtcgaagt agctgatgca ggtgccagca ttgtccagcg ccgcttgcca    6540
gtcgcgcacg gccagcgcgc gctcgtaggg gctgaggggc gtgccccagg gcatgggtg     6600 cgtgagcgcg gaggcgtaca tgccgcagat gtcgtagacg tagagggct cctcgaggac     6660 gccgatgtag gtggggtagc agcgcccccc gcggatgctg gcgcgcacgt agtcgtacag    6720
```

```
ctcgtgcgag ggcgcgagga gccccgtgcc gaggttggag cgttgcggct tttcggcgcg    6780
gtagacgatc tggcggaaga tggcgtggga gttggaggag atggtgggcc tttgaaagat    6840
gttgaagtgg gcgtggggca ggccgaccga gtccctgatg aagtgggcgt aggagtcctg    6900
cagcttggcg acgagctcgg cggtgacgag gacgtccagg gcgcagtagt cgagggtctc    6960
ttggatgatg tcatacttga gctggccctt ctgcttccac agctcgcggt tgagaaggaa    7020
ctcttcgcgg tccttccagt actcttcgag ggggaacccg tcctgatcgg cacggtaaga    7080
gcccaccatg tagaactggt tgacggcctt gtaggcgcag cagcccttct ccacggggag    7140
ggcgtaagct tgcgcggcct tgcgcaggga ggtgtgggtg agggcgaagg tgtcgcgcac    7200
catgaccttg aggaactggt gcttgaagtc gaggtcgtcg cagccgccct gctcccagag    7260
ttggaagtcc gtgcgcttct tgtaggcggg gttaggcaaa gcgaaagtaa catcgttgaa    7320
gaggatcttg cccgcgcggg gcatgaagtt gcgagtgatg cggaaaggct ggggcacctc    7380
ggcccggttg ttgatgacct gggcggcgag gacgatctcg tcgaagccgt tgatgttgtg    7440
cccgacgatg tagagttcca cgaatcgcgg gcggcccttg acgtggggca gcttcttgag    7500
ctcgtcgtag gtgagctcgg cggggtcgct gagcccgtgc tgctcgaggg cccagtcggc    7560
gacgtggggg ttggcgctga ggaaggaagt ccagagatcc acggccaggg cggtctgcaa    7620
gcggtcccga tactgacgga actgttggcc cacggccatt ttttcggggg tgacgcagta    7680
gaaggtgcgg gggtcgccgt gccagcggtc ccacttgagc tggagggcga ggtcgtgggc    7740
gagctcgacg agcggcgggt ccccggagag tttcatgacc agcatgaagg ggacgagctg    7800
cttgccgaag gaccccatcc aggtgtaggt ttccacatcg taggtgagga agagcctttc    7860
ggtgcgagga tgcgagccga tggggaagaa ctggatctcc tgccaccagt tggaggaatg    7920
gctgttgatg tgatggaagt agaaatgccg acggcgcgcc gagcactcgt gcttgtgttt    7980
atacaagcgt ccgcagtgct cgcaacgctg cacgggatgc acgtgctgca cgagctgtac    8040
ctgggttcct ttggcgagga atttcagtgg gcagtggagc gctggcggct gcatctcgtg    8100
ctgtactacg tcttggccat cggcgtggcc atcgtctgcc tcgatggtgg tcatgctgac    8160
gagcccgcgc gggaggcagg tccagacctc ggctcggacg ggtcggagag cgaggacgag    8220
ggcgcgcagg ccggagctgt ccagggtcct gagacgctgc ggagtcaggt cagtgggcag    8280
cggcggcgcg cggttgactt gcaggagctt ttccagggcg cgcgggaggt ccagatggta    8340
cttgatctcc acggcgccgt tggtggctac gtccacggct tgcagggtgc cgtgcccctg    8400
gggcgccacc accgtgcccc gtttcttctt gggcgctgct tccatgtcgg tcagaagcgg    8460
cggcgaggac gcgcgccggg cggcagggdc ggctcggggc ccggaggcag gggcggcagg    8520
ggcacgtcgg cgccgcgcgc gggcaggttc tggtactgcg cccggagaag actggcgtga    8580
gcgacgacgc gacggttgac gtcctggatc tgacgcctct gggtgaaggc cacgggaccc    8640
gtgagtttga acctgaaaga gagttcgaca gaatcaatct cggtatcgtt gacggcggcc    8700
tgccgcagga tctcttgcac gtcgcccgag ttgtcctggt aggcgatctc ggtcatgaac    8760
tgctcgatct cctcctcctg aaggtctccg cggccgcgc gctcgacggt ggccgcgagg    8820
tcgttggaga tgcggcccat gagctgcgag aaggcgttca tgccggcctc gttccagacg    8880
cggctgtaga ccacgctcc gtcggggtcg cgcgcgcgca tgaccacctg gcgaggttg    8940 agctcgacgt ggcgcgtgaa gaccgcgtag ttgcagaggc gctggtagag gtagttgagc    9000
gtggtggcga tgtgctcggt gacgaagaag tacatgatcc agcggcggag cggcatctcg    9060
ctgacgtcgc ccagggcttc caagcgttcc atggcctcgt agaagtccac ggcgaagttg    9120
```

```
aaaaactggg agttgcgcgc cgagacggtc aactcctcct ccagaagacg gatgagctcg      9180
gcgatggtgg cgcgcacctc gcgctcgaag gccccggggg gctcctcttc catctcctcc      9240
tcttcctcct ccactaacat ctcttctact tcctcctcag gaggcggtgg cgggggaggg      9300
gccctgcgtc gccggcggcg cacgggcaga cggtcgatga agcgctcgat ggtctccccg      9360
cgccggcgac gcatggtctc ggtgacggcg cgcccgtcct cgcggggccg cagcatgaag      9420
acgccgccgc gcatctccag gtggccgccg gggggtctc cgttgggcag ggagagggcg       9480
ctgacgatga tcttatcaa ttgacccgta gggactccgc gcaaggacct gagcgtctcg       9540
agatccacgg gatccgaaaa ccgctgaacg aaggcttcga gccagtcgca gtcgcaaggt      9600
aggctgagcc cggtttcttg ttcttcgggt atttggtcgg gaggcgggcg ggcgatgctg      9660
ctggtgatga agttgaagta ggcggtcctg agacggcgga tggtggcgag gagcaccagg      9720
tccttgggcc cggcttgctg gatgcgcaga cggtcggcca tgccccaggc gtggtcctga      9780
cacctggcga ggtccttgta gtagtcctgc atgagccgct ccacgggcac ctcctcctcg      9840
cccgcgcggc cgtgcatgcg cgtgagcccg aacccgcgct gcggctggac gagcgccagg      9900
tcggcgacga cgcgctcggt gaggatggcc tgctggatct gggtgagggt ggtctggaag      9960
tcgtcgaagt cgacgaagcg gtggtaggct ccggtgttga tggtgtagga gcagttggcc      10020
atgacggacc agttgacggt ctggtggccg ggtcgcacga gctcgtggta cttgaggcgc      10080
gagtaggcgc gcgtgtcgaa gatgtagtcg ttgcaggcgc gcacgaggta ctggtatccg      10140
acgaggaagt gcggcggcgg ctggcggtag agcggccatc gctcggtggc gggggcgccg      10200
ggcgcgaggt cctcgagcat gaggcggtgg tagccgtaga tgtacctgga catccaggtg      10260
atgccggcgg cggtggtgga ggcgcgcggg aactcgcgga cgcggttcca gatgttgcgc      10320
agcggcagga agtagttcat ggtggccgcg gtctggcccg tgaggcgcgc gcagtcgtgg      10380
atgctctaga catacgggca aaaacgaaag cggtcagcgg ctcgactccg tggcctggag      10440
gctaagcgaa cgggttgggc tgcgcgtgta ccccggttcg aatctcgaat caggctggag      10500
ccgcagctaa cgtggtactg gcactcccgt ctcgacccaa gcctgctaac gaaacctcca      10560
ggatacggag gcgggtcgtt ttttggcctt ggtcgctggt catgaaaaac tagtaagcgc      10620
ggaaagcggc cgcccgcgat ggctcgctgc cgtagtctgg agaaagaatc gccagggttg      10680
cgttgcggtg tgccccggtt cgagcctcag cgctcggcgc cggccggatt ccgcggctaa      10740
cgtgggcgtg gctgccccgt cgtttccaag accccttagc cagccgactt ctccagttac      10800
ggagcgagcc cctctttttt tttcttgtgt ttttgccaga tgcatcccgt actgcggcag      10860
atgcgccccc accctccacc acaaccgccc taccgcagc agcagcaaca gccggcgctt       10920
ctgcccccgc cccagcagca gccagccact accgcggcgg ccgccgtgag cggagccggc      10980
gttcagtatg acctggcctt ggaagagggc gaggggctgg cgcggctggg ggcgtcgtcg      11040
ccggagcggc acccgcgcgt gcagatgaaa agggacgctc gcgaggccta cgtgcccaag      11100
cagaacctgt tcagagacag gagcggcgag gagcccgagg agatgcgcgc ctcccgcttc      11160
cacgcggggc gggagctgcg gcgcggcctg gaccgaaagc gggtgctgag ggacgaggat      11220
ttcgaggcgg acgagctgac ggggatcagc cccgcgcgcg cgcacgtggc cgcggccaac      11280
ctggtcacgg cgtacgagca gaccgtgaag gaggagagca acttccaaaa atccttcaac      11340
aaccacgtgc gcacgctgat cgcgcgcgag gaggtgaccc tgggcctgat gcacctgtgg      11400
gacctgctgg aggccatcgt gcagaacccc acgagcaagc cgctgacggc gcagctgttt      11460
```

```
ctggtggtgc agcacagtcg ggacaacgag acgttcaggg aggcgctgct gaatatcacc    11520
gagcccgagg gccgctggct cctggacctg gtgaacattt tgcagagcat cgtggtgcag    11580
gagcgcgggc tgccgctgtc cgagaagctg gcggccatca acttctcggt gctgagtctg    11640
ggcaagtact acgctaggaa gatctacaag accccgtacg tgcccataga caaggaggtg    11700
aagatcgacg ggttttacat gcgcatgacc ctgaaagtgc tgaccctgag cgacgatctg    11760
ggggtgtacc gcaacgacag gatgcaccgc gcggtgagcg ccagccgccg gcgcgagctg    11820
agcgaccagg agctgatgca cagcctgcag cgggccctga ccggggccgg gaccgagggg    11880
gagagctact ttgacatggg cgcggacctg cgctggcagc ccagccgccg ggccttggaa    11940
gctgccggcg gttcccccta cgtggaggag gtggacgatg aggaggagga gggcgagtac    12000
ctggaagact gatggcgcga ccgtattttt gctagatgca gcaacagcca ccgccgccgc    12060
ctcctgatcc cgcgatgcgg gcggcgctgc agagccagcc gtccggcatt aactcctcgg    12120
acgattggac ccaggccatg caacgcatca tggcgctgac gacccgcaat cccgaagcct    12180
ttagacagca gcctcaggcc aaccggctct cggccatcct ggaggccgtg gtgccctcgc    12240
gctcgaaccc cacgcacgag aaggtgctgg ccatcgtgaa cgcgctggtg gagaacaagg    12300
ccatccgcgg tgacgaggcc gggctggtgt acaacgcgct gctggagcgc gtggcccgct    12360
acaacagcac caacgtgcag acgaacctgg accgcatggt gaccgacgtg cgcgaggcgg    12420
tgtcgcagcg cgagcggttc caccgcgagt cgaacctggg ctccatggtg gcgctgaacg    12480
ccttcctgag cacgcagccc gccaacgtgc ccgggggcca ggaggactac accaacttca    12540
tcagcgcgct gcggctgatg gtggccgagg tgccccagag cgaggtgtac cagtcggggc    12600
cggactactt cttccagacc agtcgccagg gcttgcagac cgtgaacctg agccaggctt    12660
tcaagaactt gcagggactg tggggcgtgc aggccccggt cggggaccgc gcgacggtgt    12720
cgagcctgct gacgccgaac tcgcgcctgc tgctgctgct ggtggcgccc ttcacggaca    12780
gcggcagcgt gagccgcgac tcgtacctgg gctacctgct taacctgtac cgcgaggcca    12840
tcggacaggc gcacgtggac gagcagacct accaggagat cacccacgtg agccgcgcgc    12900
tgggccagga ggacccgggc aacctggagg ccaccctgaa cttcctgctg accaaccggt    12960
cgcagaagat cccgcccag tacgcgctga gcaccgagga ggagcgcatc ctgcgctacg    13020
tgcagcagag cgtggggctg ttcctgatgc aggaggggc cacgcccagc gcggcgctcg    13080
acatgaccgc gcgcaacatg gagcccagca tgtacgcccg caaccgcccg ttcatcaata    13140
agctgatgga ctacttgcat cgggcggccg ccatgaactc ggactacttt accaacgcca    13200
tcttgaaccc gcactggctc ccgccgcccg ggttctacac gggcgagtac gacatgcccg    13260
accccaacga cgggttcctg tgggacacg tggacagcag cgtgttctcg ccgcgtccag    13320
gaaccaatgc cgtgtggaag aaagagggcg gggaccggcg gccgtcctcg gcgctgtccg    13380
gtcgcgcggg tgctgccgcg gcggtgccccg aggccgccag cccccttccccg agcctgccct    13440 tttcgctgaa cagcgtgcgc agcagcgagc tgggtcggct gacgcgaccg cgcctgctgg    13500
gcgaggagga gtacctgaac gactccttgt tgagggccga gcgcgagaag aacttcccca    13560
ataacgggat agagagcctg gtggacaaga tgagccgctg gaagacgtac gcgcacgagc    13620
acagggacga gccccgagct agcagcgcag gcacccgtag acgccagcgg cacgacaggc    13680
agcggggact ggtgtgggac gatgaggatt ccgccgacga cagcagcgtg ttggacttgg    13740
gtgggagtgg tggtaacccg ttcgctcacc tgcgcccccg tatcgggcgc ctgatgtaag    13800
aatctgaaaa aataaaagac ggtactcacc aaggccatgg cgaccagcgt gcgttcttct    13860
```

```
ctgttgtttg tagtagtatg atgaggcgcg tgtacccgga gggtcctcct ccctcgtacg   13920
agagcgtgat gcagcaggcg gtggcggcgg cgatgcagcc cccgctggag gcgccttacg   13980 tgccccgcg  gtacctggcg cctacggagg ggcggaacag cattcgttac tcggagctgg   14040 caccttgta  cgataccacc cggttgtacc tggtggacaa caagtcggca gacatcgcct   14100
cgctgaacta ccagaacgac cacagcaact tcctgaccac cgtggtgcag aacaacgatt   14160 tcaccccac  ggaggccagc acccagacca tcaactttga cgagcgctcg cggtggggcg   14220
gccagctgaa aaccatcatg cacaccaaca tgcccaacgt gaacgagttc atgtacagca   14280
acaagttcaa ggcgcgggtg atggtctcgc gcaagacccc caacggggtg gatgatgatt   14340
atgatggtag tcaggacgag ctgacctacg agtgggtgga gtttgagctg cccgagggca   14400
acttctcggt gaccatgacc atcgatctga tgaacaacgc catcatcgac aactacttgg   14460
cggtggggcg gcagaacggg gtgctggaga gcgacatcgg cgtgaagttc gacacgcgca   14520
acttccggct gggctgggac cccgtgaccg agctggtgat gccgggcgtg tacaccaacg   14580
aggccttcca ccccgacatc gtcctgctgc ccggctgcgg cgtggacttc accgagagcc   14640
gcctcagcaa cctgctgggc atccgcaagc ggcagcccct tccaggagggc ttccagatcc   14700 tgtacgagga cctggagggg ggcaacatcc ccgcgctctt ggatgtcgaa gcctacgaga   14760
aaagcaagga ggatagcacc gccgcggcga ccgcagccgt ggccaccgcc tctaccgagg   14820
tgcggggcga taattttgct agcgctgcgg cagcggccga ggcggctgaa accgaaagta   14880
agatagtcat ccagccggtg gagaaggaca gcaaggacag gagctacaac gtgctcgcgg   14940
acaagaaaaa caccgcctac cgcagctggt acctggccta caactacggc gaccccgaga   15000
agggcgtgcg ctcctggacg ctgctcacca cctcggacgt cacctgcggc gtggagcaag   15060
tctactggtc gctgcccgac atgatgcaag acccggtcac cttccgctcc acgcgtcaag   15120
ttagcaacta cccggtggtg ggcgccgagc tcctgcccgt ctactccaag agcttcttca   15180
acgagcaggc cgtctactcg cagcagctgc gcgccttcac ctcgctcacg cacgtcttca   15240
accgcttccc cgagaaccag atcctcgtcc gcccgccccgc gcccaccatt accaccgtca   15300
gtgaaaacgt tcctgctctc acagatcacg ggaccctgcc gctgcgcagc agtatccggg   15360
gagtccagcg cgtgaccgtc actgacgcca gacgccgcac ctgcccctac gtctacaagg   15420
ccctgggcgt agtcgcgccg cgcgtcctct cgagccgcac cttctaaaaa atgtccattc   15480
tcatctcgcc cagtaataac accggttggg gcctgcgcgc gcccagcaag atgtacgag   15540 gcgctcgcca acgctccacg caacaccccg tgcgcgtgcg cggcacttc  cgcgctccct   15600 ggggcgccct caagggccgc gtgcgctcgc gcaccaccgt cgacgacgtg atcgaccagg   15660
tggtggccga cgcgcgcaac tacacgcccg ccgccgcgcc cgtctccacc gtggacgccg   15720
tcatcgacag cgtggtggcc gacgcgcgcc ggtacgcccg caccaagagc cggcggcggc   15780
gcatcgcccg gcggcaccgg agcacccccg ccatgcgcgc ggcgcgagcc ttgctgcgca   15840
gggccaggcg cacgggacgc agggccatgc tcagggcggc cagacgcgcg gcctccggca   15900
gcagcagcgc cggcaggacc cgcagacgcg cggccacggc ggcggcggcg ccatcgcca   15960 gcatgtcccg cccgcggcgc ggcaacgtgt actgggtgcg cgacgccgcc accggtgtgc   16020
gcgtgcccgt gcgcacccgc cccctcgca  cttgaagatg ctgacttcgc gatgttgatg   16080
tgtcccagcg gcgaggagga tgtccaagcg caaatacaag gaagagatgc tccaggtcat   16140
cgcgcctgag atctacggcc ccgcggcggc ggtgaaggag gaaagaaagc cccgcaaact   16200
```

```
gaagcgggtc aaaaaggaca aaaaggagga ggaagatgac ggactggtgg agtttgtgcg   16260
cgagttcgcc ccccggcggc gcgtgcagtg gcgcgggcgg aaagtgaaac cggtgctgcg   16320
gcccggcacc acggtggtct tcacgcccgg cgagcgttcc ggctccgcct ccaagcgctc   16380
ctacgacgag gtgtacgggg acgaggacat cctcgagcag gcggtcgagc gtctgggcga   16440
gtttgcgtac ggcaagcgca gccgcccgc gcccttgaaa gaggaggcgg tgtccatccc   16500
gctggaccac ggcaacccca cgccgagcct gaagccggtg accctgcagc aggtgctacc   16560
gagcgcggcg ccgcgccggg gcttcaagcg cgagggcggc gaggatctgt acccgaccat   16620
gcagctgatg gtgcccaagc gccagaagct ggaggacgtg ctggagcaca tgaaggtgga   16680
ccccgaggtg cagcccgagg tcaaggtgcg gcccatcaag caggtggccc cgggcctggg   16740
cgtgcagacc gtggacatca agatccccac ggagcccatg gaaacgcaga ccgagcccgt   16800
gaagcccagc accagcacca tggaggtgca gacggatccc tggatgccag caccagcttc   16860
caccagcact cgccgaagac gcaagtacgg cgcggccagc ctgctgatgc caactacgc   16920
gctgcatcct tccatcatcc ccacgccggg ctaccgcggc acgcgcttct accgcggcta   16980
caccagcagc cgccgccgca agaccaccac ccgccgccgt cgtcgcagcc gccgcagcag   17040
caccgcgact tccgccttgg tgcggagagt gtatcgcagc gggcgcgagc ctctgaccct   17100
gccgcgcgcg cgctaccacc cgagcatcgc catttaacta ccgcctccta cttgcagata   17160
tggccctcac atgccgcctc cgcgtcccca ttacgggcta ccgaggaaga aagccgcgcc   17220
gtagaaggct gacggggaac gggctgcgtc gccatcacca ccggcggcgg cgcgccatca   17280
gcaagcggtt gggggggaggc ttcctgcccg cgctgatccc catcatcgcc gcggcgatcg   17340
gggcgatccc cggcatagct tccgtggcgg tgcaggcctc tcagcgccac tgagacacaa   17400
aaaagcatgg atttgtaata aaaaaaaaaa tggactgacg ctcctggtcc tgtgatgtgt   17460
gtttttagat ggaagacatc aattttttcgt ccctggcacc gcgacacggc acgcggccgt   17520
ttatgggcac ctggagcgac atcggcaaca gccaactgaa cggggcgcc ttcaattgga   17580
gcagtctctg gagcgggctt aagaatttcg ggtccacgct caaaacctat ggcaacaagg   17640
cgtggaacag cagcacaggg caggcgctga gggaaaagct gaaagaacag aacttccagc   17700
agaaggtggt tgatggcctg gcctcaggca tcaacgggt ggttgacctg gccaaccagg   17760
ccgtgcagaa acagatcaac agccgcctgg acgcggtccc gcccgcgggg tccgtggaga   17820
tgccccaggt ggaggaggag ctgcctcccc tggacaagcg cggcgacaag cgaccgcgtc   17880
ccgacgcgga ggagacgctg ctgacgcaca cggacgagcc gccccgtac gaggaggcgg   17940
tgaaactggg cctgcccacc acgcggcccg tggcgcctct ggccaccgga gtgctgaaac   18000
ccagcagcag ccagcccgcg accctggact tgcctccgcc tcgcccctcc acagtggcta   18060
agcccctgcc gccggtggcc gtcgcgtcgc gcgccccccg aggccgcccc caggcgaact   18120
ggcagagcac tctgaacagc atcgtgggtc tgggagtgca gagtgtgaag cgccgccgct   18180
gctattaaaa gacactgtag cgcttaactt gcttgtctgt gtgtatatgt atgtccgccg   18240
accagaagga ggagtgtgaa gaggcgcgtc gccgagttgc aagatggcca ccccatcgat   18300
gctgccccag tgggcgtaca tgcacatcgc cggacaggac gcttcggagt acctgagtcc   18360
gggtctggtg cagttcgccc gcgccacaga cacctacttc agtctgggga caagtttag   18420
gaaccccacg gtggcgccca cgcacgatgt gaccaccgac cgcagccagc ggctgacgct   18480
gcgcttcgtg cccgtggacc gcgaggacaa cacctactcg tacaaagtgc gctacacgct   18540
ggccgtgggc gacaaccgcg tgctggacat ggccagcacc tactttgaca tccgcggcgt   18600
```

```
gctggaccgg ggccctagct tcaaacccta ctctggcacc gcctacaaca gcctagctcc   18660
caagggagct cccaattcca gccagtggga gcaagcaaaa acaggcaatg ggggaactat   18720
ggaaacacac acatatggtg tggccccaat gggcggagag aatattacaa aagatggtct   18780
tcaaattgga actgacgtta cagcgaatca gaataaacca atttatgccg acaaaacatt   18840
tcaaccagaa ccgcaagtag gagaagaaaa ttggcaagaa actgaaaact tttatggcgg   18900
tagagctctt aaaaaagaca caaacatgaa accttgctat ggctcctatg ctagacccac   18960
caatgaaaaa ggaggtcaag ctaaacttaa agttggagat gatggagttc aaccaaaga   19020 attcgacata gacctggctt tctttgatac tcccggtggc accgtgaacg gtcaagacga   19080
gtataaagca gacattgtca tgtataccga aaacacgtat ttggaaactc cagacacgca   19140
tgtggtatac aaaccaggca aggatgatgc aagttctgaa attaacctgg ttcagcagtc   19200
tatgcccaac agacccaact acattgggtt cagggacaac tttatcggtc ttatgtacta   19260
caacagcact ggcaatatgg gtgtgcttgc tggtcaggcc tcccagctga atgctgtggt   19320
tgatttgcaa gacagaaaca ccgagctgtc ctaccagctc ttgcttgact cttgggtga   19380 cagaacccgg tatttcagta tgtggaacca ggcggtggac agttatgacc ccgatgtgcg   19440
catcatcgaa aaccatggtg tggaggatga attgccaaac tattgcttcc ccttggacgg   19500
ctctggcact aacgccgcat accaaggtgt gaaagtaaaa gatggtcaag atggtgatgt   19560
tgagagtgaa tgggaaaatg acgatactgt tgcagctcga aatcaattat gtaaaggtaa   19620
cattttcgcc atggagatta atctccaggc taacctgtgg agaagttttcc tctactcgaa   19680 cgtggccctg tacctgcccg actcctacaa gtacacgccg accaacgtca cgctgccgac   19740
caacaccaac acctacgatt acatgaatgg cagagtgaca cctccctcgc tggtagacgc   19800
ctacctcaac atcggggcgc gctggtcgct ggaccccatg gacaacgtca ccccctcaa   19860 ccaccaccgc aacgcgggcc tgcgctaccg ctccatgctc ctgggcaacg ggcgctacgt   19920
gcccttccac atccaggtgc cccaaaagtt tttcgccatc aagagcctcc tgctcctgcc   19980
cgggtcctac acctacagtg ggaacttccg caaggacgtc aacatgatcc tgcagagctc   20040
cctaggcaac gacctgcgca cggacggggc ctccatcgcc ttcaccagca tcaacctcta   20100
cgccaccttc ttccccatgg cgcacaacac cgcctccacg ctcgaggcca tgctgcgcaa   20160
cgacaccaac gaccagtcct tcaacgacta cctctcggcg ccaacatgc tctaccccat   20220 cccgccaac gccaccaacg tgcccatctc catcccctcg cgcaactggg ccgccttccg   20280
cggatggtcc ttcacgcgcc tgaagacccg cgagacgccc tcgctcggct ccgggttcga   20340 ccctacttc gtctactcgg gctccatccc ctacctagac ggcaccttct acctcaacca   20400
caccttcaag aaggtctcca tcaccttcga ctcctccgtc agctggcccg gcaacgaccg   20460
cctcctgacg cccaacgagt tcgaaatcaa gcgcaccgtc gacggagagg gatacaacgt   20520
ggcccagtgc aacatgacca aggactggtt cctggtccag atgctggccc actacaacat   20580
cggctaccag ggcttctacg tgcccgaggg ctacaaggac cgcatgtact ccttcttccg   20640
caacttccag cccatgagcc gccaggtcgt ggacgaggtc aactacaagg actaccaggc   20700 cgtcacctg gcctaccagc acaacaactc gggcttcgtc ggctacctcg cgcccaccat   20760
gcgccagggc cagccctacc ccgccaacta cccctacccg ctcatcggca gagcgccgt   20820 cgccagcgtc acccagaaaa agttcctctg cgaccgggtc atgtggcgca tccccttctc   20880
cagcaacttc atgtccatgg gcgcgctcac cgacctcggc cagaacatgc tctacgccaa   20940
```

```
ctccgcccac gcgctagaca tgaatttcga agtcgacccc atggatgagt ccacccttct   21000
ctatgttgtc ttcgaagtct tcgacgtcgt ccgagtgcac cagccccacc gcggcgtcat   21060
cgaagccgtc tacctgcgca cgcccttctc ggccggcaac gccaccacct aagccgctct   21120
tgcttcttgc aagatgacgg cgggctccgg cgagcaggag ctcagggcca tcctccgcga   21180
cctgggctgc gggccctgct tcctgggcac cttcgacaag cgcttccctg gattcatggc   21240
cccgcacaag ctggcctgcg ccatcgtgaa cacggcggc cgcgagaccg ggggcgagca   21300
ctggctggcc ttcgcctgga acccgcgctc ccacacatgc tacctcttcg acccccttcgg   21360 gttctcggac gagcgcctca agcagatcta ccagttcgag tacgagggcc tgctgcgtcg   21420
cagcgccctg gccaccgagg accgctgcgt caccctggaa aagtccaccc agaccgtgca   21480
gggtccgcgc tcggccgcct gcgggctctt ctgctgcatg ttcctgcacg ccttcgtgca   21540
ctggcccgac cgccccatgg acaagaaccc caccatgaac ttactgacgg gggtgcccaa   21600
cggcatgctc cagtcgcccc aggtggaacc caccctgcgc cgcaaccagg aagcgctcta   21660
ccgcttcctc aatgcccact ccgcctactt tcgctcccac cgcgcgcgca tcgagaaggc   21720
caccgccttc gaccgcatga atcaagacat gtaaaaaacc ggtgtgtgta tgtgaatgct   21780
ttattcataa taaacagcac atgtttatgc caccttctct gaggctctga ctttatttag   21840
aaatcgaagg ggttctgccg gctctcggca tggcccgcgg gcagggatac gttgcggaac   21900
tggtacttgg gcagccactt gaactcgggg atcagcagct tgggcacggg gaggtcgggg   21960
aacgagtcgc tccacagctt gcgcgtgagt tgcaggcgc ccagcaggtc gggcgcggag   22020
atcttgaaat cgcagttggg acccgcgttc tgcgcgcgag agttgcggta cacggggttg   22080
cagcactgga acaccatcag ggccgggtgc ttcacgcttg ccagcaccgt cgcgtcggtg   22140
atgccctcca cgtccagatc ctcggcgttg gccatcccga agggggtcat cttgcaggtc   22200
tgccgcccca tgctgggcac gcagccgggc ttgtggttgc aatcgcagtg caggggatc   22260 agcatcatct gggcctgctc ggagctcatg cccgggtaca tggccttcat gaaagcctcc   22320
agctggcgga aggcctgctg cgccttgccg ccctcggtga agaagccccc gcaggacttg   22380
ctagagaact ggttggtggc gcagccggcg tcgtgcacgc agcagcgcgc gtcgttgttg   22440
gccagctgca ccacgctgcg cccccagcgg ttctgggtga tcttggcccg ttgggggttc   22500
tccttcagcg cgcgctgccc gttctcgctc gccacatcca tctcgatagt gtgctccttc   22560
tggatcatca cggtcccgtg caggcaccgc agcttgccct cggcttcggt gcagccgtgc   22620
agccacagcg cgcagccggt gcactcccag ttcttgtggg cgatctggga gtgcgagtgc   22680
acgaagccct gcaggaagcg gcccatcatc gcggtcaggg tcttgttgct ggtgaaggtc   22740
agcgggatgc cgcggtgctc ctcgttcaca tacaggtggc agatgcggcg gtacacctcg   22800
ccctgctcgg gcatcagctg gaaggcggac ttcaggtcgc tctccacgcg gtaccggtcc   22860
atcagcagcg tcatcacttc catgcccttc tcccaggccg aaacgatcgg caggctcagg   22920
gggttcttca ccgccattgt catcttagtc gccgccgccg aggtcagggg gtcgttctcg   22980
tccagggtct caaacactcg cttgccgtcc ttctcgatga tgcgcacggg gggaaagctg   23040
aagcccacgg ccgccagctc ctcctcggcc tgcctttcgt cctcgctgtc ctggctgatg   23100
tcttgcaaag gcacatgctt ggtcttgcgg ggtttctttt tgggcggcag aggcggcggc   23160
gatgtgctgg gagagcgcga gttctcgttc accacgacta tttcttcttc ttggccgtcg   23220
tccgagacca cgcggcggta ggcatgcctc ttctggggca gaggcggagg cgacgggctc   23280
tcgcggttcg gcgggcggct ggcagagccc cttccgcgtt cggggtgcg ctcctggcgg   23340
```

```
cgctgctctg actgacttcc tccgcggccg gccattgtgt tctcctaggg agcaacaaca    23400
agcatggaga ctcagccatc gtcgccaaca tcgccatctg cccccgccgc caccgccgac    23460
gagaaccagc agcagaatga aagcttaacc gccccgccgc ccagccccac ctccgacgcc    23520
gcggccccag acatgcaaga gatggaggaa tccatcgaga ttgacctggg ctacgtgacg    23580
cccgcggagc acgaggagga gctggcagcg cgcttttcag ccccggaaga gaaccaccaa    23640
gagcagccag agcaggaagc agagaacgag cagaaccagg ctgggcacga gcatggcgac    23700
tacctgagcg gggcagagga cgtgctcatc aagcatctgg cccgccaatg catcatcgtc    23760
aaggacgcgc tgctcgaccg cgccgaggtg cccctcagcg tggcggagct cagccgcgcc    23820
tacgagcgca acctcttctc gccgcgcgtg ccccccaagc gccagcccaa cggcacctgt    23880
gagcccaacc cgcgcctcaa cttctacccg gtcttcgcgg tgcccgaggc cctggccacc    23940
taccacctct ttttcaagaa ccaaaggatc ccgtctcct gccgcgccaa ccgcacccgc    24000
gccgacgccc tgctcaacct gggccccggc gccgcctac ctgatatcac ctccttggaa    24060
gaggttccca agatcttcga gggtctgggc agcgacgaga ctcggccgc gaacgctctg    24120 caaggaagcg gagaggagca tgagcaccac agcgccctgg tggagttgga aggcgacaac    24180
gcgcgcctgg cggtcctcaa gcgcacggtc gagctgaccc acttcgccta cccggcgctc    24240
aacctgcccc ccaaggtcat gagcgccgtc atggaccagt gctcatcaa gcgcgcctcg    24300 cccctctcgg aggaggagat gcaggacccc gagagttcgg acgagggcaa gcccgtggtc    24360
agcgacgagc agctggcgcg ctggctggga gcgagtagca ccccccagag cctggaagag    24420
cggcgcaagc tcatgatggc cgtggtcctg gtgaccgtgg agctggagtg tctgcgccgc    24480
ttctttgccg acgcggagac cctgcgcaag gtcgaggaga acctgcacta cctcttcagg    24540
cacgggttcg tgcgccaggc ctgcaagatc tccaacgtgg agctgaccaa cctggtctcc    24600
tacatgggca tcctgcacga gaaccgcctg ggcaaaaacg tgctgcacac cacccctgcgc    24660 ggggaggccc gccgcgacta catccgcgac tgcgtctacc tgtacctctg ccacacctgg    24720
cagacgggca tgggcgtgtg gcagcagtgc ctggaggagc agaacctgaa agagctctgc    24780
aagctcctgc agaagaacct caaggccctg tggaccgggt tcgacagcg taccaccgcc    24840 tcggacctgg ccgacctcat cttccccgag cgcctgcggc tgacgctgcg caacgggctg    24900 cccgactta tgagccaaag catgttgcaa aactttcgct ctttcatcct cgaacgctcc    24960
gggatcctgc ccgccacctg ctccgcgctg ccctcggact tcgtgccgct gaccttccgc    25020
gagtgccccc cgccgctctg gagccactgc tacttgctgc gcctggccaa ctacctggcc    25080
taccactcgg acgtgatcga ggacgtcagc ggcgagggtc tgctggagtg ccactgccgc    25140
tgcaacctct gcacgccgca ccgctccctg gcctgcaacc ccagctgct gagcgagacc    25200 cagatcatcg gcaccttcga gttgcaaggc cccggcgacg cgcagggcaa ggggggtctg    25260
aaactcaccc cgggggctgtg gacctcggcc tacttgcgca gttcgtgcc cgaggactac    25320 catcccttcg agatcaggtt ctacgaggac caatcccagc cgcccaaggc cgagctgtcg    25380
gcctgcgtca tcacccaggg ggccatcctg gcccaattgc aagccatcca gaaatcccgc    25440
caagaatttc tgctgaaaaa gggccacggg gtctacttgg acccccagac cggagaggag    25500 ctcaaccca gcttcccca ggatgccccg aggaagcagc aagaagctga aagtggagct    25560
gccgccgccg gaggatttgg aggaagactg gagagcagt caggcagagg aggaggagat    25620
ggaagactgg gacagcactc aggcagagga ggacagcctg caagacagtc tggaggagga    25680
```

```
agacgaggtg gaggaggcag aggaagaagc agccgccgcc agaccgtcgt cctcggcgga   25740
gaaagcaagc agcacggata ccatctccgc tccgggtcgg ggtcgcggcg gccgggccca   25800
cagtaggtgg gacgagaccg ggcgcttccc gaacccacc  acccagaccg gtaagaagga   25860
gcggcaggga tacaagtcct ggcggggca  caaaaacgcc atcgtctcct gcttgcaagc   25920
ctgcggggc  aacatctcct tcacccggcg ctacctgctc ttccaccgcg gggtgaactt   25980
ccccccgcaac atcttgcatt actaccgtca cctccacagc ccctactact gtttccaaga  26040
agaggcagaa acccagcagc agcagaaaac cagcggcagc agcagctaga aaatccacag   26100
cggcggcagg tggactgagg atcgcggcga acgagccggc gcagaccggg agctgagga   26160
accggatctt tcccaccctc tatgccatct tccagcagag tcggggcag  gagcaggaac   26220
tgaaagtcaa gaaccgttct ctgcgctcgc tcacccgcag ttgtctgtat cacaagagcg   26280
aagaccaact tcagcgcact ctcgaggacg ccgaggctct cttcaacaag tactgcgcgc   26340
tcactcttaa agagtagccc gcgcccgccc acacacggaa aaaggcggga attacgtcac   26400
cacctgcgcc cttcgcccga ccatcatgag caaagagatt cccacgcctt acatgtggag   26460
ctaccagccc cagatgggcc tggccgccgg cgccgcccag gactactcca cccgcatgaa   26520
ctggctcagt gccgggcccg cgatgatctc acgggtgaat gacatccgcg cccaccgaaa   26580
ccagatactc ctagaacagt cagcgatcac cgccacgccc cgccatcacc ttaatccgcg   26640
taattggccc gccgccctgg tgtaccagga aattccccag cccacgaccg tactacttcc   26700
gcgagacgcc caggccgaag tccagctgac taactcaggt gtccagctgg ccggcggcgc   26760
cgccctgtgt cgtcaccgcc ccgctcaggg tataaagcgg ctggtgatcc gaggcagagg   26820
cacacagctc aacgacgagg tggtgagctc ttcgctgggt ctgcgacctg acggagtctt   26880
ccaactcgcc ggatcgggga gatcttcctt cacgcctcgt caggccgtcc tgactttgga   26940
gagttcgtcc tcgcagcccc gctcgggcgg catcggcact ctccagttcg tggaggagtt   27000
cactccctcg gtctacttca acccttctc  cggctccccc ggccactacc cggacgagtt   27060
catcccgaac ttcgacgcca tcagcgagtc ggtggacggc tacgattgaa tgtcccatgg   27120
tggcgcagct gacctagctc ggcttcgaca cctggaccac tgccgccgct tccgctgctt   27180
cgctcgggat ctcgccgagt ttgcctactt tgagctgccc gaggagcacc ctcagggccc   27240
agcccacgga gtgcggatca tcgtcgaagg gggcctcgac tcccacctgc ttcggatctt   27300
cagccagcga ccgatcctgg tcgagcgcga acaaggacag accttctta  ctttgtactg   27360
catctgcaac caccccggcc tgcatgaaag tctttgttgt ctgctgtgta ctgagtataa   27420
taaaagctga gatcagcgac tactccggac tcgattgtgg tgttcctgct atcaaccggt   27480
ccctgttctt caccggggaac gagaccgagc tccagctcca gtgtaagccc cacaagaagt   27540
acctcacctg gctgttccag ggctccccga tcgccgttgt caaccactgc gacaacgacg   27600
gagtcctgct gagcggccct gccaaccctta ctttttccac ccgcagaagc aagctccagc   27660
tcttccaacc cttcctcccc gggacctatc agtgcgtctc aggaccctgc catcacacct   27720
tccacctgat cccgaatacc acagcgccgc tccccgctac taacaaccaa actacccacc   27780
aacgccaccg tcgcgacctt tcctctgaat ctaataccac taccggaggt gagctccgag   27840
gtcgaccaac ctctgggatt tactacggcc cctgggaggt ggtgggtta  atagcgctag   27900
gcctagttgc gggtgggctt ttggttctct gctacctata cctcccttgc tgttcgtact   27960
tagtggtgct gtgttgctgg tttaagaaat ggggaagatc accctagtga gctgcggtgc   28020
gctggtggcg gtgttgcttt cgattgtggg actgggcggc gcggctgtag tgaaggagaa   28080
```

-continued

```
ggccgatccc tgcttgcatt tcaatcccaa caaatgccag ctgagttttc agcccgatgg    28140
caatcggtgc gcggtactga tcaagtgcgg atgggaatgc gagaacgtga gaatcgagta    28200
caataacaag actcggaaca atactctcgc gtccgtgtgg cagcccgggg accccgagtg    28260
gtacaccgtc tctgtccccg gtgctgacgg ctccccgcgc accgtgaata atactttcat    28320
ttttgcgcac atgtgcaaca cggtcatgtg gatgagcaag cagtacgata tgtggccccc    28380
cacgaaggag aacatcgtgg tcttctccat cgcttacagc ctgtgcacgg cgctaatcac    28440
cgctatcgtg tgcctgagca ttcacatgct catcgctatt cgcccagaa ataatgccga    28500 gaaagagaaa cagccataac acgttttttc acacaccttg tttttacaga caatgcgtct    28560
gttaaatttt ttaaacattg tgctcagtat tgcttatgcc tctggttatg caaacataca    28620
gaaaacccTT tatgtaggat ctgatggtac actagagggt acccaatcac aagccaaggt    28680
tgcatggtat ttttatagaa ccaacactga tccagttaaa ctttgtaagg gtgaattgcc    28740
gcgtacacat aaaactccac ttacatttag ttgcagcaat aataatctta cactttTTTc    28800
aattacaaaa caatatactg gtacttatta cagtacaaac tttcatacag acaagataa    28860 atattatact gttaaggtag aaaatcctac cactcctaga actaccacca ccaccactac    28920
tgcaaagccc actgtgaaaa ctacaactag gaccaccaca actacagaaa ccaccaccag    28980
cacaacactt gctgcaacta cacacacaca cactaagcta accttacaga ccactaatga    29040
tttgatcgcc ctgctgcaaa aggggggataa cagcaccact tccaatgagg agatacccaa    29100
atccatgatt ggcattattg ttgctgtagt ggtgtgcatg ttgatcatcg ccttgtgcat    29160
ggtgtactat gccttctgct acagaaagca cagactgaac gacaagctgg aacacttact    29220
aagtgttgaa ttttaatttt ttagaaccat gaagatccta ggcctttta gttttttctat    29280 cattacctct gctctttgtg aatcagtgga tagagatgtt actattacca ctggttctaa    29340
ttatacactg aaagggccac cctcaggtat gctttcgtgg tattgctatt ttggaactga    29400
cactgatcaa actgaattat gcaattttca aaaaggcaaa acctcaaact ctaaaatctc    29460
taattatcaa tgcaatggca ctgatctgat actactcaat gtcacgaaag catatggtgg    29520
cagttattat tgccctggac aaaacactga agaaatgatt tttacaaag tggaagtggt    29580 tgatcccact acaccaccca ccaccacaac tattcatacc acacacacag aacaaacacc    29640
agaggcaaca gaagcagagt tggccttcca ggttcacgga gattcctttg ctgtcaatac    29700
ccctacaccc gatcagcggt gtccggggcc gctagtcagc ggcattgtcg gtgtgctttc    29760
gggattagca gtcataatca tctgcatgtt cattttTgct tgctgctata gaaggcttta    29820
ccgacaaaaa tcagacccac tgctgaacct ctatgtttaa tttttTccag agccatgaag    29880
gcagttagcg ctctagtttt ttgttctttg attggcattg tttTTaatag taaaattacc    29940
agagttagct ttattaaaca tgttaatgta actgaaggag ataacatcac actagcaggt    30000
gtagaaggtg ctcaaaacac cacctggaca aaataccatc taggatggag agatatttgc    30060
acctggaatg taacttatta ttgcatagga gttaatctta ccattgttaa cgctaaccaa    30120
tctcagaatg ggttaattaa aggacagagt gttagtgtga ccagtgatgg gtactatacc    30180
cagcatagtt ttaactacaa cattactgtc ataccactgc ctacgcctag cccacctagc    30240
actaccacac agacaaccac atacagtaca tcaaatcagc ctaccaccac tacagcagca    30300
gaggttgcca gctcgtctgg ggtccgagtg gcatttttga tgttggcccc atctagcagt    30360
cccactgcta gtaccaatga gcagactact gaattttgt ccactgtcga gagccacacc    30420
```

```
acagctacct ccagtgcctt ctctagcacc gccaatctct cctcgctttc ctctacacca   30480
atcagccccg ctactactcc tagccccgct cctcttccca ctcccctgaa gcaaacagac   30540
ggcggcatgc aatggcagat caccctgctc attgtgatcg ggttggtcat cctggccgtg   30600
ttgctctact acatcttctg ccgccgcatt cccaacgcgc accgcaagcc ggcctacaag   30660
cccatcgtta tcgggcagcc ggagccgctt caggtggaag ggggtctaag gaatcttctc   30720 ttctcttta cagtatggtg attgaactat gattcctaga caattcttga tcactattct    30780
tatctgcctc ctccaagtct gtgccaccct cgctctggtg ccaacgcca gtccagactg     30840 tattgggccc ttcgcctcct acgtgctctt tgccttcgtc acctgcatct gctgctgtag   30900
catagtctgc ctgcttatca ccttcttcca gttcattgac tggatctttg tgcgcatcgc   30960
ctacctgcgc caccaccccc agtaccgcga ccagcgagtg gcgcagctgc tcaggctcct   31020
ctgataagca tgcgggctct gctacttctc gcgcttctgc tgttagtgct ccccgtccc    31080 gtcgacccc ggtcccccac tcagtccccc gaggaggttc gcaaatgcaa attccaagaa    31140
ccctggaaat tcctcaaatg ctaccgccaa aaatcagaca tgcatcccag ctggatcatg   31200
atcattggga tcgtgaacat tctggcctgc accctcatct cctttgtgat ttaccccttgc  31260 tttgactttg gttggaactc gccagaggcg ctctatctcc cgcctgaacc tgacacacca   31320
ccacagcagc aacctcaggc acacgcacta ccaccaccac agcctaggcc acaatacatg   31380
cccatattag actatgaggc cgagccacag cgacccatgc tccccgctat tagttacttc   31440
aatctaaccg gcggagatga ctgacccact ggccaataac aacgtcaacg accttctcct   31500
ggacatggac ggccgcgcct cggagcagcg actcgcccaa cttcgcattc gtcagcagca   31560
ggagagagcc gtcaaggagc tgcaggacgg catagccatc caccagtgca agagaggcat   31620
cttctgcctg gtgaaacagg ccaagatctc ctacgaggtc acccagaccg accatcgcct   31680
ctcctacgag ctcctgcagc agcgccagaa gttcacctgc ctggtcggag tcaaccccat   31740
cgtcatcacc cagcagtcgg gcgataccaa ggggtgcatc cactgctcct gcgactcccc   31800
cgactgcgtc cacactctga tcaagaccct ctgcggcctc cgcgacctcc tccccatgaa   31860
ctaatcaccc ccttatccag tgaaataaag atcatattga tgatgattta aataaaaaaa   31920
ataatcattt gatttgaaat aaagatacaa tcatattgat gatttgagtt taacaaaaat   31980
aaagaatcac ttacttgaaa tctgatacca ggtctctgtc catgttttct gccaacacca   32040
cctcactccc ctcttcccag ctctggtact gcaggcccg gcgggctgca aacttcctcc    32100
acacgctgaa ggggatgtca aattcctcct gtccctcaat cttcatttta tcttctatca   32160
gatgtccaaa aagcgcgtcc gggtggatga tgacttcgac cccgtctacc cctacgatgc   32220
agacaacgca ccgaccgtgc ccttcatcaa ccccccttc gtctcttcag atggattcca    32280
agagaagccc ctgggggtgt tgtccctgcg actggctgac cccgtcacca ccaagaacgg   32340
ggaaatcacc ctcaagctgg gagaggggt ggacctcgac tcgtcgggaa aactcatctc    32400
caacacggcc accaaggccg ccgcccctct cagtatttca acaacacca tttcccttaa    32460 aactgctgcc cctttctaca caacaatgg aactttaagc ctcaatgtct ccacaccatt    32520
agcagtattt cccacattta acactttagg cataagtctt ggaaacggtc ttcagacttc   32580
aaataagttg ttgactgtac aactaactca tcctcttaca ttcagctcaa atagcatcac   32640
agtaaaaaca gacaaagggc tatatattaa ctccagtgga aacagaggac ttgaggctaa   32700
tataagccta aaaagaggac tagttttga cggtaatgct attgcaacat atattggaaa   32760
tggcttagac tatggatctt atgatagtga tggaaaaaca agacccgtaa ttaccaaaat   32820
```

```
tggagcagga ttaaattttg atgctaacaa agcaatagct gtcaaactag gcacaggttt    32880
aagttttgac tccgctggtg ccttgacagc tggaaacaaa caggatgaca agctaacact    32940
ttggactacc cctgacccaa gccctaattg tcaattactt tcagacagag atgccaaatt    33000
tactctctgt cttacaaaat gcggtagtca aatactaggc actgtggcag tggcggctgt    33060
tactgtagga tcagcactaa atccaattaa tgacacagtc aaaagcgcca tagttttcct    33120
tagatttgat tccgatggtg tactcatgtc aaactcatca atggtaggtg attactggaa    33180
ctttagggag ggacagacca ctcaaagtgt agcctataca aatgctgtgg gattcatgcc    33240
aaatataggt gcatatccaa aacccaaag taaaacacct aaaaatagca tagtcagtca    33300
ggtatattta actggagaaa ctactatgcc aatgacacta accataactt tcaatggcac    33360
tgatgaaaaa gacacaaccc cagttagcac ctactctatg acttttacat ggcagtggac    33420
tggagactat aaggacaaaa atattacctt tgctaccaac tcattctctt tttcctacat    33480
cgcccaggaa taatcccacc cagcaagcca accccttttc ccaccacctt tgtctatatg    33540
gaaactctga acagaaaaa taaagttcaa gtgttttatt gaatcaacag ttttacagga    33600
ctcgagcagt tattttttcct ccaccctccc aggacatgga atacaccacc ctctccccccc    33660 gcacagcctt gaacatctga atgccattgg tgatggacat gcttttggtc tccacgttcc    33720
acacagtttc agagcgagcc agtctcggat cggtcaggga gatgaaaccc tccgggcact    33780
cccgcatctg cacctcacag ctcaacagct gaggattgtc ctcggtggtc gggatcacgg    33840
ttatctggaa gaagcagaag agcggcggtg ggaatcatag tccgcgaacg ggatcggccg    33900
gtggtgtcgc atcaggcccc gcagcagtcg ctgccgccgc cgctccgtca agctgctgct    33960 caggggggttc gggtccaggg actccctcag catgatgccc acggccctca gcatcagtcg    34020
tctggtgcgg cgggcgcagc agcgcatgcg aatctcgctc aggtcactgc agtacgtgca    34080
acacaggacc accaggttgt tcaacagtcc atagttcaac acgctccagc cgaaactcat    34140
cgcgggaagg atgctaccca cgtggccgtc gtaccagatc ctcaggtaaa tcaagtggcg    34200
ctccctccag aagacgctgc ccatgtacat gatctccttg ggcatgtggc ggttcaccac    34260 ctccggtac cacatcaccc tctggttgaa catgcagccc cggatgatcc tgcggaacca    34320
cagggccagc accgccccgc ccgccatgca gcgaagagac cccggatccc ggcaatgaca    34380
atggaggacc caccgctcgt acccgtggat catctgggag ctgaacaagt ctatgttggc    34440
acagcacagg catatgctca tgcatctctt cagcactctc agctcctcgg gggtcaaaac    34500
catatcccag ggcacgggga actcttgcag gacagcgaac cccgcagaac agggcaatcc    34560
tcgcacataa cttacattgt gcatggacag ggtatcgcaa tcaggcagca ccgggtgatc    34620
ctccaccaga gaagcgcggg tctcggtctc ctcacagcgt ggtaaggggg ccggccgata    34680
cgggtgatgg cgggacgcgg ctgatcgtgt tctcgaccgt gtcatgatgc agttgctttc    34740
ggacattttc gtacttgctg tagcagaacc tggtccgggc gctgcacacc gatcgccggc    34800
ggcggtctcg gcgcttggaa cgctcggtgt taaagttgta aaacagccac tctctcagac    34860
cgtgcagcag atctagggcc tcaggagtga tgaagatccc atcatgcctg atagctctga    34920
tcacatcgac caccgtggaa tgggccaggc ccagccagat gatgcaattt tgttgggttt    34980
cggtgacggc gggggaggga agaacaggaa gaaccatgat taacttttaa tccaaacggt    35040
ctcggagcac ttcaaaatga aggtcacgga gatggcacct ctcgcccccg ctgtgttggt    35100
ggaaaataac agccaggtca aaggtgatac ggttctcgag atgttccacg gtggcttcca    35160
```

-continued

```
gcaaagcctc cacgcgcaca tccagaaaca agacaatagc gaaagcggga gggttctcta    35220
attcctcaac catcatgtta cactcctgca ccatccccag ataattttca tttttccagc    35280
cttgaatgat tcgaactagt tcctgaggta atccaagcc agccatgata aaaagctcgc    35340
gcagagcacc ctccaccggc attcttaagc acaccctcat aattccaaga tattctgctc    35400
ctggttcacc tgcagcagat tgacaagcgg aatatcaaaa tctctgccgc gatccctgag    35460
ctcctccctc agcaataact gtaagtactc tttcatatcg tctccgaaat ttttagccat    35520
aggaccccca ggaataagag aagggcaagc cacattacag ataaaccgaa gtccccccca    35580
gtgagcattg ccaaatgtaa gattgaaata agcatgctgg ctagacccgg tgatatcttc    35640
cagataactg gacagaaaat cgggtaagca attttttaaga aaatcaacaa aagaaaaatc    35700
ttccaggtgc acgtttaggg cctcgggaac aacgatggag taagtgcaag gggtgcgttc    35760
cagcatggtt agttagctga tctgtaaaaa aacaaaaaat aaaacattaa accatgctag    35820
cctggcgaac aggtgggtaa atcgttctct ccagcaccag gcaggccacg gggtctccgg    35880
cgcgaccctc gtaaaaattg tcgctatgat tgaaaaccat cacagagaga cgttcccggt    35940
ggccggcgtg aatgattcga gaagaagcat acaccccccgg aacattggag tccgtgagtg    36000
aaaaaaagcg gccgaggaag caatgaggca ctacaacgct cactctcaag tccagcaaag    36060
cgatgccatg cggatgaagc acaaaatttt caggtgcgta aaaaatgtaa ttactcccct    36120
cctgcacagg cagcgaagct cccgatccct ccagatacac atacaaagcc tcagcgtcca    36180
tagcttaccg agcggcagca gcagcggcac acaacaggcg caagagtcag agaaaagact    36240
gagctctaac ctgtccgccc gctctctgct caatatatag ccccagatct acactgacgt    36300
aaaggccaaa gtctaaaaat acccgccaaa taatcacaca cgcccagcac acgcccagaa    36360
accggtgaca cactcagaaa aatacgcgca cttcctcaaa cggccaaact gccgtcattt    36420
ccgggttccc acgctacgtc atcaaaacac gactttcaaa ttccgtcgac cgttaaaaac    36480
atcacccgcc ccgccccctaa cggtcgccgc tcccgcagcc aatcaccttc ctccctcccc    36540
aaattcaaac agctcatttg catattaacg cgcaccaaaa gtttgaggta tattattgat    36600
gatg                                                                 36604
```

<210> SEQ ID NO 3
<211> LENGTH: 36535
<212> TYPE: DNA
<213> ORGANISM: chimpanzee adenovirus serotype Pan7

<400> SEQUENCE: 3

```
catcatcaat aatataccte aaacttttgg tgcgcgttaa tatgcaaatg agctgtttga     60
atttggggag ggaggaaggt gattggccga gagacgggcg accgttaggg gcggggcggg    120
tgacgttttt aatacgtggc cgtgaggcgg agccggtttg caagttctcg tgggaaaagt    180
gacgtcaaac gaggtgtggt ttgaacacgg aaatactcaa ttttcccgcg ctctctgaca    240
ggaaatgagg tgtttctggg cggatgcaag tgaaaacggg ccattttcgc gcgaaaactg    300
aatgaggaag tgaaaatctg agtaatttcg cgtttatggc agggaggagt atttgccgag    360
ggccgagtag actttgaccg attacgtggg ggtttcgatt accgtatttt tcacctaaat    420
ttccgcgtac ggtgtcaaag tccggtgttt ttacgtaggc gtcagctgat cgccaggta    480
tttaaacctg cgctctctag tcaagaggcc actcttgagt gccagcgagt agagttttct    540
cctccgcgcc gcgagtcaga tctacacttt gaaagatgag gcacctgaga gacctgcccg    600
gtaatgtttt cctggctact gggaacgaga ttctggaatt ggtggtggac gccatgatgg    660
```

```
gtggcgaccc tcctgagccc cctacccat  ttgaggcgcc ttcgctgtac gatttgtatg    720
atctggaggt ggatgtgccc gagaacgacc ccaacgagga ggcggtgaat gatttgttta    780
gcgatgccgc gctgctggct gccgagcagg ctaatacgga ctctggctca gacagcgatt    840
cctctctcca taccccgaga cccggcagag gtgagaaaaa gatccccgag cttaaagggg    900
aagagctcga cctgcgctgc tatgaggaat gcttgcctcc gagcgatgat gaggaggacg    960
aggaggcgat tcgagctgca tcgaaccagg gagtgaaagc tgcgggcgaa agctttagcc   1020
tggactgtcc tactctgccc ggacacggct gtaagtcttg tgaatttcat cgcatgaata   1080
ctggagataa gaatgtgatg tgtgccctgt gctatatgag agcttacaac cattgtgttt   1140
acagtaagtg tgattaactt tagttgggaa ggcagagggt gactgggtgc tgactggttt   1200
atttatgtat atgtttttt  atgtgtaggt cccgtctctg acgtagatga acccccact    1260
tcagagtgca tttcatcacc cccagaaatt ggcgaggaac cgcccgaaga tattattcat   1320
agaccagttg cagtgagagt caccgggcgg agagcagctg tggagagttt ggatgacttg   1380
ctacagggtg gggatgaacc tttggacttg tgtacccgga aacgcccag  gcactaagtg   1440
ccacacatgt gtgtttactt aaggtgatgt cagtatttat agggtgtgga gtgcaataaa   1500
atccgtgttg actttaagtg cgtggtttat gactcagggg tggggactgt gggtatataa   1560
gcaggtgcag acctgtgtgg tcagttcaga gcaggactca tggagatctg acggtcttg    1620
gaagactttc accagactag acagctgcta gagaactcat cggaggggt  ctcttacctg   1680
tggagattct gcttcggtgg gcctctagct aagctagtct ataggccaa  acaggattat   1740
aaggatcaat ttgaggatat tttgagagag tgtcctggta tttttgactc tctcaacttg   1800
ggccatcagt ctcactttaa ccagagtatt ctgagagccc ttgacttttc tactcctggc   1860
agaactaccg ccgcggtagc ctttttgcc  tttatccttg acaaatggag tcaagaaacc   1920
catttcagca gggattaccg tctggactgc ttagcagtag ctttgtggag aacatggagg   1980
tgccagcgcc tgaatgcaat ctccggctac ttgccagtac agccggtaga cacgctgagg   2040
atcctgagtc tccagtcacc ccaggaacac caacgccgcc agcagccgca gcaggagcag   2100
cagcaagagg aggaggagga tcgagaagag aacccgagag ccggtctgga ccctccggtg   2160
gcggaggagg aggagtagct gacttgtttc ccgagctgcg ccggggtgctg actaggtctt   2220
ccagtggacg ggagaggggg attaagcggg agaggcatga ggagactagc cacagaactg   2280
aactgactgt cagtctgatg agccgcaggc gcccagaatc ggtgtggtgg catgaggttc   2340
agtcgcaggg gatagatgag gtctcggtga tgcatgagaa atattccctg gaacaagtca   2400
agacttgttg gttggagcct gaggatgatt gggaggtagc catcaggaat tatgccaagc   2460
tggctctgaa gccagacaag aagtacaaga ttaccaaact gattaatatc agaaattcct   2520
gctacatttc agggaatggg gccgaggtgg agatcagtac ccaggagagg gtggccttca   2580
gatgttgtat gatgaatatg taccggggg  tggtgggcat ggagggagtc acctttatga   2640
acgcgaggtt caggggtgat gggtataatg gggtggtctt tatggccaac accaagctga   2700
cagtgcacgg atgctccttc tttgggttca ataacatgtg catcgaggcc tggggcagtg   2760
tttcagtgag gggatgcagc ttttcagcca actggatggg ggtcgtgggc agaaccaaga   2820
gcaaggtgtc agtgaagaaa tgcctgttcg agaggtgcca cctgggggtg atgagcgagg   2880
gcgaagccaa agtcaaacac tgcgcctcta ctgagacggg ctgctttgtg ctgatcaagg   2940
gcaatgccca agtcaagcat aacatgatct gtggggcctc ggatgagcgc ggctaccaga   3000
```

```
tgctgacctg cgccggtggg aacagccata tgctggccac cgtgcatgtg acctcgcacc    3060
cccgcaagac atggcccgag ttcgagcaca acgtcatgac ccgatgcaat gtgcacctgg    3120
ggtcccgccg aggcatgttc atgccctacc agtgcaacat gcaatttgtg aaggtgctgc    3180
tggagcccga tgccatgtcc agagtgagcc tgacgggggt gtttgacatg aatgtggagc    3240
tgtggaaaat tctgagatat gatgaatcca agaccaggtg ccgggcctgc gaatgcggag    3300
gcaagcacgc caggcttcag cccgtgtgtg tggaggtgac ggaggacctg cgacccgatc    3360
atttggtgtt gtcctgcaac gggacggagt tcggctccag cggggaagaa tctgactaga    3420
gtgagtagtg tttgggggag gtggagggct tgtatgaggg gcagaatgac taaaatctgt    3480 gttttctgt gtgttgcagc agcatgagcg gaagcgcctc ctttgaggga ggggtattca    3540
gcccttatct gacggggcgt ctcccctcct gggcgggagt gcgtcagaat gtgatgggat    3600
ccacggtgga cggccggccc gtgcagcccg cgaactcttc aaccctgacc tacgcgaccc    3660
tgagctcctc gtccgtggac gcagctgccg ccgcagctgc tgcttccgcc gccagcgccg    3720
tgcgcggaat ggccctgggc gccggctact acagctctct ggtggccaac tcgacttcca    3780
ccaataatcc cgccagcctg aacgaggaga agctgctgct gctgatggcc cagctcgagg    3840
ccctgaccca gcgcctgggc gagctgaccc agcaggtggc tcagctgcag gcggagacgc    3900
gggccgcggt tgccacggtg aaaaccaaat aaaaaatgaa tcaataaata aacgagacg    3960 gttgttgatt ttaacacaga gtcttgaatc tttatttgat ttttcgcgcg cggtaggccc    4020
tggaccaccg gtctcgatca ttgagcaccc ggtggatttt ttccaggacc cggtagaggt    4080
gggcttggat gttgaggtac atgggcatga gcccgtcccg ggggtggagg tagctccatt    4140
gcagggcctc gtgctcgggg gtggtgttgt aaatcaccca gtcatagcag gggcgcaggg    4200
cgtggtgctg cacgatgtcc ttgaggagga gactgatggc cacgggcagc cccttggtgt    4260
aggtgttgac gaacctgttg agctgggagg gatgcatgcg gggggagatg agatgcatct    4320
tggcctggat cttgagattg gcgatgttcc cgcccagatc ccgccggggg ttcatgttgt    4380
gcaggaccac cagcacggtg tatccggtgc acttggggaa tttgtcatgc aacttggaag    4440
ggaaggcgtg aaagaatttg gagacgccct tgtgaccgcc caggttttcc atgcactcat    4500
ccatgatgat ggcgatgggc ccgtgggcgg cggcctgggc aaagacgttt cggggtcgg    4560 acacatcgta gttgtggtcc tgggtgagct cgtcataggc cattttaatg aatttggggc    4620
ggagggtgcc cgactggggg acgaaggtgc cctcgatccc gggggcgtag ttgccctcgc    4680
agatctgcat ctcccaggcc ttgagctcgg agggggggat catgtccacc tgcggggcga    4740
tgaaaaaaac ggtttccggg gcgggggaga tgagctgggc cgaaagcagg ttccggagca    4800
gctgggactt gccgcagccg gtgggccgt agatgacccc gatgaccggc tgcaggtggt    4860
agttgaggga gagacagctg ccgtcctcgc ggaggagggg ggccacctcg ttcatcatct    4920
cgcgcacatg catgttctcg cgcacgagtt ccgccaggag gcgctcgccc ccagcgaga    4980 ggagctcttg cagcgaggcg aagttttttca gcggcttgag yccgtcggcc atgggcattt    5040
tggagagggt ctgttgcaag agttccagac ggtcccagag ctcggtgatg tgctctaggg    5100
catctcgatc cagcagacct cctcgtttcg cgggttgggg cgactgcggg agtagggcac    5160
caggcgatgg gcgtccagcg aggccaggt ccggtcctcc cagggtcgca gggtccgcgt    5220
cagcgtggtc tccgtcacgg tgaaggggtg cgcgccgggc tgggcgcttg cgagggtgcg    5280
cttcaggctc atccggctgg tcgagaaccg ctcccggtcg gcgccctgcg cgtcggccag    5340
gtagcaattg agcatgagtt cgtagttgag cgcctcggcc gcgtggccct tggcgcggag    5400
```

```
cttacctttg gaagtgtgtc cgcagacggg acagaggagg gacttgaggg cgtagagctt   5460
gggggcgagg aagacggact cgggggcgta ggcgtccgcg ccgcagctgg cgcagacggt   5520
ctcgcactcc acgagccagg tgaggtcggg ccggttgggg tcaaaaacga ggtttcctcc   5580
gtgctttttg atgcgtttct tacctctggt ctccatgagc tcgtgtcccc gctgggtgac   5640
aaagaggctg tccgtgtccc cgtagaccga ctttatgggc cggtcctcga gcggggtgcc   5700
gcggtcctcg tcgtagagga accccgccca ctccgagacg aaggcccggg tccaggccag   5760
cacgaaggag gccacgtggg aggggtagcg gtcgttgtcc accagcgggt ccaccttctc   5820
cagggtatgc aagcacatgt ccccctcgtc cacatccagg aaggtgattg gcttgtaagt   5880
gtaggccacg tgaccggggg tcccggccgg ggggtataa aaggggggcgg gcccctgctc   5940
gtcctcactg tcttccggat cgctgtccag gagcgccagc tgttggggta ggtattccct   6000
ctcgaaggct ggcataacct cggcactcag gttgtcagtt tctagaaacg aggaggattt   6060
gatattgacg gtgccgttgg agacgccttt catgagcccc tcgtccatct ggtcagaaaa   6120
gacgatcttt ttgttgtcga gcttggtggc gaaggagccg tagagggcgt tggagaggag   6180
cttggcgatg gagcgcatgg tctggttctt ttccttgtcg gcgcgctcct tggcggcgat   6240
gttgagctgc acgtactcgc gcgccacgca cttccattcg gggaagacgg tggtgagctc   6300
gtcgggcacg attctgaccc gccagccgcg gttgtgcagg gtgatgaggt ccacgctggt   6360
ggccacctcg ccgcgcaggg gctcgttggt ccagcagagg cgcccgccct tgcgcgagca   6420
gaaggggggc agcgggtcca gcatgagctc gtcggggggg tcggcgtcca cggtgaagat   6480
gccgggcaga agctcggggt cgaagtagct gatgcaggtg tccagatcgt ccagcgccgc   6540
ttgccagtcg cgcacggcca gcgcgcgctc gtaggggctg aggggcgtgc cccagggcat   6600
ggggtgcgtg agcgcggagg cgtacatgcc gcagatgtcg tagacgtaga ggggctcctc   6660
gaggacgccg atgtaggtgg ggtagcagcg cccccccgcgg atgctggcgc gcacgtagtc   6720
gtacagctcg tgcgagggcg cgaggagccc cgtgccgagg ttggagcgtt gcggcttttc   6780
ggcgcggtag acgatctggc ggaagatggc gtgggagttg gaggagatgg tgggcctctg   6840
gaagatgttg aagtgggcgt ggggcaggcc gaccgagtcc ctgatgaagt gggcgtagga   6900
gtcctgcagc ttggcgacga gctcggcggt gacgaggacg tccagggcgc agtagtcgag   6960
ggtctcttgg atgatgtcgt acttgagctg gcccttctgc ttccacagct cgcggttgag   7020
aaggaactct tcgcggtcct tccagtactc ttcgaggggg aacccgtcct gatcggcacg   7080
gtaagagccc accatgtaga actggttgac ggccttgtag gcgcagcagc ccttctccac   7140
ggggagggcg taagcttgtg cggccttgcg caggaggtg tgggtgaggg cgaaggtgtc   7200
gcgcaccatg accttgagga actggtgctt gaagtcgagg tcgtcgcagc cgccctgctc   7260
ccagagctga aagtccgtgc gcttcttgta ggcggggttg ggcaaagcga aagtaacatc   7320
gttgaagagg atcttgcccg cgcggggcat gaagttgcga gtgatgcgga aaggctgggg   7380
cacctcggcc cggttgttga tgacctgggc ggcgaggacg atctcgtcga agccgttgat   7440
gttgtgcccg acgatgtaga gttccacgaa tcgcgggcgg cccttaacgt ggggcagctt   7500
cttgagctcg tcgtaggtga gctcggcggg gtcgctgagc ccgtgctgct cgagggccca   7560
gtcggcgacg tgggggttgg cgctgaggaa ggaagtccag agatccacgg ccagggcggt   7620
ctgcaagcgg tcccggtact gacggaactg ctggcccacg gccattttt cggggggtgac   7680
gcagtagaag gtgcgggggt cgccgtgcca gcggtcccac ttgagctgga gggcgaggtc   7740
```

```
gtgggcgagc tcgacgagcg gcgggtcccc ggagagtttc atgaccagca tgaaggggac    7800
gagctgcttg ccgaaggacc ccatccaggt gtaggtttcc acatcgtagg tgaggaagag    7860
cctttcggtg cgaggatgcg agccgatggg gaagaactgg atctcctgcc accagttgga    7920
ggaatggctg ttgatgtgat ggaagtagaa atgccgacgg cgcgccgagc actcgtgctt    7980
gtgtttatac aagcgtccgc agtgctcgca acgctcacg ggatgcacgt gctgcacgag    8040
ctgtacctgg gttcctttga cgaggaattt cagtgggcag tggagcgctg gcggctgcat    8100
ctggtgctgt actacgtcct ggccatcggc gtggccatcg tctgcctcga tggtggtcat    8160
gctgacgagc ccgcgcggga ggcaggtcca gacttcggct cggacgggtc ggagagcgag    8220
gacgagggcg cgcaggccgg agctgtccag ggtcctgaga cgctgcggag tcaggtcagt    8280
gggcagcggc ggcgcgcggt tgacttgcag gagcttttcc agggcgcgcg ggaggtccag    8340
atggtacttg atctccacgg cgccgttggt ggcgacgtcc acggcttgca gggtcccgtg    8400
cccctggggc gccaccaccg tgccccgttt cttcttgggc gctgcttcca tgccggtcag    8460
aagcggcggc gaggacgcgc gccgggcggc aggggcggct cgggacccgg aggcaggggc    8520
ggcaggggca cgtcggcgcc gcgcgcgggc aggttctggt actgcgcccg gagaagactg    8580
gcgtgagcga cgacgcgacg gttgacgtcc tggatctgac gcctctgggt gaaggccacg    8640
ggacccgtga gtttgaacct gaaagagagt tcgacagaat caatctcggt atcgttgacg    8700
gcggcctgcc gcaggatctc ttgcacgtcg cccgagttgt cctggtaggc gatctcggtc    8760
atgaactgct cgatctcctc ctcctgaagg tctccgcggc cggcgcgctc gacggtggcc    8820
gcgaggtcgt tggagatgcg gcccatgagc tgcgagaagg cgttcatgcc ggcctcgttc    8880
cagacgcggc tgtagaccac ggctccgtcg ggtcgcgcg cgcgcatgac cacctgggcg    8940
aggttgagct cgacgtggcg cgtgaagacc gcgtagttgc agaggcgctg gtagaggtag    9000
ttgagcgtgg tggcgatgtg ctcggtgacg aagaagtaca tgatccagcg gcggagcggc    9060
atctcgctga cgtcgcccag ggcttccaag cgctccatgg cctcgtagaa gtccacggcg    9120
aagttgaaaa actgggagtt gcgcgccgag acggtcaact cctcctccag aagacggatg    9180
agctcagcga tggtggcgcg cacctcgcgc tcgaaggccc cggggggctc ctcttcttcc    9240
atctcttcct cctccactaa catctcttct acttcctcct caggaggcgg cggcggggga    9300
ggggccctgc gtcgccggcg gcgcacgggc agacggtcga tgaagcgctc gatggtctcc    9360
ccgcgccggc gacgcatggt ctcggtgacg gcgcgcccgt cctcgcgggg ccgcagcgtg    9420
aagacgccgc cgcgcatctc caggtggccg ccgggggggt ctccgttggg cagggagagg    9480
gcgctgacga tgcatcttat caattggccc gtagggactc cgcgcaagga cctgagcgtc    9540
tcgagatcca cgggatccga aaaccgctga acgaaggctt cgagccagtc gcagtcgcaa    9600
ggtaggctga gcccggtttc ttgttcttcg gggatttcgg gaggcgggcg gcgatgctg    9660
ctggtgatga agttgaagta gcggtcctg agacggcgga tggtggcgag gagcaccagg    9720
tccttgggcc cggcttgctg gatgcgcaga cggtcggcca tgccccaggc gtggtcctga    9780
cacctggcga ggtccttgta gtagtcctgc atgagccgct ccacgggcac ctcctcctcg    9840
cccgcgcggc cgtgcatgcg cgtgagcccg aacccgcgct ggggctggac gagcgccagg    9900
tcggcgacga cgcgctcggc gaggatggcc tgctgtatct gggtgagggt ggtctggaag    9960
tcgtcgaagt cgacgaagcg gtggtaggct ccggtgttga tggtatagga gcagttggcc   10020
atgacggacc agttgacggt ctggtggccg ggtcgcacga gctcgtggta cttgaggcgc   10080
gagtaggcgc gcgtgtcgaa gatgtagtcg ttgcaggtgc gcacgaggta ctggtatccg   10140
```

```
acgaggaagt gcggcggcgg ctggcggtag agcggccatc gctcggtggc ggggcgccg    10200
ggcgcgaggt cctcgagcat gaggcggtgg tagccgtaga tgtacctgga catccaggtg   10260
atgccggcgg cggtggtgga ggcgcgcggg aactcgcgga cgcggttcca gatgttgcgc   10320
agcggcagga agtagttcat ggtggccgcg gtctggcccg tgaggcgcgc gcagtcgtgg   10380
atgctctaga catacgggca aaaacgaaag cggtcagcgg ctcgactccg tggcctggag   10440
gctaagcgaa cgggttgggc tgcgcgtgta ccccggttcg aatctcgaat caggctggag   10500
ccgcagctaa cgtggtactg gcactcccgt ctcgacccaa gcctgctaac gaaacctcca   10560
ggatacggag gcgggtcgtt ttttggcctt ggtcgctggt catgaaaaac tagtaagcgc   10620
ggaaagcgac cgcccgcgat ggctcgctgc cgtagtctgg agaaagaatc gccagggttg   10680
cgttgcggtg tgccccggtt cgagcctcag cgctcggcgc cggccggatt ccgcggctaa   10740
cgtgggcgtg gctgccccgt cgtttccaag acccccttagc cagccgactt ctccagttac   10800
ggagcgagcc cctcttttc ttgtgttttt gccagatgca tcccgtactg cggcagatgc    10860
gccccacccc tccacctcaa ccgccccta cgccgcagca gcagcaacag ccggcgcttc    10920
tgcccccgcc ccagcagcag ccagccacta ccgcggcggc cgccgtgagc ggagccggcg    10980
ttcagtatga cctggccttg aagagggcg aggggctggc gcggctgggg gcgtcgtcgc    11040
cggagcggca cccgcgcgtg cagatgaaaa gggacgctcg cgaggcctac gtgcccaagc    11100
agaacctgtt cagagacagg agcggcgagg agcccgagga gatgcgcgcc tcccgcttcc    11160
acgcggggcg ggagctgcgg cgcggcctgg accgaaagcg ggtgctgagg gacgaggatt    11220
tcgaggcgga cgagctgacg gggatcagcc ccgcgcgcgc gcacgtggcc gcggccaacc    11280
tggtcacggc gtacgagcag accgtgaagg aggagagcaa cttccaaaaa tccttcaaca    11340
accacgtgcg cacgctgatc gcgcgcgagg aggtgaccct gggcctgatg cacctgtggg    11400
acctgctgga ggccatcgtg cagaacccca cgagcaagcc gctgacggcg cagctgtttc    11460
tggtggtgca gcacagtcgg gacaacgaga cgttcaggga ggcgctgctg aatatcaccg    11520
agcccgaggg ccgctggctc ctggacctgg tgaacattct gcagagcatc gtggtgcagg    11580
agcgcgggct gccgctgtcc gagaagctgg cggctatcaa cttctcggtg ctgagcctgg    11640
gcaagtacta cgctaggaag atctacaaga ccccgtacgt gcccatagac aaggaggtga    11700
agatcgacgg gttttacatg cgcatgaccc tgaaagtgct gaccctgagc gacgatctgg    11760
gggtgtaccg caacgacagg atgcaccgcg cggtgagcgc cagccgccgg cgcgagctga    11820
gcgaccagga gctgatgcac agcctgcagc gggccctgac cggggccggg accgagggg    11880
agagctactt tgacatgggc gcggacctgc gctggcagcc cagccgccgg gccttggaag    11940
ctgccggcgg ttcccctac gtggaggagg tggacgatga ggaggaggag ggcgagtacc     12000
tggaagactg atggcgcgac cgtattttg ctagatgcag caacagccac cgcctcctga     12060
tcccgcgatg cgggcggcgc tgcagagcca gccgtccggc attaactcct cggacgattg    12120
gacccaggcc atgcaacgca tcatggcgct gacgacccgc aatcccgaag cctttagaca    12180
gcagcctcag gccaaccggc tctcggccat cctggaggcc gtggtgccct cgcgctcgaa    12240
ccccacgcac gagaaggtgc tggccatcgt gaacgcgctg gtgagaacaa aggccatccg    12300
cggcgacgag gccgggctgg tgtacaacgc gctgctggag cgcgtggccc gctacaacag    12360
caccaacgtg cagacgaacc tggaccgcat ggtgaccgac gtgcgcgagg cggtgtcgca    12420
gcgcgagcgg ttccaccgcg agtcgaacct gggctccatg gtggcgctga acgccttcct    12480
```

```
gagcacgcag cccgccaacg tgccccgggg ccaggaggac tacaccaact tcatcagcgc  12540
gctgcggctg atggtggccg aggtgcccca gagcgaggtg taccagtcgg ggccggacta  12600
cttcttccag accagtcgcc agggcttgca gaccgtgaac ctgagccagg cttcaagaa   12660 cttgcaggga ctgtggggcg tgcaggcccc ggtcgggac  cgcgcgacgg tgtcgagcct  12720
gctgacgccg aactcgcgcc tgctgctgct gctggtggcg cccttcacgg acagcggcag  12780
cgtgagccgc gactcgtacc tgggctacct gcttaacctg taccgcgagg ccatcgggca  12840
ggcgcacgtg gacgagcaga cctaccagga gatcacccac gtgagccgcg cgctgggcca  12900
ggaggacccg ggcaacctgg aggccaccct gaacttcctg ctgaccaacc ggtcgcagaa  12960
gatcccgccc cagtacgcgc tgagcaccga ggaggagcgc atcctgcgct acgtgcagca  13020
gagcgtgggg ctgttcctga tgcaggaggg ggccacgccc agcgccgcgc tcgacatgac  13080
cgcgcgcaac atggagccca gcatgtacgc tcgcaaccgc ccgttcatca ataagctgat  13140
ggactacttg catcgggcgg ccgccatgaa ctcggactac tttaccaacg ccatcttgaa  13200
cccgcactgg ctcccgccgc ccgggttcta cacgggcgag tacgacatgc ccgaccccaa  13260
cgacgggttc ctgtgggacg acgtggacag cagcgtgttc tcgccgcgcc ccgccaccac  13320
cgtgtggaag aaagagggcg gggaccggcg gccgtcctcg gcgctgtccg gtcgcgcggg  13380
tgctgccgcg gcggtgcctg aggccgccag ccccttcccg agcctgccct tttcgctgaa  13440
cagcgtgcgc agcagcgagc tgggtcggct gacgcggccg cgcctgctgg gcgaggagga  13500
gtacctgaac gactccttgt tgaggcccga gcgcgagaag aacttcccca ataacgggat  13560
agagagcctg gtgacaaga  tgagccgctg gaagacgtac gcgcacgagc acagggacga  13620
gccccgagct agcagcagcg caggcacccg tagacgccag cgacacgaca ggcagcgggg  13680
tctggtgtgg gacgatgagg attccgccga cgacagcagc gtgttggact tgggtgggag  13740
tggtggtggt aacccgttcg ctcacttgcg ccccgtatc  gggcgcctga tgtaagaatc  13800
tgaaaaaata aaaacggta  ctcaccaagg ccatggcgac cagcgtgcgt tcttctctgt  13860
tgtttgtagt agtatgatga ggcgcgtgta cccggagggt cctcctccct cgtacgagag  13920
cgtgatgcag caggcggtgg cggcggcgat gcagcccccg ctggaggcgc cttacgtgcc  13980
cccgcggtac ctggcgccta cggaggggcg gaacagcatt cgttactcgg agctggcacc  14040
cttgtacgat accacccggt tgtacctggt ggacaacaag tcggcggaca tcgcctcgct  14100
gaactaccag aacgaccaca gcaacttcct gaccaccgtg gtgcagaaca acgatttcac  14160
ccccacggag gccagcaccc agaccatcaa ctttgacgag cgctcgcggt ggggcggcca  14220
gctgaaaacc atcatgcaca ccaacatgcc caacgtgaac gagttcatgt acagcaacaa  14280
gttcaaggcg cgggtgatgg tctcgcgcaa gaccccccaat ggggtcgcgg tggatgagaa  14340
ttatgatggt agtcaggacg agctgactta cgagtgggtg gagtttgagc tgcccgaggg  14400
caacttctcg gtgaccatga ccatcgatct gatgaacaac gccatcatcg acaactactt  14460
ggcggtgggg cgtcagaacg gggtgctgga gagcgacatc ggcgtgaagt tcgacacgcg  14520
caacttccgg ctgggctggg accccgtgac cgagctggtg atgccgggcg tgtacaccaa  14580
cgaggccttc caccccgaca tcgtcctgct gcccggctgc ggcgtggact tcaccgagag  14640
ccgcctcagc aacctgctgg gcatccgcaa gcggcagccc ttccaggagg gcttccagat  14700
cctgtacgag gacctggagg ggggcaacat ccccgcgctc ttggatgtcg aagcctatga  14760
gaaaagcaag gaggaggccg ccgcagcggg gaccgcagcc gtggccaccg cctctaccga  14820
ggtgcggggc gataattttg ctagcgccgc ggcagtggcc gaggcggctg aaaccgaaag  14880
```

```
taagatagtc atccagccgg tggagaagga cagcaaggac aggagctaca acgtgctcgc   14940
ggacaagaaa aacaccgcct accgcagctg gtacctggcc tacaactacg gcgaccccga   15000
gaagggcgtg cgctcctgga cgctgctcac cacctcggac gtcacctgcg cgtggagca    15060
agtctactgg tcgctgcccg acatgatgca agacccggtc accttccgct ccacgcgtca   15120
agttagcaac tacccggtgg tgggcgccga gctcctgccc gtctactcca agagcttctt   15180
caacgagcag gccgtctact cgcagcagct gcgcgccttc acctcgctca cgcacgtctt   15240
caaccgcttc cccgagaacc agatcctcgt ccgcccgccc gcgcccacca ttaccaccgt   15300
cagtgaaaac gttcctgctc tcacagatca cgggaccctg ccgctgcgca gcagtatccg   15360
gggagtccag cgcgtgaccg tcactgacgc cagacgccgc acctgcccct acgtctacaa   15420
ggccctgggc gtagtcgcgc cgcgcgtcct ctcgagccgc accttctaaa aaatgtccat   15480
tctcatctcg cccagtaata acaccggttg gggcctgcgc gcgcccagca agatgtacgg   15540
aggcgctcgc caacgctcca cgcaacaccc cgtgcgcgtg cgcgggcact tccgcgctcc   15600
ctggggcgcc ctcaagggcc gcgtgcgctc gcgcaccacc gtcgacgacg tgatcgacca   15660
ggtggtggcc gacgcgcgca actacacgcc cgccgccgcg cccgcctcca ccgtggacgc   15720
cgtcatcgac agcgtggtgg ccgatgcgcg ccggtacgcc cgcgccaaga gccggcggcg   15780
gcgcatcgcc cggcggcacc ggagcacccc cgccatgcgc gcggcgcgag ccttgctgcg   15840
cagggccagg cgcacgggac gcagggccat gctcagggcg ccagacgcg cggcctccgg    15900
cagcagcagc gccggcagga cccgcagacg cgcggccacg gcggcggcgg cggccatcgc   15960
cagcatgtcc cgcccgcggc gcggcaacgt gtactgggtg cgcgacgccg ccaccggtgt   16020
gcgcgtgccc gtgcgcaccc gcccccctcg cacttgaaga tgctgacttc gcgatgttga   16080
tgtgtcccag cggcgaggag gatgtccaag cgcaaataca aggaagagat gctccaggtc   16140
atcgcgcctg agatctacgg ccccgcggtg aaggaggaaa gaaagccccg caaactgaag   16200
cgggtcaaaa aggacaaaaa ggaggaggaa gatgtggacg gactggtgga gtttgtgcgc   16260
gagttcgccc ccggcggcg cgtgcagtgg cgcgggcgga aagtgaaacc ggtgctgcgg    16320
cccggcacca cggtggtctt cacgcccggc gagcgttccg gctccgcctc caagcgctcc   16380
tacgacgagg tgtacgggga cgaggacatc ctcgagcagg cggtcgagcg tctgggcgag   16440
tttgcttacg gcaagcgcag ccgccccgcg cccttgaaag aggaggcggt gtccatcccg   16500
ctggaccacg gcaaccccac gccgagcctg aagccggtga ccctgcagca ggtgctgccg   16560
agcgcggcgc cgcgccgggg cttcaagcgc gagggcggcg aggatctgta cccgaccatg   16620
cagctgatgg tgcccaagcg ccagaagctg gaggacgtgc tggagcacat gaaggtggac   16680
cccgaggtgc agcccgaggt caaggtgcgg cccatcaagc aggtggcccc gggcctgggc   16740
gtgcagaccg tggacatcaa gatccccacg gagcccatgg aaacgcagac cgagcccgtg   16800
aagcccagca ccagcaccat ggaggtgcag acggatccct ggatgccggc gccggcttcc   16860
accactcgcc gaagacgcaa gtacggcgcg ccagcctgc tgatgcccaa ctacgcgctg    16920
catccttcca tcatccccac gccgggctac cgcggcacgc gcttctaccg cggctacacc   16980
agcagccgcc gcaagaccac cacccgccgc cgccgtcgtc gcaccgccg cagcagcacc     17040
gcgacttccg ccgccgccct ggtgcggaga gtgtaccgca gcgggcgcga gcctctgacc   17100
ctgccgcgcg cgcgctacca cccgagcatc gccatttaac tctgccgtcg cctcctactt   17160
gcagatatgg ccctcacatg ccgcctccgc gtccccatta cgggctaccg aggaagaaag   17220
```

```
ccgcgccgta gaaggctgac ggggaacggg ctgcgtcgcc atcaccaccg gcggcggcgc    17280
gccatcagca agcggttggg gggaggcttc ctgcccgcgc tgatccccat catcgccgcg    17340
gcgatcgggg cgatcccgg  catagcttcc gtggcggtgc aggcctctca gcgccactga    17400
gacacagctt ggaaaatttg taataaaaaa atgactgac  gctcctggtc ctgtgatgtg    17460 tgttttaga  tggaagacat caattttttcg tccctggcac cgcgacacgg cacgcggccg    17520
tttatgggca cctggagcga catcggcaac agccaactga acggggcgc  cttcaattgg    17580 agcagtctct ggagcgggct taagaatttc gggtccacgc tcaaaaccta tggcaacaag    17640
gcgtggaaca gcagcacagg gcaggcgctg agggaaaagc tgaaagagca gaacttccag    17700
cagaaggtgg tcgatggcct ggcctcgggc atcaacgggg tggtggacct ggccaaccag    17760
gccgtgcaga aacagatcaa cagccgcctg gacgcggtcc cgcccgcggg gtccgtggag    17820
atgccccagg tggaggagga gctgcctccc ctggacaagc gcggcgacaa gcgaccgcgt    17880
cccgacgcgg aggagacgct gctgacgcac acggacgagc cgccccgta  cgaggaggcg    17940 gtgaaactgg gtctgcccac cacgcggccc gtggcgcctc tggccaccgg ggtgctgaaa    18000
cccagcagca gcagccagcc cgcgaccctg gacttgcctc cgcctgcttc ccgcccctcc    18060
acagtggcta agcccctgcc gccggtggcc gtcgcgtcgc gcgcccccg  aggccgcccc    18120 caggcgaact ggcagagcac tctgaacagc atcgtgggtc tgggagtgca gagtgtgaag    18180
cgccgccgct gctattaaaa gacactgtag cgcttaactt gcttgtctgt gtgtatatgt    18240
atgtccgccg accagaagga ggaagaggcg cgtcgccgag ttgcaagatg gccacccccat    18300 cgatgctgcc ccagtgggcg tacatgcaca tcgccggaca ggacgcttcg gagtacctga    18360
gtccgggtct ggtgcagttc gcccgcgcca cagacaccta cttcagtctg gggaacaagt    18420
ttaggaaccc cacggtggcg cccacgcacg atgtgaccac cgaccgcagc cagcggctga    18480
cgctgcgctt cgtgcccgtg gaccgcgagg acaacaccta ctcgtacaaa gtgcgctaca    18540
cgctggccgt gggcgacaac cgcgtgctgg acatggccag cacctacttt gacatccgcg    18600
gcgtgctgga tcgggggccc agcttcaaac cctactccgg caccgcctac aacagcctgg    18660
ctcccaaggg agcgcccaac acttgccagt ggacatataa agctggtgat actgatacag    18720
aaaaaaccta tacatatgga aatgcacctg tgcaaggcat tagcattaca aaggatggta    18780
ttcaacttgg aactgacagc gatggtcagg caatctatgc agacgaaact tatcaaccag    18840
agcctcaagt gggtgatgct gaatggcatg acatcactgg tactgatgaa aaatatggag    18900
gcagagctct taagcctgac accaaaatga agccttgcta tggttctttt gccaagccta    18960
ccaataaaga aggaggccag gcaaatgtga aaaccgaaac aggcggtacc aaagaatatg    19020
acattgacat ggcattcttc gataatcgaa gtgcagctgc cgccggccta gccccagaaa    19080 ttgtttttgta tactgagaat gtggatctgg aaactccaga tacccatatt gtatacaagg    19140
caggtacaga tgacagtagc tcttctatca atttgggtca gcagtccatg cccaacagac    19200
ccaactacat tggcttcaga gacaactttta tcggtctgat gtactacaac agcactggca    19260
atatgggtgt actggctgga caggcctccc agctgaatgc tgtggtggac ttgcaggaca    19320
gaaacaccga actgtcctac cagctcttgc ttgactctct gggtgacaga accaggtatt    19380
tcagtatgtg gaatcaggcg gtggacagtt atgaccccga tgtgcgcatt attgaaaatc    19440
acggtgtgga ggatgaactt cctaactatt gcttccccct ggatgctgtg ggtagaactg    19500
atacttacca gggaattaag gccaatggtg ataatcaaac cacctggacc aaagatgata    19560
ctgttaatga tgctaatgaa ttgggcaagg gcaatccttt cgccatggag atcaacatcc    19620
```

```
aggccaacct gtggcggaac ttcctctacg cgaacgtggc gctgtacctg cccgactcct    19680
acaagtacac gccggccaac atcacgctgc ccaccaacac caacacctac gattacatga    19740
acggccgcgt ggtggcgccc tcgctggtgg acgcctacat caacatcggg gcgcgctggt    19800
cgctggaccc catggacaac gtcaacccct tcaaccacca ccgcaacgcg ggcctgcgat    19860
accgctccat gctcctgggc aacgggcgct acgtgcccct tccacatccag gtgcccaaa    19920 agttttcgc catcaagagc ctcctgctcc tgcccgggtc ctacacctac gagtggaact    19980
tccgcaagga cgtcaacatg atcctgcaga gctccctcgg caacgacctg cgcacggacg    20040
gggcctccat cgccttcacc agcatcaacc tctacgccac cttcttcccc atggcgcaca    20100
acaccgcctc cacgctcgag gccatgctgc gcaacgacac caacgaccag tccttcaacg    20160
actacctctc ggcggccaac atgctctacc ccatcccggc caacgccacc aacgtgccca    20220
tctccatccc ctcgcgcaac tgggccgcct tccgcggctg gtccttcacg cgcctcaaga    20280
cccgcgagac gccctcgctc ggctccgggt tcgaccccta cttcgtctac tcgggctcca    20340 tccctacct cgacggcacc ttctacctca accacacctt caagaaggtc tccatcacct    20400
tcgactcctc cgtcagctgg cccggcaacg accgcctcct gacgcccaac gagttcgaaa    20460
tcaagcgcac cgtcgacgga gaggggtaca acgtggccca gtgcaacatg accaaggact    20520
ggttcctggt ccagatgctg gccactaca acatcggcta ccagggcttc tacgtgcccg    20580
agggctacaa ggaccgcatg tactccttct tccgcaactt ccagcccatg agccgccagg    20640
tcgtggacga ggtcaactac aaggactacc aggccgtcac cctggcctac cagcacaaca    20700
actcgggctt cgtcggctac ctcgcgccca ccatgcgcca gggccagccc taccccgcca    20760 actacccta cccgctcatc ggcaagacg ccgtcgccag cgtcacccag aaaaagttcc    20820
tctgcgaccg ggtcatgtgg cgcatcccct tctccagcaa cttcatgtcc atgggcgcgc    20880
tcaccgacct cggccagaac atgctctacg ccaactccgc ccacgcgcta gacatgaatt    20940
tcgaagtcga ccccatggat gagtccaccc ttctctatgt tgtcttcgaa gtcttcgacg    21000
tcgtccgagt gcaccagccc caccgcgcg tcatcgaggc cgtctacctg cgcacgccct    21060
tctcggccgg caacgccacc acctaagcct cttgcttctt gcaagatgac ggcctgcgcg    21120
ggctccggcg agcaggagct cagggccatc ctccgcgacc tgggctgcgg gccctgcttc    21180
ctgggcacct tcgacaagcg cttcccggga ttcatggccc cgcacaagct ggcctgcgcc    21240
atcgtcaaca cggccggccg cgagaccggg ggcgagcact ggctggcctt cgcctggaac    21300
ccgcgctccc acacctgcta cctcttcgac ccctgcggt tctcggacga cgcctcaag    21360 cagatctacc agttcgagta ccagggcctg ctgcgtcgca cgccctggc caccgaggac    21420 cgctgcgtca ccctggaaaa gtccacccag accgtgcagg gtccgcgctc ggccgcctgc    21480
gggctcttct gctgcatgtt cctgcacgcc ttcgtgcact ggcccgaccg ccccatggac    21540
aagaacccca ccatgaactt gctgacgggg gtgcccaacg gcatgctcca gtcgcccag    21600 gtggaaccca ccctgcgccg caaccaggag gcgctctacc gcttcctcaa cgcccactcc    21660
gcctactttc gctcccaccg cgcgcgcatc gagaaggcca ccgccttcga ccgcatgaat    21720
caagacatgt aatccggtgt gtgtatgtga atgctttatt catcataata aacagcacat    21780
gtttatgcca ccttctctga ggctctgact ttattaaga atcgaagggg ttctgccggc    21840
tctcggcatg gcccgcggc agggatacgt tgcggaactg gtacttgggc agccacttga    21900
actcggggat cagcagcttc ggcacgggga ggtcggggaa cgagtcgctc cacagcttgc    21960
```

```
gcgtgagttg cagggcgccc agcaggtcgg gcgcggagat cttgaaatcg cagttgggac   22020
ccgcgttctg cgcgcgagag ttacggtaca cggggttgca gcactggaac accatcaggg   22080
ccgggtgctt cacgctcgcc agcaccgtcg cgtcggtgat gccctccacg tccagatcct   22140
cggcgttggc catcccgaag ggggtcatct tgcaggtctg ccgccccatg ctgggcacgc   22200
agccgggctt gtggttgcaa tcgcagtgca gggggatcag catcatctgg gcctgctcgg   22260
agctcatgcc cgggtacatg gccttcatga aagcctccag ctggcggaag gcctgctgcg   22320
ccttgccgcc ctcggtgaag aagaccccgc aggacttgct agagaactgg ttggtggcgc   22380
agccagcgtc gtgcacgcag cagcgcgcgt cgttgttggc cagctgcacc acgctgcgcc   22440
cccagcggtt ctgggtgatc ttggcccggt cggggttctc cttcagcgcg cgctgcccgt   22500
tctcgctcgc cacatccatc tcgatcgtgt gctccttctg gatcatcacg gtcccgtgca   22560
ggcaccgcag cttgccctcg gcctcggtgc accgtgcag ccacagcgcg cagccggtgc   22620
tctcccagtt cttgtgggcg atctgggagt gcgagtgcac gaagccctgc aggaagcggc   22680
ccatcatcgt ggtcagggtc ttgttgctgg tgaaggtcag cggaatgccg cggtgctcct   22740
cgttcacata caggtggcag atacggcggt acacctcgcc ctgctcgggc atcagctgga   22800
aggcggactt caggtcgctc tccacgcggt accggtccat cagcagcgtc atcacttcca   22860
tgcccttctc ccaggccgaa acgatcggca ggctcagggg gttcttcacc gttgtcatct   22920
tagtcgccgc cgccgaagtc aggggggtcgt tctcgtccag ggtctcaaac actcgcttgc   22980
cgtccttctc ggtgatgcgc acgggggggaa agctgaagcc cacggccgcc agctcctcct   23040
cggcctgcct ttcgtcctcg ctgtcctggc tgatgtcttg caaaggcaca tgcttggtct   23100
tgcgggggttt cttttttgggc ggcagaggcg gcggcggaga cgtgctgggc gagcgcgagt   23160
tctcgctcac cacgactatt tcttctcctt ggccgtcgtc cgagaccacg cggcggtagg   23220
catgcctctt ctggggcaga ggcggaggcg acgggctctc gcggttcggc gggcggctgg   23280
cagagcccct tccgcgttcg ggggtgcgct cctggcggcg ctgctctgac tgacttcctc   23340
cgcggccggc cattgtgttc tcctagggag caagcatgga gactcagcca tcgtcgccaa   23400
catcgccatc tgccccgcc gccgccgacg agaaccagca gcagcagaat gaaagcttaa   23460
ccgccccgcc gcccagcccc acctccgacg ccgcagcccc agacatgcaa gagatggagg   23520
aatccatcga gattgacctg ggctacgtga cgcccgcgga gcacgaggag gagctggcag   23580
cgcgcttttc agccccggaa gagaaccacc aagagcagcc agagcaggaa gcagagagcg   23640
agcagaacca ggctgggctc gagcatggcg actacctgag cggggcagag gacgtgctca   23700
tcaagcatct ggcccgccaa tgcatcatcg tcaaggacgc gctgctcgac cgcgccgagg   23760
tgcccctcag cgtggcggag ctcagccgcg cctacgagcg caacctcttc tcgccgcgcg   23820
tgccccccaa gcgccagccc aacggcacct gcgagcccaa cccgcgcctc aacttctacc   23880
cggtcttcgc ggtgcccgag ccctggcca cctaccacct cttttttcaag aaccaaagga   23940
tccccgtctc ctgccgcgcc aaccgcaccc gcgccgacgc cctgctcaac ctgggccccg   24000
gcgcccgcct acctgatatc gcctccttgg aagaggttcc caagatcttc gagggtctgg   24060
gcagcgacga gactcgggcc gcgaacgctc tgcaaggaag cggagaggag catgagcacc   24120
acagcgccct ggtggagttg gaaggcgaca acgcgcgcct ggcggtcctc aagcgcacgg   24180
tcgagctgac ccacttcgcc tacccggcgc tcaacctgcc ccccaaggtc atgagcgccg   24240
tcatggacca ggtgctcatc aagcgcgcct cgccctctc ggaggaggag atgcaggacc   24300
ccgagagctc ggacgagggc aagcccgtgg tcagcgacga gcagctggcg cgctggctgg   24360
```

```
gagcgagtag caccccccag agcctggaag agcggcgcaa gctcatgatg gccgtggtcc   24420
tggtgaccgt ggagctggag tgtctgcgcc gcttcttcgc cgacgcggag accctgcgca   24480
aggtcgagga gaacctgcac tacctcttca gacacgggtt cgtgcgccag gcctgcaaga   24540
tctccaacgt ggagctgacc aacctggtct cctacatggg catcctgcac gagaaccgcc   24600
tggggcagaa cgtgctgcac accaccctgc gcggggaggc ccgccgcgac tacatccgcg   24660
actgcgtcta cctgtacctc tgccacacct ggcagacggg catgggcgtg tggcagcagt   24720
gcctggagga gcagaacctg aaagagctct gcaagctcct gcagaagaac ctcaaggccc   24780
tgtggaccgg gttcgacgag cgcaccaccg ccgcggacct ggccgacctc atcttccccg   24840
agcgcctgcg gctgacgctg cgcaacgggc tgcccgactt tatgagccaa agcatgttgc   24900
aaaactttcg ctctttcatc ctcgaacgct ccgggatcct gcccgccacc tgctccgcgc   24960
tgccctcgga cttcgtgccg ctgaccttcc gcgagtgccc ccgccgctc tggagccact   25020 gctacctgct gcgcctggcc aactacctgg cctaccactc ggacgtgatc gaggacgtca   25080
gcggcgaggg cctgctcgag tgccactgcc gctgcaacct ctgcacgccg caccgctccc   25140
tggcctgcaa cccccagctg ctgagcgaga cccagatcat cggcaccttc gagttgcaag   25200
gccccggcga gggcaagggg ggtctgaaac tcacccgggg gctgtggacc tcggcctact   25260
tgcgcaagtt cgtgcccgag gactaccatc ccttcgagat caggttctac gaggaccaat   25320
cccagccgcc caaggccgag ctgtcggcct gcgtcatcac ccaggggcc atcctggccc   25380 aattgcaagc catccagaaa tcccgccaag aatttctgct gaaaaagggc cacggggtct   25440
acttggaccc ccagaccgga gaggagctca accccagctt cccccaggat gccccgagga   25500
agcagcaaga agctgaaagt ggagctgccg ccgccgccgg aggatttgga ggaagactgg   25560
gagagcagtc aggcagagga ggaggagatg gaagactggg acagcactca ggcagaggag   25620
gacagcctgc aagacagtct ggaggaggaa gacgaggtgg aggaggcaga ggaagaagca   25680
gccgccgcca gaccgtcgtc ctcggcggag gaggagaaag caagcagcac ggataccatc   25740
tccgctccgg gtcggggtcg cggcggccgg gcccacagta gatgggacga gaccgggcgc   25800
ttcccgaacc ccaccaccca gaccggtaag aaggagcggc agggatacaa gtcctggcgg   25860
gggcacaaaa acgccatcgt ctcctgcttg caagcctgcg ggggcaacat ctccttcacc   25920
cggcgctacc tgctcttcca ccgcggggtg aacttccccc gcaacatctt gcattactac   25980
cgtcacctcc acagcccta ctactgtttc caagaagagg cagaaaccca gcagcagcag   26040
cagcagcaga aaaccagcgg cagcagctag aaaatccaca gcggcggcag gtggactgag   26100
gatcgcggcg aacgagccgg cgcagacccg ggagctgagg aaccggatct ttcccaccct   26160
ctatgccatc ttccagcaga gtcggggca agagcaggaa ctgaaagtca agaaccgttc   26220
tctgcgctcg ctcacccgca gttgtctgta tcacaagagc gaagaccaac ttcagcgcac   26280
tctcgaggac gccgaggctc tcttcaacaa gtactgcgcg ctcactctta aagagtagcc   26340
cgcgcccgcc cacacacgga aaaggcggg aattacgtca ccacctgcgc ccttcgcccg   26400
accatcatca tgagcaaaga gattcccacg ccttacatgt ggagctacca gccccagatg   26460
ggcctggccg ccggcgccgc ccaggactac tccacccgca tgaactggct cagtgccggg   26520
cccgcgatga tctcacgggt gaatgacatc cgcgcccacc gaaaccagat actcctagaa   26580
cagtcagcga tcaccgccac gccccgccat caccttaatc cgcgtaattg gccgccgcc   26640 ctggtgtacc aggaaattcc ccagcccacg accgtactac ttccgcgaga cgcccaggcc   26700
```

```
gaagtccagc tgactaactc aggtgtccag ctggccggcg gcgccgccct gtgtcgtcac   26760
cgccccgctc agggtataaa gcggctggtg atccgaggca gaggcacaca gctcaacgac   26820
gaggtggtga gctcttcgct gggtctgcga cctgacggag tcttccaact cgccggatcg   26880
gggagatctt ccttcacgcc tcgtcaggcc gtcctgactt tggagagttc gtcctcgcag   26940
ccccgctcgg gtggcatcgg cactctccag ttcgtggagg agttcactcc ctcggtctac   27000
ttcaacccct tctccggctc ccccggccac tacccggacg agttcatccc gaacttcgac   27060
gccatcagcg agtcggtgga cggctacgat tgaatgtccc atggtggcgc ggctgaccta   27120
gctcggcttc gacacctgga ccactgccgc cgcttccgct gcttcgctcg ggatctcgcc   27180
gagtttgcct actttgagct gcccgaggag caccctcagg gcccggccca cggagtgcgg   27240
atcgtcgtcg aaggggtct cgactccac ctgcttcgga tcttcagcca gcgtccgatc   27300
ctggccgagc gcgagcaagg acagacccct ctgaccctgt actgcatctg caaccacccc   27360
ggcctgcatg aaagtctttg ttgtctgctg tgtactgagt ataataaaag ctgagatcag   27420
cgactactcc ggacttccgt gtgttcctgc tatcaaccag tccctgttct tcaccgggaa   27480
cgagaccgag ctccagctcc agtgtaagcc ccacaagaag tacctcacct ggctgttcca   27540
gggctctccg atcgccgttg tcaaccactg cgacaacgac ggagtcctgc tgagcggccc   27600
tgccaacctt acttttttcca cccgcagaag caagctccag ctcttccaac ccttcctccc   27660
cgggacctat cagtgcgtct cgggaccctg ccatcacacc ttccacctga tcccgaatac   27720
cacagcgtcg ctccccgcta ctaacaacca aactacccac caacgccacc gtcgcgacct   27780
ttcctctggg tctaatacca ctaccggagg tgagctccga ggtcgaccaa cctctgggat   27840
ttactacggc ccctgggagg tggtagggtt aatagcgcta ggcctagttg cgggtgggct   27900
tttggctctc tgctacctat acctcccttg ctgttcgtac ttagtggtgc tgtgttgctg   27960
gtttaagaaa tggggaagat cacccctagt agctgcggtg tgctggtggc ggtggtgctt   28020
tcgattgtgg gactgggcgg cgcggctgta gtgaaggaga aggccgatcc ctgcttgcat   28080
ttcaatcccg acaaatgcca gctgagtttt cagcccgatg gcaatcggtg cgcggtgctg   28140
atcaagtgcg gatgggaatg cgagaacgtg agaatcgagt acaataacaa gactcggaac   28200
aatactctcg cgtccgtgtg gcagcccggg gaccccgagt ggtacaccgt ctctgtcccc   28260
ggtgctgacg gctccccgcg caccgtgaat aatactttca ttttgcgca catgtgcgac   28320 acggtcatgt ggatgagcaa gcagtacgat atgtggcccc ccacgaagga gaacatcgtg   28380
gtcttctcca tcgcttacag cgtgtgcacg gcgctaatca ccgctatcgt gtgcctgagc   28440
attcacatgc tcatcgctat tcgccccaga aataatgccg aaaagaaaa acagccataa   28500 cacgtttttt cacacacctt tttcagacca tggcctctgt taaattttttg cttttatttg   28560 ccagtctcat tgccgtcatt catggaatga gtaatgagaa aattactatt tacactggca   28620
ctaatcacac attgaaaggt ccagaaaaag ccacagaagt ttcatggtat tgttatttta   28680
atgaatcaga tgtatctact gaactctgtg gaaacaataa caaaaaaat gagagcatta   28740 ctctcatcaa gtttcaatgt ggatctgact aacccctaat taacatcact agagactatg   28800
taggtatgta ttatggaact acagcaggca tttcggacat ggaattttat caagtttctg   28860
tgtctgaacc caccacgcct agaatgacca caaccacaaa aactacacct gttaccacta   28920
tacagctcac taccaatggc tttcttgcca tgcttcaagt ggctgaaaat agcaccagca   28980
ttcaacccac cccacccagt gaggaaattc ccagatccat gattggcatt attgttgctg   29040
tagtggtgtg catgttgatc atcgccttgt gcatggtgta ctatgccttc tgctacagaa   29100
```

```
agcacagact gaacgacaag ctggaacact tactaagtgt tgaattttaa ttttttagaa   29160
ccatgaagat cctaggcctt ttagtttttt ctatcattac ctctgctcta tgcaattctg   29220
acaatgagga cgttactgtc gttgtcggat caaattatac actaaaaggt ccagcaaaag   29280
gtatgctttc gtggtattgt tggttcggaa ctgacgagca acagacagaa ctttgcaatg   29340
ctcaaaaagg caaaacctca aattctaaaa tctctaatta tcaatgcaat ggcactgact   29400
tagtattgct caatgtcacg aaagcatatg ctggcagtta cacctgccct ggagatgatg   29460
ccgacaatat gatttttac aaagtggaag tggttgatcc cactactcca ccgcccacca   29520
ccacaactac tcataccaca cacacagaac aaacaccaga ggcagcagaa gcagagttgg   29580
ccttccaggt tcacggagat tcctttgctg tcaatacccc tacacccgat cagcggtgtc   29640
cggggctgct cgtcagcggc attgtcggtg tgctttcggg attagcagtc ataatcatct   29700
gcatgttcat ttttgcttgc tgctatagaa ggctttaccg acaaaaatca gacccactgc   29760
tgaacctcta tgtttaattt tttccagagc catgaaggca gttagcgctc tagttttttg   29820
ttctttgatt ggcattgttt ttagtgctgg gttttgaaa atcttacca tttatgaagg   29880 tgagaatgcc actctagtgg gcatcagtgg tcaaaatgtc agctggctaa ataccatct   29940 agatgggtgg aaagacattt gcgattggaa tgtcactgtg tatacatgta atggagttaa   30000
cctcaccatt actaatgcca cccaagatca gaatggtagg tttaagggcc agagtttcac   30060
tagaaataat gggtatgaat cccataacat gtttatctat gacgtcactg tcatcagaaa   30120
tgagactgcc accaccacac agatgccac tacacacagt tctaccacta ctaccatgca   30180
aaccacacag acaaccacta catcaactca gcatatgacc accactacag cagcaaagcc   30240
aagtagtgca gcgcctcagc cccaggcttt ggctttgaaa gctgcacaac ctagtacaac   30300
tactaggacc aatgagcaga ctactgaatt tttgtccact gtcgagagcc acaccacagc   30360
tacctccagt gccttctcta gcaccgccaa tctctcctcg ctttcctcta caccaatcag   30420
tcccgctact actcccaccc cagctcttct ccccactccc ctgaagcaaa ctgaggacag   30480
cggcatgcaa tggcagatca ccctgctcat tgtgatcggg ttggtcatcc tggccgtgtt   30540
gctctactac atcttctgcc gccgcattcc caacgcgcac cgcaaaccgg cctacaagcc   30600
catcgttatc gggcagccgg agccgcttca ggtggaaggg ggtctaagga atcttctctt   30660
ctcttttaca gtatggtgat tgaactatga ttcctagaca attcttgatc actattctta   30720
tctgcctcct ccaagtctgt gccaccctcg ctctggtggc caacgccagt ccagactgta   30780
ttgggccctt cgcctcctac gtgctctttg ccttcatcac ctgcatctgc tgctgtagca   30840
tagtctgcct gcttatcacc ttcttccagt tcattgactg gatctttgtg cgcatcgcct   30900
acctgcgcca ccaccccag taccgcgacc agcgagtggc gcggctgctc aggctcctct   30960
gataagcatg cgggctctgc tacttctcgc gcttctgctg ttagtgctcc cccgcccgt   31020 cgacccccgg tccccactc agtcccccga agaggtccgc aaatgcaaat tccaagaacc   31080
ctggaaattc ctcaaatgct accgccaaaa atcagacatg cttcccagct ggatcatgat   31140
cattgggatc gtgaacattc tggcctgcac cctcatctcc tttgtgattt acccctgctt   31200
tgactttggt tggaactcgc cagaggcgct ctatctcccg cctgaacctg acacaccacc   31260
acagcaacct caggcacacg cactaccacc accacagcct aggccacaat acatgccat   31320 attagactat gaggccgagc cacagcgacc catgctcccc gctattagtt acttcaatct   31380
aaccggcgga gatgactgac ccactggcca acaacaacgt caacgacctt ctcctggaca   31440
```

```
tggacggccg cgcctcggag cagcgactcg cccaacttcg cattcgccag cagcaggaga    31500
gagccgtcaa ggagctgcag gacggcatag ccatccacca gtgcaagaaa ggcatcttct    31560
gcctggtgaa acaggccaag atctcctacg aggtcacccc gaccgaccat cgcctctcct    31620
acgagctcct gcagcagcgc cagaagttca cctgcctggt cggagtcaac cccatcgtca    31680
tcacccagca gtcgggcgat accaaggggt gcatccactg ctcctgcgac tcccccgact    31740
gcgtccacac tctgatcaag accctctgcg gcctccgcga cctcctcccc atgaactaat    31800
caccccctta tccagtgaaa taaatatcat attgatgatg atttaaataa aaaataatca    31860
tttgatttga aataaagata caatcatatt gatgatttga gttttaaaaa ataaagaatc    31920
acttacttga aatctgatac caggtctctg tccatgtttt ctgccaacac cacctcactc    31980
ccctcttccc agctctggta ctgcagaccc cggcgggctg caaacttcct ccacacgctg    32040
aaggggatgt caaattcctc ctgtccctca atcttcattt tatcttctat cagatgtcca    32100
aaaagcgcgt ccgggtggat gatgacttcg accccgtcta cccctacgat gcagacaacg    32160
caccgaccgt gcccttcatc aaccccccct tcgtctcttc agatggattc aagagaagc     32220 ccctgggggt gctgtccctg cgactggctg accccgtcac caccaagaac ggggaaatca    32280
ccctcaagct gggagagggg gtggacctcg actcctcggg aaaactcatc tccaacacgg    32340
ccaccaaggc cgccgcccct ctcagttttt ccaacaacac catttccctt aacatggata    32400
cccctcttta taccaaagat ggaaaattat ccttacaagt ttctccaccg ttaaacatat    32460
taaaatcaac cattctgaac acattagctg tagcttatgg atcaggttta ggactgagtg    32520
gtggcactgc tcttgcagta cagttggcct ctccactcac ttttgatgaa aaaggaaata    32580
ttaaaattaa cctagccagt ggtccattaa cagttgatgc aagtcgactt agtatcaact    32640
gcaaaagagg ggtcactgtc actacctcag gagatgcaat tgaaagcaac ataagctggc    32700
ctaaaggtat aagatttgaa ggtaatggca tagctgcaaa cattggcaga ggattggaat    32760
ttggaaccac tagtacagag actgatgtca cagatgcata cccaattcaa gttaaattgg    32820
gtactggcct taccttttgac agtacaggcg ccattgttgc ttggaacaaa gaggatgata    32880
aacttacatt atggaccaca gccgacccct cgccaaattg caaaatatac tctgaaaaag    32940
atgccaaact cacactttgc ttgacaaagt gtggaagtca aattctgggt actgtgactg    33000
tattggcagt gaataatgga agtctcaacc caatcacaaa cacagtaagc actgcactcg    33060
tctccctcaa gtttgatgca agtggagttt tgctaagcag ctccacatta gacaaagaat    33120
attggaactt cagaaaggga gatgttacac ctgctgagcc ctatactaat gctataggtt    33180
ttatgcctaa cataaaggcc tatcctaaaa acacatctgc agcttcaaaa agccatattg    33240
tcagtcaagt ttatctcaat ggggatgagg ccaaaccact gatgctgatt attactttta    33300
atgaaactga ggatgcaact tgcacctaca gtatcacttt tcaatggaaa tgggatagta    33360
ctaagtacac aggtgaaaca cttgctacca gctccttcac cttctcctac atcgcccaag    33420
aatgaacact gtatcccacc ctgcatgcca accttccca ccccactctg tctatggaaa    33480
aaactctgaa gcacaaaata aaataaagtt caagtgtttt attgattcaa cagttttaca    33540
ggattcgagc agttattttt cctccaccct cccaggacat ggaatacacc accctctccc    33600
cccgcacagc cttgaacatc tgaatgccat tggtgatgga catgcttttg gtctccacgt    33660
tccacacagt ttcagagcga gccagtctcg ggtcggtcag ggagatgaaa ccctccgggc    33720
actcccgcat ctgcacctca cagctcaaca gctgaggatt gtcctcggtg gtcgggatca    33780
cggttatctg gaagaagcag aagagcggcg gtgggaatca tagtccgcga acgggatcgg    33840
```

```
ccggtggtgt cgcatcaggc cccgcagcag tcgctgccgc cgccgctccg tcaagctgct    33900
gctcaggggg tccgggtcca gggactccct cagcatgatg cccacggccc tcagcatcag    33960
tcgtctggtg cggcgggcgc agcagcgcat gcggatctcg ctcaggtcgc tgcagtacgt    34020
gcaacacagg accaccaggt tgttcaacag tccatagttc aacacgctcc agccgaaact    34080
catcgcggga aggatgctac ccacgtggcc gtcgtaccag atcctcaggt aaatcaagtg    34140
gcgctccctc cagaacacgc tgcccacgta catgatctcc ttgggcatgt ggcggttcac    34200
cacctcccgg taccacatca ccctctggtt gaacatgcag cccgatga tcctgcggaa    34260 ccacagggcc agcaccgccc cgcccgccat gcagcgaaga ccccgggt cccggcaatg    34320 gcaatggagg acccaccgct cgtacccgtg gatcatctgg gagctgaaca agtctatgtt    34380
ggcacagcac aggcatatgc tcatgcatct cttcagcact ctcagctcct cgggggtcaa    34440
aaccatatcc cagggcacgg ggaactcttg caggacagcg aaccccgcag aacagggcaa    34500
tcctcgcaca taacttacat tgtgcatgga cagggtatcg caatcaggca gcaccgggtg    34560
atcctccacc agagaagcgc gggtctcggt ctcctcacag cgtggtaagg gggcggccg    34620 atacgggtga tggcgggacg cggctgatcg tgttcgcgac cgtgtcatga tgcagttgct    34680
ttcggacatt ttcgtacttg ctgtagcaga acctggtccg ggcgctgcac accgatcgcc    34740
ggcggcggtc ccggcgcttg gaacgctcgg tgttgaaatt gtaaaacagc cactctctca    34800
gaccgtgcag cagatctagg gcctcaggag tgatgaagat cccatcatgc ctgatagctc    34860
tgatcacatc gaccaccgtg gaatgggcca gacccagcca gatgatgcaa ttttgttggg    34920
tttcggtgac ggcggggag ggaagaacag gaagaaccat gattaactt taatccaaac    34980 ggtctcggag cacttcaaaa tgaaggtcgc ggagatggca cctctcgccc ccgctgtgtt    35040
ggtggaaaat aacagccagg tcaaggtga tacggttctc gagatgttcc acggtggctt    35100
ccagcaaagc ctccacgcgc acatccagaa acaagacaat agcgaaagcg ggagggttct    35160
ctaattcctc aatcatcatg ttacactcct gcaccatccc cagataattt tcattttcc    35220 agccttgaat gattcgaact agttcctgag gtaaatccaa gccagccatg ataaagagct    35280
cgcgcagagc gccctccacc ggcattctta agcacaccct cataattcca agatattctg    35340
ctcctggttc acctgcagca gattgacaag cggaatatca aaatctctgc cgcgatcct    35400 aagctcctcc ctcagcaata actgtaagta ctctttcata tcctctccga aattttagc    35460 cataggacca ccaggaataa gattagggca agccacagta cagataaacc gaagtcctcc    35520
ccagtgagca ttgccaaatg caagactgct ataagcatgc tggctagacc cggtgatatc    35580
ttccagataa ctggacagaa aatcacccag gcaattttta agaaaatcaa caaagaaaa    35640 atcctccagg tgcacgttta gagcctcggg aacaacgatg aagtaaatgc aagcggtgcg    35700
ttccagcatg gttagttagc tgatctgtaa aaaacaaaaa ataaaacatt aaaccatgct    35760
agcctggcga acaggtgggt aaatcgttct ctccagcacc aggcaggcca cggggtctcc    35820
ggcgcgaccc tcgtaaaaat tgtcgctatg attgaaaacc atcacagaga acgttcccg    35880 gtggccggcg tgaatgattc gacaagatga atacaccccc ggaacattgg cgtccgcgag    35940
tgaaaaaaag cgcccgagga agcaataagg cactacaatg ctcagtctca agtccagcaa    36000
agcgatgcca tgcggatgaa gcacaaaatc ctcaggtgcg tacaaaatgt aattactccc    36060
ctcctgcaca ggcagcgaag cccccgatcc ctccagatac acatacaaag cctcagcgtc    36120
catagcttac cgagcagcag cacacaacag gcgcaagagt cagagaaagg ctgagctcta    36180
```

```
acctgtccac ccgctctctg ctcaatatat agcccagatc tacactgacg taaaggccaa    36240
agtctaaaaa tacccgccaa ataatcacac acgcccagca cacgcccaga aaccggtgac    36300
acactcaaaa aaatacgcgc acttcctcaa acgcccaaac tgccgtcatt tccgggttcc    36360
cacgctacgt catcggaatt cgactttcaa attccgtcga ccgttaaaaa cgtcacccgc    36420
cccgccccta acgtcgccc gtctctcggc caatcacctt cctccctccc caaattcaaa    36480
cagctcattt gcatattaac gcgcaccaaa agtttgaggt atattattga tgatg         36535

<210> SEQ ID NO 4
<211> LENGTH: 34264
<212> TYPE: DNA
<213> ORGANISM: simian adenovirus SV-1

<400> SEQUENCE: 4
tccttattct ggaaacgtgc caatatgata atgagcgggg aggagcgagg cggggccggg      60
gtgacgtgcg gtgacgtggg gtgacgcggg gtggcgcgag ggcggggcgg gagtggggag     120
gcgcttagtt tttacgtatg cggaaggagg ttttataccg gaagttgggt aatttgggcg     180
tatacttgta agttttgtgt aatttggcgc gaaaaccggg taatgaggaa gttgaggtta     240
atatgtactt tttatgactg ggcggaattt ctgctgatca gcagtgaact ttgggcgctg     300
acggggaggt ttcgctacgt ggcagtacca cgagaaggct caaaggtccc atttattgta     360
ctcctcagcg ttttcgctgg gtatttaaac gctgtcagat catcaagagg ccactcttga     420
gtgccggcga gtagagtttt ctcctccgcg ctgccgcgat gaggctggtt cccgagatgt     480
acggtgtttt ctgcagcgag acggcccgga actcagatga gctgcttaat acagatctgc     540
tggatgttcc caactcgcct gtggcttcgc ctccgtcgct tcatgatctt ttcgatgtgg     600
aagtggatcc accgcaagat cccaacgagg acgcggtaaa cagtatgttc cctgaatgtc     660
tgtttgaggc ggctgaggag ggttctcaca gcagtgaaga gagcagacgg ggagaggaac     720
tggacttgaa atgctacgag gaatgtctgc cttctagcga ttctgaaacg gaacagacag     780
ggggagacgg ctgtgagtcg gcaatgaaaa atgaacttgt attagactgt ccagaacatc     840
ctggtcatgg ctgccgtgcc tgtgcttttc atagaaatgc cagcggaaat cctgagactc     900
tatgtgctct gtgttatctg cgccttacca gcgattttgt atacagtaag taaagtgttt     960
tcattggcgt acggtagggg attcgttgaa gtgctttgtg acttattatg tgtcattatt    1020
tctaggtgac gtgtccgacg tggaagggga aggagataga tcaggggctg ctaattctcc    1080
ttgcactttg gggctgtgg ttccagttgg cattttaaa ccgagtggtg gaggagaacg    1140
agccggagga gaccgagaat ctgagagccg gcctggaccc tccagtggaa gactaggtgc    1200
tgaggatgat cctgaagagg ggactagtgg gggtgctagg aaaaagcaaa aaactgagcc    1260
tgaacctaga aacttttga atgagttgac tgtaagccta atgaatcggc agcgtcctga    1320
gacggtgttt tggactgagt tggaggatga gttcaagaag ggggaattaa acctcttgta    1380
caagtatggg tttgagcagt tgaaaactca ctggttggag ccgtgggagg atatggaaat    1440
ggctctagac acctttgcta aagtggctct gcggccggat aaagtttaca ctattcgccg    1500
cactgttaat ataaaaaaga gtgtttatgt tatcggccat ggagctctgg tgcaggtgca    1560
gaccccagac cggtggcctt tcaattgcgg catgcagagt ttgggcccccg ggtgatagg    1620 tttgaatgga gttacatttc aaaatgtcag gtttactggt gatgatttta atggctctgt    1680
gtttgtgact agcaccccagc taaccctcca cggtgtttac tttttttaact ttaacaatac    1740 atgtgtggag tcatggggta gggtgtctct gaggggctgc agttttcatg gttgctggaa    1800
```

```
ggcggtggtg ggaagaatta aaagtgtcat gtctgtgaag aaatgcatat ttgaacgctg    1860
tgtgatagct ctagcagtag aggggtacgg acggatcagg aataacgccg catctgagaa    1920
tggatgtttt cttttgctga aaggtacggc cagcgttaag cataatatga tttgcggcag    1980
cggcctgtgc ccctcgcagc tcttaacttg cgcagatgga aactgtcaca ccttgcgcac    2040
cgtgcacata tgtcccact cgcgccgcac ctggccaaca tttgagcaca atatgctcat    2100
gcgttgcgcc gttcacctag gtgctagacg cggcgtgttt atgccttatc aatgtaactt    2160
tagtcatact aagattttgc tggaaactga ttccttccct cgagtatgtt tcaatggggt    2220
gtttgacatg tcaatggaac tttttaaagt gataagatat gatgaaacca agtctcgttg    2280
tcgctcatgt gaatgcggag ctaatcattt gaggttgtat cctgtaaccc tgaacgttac    2340
cgaggagctg aggacggacc accacatgct gtcttgcctg cgtaccgact atgaatccag    2400
cgatgaggag tgaggtgagg ggcggagcca caaagggtat aaaggggcat gaggggtggg    2460
cgcggtgttt caaaatgagc gggacgacgg acggcaatgc gtttgagggg ggagtgttca    2520
gcccatatct gacatctcgt cttccttcct gggcaggagt tcgtcagaat gtagtgggct    2580
ccaccgtgga cggacggccg gtcgcccctg caaattccgc caccctcacc tatgccaccg    2640
tgggatcatc gttggacact gccgcggcag ctgccgcttc tgctgccgct tctactgctc    2700
gcggcatggc ggctgatttt ggactatata accaactggc cactgcagct gtggcgtctc    2760
ggtctctggt tcaagaagat gccctgaatg tgatcttgac tcgcctggag atcatgtcac    2820
gtcgcctgga cgaactggct gcgcagatat cccaagctaa ccccgatacc gcttcagaat    2880
cttaaaataa agacaaacaa atttgttgaa aagtaaaatg gctttatttg ttttttttgg    2940
ctcggtaggc tcgggtccac ctgtctcggt cgttaaggac tttgtgtatg ttttccaaaa    3000
cacggtacag atgggcttgg atgttcaagt acatgggcat gaggccatct ttggggtgga    3060
gataggacca ctgaagagcg tcatgttccg gggtggtatt gtaaatcacc cagtcgtagc    3120 agggttttg agcgtggaac tggaatatgt ccttcaggag caggctaatg ccaagggta    3180 gacccttagt gtaggtgttt acaaagcggt tgagctggga gggatgcatg cggggggaga    3240
tgatatgcat cttggcttgg attttgaggt tagctatgtt accacccagg tctctgcggg    3300
ggttcatgtt atgaaggacc accagcacgg tatagccagt gcatttgggg aacttgtcat    3360
gcagtttgga ggggaaggcg tggaagaatt tagatacccc cttgtgcccc cctaggtttt    3420
ccatgcactc atccataata atggcaatgg accctggc ggccgcttta gcaaacacgt    3480
tttgggggtt ggaaacatca tagttttgct ctagagtgag ctcatcatag gccatcttta    3540
caaagcgggg taggagggtg cccgactggg ggatgatagt tccatctggg cctgagcgt    3600 agttgccctc acagatctgc atctcccagg ccttaatttc cgaggggggg atcatgtcca    3660 cctgggggc gataaaaaac acggtttctg gcggggggtt aatgagctgg gtggaaagca    3720
agttacgcaa cagctgggat tgccgcaac cggtgggacc gtagatgacc ccgatgacgg    3780
gttgcagctg gtagttcaga gaggaacagc tgccgtcggg gcgcaggagg ggagctacct    3840
cattcatcat gcttctgaca tgtttatttt cactcactaa gttttgcaag agcctctccc    3900
cacccaggga taagagttct tccaggctgt tgaagtgttt cagcggtttc aggccgtcgg    3960
ccatgggcat cttttcaagc gactgacgaa gcaagtacag tcggtcccag agctcggtga    4020
cgtgctctat ggaatctcga tccagcagac ttcttggttt cggggttgg gccgactttc    4080 gctgtagggc accagccggt gggcgtccag ggccgcgagg gttctgtcct tccagggtct    4140
```

```
cagcgttcgg gtgagggtgg tctcggtgac ggtgaaggga tgagcccgg gctgggcgct      4200 tgcgagggtg cgcttcaggc tcatcctgct ggtgctgaag cgggcgtcgt ctccctgtga      4260
gtcggccaga tagcaacgaa gcatgaggtc gtagctgagg gactcggccg cgtgtccctt      4320
ggcgcgcagc tttcccttgg aaacgtgctg acatttggtg cagtgcagac acttgagggc      4380
gtagagtttt ggggccagga agaccgactc gggcgagtag gcgtcggctc cgcactgagc      4440
gcagacggtc tcgcactcca ccagccacgt gagctcgggt ttagcgggat caaaaaccaa      4500
gttgcctcca ttttttttga tgcgtttctt accttgcgtc tccatgagtc tgtgtcccgc      4560
ttccgtgaca aaaaggctgt cggtatcccc gtagaccgac ttgaggggc gatcttccaa      4620 aggtgttccg aggtcttccg cgtacaggaa ctgggaccac tccgagacaa aggctcgggt      4680
ccaggctaac acgaaggagg cgatctgcga ggggtatctg tcgttttcaa tgaggggtc      4740 caccttttcc agggtgtgca gacacaggtc gtcctcctcc gcgtccacga aggtgattgg      4800
cttgtaagtg taggtcacgt gacccgcacc cccccaaggg gtataaaagg gggcgtgccc      4860
actctccccg tcactttctt ccgcatcgct gtggaccaga gccagctgtt cgggtgagta      4920
ggccctctca aaagccggca tgatttcggc gctcaagttg tcagtttcta caaacgaggt      4980
ggatttgata ttcacgtgcc ccgcggcgat gcttttgatg gtggaggggt ccatctgatc      5040
agaaaacacg atctttttat tgtcaagttt ggtggcgaaa gacccgtaga gggcgttgga      5100
aagcaacttg gcgatggagc gcagggtctg attttctcc cgatcggccc tctccttggc      5160
ggcgatgttg agttgcacgt actcgcgggc cacgcaccgc cactcgggga acacggcggt      5220
gcgctcgtcg ggcaggatgc gcacgcgcca gccgcggttg tgcagggtga tgaggtccac      5280
gctggtggcc acctccccgc ggagggctc gttggtccaa cacaatcgcc cccttttct      5340 ggagcagaac ggaggcaggg gatctagcaa gttggcgggc gggggtcgg cgtcgatggt      5400 aaatatgccg ggtagcagaa ttttattaaa ataatcgatt tcggtgtccg tgtcttgcaa      5460
cgcgtcttcc cacttcttca ccgccagggc cctttcgtag ggattcaggg gcggtcccca      5520
gggcatgggg tgggtcaggg ccgaggcgta catgccgcag atgtcgtaca cgtacagggg      5580
ctccctcaac accccgatgt aagtggggta acagcgcccc ccgcggatgc tggctcgcac      5640
gtagtcgtac atctcgtgag agggagccat gagcccgtct cccaagtggg tcttgtgggg      5700
tttttcggcc cggtagagga tctgcctgaa gatggcgtgg gagttggaag agatagtggg      5760
gcgttggaag acgttaaagt tggctccggg cagtcccacg gagtcttgga tgaactgggc      5820
gtaggattcc cggagcttgt ccaccagggc tgcggttacc agcacgtcga gagcgcagta      5880
gtccaacgtc tcgcggacca ggttgtaggc cgtctcttgt tttttctccc acagttcgcg      5940
attgaggagg tattcctcgc ggtctttcca gtactcttcg gcgggaaatc cttttcgtc      6000 cgctcggtaa gaacctaaca tgtaaaattc gttcacggct ttgtatggac aacagccttt      6060
ttctaccggc agggcgtacg cttgagcggc ctttctgaga gaggtgtggg tgagggcgaa      6120
ggtgtcccgc accatcactt tcaggtactg atgtttgaag tccgtgtcgt cgcaggcgcc      6180
ctgttcccac agcgtgaagt cggtgcgctt tttctgcctg ggattgggga gggcgaatgt      6240
gacgtcgtta aagaggattt tcccggcgcg gggcatgaag ttgcgagaga tcctgaaggg      6300
tccgggcacg tccgagcggt tgttgatgac ttgcgccgcc aggacgatct cgtcgaagcc      6360
gttgatgttg tggcccacga tgtaaagttc gataaagcgc ggctgtccct tgagggccgg      6420
cgcttttttc aactcctcgt aggtgagaca gtccggcgag gagagaccca gctccgcccg      6480
ggcccagtcg gagagctgag ggttagccgc gaggaaagag ctccacaggt caagggctag      6540
```

```
cagagtttgc aagcggtcgc ggaactcgcg aaacttttc cccacggcca ttttctccgg    6600
cgtcaccacg tagaaagtgc aggggcggtc gttccagacg tcccatcgga gctctagggc    6660
cagctcgcag gcttgacgaa cgagggtctc ctcgcccgag acgtgcatga ccagcatgaa    6720
gggtaccaac tgtttcccga acgagcccat ccatgtgtag gtttctacgt cgtaggtgac    6780
aaagagccgc tgggtgcgcg cgtgggagcc gatcggaag aagctgatct cctgccacca    6840
gttggaggaa tgggtgttga tgtggtgaaa gtagaagtcc cgccggcgca cagagcattc    6900
gtgctgatgt ttgtaaaagc gaccgcagta gtcgcagcgc tgcacgctct gtatctcctg    6960
aatgagatgc gcttttcgcc cgcgcaccag aaaccggagg gggaagttga gacgggggct    7020
tggtggggcg gcatcccctt cgccttggcg gtgggagtct gcgtctgcgc cctccttctc    7080
tgggtggacg acggtgggga cgacgacgcc ccgggtgccg caagtccaga tctccgccac    7140
ggaggggcgc aggcgttgca ggaggggacg cagctgcccg ctgtccaggg agtcgagggc    7200
ggccgcgctg aggtcggcgg gaagcgtttg caagttcact ttcagaagac cggtaagagc    7260
gtgagccagg tgcacatggt acttgatttc cagggggtg ttggaagagg cgtccacggc    7320
gtagaggagg ccgtgtccgc gcggggccac caccgtgccc cgaggaggtt ttatctcact    7380
cgtcgagggc gagcgccggg gggtagaggc ggctctgcgc cgggggggcag cggaggcagt    7440 ggcacgtttt cgtgaggatt cggcagcggt tgatgacgag cccggagact gctggcgtgg    7500
gcgacgacgc ggcggttgag gtcctggatg tgccgtctct gcgtgaagac caccggcccc    7560
cgggtcctga acctgaaaga gagttccaca gaatcaatgt ctgcatcgtt aacgcggcc    7620 tgcctgagga tctcctgtac gtcgcccgag ttgtcttgat aggcgatctc ggccatgaac    7680
tgctccactt cttcctcgcg gaggtcgccg tggcccgctc gctccacggt ggcggccagg    7740
tcgttggaga tgcgacgcat gagttgagag aaggcgttga ggccgttctc gttccacacg    7800
cggctgtaca ccacgtttcc gaaggagtcg cgcgctcgca tgaccacctg gccacgttg    7860 agttccacgt ggcgggcgaa gacggcgtag tttctgaggc gctggaagag gtagttgagc    7920
gtggtggcga tgtgctcgca gacgaagaag tacatgatcc agcgccgcag ggtcatctcg    7980
ttgatgtctc cgatggcttc gagacgctcc atggcctcgt agaagtcgac ggcgaagttg    8040
aaaaattggg agttgcgggc ggccaccgtg agttcttctt gcaggaggcg gatgagatcg    8100
gcgaccgtgt cgcgcacctc ctgctcgaaa gcgccccgag gcgcctctgc ttcttcctcc    8160
ggctcctcct cttccagggg cacgggttcc tccggcagct ctgcgacggg gacggggcgg    8220
cgacgtcgtc gtctgaccgg caggcggtcc acgaagcgct cgatcatttc gccgcgccgg    8280
cgacgcatgt tctcggtgac ggcgcgtccg ttttcgcgag gtcgcagttc gaagacgccg    8340
ccgcgcagag cgcccccgtg cagggagggt aagtggttag ggccgtcggg cagggacacg    8400
gcgctgacga tgcattttat caattgctgc gtaggcactc cgtgcaggga tctgagaacg    8460
tcgaggtcga cgggatccga gaacttctct aggaaagcgt ctatccaatc gcagtcgcaa    8520
ggtaagctga ggacggtggg ccgctggggg gcgtccgcgg gcagttggga ggtgatgctg    8580
ctgatgatgt aattaaagta ggcggtcttc aggcggcgga tggtggcgag gaggaccacg    8640
tctttgggcc cggcctgttg aatgcgcagg cgctcggcca tgcccaggc ctcgctctga    8700 cagcgacgca ggtctttgta gtagtcttgc atcagtctct ccaccggaac ctctgcttct    8760
cccctgtctg ccatgcgagt cgagccgaac ccccgcaggg gctgcagcaa cgctaggtcg    8820
gccacgaccc tctcggccag cacggcctgt tggatctgcg tgagggtggt ctggaagtcg    8880
```

```
tccaggtcca cgaagcggtg ataggccccc gtgttgatgg tgtaggtgca gttggccatg   8940
acggaccagt tgacgacttg catgccgggt tgggtgatct ccgtgtactt gaggcgcgag   9000
taggcgcggg actcgaacac gtagtcgttg catgtgcgta ccagatactg gtagccaacc   9060
aggaagtggg gaggcggttc tcggtacagg ggccagccga ctgtggcggg ggcgccgggg   9120
gacaggtcgt ccagcatgag gcgatggtag tggtagatgt agcggagag ccaggtgatg    9180 ccggccgagg tggtcgcggc cctggtgaat tcgcggacgc ggttccagat gttgcgcagg   9240
gggcgaaagc gctccatggt gggcacgctc tgccccgtga ggcgggcgca atcttgtacg   9300
ctctagatgg aaaaaagaca gggcggtcat cgactccctt ccgtagctcg ggggtaaag    9360 tcgcaagggt gcggcggcgg ggaaccccgg ttcgagaccg gccggatccg ccgctcccga   9420
tgcgcctggc cccgcatcca cgacgtccgc gtcgagaccc agccgcgacg ctccgcccca   9480
atacggaggg gagtcttttg gtgttttttc gtagatgcat ccggtgctgc ggcagatgcg   9540
acctcagacg cccaccacca ccgccgcggc ggcagtaaac ctgagcggag gcggtgacag   9600
ggaggaggag gagctggctt tagacctgga agagggagag gggctggccc ggctgggagc   9660
gccgtcccca gagagacacc ctagggttca gctcgtgagg gacgccaggc aggcttttgt   9720
gccgaagcag aacctgttta gggaccgcag cggtcaggag gcggaggaga tgcgcgattg   9780
caggtttcgg gcgggtagag agctgagggc gggcttcgat cgggagcggc tcctgagggc   9840
ggaggatttc gagcccgacg agcgttctgg ggtgagcccg gcccgcgctc acgtctcggc   9900
ggccaacctg gtgagcgcgt acgagcagac ggtgaacgag gagcgcaact tccaaaagag   9960
ctttaacaat cacgtgagga ccctgatcgc gagggaggag gtgaccatcg ggctgatgca  10020
tctgtgggac ttcgtggagg cctacgtgca gaacccggcc agcaaacctc tgacggccca  10080
gctgttcctg atcgtgcagc acagccgcga caacgagacg ttccgcgacg ccatgttgaa  10140
catcgcggag cccgagggtc gctggctctt ggatctgatt aacatcctgc agagcatcgt  10200
ggtgcaggag aggggcctca gcttagcgga caaggtggcg gccattaact attcgatgca  10260
gagcctgggg aagttctacg ctcgcaagat ctacaagagc ccttacgtgc ccatagacaa  10320
ggaggtgaag atagacagct tttacatgcg catggcgctg aaggtgctga cgctgagcga  10380
cgacctcggc gtgtaccgta acgacaagat ccacaaggcg gtgagcgcca gccgccggcg  10440
ggagctgagc gacagggagc tgatgcacag cctgcagagg gcgctggcgg gcgccgggga  10500
cgaggagcgc gaggcttact tcgacatggg agccgatctg cagtggcgtc ccagcgcgcg  10560
cgccttggag gcggcgggct accccgacga ggaggatcgg gacgatttgg aggaggcagg  10620
cgagtacgag gacgaagcct gaccgggcag gtgttgtttt agatgcagcg gccggcggac  10680
ggggccaccg cggatcccgc acttttggca tccatgcaga gtcaaccttc gggcgtgacc  10740
gcctccgatg actgggcggc ggccatggac cgcattatgg cgctgactac ccgcaacccc  10800
gaggctttta gacagcaacc ccaggccaac cgttttttcgg ccatcttgga agcggtggtg  10860
ccctcccgca ccaaccccac acacgagaaa gtcctgacta tcgtgaacgc cctggtagac  10920
agcaaggcca tccgccgcga cgaggcgggc ttgatttaca acgctctgct ggaacgggtg  10980
gcgcgctaca acagcactaa cgttcagacc aatctggatc gcctcaccac cgacgtgaag  11040
gaggcgctgg ctcagaagga gcggtttctg agggacagca atctgggctc tctggtggca  11100
ctcaacgcct tcctgagcac gcagccggcc aacgtgcccc gcgggcagga ggactacgtg  11160
agcttcatca gcgctctgag gctgctggtg tccgaggtgc cccagagcga ggtgtatcag  11220
tctgggccgg attacttctt ccagacgtcc cgacagggct tgcaaacggt gaacctgact  11280
```

```
caggccttta aaaacttgca aggcatgtgg ggcgttaagg ccccggtggg cgatcgagcc  11340
accatctcca gtctgctgac ccccaacact cgcctgctgc tgctcttgat cgcgccgttc  11400
accaacagta gcactatcag ccgtgactcg tacctgggtc atctcatcac tttgtaccgc  11460
gaggccatcg gtcaggctca gatcgacgag cacacatatc aggagatcac taacgtgagc  11520
cgggccctgg gtcaggaaga taccggcagc ctggaagcca cgttgaactt tttgctaacc  11580
aaccggaggc aaaaaatacc ctcccagttt acgttaagcg ccgaggagga gaggattctg  11640
cgatacgtgc agcagtccgt gagtctgtac ttgatgcggg agggcgccac cgcttccacg  11700
gctttagaca tgacggctcg gaacatggaa ccgtccttt actccgccca ccggccgttc  11760
attaaccgtc tgatggacta cttccatcgc gcggccgcca tgaacgggga gtacttcacc  11820
aatgccatcc tgaatccgca ttggatgccc ccgtccggct tctacaccgg cgagtttgac  11880
ctgcccgaag ccgacgacgg ctttctttgg gacgacgtgt ccgacagcat tttcacgccg  11940
ggcaatcgcc gattccagaa gaaggagggc ggagacgagc tcccctctc cagcgtggag  12000
gcggcctcta ggggagagag tccctttccc agtctgtctt ccgccagcag tggtcgggta  12060
acgcgcccgc ggttgccggg ggagagcgac tacctgaacg accccttgct gcggccggct  12120
aggaagaaaa atttcccaa caacggggtg gaaagcttgg tggataaaat gaatcgttgg  12180
aagacctacg cccaggagca gcgggagtgg gaggacagtc agccgcgacc gctggttccg  12240
ccgcactggc gtcgtcagag agaagacccg gacgactccg cagacgatag tagcgtgttg  12300
gacctgggag ggagcggagc caacccctt gctcacttgc aacccaaggg gcgttccagt  12360
cgcctctact aataaaaaag acgcggaaac ttaccagagc catggccaca gcgtgtgtcc  12420
tttcttcctc tctttcttcc tcggcgcggc agaatgagaa gagcggtgag agtcacgccg  12480
gcggcgtatg agggtccgcc cccttcttac gaaagcgtga tgggatcagc gaacgtgccg  12540
gccacgctgg aggcgcctta cgttcctccc agatacctgg gacctacgga gggcagaaac  12600
agcatccgtt actccgagct ggcacccctg tacgatacca ccaaggtgta cctggtggac  12660
aacaagtcgg cggacatcgc ctccctgaat tatcaaaacg atcacagcaa ttttctgact  12720
accgtggtgc agaacaatga cttcaccccg acggaggcgg gcacgcagac cattaacttt  12780
gacgagcgtt cccgctgggg cggtcagctg aaaaccatcc tgcacaccaa catgcccaac  12840
atcaacgagt tcatgtccac caacaagttc agggccaggc tgatggttaa aaaggctgaa  12900
aaccagcctc ccgagtacga atggtttgag ttcaccattc ccgagggcaa ctattccgag  12960
accatgacta tcgatctgat gaacaatgcg atcgtggaca attacctgca agtggggagg  13020
cagaacgggg tattggaaag cgatatcggc gtaaaatttg ataccagaaa cttccgactg  13080
gggtgggatc ccgtgaccaa gctggtgatg ccaggcgtgt acaccaacga ggcttttcac  13140
cccgacatcg tgctgctgcc ggggtgcggt gtggacttca ctcagagccg tttgagtaac  13200
ctgttaggga tcagaaagcg ccgccccttc aagagggct ttcagatcat gtatgaggac  13260
ctggaaggag gtaacattcc aggtttgcta gacgtgccgg cgtatgaaga gagtgttaaa  13320
caggcggagg cgcagggacg agagattcga ggcgacacct tgccacggga acctcacgaa  13380
ctggtaataa aacctctgga acaagacagt aaaaaacgga gttacaacat tatatccggc  13440
actatgaata ccttgtaccg gagctggttt ctggcttaca actacgggga tcccgaaaag  13500
ggagtgagat catggaccat actcaccacc acgacgtga cctgcggctc gcagcaagtg  13560
tactggtccc tgccggatat gatgcaagac ccggtcacct tccgcccctc cacccaagtc  13620
```

```
agcaacttcc cggtggtggg caccgagctg ctgcccgtcc atgccaagag cttctacaac   13680
gaacaggccg tctactcgca actcattcgc cagtccaccg cgcttaccca cgtgttcaat   13740
cgctttcccg agaaccagat tctggtgcgc cctcccgctc ctaccattac caccgtcagt   13800
gaaaacgttc ccgccctcac agatcacgga accctgccgc tgcgcagcag tatcagtgga   13860
gttcagcgcg tgaccatcac cgacgccaga cgtcgaacct gtccctacgt ttacaaagct   13920
cttggcgtag tggctcctaa agtgctctct agtcgcacct tctaaacatg tccatcctca   13980
tctctcccga taacaacacc ggctggggac tgggctccgg caagatgtac ggcggagcca   14040
aaaggcgctc cagtcagcac ccagttcgag ttcgggggcca cttccgtgct ccctggggag   14100
cttacaagcg aggactctcg ggccgaacgg cggtagacga taccatagat gccgtgattg   14160
ccgacgcccg ccggtacaac cccggaccgg tcgctagcgc cgcctccacc gtggattccg   14220
tgatcgacag cgtggtagct ggcgctcggg cctatgctcg ccgcaagagg cggctgcatc   14280
ggagacgtcg ccccaccgcc gccatgctgg cagccagggc cgtgctgagg cgggcccgga   14340
gggtaggcag aagggctatg cgccgcgctg ccgccaacgc cgccgccggg agggcccgcc   14400
gacaggctgc ccgccaggct gctgccgcca tcgctagcat ggccagaccc aggagaggga   14460
acgtgtactg ggtgcgcgat tctgtgacgg gagtccgagt gccggtgcgc agccgacctc   14520
cccgaagtta aagatccaa gctgcgaaga cggcggtact gagtctccct gttgttatca   14580
gcccaacatg agcaagcgca agtttaaaga agaactgctg cagacgctgg tgcctgagat   14640
ctatggccct ccggacgtga agcctgacat taagccccgc gatatcaagc gtgttaaaaa   14700
gcgggaaaag aaagaggaac tcgcggtggt agacgatggc ggagtggaat ttattaggag   14760
tttcgccccg cgacgcaggg ttcaatggaa agggcggcgg gtacaacgcg ttttgaggcc   14820
gggcaccgcg gtagtttttta ccccgggaga gcggtcggcc gttaggggtt tcaaaaggca   14880
gtacgacgag gtgtacggcg acgaggacat attggaacag gcggctcaac agatcggaga   14940
atttgcctac ggaaagcgtt cgcgtcgcga agacctggcc atcgctttag acagcggcaa   15000
ccccacgccc agcctcaaac ctgtgacgct gcagcaggtg ctccccgtga gcgccagcac   15060
ggacagcaag aggggaataa aaagagaaat ggaagatctg cagcccacca tccagctcat   15120
ggtccctaaa cggcagaggc tggaagaggt cctggagaaa atgaaagtgg acccaagcat   15180
agagccggac gtcaaagtca ggccgatcaa agaagtggcc cctggtctcg gggtgcagac   15240
ggtggatatc cagatccccg tcacgtcagc ttcgaccgcc gtggaagcca tggaaacgca   15300
aacggaaacc cctgccgcga tcggtaccag ggaagtggcg ttgcaaaccg acccctggta   15360
cgaatacgcc gcccctcggc gtcagaggcg acccgctcgt tacggccccg ccaacgccat   15420
catgccagaa tatgcgctgc atccgtctat cctgcccacc cccggctacc ggggagtgac   15480
gtatcgcccg tcaggaaccc gccgccgaac ccgtcgccgc cgccgctccc gtcgtgctct   15540
ggcccccgtg tcggtgcgcc gcgtaacacg ccggggaaag acagttacca ttcccaaccc   15600
gcgctaccac cctagcatcc tttaatgact ctgccgtttt gcagatggct ctgacttgcc   15660
gcgtgcgcct tcccgttccg cactatcgag gaagatctcg tcgtaggaga ggcatggcgg   15720
gtagtggtcg ccggcgggct ttgcgcaggc gcatgaaagg cggaatttta cccgctctga   15780
tacccataat cgccgccgcc atcggtgcca taccgcgcgt cgcttcagtg gccttgcaag   15840
cagctcgtaa taaataaacg aaggcttttg cacttatgtc ctggtcctga ctattttatg   15900
cagaaagagc atgaagacat caatttttac gtcgctggct ccgcggcacg gctcgcggcc   15960
gctcatgggc acctggaacg acatcggcac cagtcagctc aacgggggcg ctttcaattg   16020
```

```
ggggagccctt tggagcggca ttaaaaactt tggctccacg attaaatcct acggcagcaa   16080
agcctggaac agtagtgctg gtcagatgct ccgagataaa ctgaaggaca ccaacttcca   16140
agaaaaagtg gtcaatgggg tggtgaccgg catccacggc gcggtagatc tcgccaacca   16200
agcggtgcag aaagagattg acaggcgttt ggaaagctcg cgggtgccgc cgcagagagg   16260
ggatgaggtg gaggtcgagg aagtagaagt agaggaaaag ctgcccccgc tggagaaagt   16320
tcccggtgcg cctccgagac cgcagaagcg acccaggcca gaactagaag aaactctggt   16380 gacgagagc aaggagcctc cctcgtacga gcaagccttg aaagagggcg cctctccacc   16440
ctacccaatg acaaaaccga tcgcgcctat ggctcggccg gtgtacggga aggactacaa   16500
gcctgtcacg ctagagctcc ccccgccgcc accgccgccc ccacgcgcc cgaccgttcc   16560 ccccccctg ccggctccgt cggcgggacc cgtgtccgca cccgtcgccg tgcctctgcc   16620
agccgcccgc ccagtggccg tggccactgc cagaaacccc agaggccaga gaggagccaa   16680
ctggcaaagc acgctgaaca gcatcgtggg cctgggagtg aaaagcctga acgccgccg   16740 ttgctattat taaaagtgta gctaaaaaat ttcccgttgt atacgcctcc tatgttaccg   16800
ccagagacgc gtgactgtcg ccgcgagcgc cgctttcaag atggccaccc catcgatgat   16860
gccgcagtgg tcttacatgc acatcgccgg gcaggacgcc tcggagtacc tgagccccgg   16920
tctcgtgcag ttcgcccgcg ccaccgacac ctacttcagc ttgggaaaca gtttagaaa   16980 ccccaccgtg gccccccaccc acgatgtaac cacggaccgc tcgcaaaggc tgaccctgcg   17040
ttttgtgccc gtagaccggg aggacaccgc gtactcttac aaagtgcgct acacgctggc   17100
cgtaggggac aaccgagtgc tggacatggc cagcacctac tttgacatcc ggggagtgct   17160
ggatcgcggt cccagttta gccctactc gggtaccgcg tacaattccc tggctcccaa   17220
gggcgctccc aaccctgcag aatggacgaa ttcagacagc aaagttaaag tgagggcaca   17280 ggcgccttt gttagctcgt atggtgctac agcgattaca aaagagggta ttcaggtggg   17340 agtaaccta acagactccg gatcaacacc acagtatgca gataaaacgt atcagcctga   17400
gccgcaaatt ggagaactac agtggaacag cgatgttgga accgatgaca aaatagcagg   17460
aagagtgcta aagaaaacaa cgcccatgtt cccttgttac ggctcatatg ccaggcccac   17520
taatgaaaaa ggaggacagg caacaccgtc cgctagtcaa gacgtgcaaa atcccgaatt   17580 acaattttt gcctctacta atgtcgccaa tacaccaaaa gcagttctat atgcggagga   17640
cgtgtcaatt gaagcgccag acactcactt ggtgttcaaa ccaacagtca ctgaaggcat   17700
tacaagttca gaggctctac tgacccaaca agctgctccc aaccgtccaa actacatagc   17760
ctttagagat aattttattg gtctcatgta ctacaatagc acaggtaaca tgggagtact   17820
ggcaggccag gcttctcagc taaatgcagt tgttgacctg caagacagaa atactgagct   17880
gtcctaccaa ctcatgttgg acgccctcgg agaccgcagt cggtacttt ctatgtggaa   17940 ccaagctgtg gatagttacg atcctgatgt aagaatcata gaaaaccatg gcgtagaaga   18000
tgaattgcct aattattgct ttcctttggg aggcatggca gtaaccgaca cctactcgcc   18060
tataaaggtt aatggaggag gcaatggatg ggaagccaat aacggcgttt tcaccgaaag   18120
aggagtggaa ataggttcag ggaacatgtt tgccatggag attaacctgc aagccaacct   18180
atggcgtagc tttctgtact ccaatattgg gctgtacctg ccagactctc tcaaaatcac   18240
tcctgacaac atcacactcc cagagaacaa aaacacctat cagtatatga acggtcgcgt   18300
gacgccaccc gggctggttg acaccttacgt taacgtgggc gcgcgctggt ccccccgatgt   18360
```

```
catggacagt attaaccctt ttaatcacca ccgcaacgcc ggactccgct accgttccat   18420
gctcctggga aacggacgct acgtgccctt ccacatccag gtgccccaga aattctttgc   18480
aattaaaaac ctgctgctgc tccccggttc ctacacctac gagtggaact tccgcaagga   18540
cgtgaacatg atcttgcaga gctcgctggg caatgacctg cgagtggacg gggccagcat   18600
ccgcttcgac agcatcaacc tgtacgccaa cttttccccc atgcccacac acacggcctc   18660
caccctggaa gccatgctgc gcaacgacac caacgaccaa tctttcaacg actacctgtg   18720
cgcggccaac atgctgtacc ccatccccgc caacgccacc agcgtgccca tctccattcc   18780
ctctcgcaac tgggcagcct tcaggggctg gagtttcacc cgcctcaaaa ccaaggagac   18840
cccctcgctg ggctccgggt tcgaccccta cttcgtctac tccggctcca tccctacct   18900
ggacggcacc ttctacctca accatacttt caaaaaggtg tcaatcatgt tcgactcctc   18960
cgtcagctgg cccggcaacg accgtctgct gacgcccaac gagttcgaaa tcaagcgttc   19020
ggtggacggt gaagggtaca acgtggctca gagcaacatg accaaggact ggttcctgat   19080
tcagatgctc agccactaca acatcggcta ccagggcttc tacgtgcccg aaaattacaa   19140
ggaccgcatg tactctttct tcagaaactt ccaacccatg agccgccaaa ttgtagattc   19200
aacggcttac actaattatc aggatgtgaa actgccatac cagcataaca actcagggtt   19260
cgtgggctac atgggaccca ccatgcgaga ggggcaggcc tacccggcca actatcccta   19320
tccctgatt ggggccaccg ccgtgcccag cctcacgcag aaaaagttcc tctgcgaccg   19380
ggtgatgtgg aggatcccct tctctagcaa cttcatgtct atgggctccc tcaccgacct   19440
ggggcagaac atgctgtacg ccaactccgc tcacgccttg gatatgacct ttgaggtgga   19500
tcccatggat gagcccacgc ttctctatgt tctgttgaa gtcttcgacg tggtgcgcat   19560
ccaccagccg caccgcggcg tcatcgaggc cgtctacctg cgcacacctt tctctgccgg   19620
taacgccacc acctaaagaa gccgatgggc tccagcgaac aggagctgca ggccattgtt   19680
cgcgacctgg gctgcgggcc ctactttttg ggcaccttcg acaagcgttt tcccggcttc   19740
atgtccccc acaagccggc ctgtgccatc gttaacacgg ccggacggga gaccgggggg   19800
gtccactggc tcgccttcgc ctggaacccg cgtaaccgca cctgctacct gttcgaccct   19860
tttggttttct ccgacgaaag gctgaagcag atctaccagt tcgagtacga ggggctcctc   19920
aagcgcagcg ctctggcctc cacgcccgac cactgcgtca ccctggaaaa gtccacccaa   19980
acggtccagg ggccccctctc ggccgcctgc gggctcttct gttgcatgtt tttgcacgcc   20040
ttcgtgcact ggcctcacac ccccatggat cacaacccca ccatggatct gctcaccgga   20100
gtgcccaaca gcatgcttca cagccccccag gtcgccccca ccctgcgccg taaccaggaa   20160
cacctgtatc gctttctggg gaaacactct gcctattttc gccgccaccg gcagcgcatc   20220
gaacgggcca cggccttcga aagcatgagc caaagagtgt aatcaataaa aaacattttt   20280
atttgacatg atacgcgctt ctggcgtttt attaaaaatc gaagggttcg agggaggggt   20340
cctcgtgccc gctggggagg acacgttgc gatactggaa acgggcgctc caacgaaact   20400
cggggatcac cagccgcggc aggggcacgt cttctaggtt ctgcttccaa aactgccgca   20460
ccagctgcag ggctcccatg acgtcgggcg ccgatatctt gaagtcgcag ttagggccgg   20520
agctcccgcg gctgttgcgg aacacggggt tggcacactg gaacaccagc acgccgggt   20580
tgtggatact ggccagggcc gtcgggtcgg tcacctccga cgcatccaga tcctcggcgt   20640
tgctcagggc aaacgggggtc agcttgcaca tctgccgccc aatctgggt actaggtcgc   20700
gcttgttgag gcagtcgcag cgcagaggga tcaggatgcg tcgctgcccg cgttgcatga   20760
```

```
tagggtaact cgccgccagg aactcctcca tttgacggaa ggccatctgg gctttgccgc   20820
cctcggtgta gaatagcccg caggacttgc tagagaatac gttatgaccg cagttgacgt   20880
cctccgcgca gcagcgggcg tcttcgttct tcagctgaac cacgttgcgg ccccaacggt   20940
tctggaccac cttggctcta gtggggtgct ccttcagcgc ccgctgtccg ttctcgctgg   21000
ttacatccat ttccaacacg tgctccttgc agaccatctc cactccgtgg aagcaaaaca   21060
ggacgccctc ctgctgggta ctgcgatgct cccatacggc gcatccggtg ggctcccagc   21120
tcttgtgttt taccccgcg taggcttcca tgtaagccat aaggaatctg cccatcagct   21180
cggtgaaggt cttctggttg gtgaaggtta gcggcaggcc gcggtgctcc tcgttcaacc   21240
aagtttgaca gatcttgcgg tacaccgctc cctggtcggg cagaaactta aaagccgctc   21300
tgctgtcgtt gtctacgtgg aacttctcca ttaacatcat catggtttcc ataccccttct  21360 cccacgctgt caccagtggt ttgctgtcgg ggttcttcac caacacgcg gtagaggggc    21420 cctcgccggc cccgacgtcc ttcatggtca ttctttgaaa ctccacggag ccgtccgcgc   21480
gacgtactct cgcaccgga gggtagctga agcccacctc caccacgtg ccttcgccct     21540 cgctgtcgga gacaatctcc ggggatggcg gcggcgcggg tgtcgccttg cgagccttct   21600
tcttgggagg gagctgaggc gcctcctgct cgcgctcggg gctcatctcc cgcaagtagg   21660
gggtaatgga gctgcctgct tggttctgac ggttggccat tgtatcctag gcagaaagac   21720
atggagctta tgcgcgagga aactttaacc gccccgtccc ccgtcagcga cgaagatgtc   21780
atcgtcgaac aggacccggg ctacgttacg ccgcccgagg atctggaggg gcctgaccgg   21840
cgcgacgcta gtgagcggca ggaaaatgag aaagaggagg cctgctacct cctggaaggc   21900
gacgttttgc taaagcattt cgccaggcag agcaccatag ttaaggaggc cttgcaagac   21960
cgctccgagg tgcccttgga cgtcgccgcg ctctcccagg cctacgaggc gaaccttttc   22020
tcgcctcgag tgcctccgaa gagacagccc aacggcacct gcgagcccaa cccgcgactc   22080
aacttctacc ccgtgttcgc cgtaccagag gcgctggcca cctatcacat ttttttcaaa   22140
aaccaacgca tcccctatc gtgccgggcc aaccgcaccg cggccgatag gaatctcagg    22200
cttaaaaacg gagccaacat acctgatatc acgtcgctgg aggaagtgcc caagattttc    22260
gagggtctgg gtcgagatga gaagcgggcg gcgaacgctc tgcagaaaga acagaaagag   22320
agtcagaacg tgctggtgga gctggagggg gacaacgcgc gtctggccgt cctcaaacgc   22380
tgcatagaag tctcccactt cgcctacccc gccctcaact tgccaccaa agttatgaaa    22440 tcggtcatgg atcagctgct catcaagaga gctgagcccc tggatcccga ccaccccgag   22500
gcggaaaact cagaggacgg aaagcccgtc gtcagcgacg aggagctcga gcggtggctg   22560
gaaaccaggg accccaaca gttgcaagag aggcgcaaga tgatgatggc ggccgtgctg    22620
gtcaccgtgg agctggaatg cctgcaacgg ttttttcagcg acgtggagac gctacgcaaa   22680
atcggggaat ccctgcacta caccttccgc cagggctacg tccgccaggc ctgcaagatc   22740
tccaacgtgg agctcagcaa cctggtctcc tacatgggca tcctccacga gaaccggctg   22800
gggcagagcg tgctgcactg caccttgcaa ggcgaggcgc ggcgggacta cgtgcgagac   22860
tgcatctacc tcttcctcac cctcacctgg cagaccgcca tgggcgtctg gcagcagtgc   22920
ttggaagaga gaaacctcaa agagctagac aaactcctct gccgcagcg gcgcgccctg   22980 tggtccggtt tcagcgagcg cacggtcgcc agcgctctgg cggacatcat cttcccggag   23040
cgcctgatga aaaaccttgca aaacggcctg ccggatttca tcagtcaaag cattttgcaa   23100
```

```
aacttccgct cttttgtcct ggaacgctcc gggatcttgc cgccatgag ctgcgcgcta    23160 ccttctgact ttgtccccct ctcctaccgc gagtgccctc ccccactgtg gagccactgc    23220
tacctcttcc aactggccaa ctttctggcc taccactccg acctcatgga agacgtaagc    23280
ggagagggtt tactggagtg ccactgccgc tgcaacctgt gcaccccca cagatcgctg    23340 gcctgcaaca ccgagctact cagcgaaacc caggtcatag gtaccttcga gatccagggg    23400
ccccagcagc aagagggtgc ttccggcttg aagctcactc cggcgctgtg gacctcggct    23460
tacttacgca aatttgtagc cgaggactac cacgcccaca aaattcagtt ttacgaagac    23520
caatctcgac caccgaaagc cccctcacg gcctgcgtca tcacccagag caagatcctg    23580
gcccaattgc aatccatcaa ccaagcgcgc cgcgatttcc ttttgaaaaa gggtcggggg    23640
gtgtacctgg accccagac cggcgaggaa ctcaacccgt ccacactctc cgtcgaagca    23700 gccccccga gacatgccgc ccagggaac cgccaagcag ctgatcgctc ggcagagagc    23760
gaagaagcaa gagctgctcc agcagcaggt ggaggacgag gaagagatgt gggacagcca    23820
ggcagaggag gtgtcagagg acgaggagga gatggaaagc tgggacagcc tagacgagga    23880
ggaggacgag ctttcagagg aagaggcgac cgaagaaaaa ccacctgcat ccagcgcgcc    23940
ttctctgagc cgacagccga agccccggcc cccgacgccc ccggccggct cactcaaagc    24000
cagccgtagg tgggacgcca ccgaatctcc agcggcagcg gcaacggcag cgggtaaggc    24060
caaacgcgag cggcgggggt attgctcctg gcgggcccac aaaagcagta ttgtgaactg    24120
cttgcaacac tgcgggggaa acatctcctt tgcccgacgc tacctcctct tccatcacgg    24180
tgtggccttc cctcgcaacg ttctctatta ttaccgtcat ctctacagcc cctacgaaac    24240
gctcggagaa aaaagctaag gcctcctccg ccgcgaggaa aaactccgcc gccgctgccg    24300
ccgccaagga tccaccggcc accgaagagc tgagaaagcg catctttccc actctgtatg    24360
ctatctttca gcaaagccgc gggcagcacc ctcagcgcga actgaaaata aaaaaccgct    24420
ccttccgctc gctcacccgc agctgtctgt accacaagag agaagaccag ctgcagcgca    24480
ccctggacga cgccgaagca ctgttcagca aatactgctc agcgtctctt aaagactaaa    24540
agacccgcgc ttttttcccc tcggccgcca aaacccacgt catcgccagc atgagcaagg    24600
agattcccac cccctacatg tggagctatc agccccagat gggcctggcc gcggggggccg    24660 cccaggacta ctccagcaag atgaactggc tcagcgccgg ccccccacatg atctcacgag    24720 ttaacggcat ccgagcccac cgaaaccaga ttctcttaga acaggcggca atcaccgcca    24780 cacccccggcg ccaactcaac ccgcctagtt ggcccgccgc ccaggtgtat caggaaaatc    24840
cccgcccgac cacagtcctc ctgccacgcg acgcggaggc cgaagtcctc atgactaact    24900
ctggggtaca attagcgggc gggtccaggt acgccaggta cagaggtcgg gccgctcctt    24960
actctcccgg gagtataaag agggtgatca ttcgaggccg aggtatccag ctcaacgacg    25020
agacggtgag ctcctcaacc ggtctcagac ctgacggagt cttccagctc ggaggagcgg    25080
gccgctcttc cttcaccact cgccaggcct acctgaccct gcagagctct tcctcgcagc    25140
cgcgctccgg gggaatcggc actctccagt tcgtggaaga gttcgttccc tccgtctact    25200
tcaacccctt ctccggctcg cctggacgct acccggacgc cttcattccc aactttgacg    25260
cagtgagtga atccgtggac ggctacgact gatgacagat ggtgcggccg tgagagctcg    25320
gctgcgacat ctgcatcact gccgtcagcc tcgctgctac gctcgggagg cgatcgtctt    25380
cagctacttt gagctgccgg acgagcaccc tcagggtccg gctcacgggt tgaaactcga    25440
gatcgagaac gcgctcgagt ctcgcctcat cgacaccttc accgcccgac ctctcctggt    25500
```

```
agaaatccaa cggggggatca ctaccatcac cctgttctgc atctgcccca cgcccggatt   25560
acatgaagat ctgtgttgtc atctttgcgc tcagtttaat aaaaactgaa cttttttgccg   25620 caccttcaac gccatctgtg atttctacaa caaaaagttc ttctggcaaa ggtacacaaa   25680
ctgtatttta ttctaattct acctcatcta tcgtgctgaa ctgcgcctgc actaacgaac   25740
ttatccagtg gattgcaaac ggtagtgtgt gcaagtactt ttgggggaac gatatagtta   25800
gtagaaataa cagcctttgc gagcactgca actcctccac actaatcctt tatccccat    25860 ttgttactgg atggtatatg tgcgttggct ccggtttaaa tcctagttgc tttcataagt   25920
ggtttctaca aaagagacc cttcccaaca attctgtttc tttttttcgcc ctatcctact   25980 gctgttctcc ctctggttac tctttcaaac ctctaattgg tattttagct ttgatactca   26040
taatctttat taactttata ataattaaca acttacagta acatgcttg ttctactgct    26100 cgccacatct ttcgctctct ctcacgccag aacaagtatt gttggcgcag gttacaatgc   26160
aactcttcaa tctgcttaca tgccagattc cgaccagata ccccatatta cgtggtactt   26220
acaaacctcc aaacctaatt cttcatttta tgaaggaaac aaactctgcg atgactccga   26280
caacagaacg cacacatttc cccacccttc actacaattc gaatgcgtaa acaaaagctt   26340
gaagctttac aacttaaagc cttcagattc tggcttgtac catgctgtag ttgaaaaaag   26400
taatttagaa gtccacagtg attacattga attgacggtt gtggacctgc cacctccaaa   26460
atgtgaggtt tcctcctctt accttgaagt tcaaggcgtg gatgcctact gcctcataca   26520
cattaactgc agcaactcta aatatccagc tagaatttac tataatggac aggaaagtaa   26580
tcttttttat tatttaacaa caagcgctgg taacggtaaa cagttacctg actatttac    26640 tgctgttgtt gaattttcca cctacagaga aacgtatgcc aagcggcctt acaatttctc   26700
atacccgttt aacgaccttt gcaatgaaat acaagcgctc gaaactggaa ctgattttac   26760
tccaattttc attgctgcca ttgttgtaag cttaattacc attattgtca gcctagcatt   26820
ttactgcttt tacaagccca aaaaccctaa gtttgaaaaa cttaaactaa aacctgtcat   26880
tcaacaagtg tgattttgtt ttccagcatg gtagctgcat ttctacttct cctctgtcta   26940
cccatcattt tcgtctcttc aactttcgcc gcagtttccc acctggaacc agagtgccta   27000
ccgccttttg acgtgtatct gattctcacc tttgtttgtt gtatatccat ttgcagtata   27060
gcctgctttt ttataacaat ctttcaagcc gccgactatt tttacgtgcg aattgcttac   27120
tttagacacc atcctgaata cagaaatcaa aacgttgcct ccttactttg tttggcatga   27180
ttaagttatt gctgatactt aattatttac ccctaatcaa ctgtaattgt ccattcacca   27240
aaccctggtc attctacacc tgttatgata aaatccccga cactcctgtt gcttggcttt   27300
acgcagccac cgccgctttg gtatttatat ctacttgcct tggagtaaaa ttgtatttta   27360
ttttacacac tgggtggcta catcccagag aagatttacc tagatatcct cttgtaaacg   27420
cttttcaatt acagcctctg cctcctcctg atcttcttcc tcgagctccc tctattgtga   27480
gctactttca actcaccggt ggagatgact gactctcagg acattaatat tagtgtggaa   27540
agaatagctg ctcagcgtca gcgagaaacg cgagtgttgg aatacctgga actacagcaa   27600
cttaaagagt cccactggtg tgagaaagga gtgctgtgcc atgttaagca ggcagccctt   27660
tcctacgatg tcagcgttca gggacatgaa ctgtcttaca ctttgccttt gcagaaacaa   27720
accttctgca ccatgatggg ctctacctcc atcacaatca cccaacaagc cgggcctgta   27780 gaggggggcta tcctctgtca ctgtcacgca cctgattgca tgtccaaact aatcaaaact   27840
```

```
ctctgtgctt taggtgatat ttttaaggtg taaatcaata ataaacttac cttaaatttg   27900
acaacaaatt tctggtgaca tcattcagca gcaccacttt accctcttcc cagctctcgt   27960
atgggatgcg atagtgggtg gcaaacttcc tccaaaccct aaaagaaata ttggtatcca   28020
cttccttgtc ctcacccaca attttcatct tttcatagat gaaaagaacc agagttgatg   28080
aagacttcaa ccccgtctac ccctatgaca ccacaaccac tcctgcagtt ccctttatat   28140
cacccccctt tgtaaacagc gatggtcttc aggaaaaccc cccaggtgtt ttaagtctgc   28200
gaatagctaa acccctatat ttcgacatgg agagaaaact agccctttca cttggaagag   28260
ggttgacaat taccgccgcc ggacaattag aaagtacgca gagcgtacaa accaacccac   28320
cgttgataat taccaacaac aacacactga ccctacgtca ttctccccc ttaaacctaa   28380 ctgacaatag cttagtgcta ggctactcga gtcctctccg cgtcacagac aacaaactta   28440
catttaactt cacatcacca ctccgttatg aaaatgaaaa ccttactttt aactatacag   28500
agcctcttaa acttataaat aacagccttg ccattgacat caattcctca aaaggcctta   28560
gtagcgtcgg aggctcacta gctgtaaacc tgagttcaga cttaaagttt gacagcaacg   28620
gatccatagc ttttggcata caaaccctgt ggaccgctcc gacctcgact ggcaactgca   28680
ccgtctacag cgagggcgat tccctactta gtctctgttt aaccaaatgc ggagctcacg   28740
tcttaggaag tgtaagttta accggtttaa caggaaccat aacccaaatg actgatattt   28800
ctgtcaccat tcaatttaca tttgacaaca atggtaagct actaagctct ccacttataa   28860
acaacgcctt tagtattcga cagaatgaca gtacggcctc aaaccctacc tacaacgccc   28920
tggcgtttat gcctaacagt accatatatg caagagggg aggtggtgaa ccacgaaaca   28980
actactacgt ccaaacgtat cttaggggaa atgttcaaaa accaatcatt cttactgtaa   29040
cctacaactc agtcgccaca ggatattcct tatcttttaa gtggactgct cttgcacgtg   29100
aaaagtttgc aacccaaca acctcgtttt gctacattac agaacaataa aaccgtgtac   29160
cccaccgttt cgttttttc agatgaaacg ggcgagagtt gatgaagact caacccagt   29220 gtacccttat gacccccac atgctcctgt tatgccttc attaccac cttttacctc   29280 ctcggatggg ttgcaggaaa aaccacttgg agtgttaagt ttaaactaca gagatcccat   29340
tactacgcaa aatgagtctc ttacaattaa actaggaaac ggcctcactc tagcaaacca   29400
gggacaacta acatcaaccg ctggcgaagt agaacctcca ctcactaacg ctaacaacaa   29460
acttgcactg gtctatagcg atcctttagc agtaaagcgc aacagcctaa ccttatcgca   29520
caccgctccc cttgttattg ctgataactc tttagcattg caagtttcag agcctatttt   29580
tataaatgac aaggacaaac tagccctgca aacagccgcg cccttgtaa ctaacgctgg   29640 caccctcgc ttacaaagcg ccgccccttt aggcattgca gaccaaaccc taaaactcct   29700
gtttaccaac cctttgtact tgcagaataa ctttctcacg ttagccattg aacgaccct   29760 tgccattacc aatactggaa agctggctct acagctctcc ccaccgctac aaacagcaga   29820
cacaggcttg actttgcaaa ccaacgtgcc attaactgta agcaacggga ccctaggctt   29880
agccataaag cgcccactta ttattcagga caacaacttg ttttggact tcagagctcc   29940 cctgcgtctt ttcaacagcg acccagtact agggcttaac ttttacacc ctcttgcggt   30000 acgcgatgag gcgctcactg ttaacacagg ccgcggcctc acagtgagtt acgatggttt   30060
aattttaaat cttggtaagg atcttcgctt tgacaacaac accgtttctg tcgctcttag   30120
tgctgctttg cctttacaat acactgatca gcttcgcctt aacgtgggcg ctgggctgcg   30180
ttacaatcca gtgagtaaga aattggacgt gaaccccaat caaaacaagg gtttaacctg   30240
```

```
ggaaaatgac tacctcattg taaagctagg aaatggatta ggttttgatg gcgatggaaa   30300
catagctgtt tctcctcaag ttacatcgcc tgacaccttg tggaccactg ccgacccatc   30360
ccccaattgt tccatctaca ctgatttaga tgccaaaatg tggctctcgt tggtaaaaca   30420 aggggggtgtg gttcacggtt ctgttgcttt aaaagcattg aaaggaaccc tattgagtcc   30480 tacgaaagc gccattgtta ttatactaca ttttgacaat tatggagtgc gaattctcaa   30540
ttatcccact ttgggcactc aaggcacgtt gggaaataat gcaacttggg gttataggca   30600
gggagaatct gcagacacta atgtactcaa tgcactagca tttatgccca gttcaaaaag   30660
gtacccaaga gggcgtggaa gcgaagttca gaatcaaact gtgggctaca cttgtataca   30720
gggtgacttt tctatgcccg taccgtacca aatacagtac aactatggac caactggcta   30780
ctcctttaaa tttatttgga gaactgtttc aagacaacca tttgacatcc catgctgttt   30840
tttctcttac attacggaag aataaaacaa ctttttcttt ttattttctt tttattttac   30900
acgcacagta aggcttcctc caccctccca tctcacagca tacaccagcc tctcccctt   30960 catggcagta aactgttgtg agtcagtccg gtatttggga gttaagatcc aaacagtctc   31020
tttggtgatg aaacatggat ccgtgatgga cacaaatccc tgggacaggt tctccaacgt   31080
ttcggtaaaa aactgcatgc cgccctacaa aacaaacagg ttcaggctct ccacgggtta   31140
tctccccgat caaactcaga cagagtaaag gtgcgatgat gttccactaa ccacgcagg   31200 tggcgctgtc tgaacctctc ggtgcgactc ctgtgaggct ggtaagaagt tagattgtcc   31260
agcagcctca cagcatggat catcagtcta cgagtgcgtc tggcgcagca gcgcatctga   31320
atctcactga gattccggca agaatcgcac accatcacaa tcaggttgtt catgatccca   31380
tagctgaaca cgctccagcc aaagctcatt cgctccaaca cgccaccgc gtgtccgtcc   31440 aaccttactt taacataaat caggtgtctg ccgcgtacaa acatgctacc cgcatacaga   31500
acctcccggg gcaaaccct gttcaccacc tgcctgtacc agggaaacct cacatttatc   31560
agggagccat agatagccat tttaaaccaa ttagctaaca ccgccccacc agctctacac   31620
tgaagagaac cgggagagtt acaatgcagn tgaataatcc atctctcata acccctaatg   31680
gtctgatgga aatccagatc taacgtggca cagcagatac acactttcat atacattttc   31740
atcacatgtt tttcccaggc cgttaaaata caatcccaat acacgggcca ctcctgcagt   31800
acaataaagc taatacaaga tggtatactc ctcacctcac taacattgtg catgttcata   31860
ttttcacatt ctaagtaccg agagttctcc tctacaacag cactgccgcg gtcctcacaa   31920
ggtggtagct ggtgacgatt gtaaggagcc agtctgcagc gataccgtct gtcgcgttgc   31980
atcgtagacc agggaccgac gcacttcctc gtacttgtag tagcagaacc acgtccgctg   32040
ccagcacgtc tccaagtaac gccggtccct gcgtcgctca cgctccctcc tcaacgcaaa   32100
gtgcaaccac tcttgtaatc cacacagatc cctctcggcc tccggggcga tgcacacctc   32160
aaacctacag atgtctcggt acagttccaa acacgtagtg agggcgagtt ccaaccaaga   32220
cagacagcct gatctatccc gacacactgg aggtggagga agacacgaa gaggcatgtt   32280 attccaagcg attcaccaac gggtcgaaat gaagatcccg aagatgacaa cggtcgcctc   32340
cggagccctg atggaattta acagccagat caaacattat gcgatttttcc aggctatcaa   32400 tcgcggcctc caaaagagcc tggacccgca cttccacaaa caccagcaaa gcaaaagcgt   32460
tattatcaaa ctcttcgatc atcaagctgc aggactgtac aatgcccaag taattttcat   32520
ttctccactc gcgaatgatg tcgcggcaaa tagtctgaag gttcatgccg tgcatattaa   32580
```

-continued

```
aaagctccga aagggcgccc tctatagcca tgcgtagaca caccatcatg actgcaagat    32640
atcgggctcc tgagacacct gcagcagatt taacagaccc aggtcaggtt gctctccgcg    32700
atcgcgaatc tccatccgca aagtcatttg caaataatta aatagatctg cgccgactaa    32760
atctgttaac tccgcgctag gaactaaatc aggtgtggct acgcagcaca aaagttccag    32820
ggatggcgcc aaactcacta gaaccgctcc cgagtagcaa aactgatgaa tgggagtaac    32880
acagtgtaaa atgttcagcc aaaaatcact aagctgctcc tttaaaaagt ccagtacttc    32940
tatattcagt tcgtgcaagt actgaagcaa ctgtgcggga atatgcacag caaaaaaaat    33000
agggcggctc agatacatgt tgacctaaaa taaaagaat cattaaacta agaagcctg     33060
gcgaacggtg ggatatatga cacgctccag cagcaggcaa gcaaccggct gtccccggga    33120
accgcggtaa aattcatccg aatgattaaa aagaacaaca gagacttccc accatgtact    33180
cggttggatc tcctgagcac agagcaatac ccccctcaca ttcatatccg ctacagaaaa    33240
aaaacgtccc agatacccag cgggaatatc caacgacagc tgcaaagaca gcaaaacaat    33300
ccctctggga gcaatcacaa aatcctccgg tgaaaaaagc acatacatat tagaataacc    33360
ctgttgctgg ggcaaaaagg cccgtcgtcc cagcaaatgc acataaatat gttcatcagc    33420
cattgccccg tcttaccgcg taaacagcca cgaaaaaatc gagctaaaat ccacccaaca    33480
gcctatagct atatatacac tccacccaat gacgctaata ccgcaccacc cacgaccaaa    33540
gttcacccac acccacaaaa cccgcgaaaa tccagcgccg tcagcacttc cgcaatttca    33600
gtctcacaac gtcacttccg cgcgcctttt cactttccca cacacgccct tcgcccgccc    33660
gccctcgcgc caccccgcgt caccccacgt caccgcacgt caccccggcc ccgcctcgct    33720
cctcccgct cattatcata ttggcacgtt tccagaataa ggtatattat tgatgcagca    33780
aaacaatccc tctgggagca atcacaaaat cctccggtga aaaagcaca tacatattag    33840
aataaccctg ttgctggggc aaaaaggccc gtcgtcccag caaatgcaca taaatatgtt    33900
catcagccat tgccccgtct taccgcgtaa acagccacga aaaaatcgag ctaaaatcca    33960
cccaacagcc tatagctata tatacactcc acccaatgac gctaataccg caccaccac    34020
gaccaaagtt cacccacacc cacaaaaccc gcgaaaatcc agcgccgtca gcacttccgc    34080
aatttcagtc tcacaacgtc acttccgcgc gccttttcac tttcccacac acgcccttcg    34140
cccgccgcc ctcgcgccac cccgcgtcac cccacgtcac gcacgtcac cccggccccg    34200
cctcgctcct ccccgctcat tatcatattg gcacgtttcc agaataaggt atattattga    34260
tgca                                                                 34264
```

<210> SEQ ID NO 5
<211> LENGTH: 31044
<212> TYPE: DNA
<213> ORGANISM: simian adenovirus SV-25

<400> SEQUENCE: 5

```
catcatcaat aatataccttattctggaaa cgtgccaata tgataatgag cggggaggag      60
cgaggcgggg ccggggtgac gtgcggtgac gcggggtggc gcgagggcgg ggcgaagggc    120
gcgggtgtgt gtgtgggagg cgcttagttt ttacgtatgc ggaaggaggt tttataccgg    180
aagatgggta atttgggcgt atacttgtaa gttttgtgta atttggcgcg aaaactgggt    240
aatgaggaag ttgaggttaa tatgtacttt ttatgactgg gcggaatttc tgctgatcag    300
cagtgaactt tgggcgctga cggggaggtt tcgctacgtg acagtaccac gagaaggctc    360
aaaggtccca tttattgtac tcttcagcgt tttcgctggg tatttaaacg ctgtcagatc    420
```

-continued

```
atcaagaggc cactcttgag tgctggcgag aagagttttc tcctccgtgc tgccacgatg    480
aggctggtcc ccgagatgta cggtgttttt agcgacgaga cggtgcgtaa ctcagatgac    540
ctgctgaatt cagacgcgct ggaaatttcc aattcgcctg tgctttcgcc gccgtcactt    600
cacgacctgt ttgtgttttg gctcaacgct tagcaacgtg ttatataggg tcaagaagga    660
gcaggagacg cagtttgcta ggctgttggc cgatactcct ggagttttg tggctctgga     720 tctaggccat cactctcttt tccaagagaa aattatcaaa aacttaactt ttacgtctcc    780
tggtcgcacg gttgcttccg ctgcctttat tacctatatt ttggatcaat ggagcaacag    840
cgacagccac ctgtcgtggg agtacatgct ggattacatg tcgatggcgc tgtggagggc    900
catgctgcgg aggagggttt gcatttactt gcgggcgcag cctccgcggc tggaccgagt    960
ggaggaggag gacgagccgg gggagaccga gaacctgagg gccgggctgg accctccaac   1020
ggaggactag gtgctgagga tgatcccgaa gaggggacta gtgggctag gaagaagcaa    1080 aagactgagt ctgaacctcg aaactttttg aatgagttga ctgtgagttt gatgaatcgt   1140
cagcgtccgg agacaatttt ctggtctgaa ttggaggagg aattcaggag ggggaactg    1200 aacctgctat acaagtatgg gtttgaacag ttaaaaactc actggttgga gccgtgggag   1260
gattttgaaa ccgccttgga cacttttgct aaagtggctc tgcggccgga taaggtttac   1320
actatccgcc gcactgttaa cataaagaag agtgtttatg ttataggcca tggagctctg   1380
gtgcaggtgc aaaccgtcga ccgggtggcc tttagttgcg gtatgcaaaa tctgggcccc   1440
ggggtgatag gcttaaatgg tgtaacattt cacaatgtaa ggtttactgg tgaaagtttt   1500
aacggctctg tgtttgcaaa taacacacag ctgacgctcc acggcgttta cttttttaac   1560
tttaataaca catgtgtgga gtcgtggggc agggtgtctt tgaggggctg ctgttttcac   1620
ggctgctgga aggcggtggt gggaagactt aaaagtgtaa catctgtaaa aaaatgcgtg   1680
tttgagcggt gtgtgttggc tttaactgtg gagggctgtg gacgcattag gaataatgcg   1740
gcgtctgaga atggatgttt tcttttgcta aaaggcacgg ctagtattaa gcataacatg   1800
atatgcggca gcggtctgta cccttcacag ctgttaactt gcgcggatgg aaactgtcag   1860
accttgcgca ccgtgcacat agcgtcccac cagcgccgcg cctggccaac attcgagcac   1920
aatatgctta tgcgttgtgc cgtccacttg ggccctaggc gaggcgtgtt tgtgccttac   1980
cagtgtaact ttagccatac caagattta ctagaacctg ataccttctc tcgagtgtgt   2040
ttcaatgggt gtttgacat gtcaatgaa ctgtttaaag tgataagata tgatgaatcc    2100
aagtctcgtt gtcgcccatg tgaatgcgga gctaatcatc tgaggttgta tcctgtaacc   2160
ctaaacgtta ccgaggagct gaggacggat caccacatgt tgtcctgcct gcgcaccgac   2220
tatgaatcca gcgacgagga gtgaggtgag gggcggagcc acaaagggta taaggggcg    2280 tgaggggtgg gtgtgatgat tcaaaatgag cgggacgacg gacggcaacg cgtttgaggg   2340
tggagtgttc agcccttatc tgacatctcg tcttccttcc tgggcaggag tgcgtcagaa   2400
tgtagtgggc tccaccgtgg acggacgacc ggtcgcccct gcaaattccg ccaccctcac   2460
ctatgccacc gtgggatcat cgttggacac tgccgcggca gctgccgctt ctgctgccgc   2520
ttctactgct cgcggcatgg cggctgattt tggactgtat aaccaactgg ccactgcagc   2580
tgtggcgtct cggtctctgg ttcaagaaga tgccctgaat gtgatcctga ctcgcctgga   2640
gatcatgtca cgtcgcttgg acgaactggc tgcgcagata tcccaagcta accccgatac   2700
cacttcagaa tcctaaaata aagacaaaca aatatgttga aaagtaaaat ggctttattt   2760
```

```
gttttttttg gctcggtagg ctcgggtcca cctgtctcgg tcgttaagaa ctttgtgtat    2820
gttttccaaa acacggtaca gatgggcttg gatgttcaag tacatgggca tgaggccatc    2880
tttggggtga agataggacc attgaagagc gtcatgctcc ggggtggtgt tgtaaattac    2940
ccagtcgtag cagggtttct gggcgtggaa ctggaagatg tcctttagga gtaggctgat    3000
ggccaagggc aggcccttag tgtaggtgtt tacaaagcgg ttaagctggg agggatgcat    3060 gcgggggag atgatatgca tcttggcttg gatcttgagg ttagctatgt taccacccag    3120
gtctctgcgg gggttcatgt tatgaaggac caccagcacg gtgtagccgg tgcatttggg    3180
gaacttgtca tgcagtttgg aggggaaggc gtggaagaat ttagagaccc ccttgtggcc    3240
ccctaggttt tccatgcact catccataat gatggcaatg ggaccctgg cggccgcttt    3300 ggcaaacacg ttttgggggt tggaaacatc atagttttgc tctagagtga gctcatcata    3360
ggccatctta acaaagcggg gtaggagggt gcccgactgg gggatgatag ttccatctgg    3420
gcctggggcg tagttaccct cacagatctg catctcccag gccttaattt ccgaggggg    3480 tatcatgtcc acctgggggg caataaagaa cacggtttct ggcgggggat tgatgagctg    3540
ggtggaaagc aagttacgca gcagttgaga tttgccacag ccggtggggc cgtagatgac    3600
cccgatgacg ggttgcagct ggtagttgag agaggaacag ctgccgtcgg ggcgcaggag    3660
gggggctacc tcattcatca tgcttctaac atgtttattt tcactcacta agttttgcaa    3720
gagcctctcc ccacccaggg ataagagttc ttccaggctg ttgaagtgtt tcagcggttt    3780
taggccgtcg gccatgggca tcttttcgag cgactgacga agcaagtaca gtcggtccca    3840
gagctcggtg acgtgctcta tggaatctcg atccagcaga cttcttggtt gcggggttg    3900 ggtcgacttt cgctgtaggg caccagccgg tgggcgtcca gggccgcgag ggttctgtcc    3960
ttccagggtc tcagcgtccg ggtgagggtg gtctcggtga cggtgaaggg atgagcccg    4020 ggctgggcgc ttgcgagggt gcgcttcagg ctcatcctgc tggtgctgaa gcggacgtcg    4080
tctccctgtg agtcggccag atagcaacga agcatgaggt cgtagctgag ggactcggcc    4140
gcgtgtccct ggcgcgcag ctttcccttg gaaacgtgct gacatttggt gcagtgcaga    4200
cattggaggg cgtagagttt gggggccagg aagaccgact cgggcgagta ggcgtcggct    4260
ccgcactgag cgcagacggt ctcgcactcc actagccacg tgagctcggg tttagcggga    4320
tcaaaaacca agttgcctcc attttttttg atgcgtttct taccttgcgt ttccatgagt    4380
ttgtggcccg cttccgtgac aaaaaggctg tcggtgtctc cgtagacaga cttgaggggg    4440
cgatcttcca aaggtgttcc gaggtcttcc gcgtacagga actgggacca ctccgagacg    4500
aaggctctgg tccaggctaa cacgaaggag gcaatctgcg aggggtatct gtcgttttca    4560 atgaggggt ccaccttttc cagggtgtgc agacacaggt cgtcctcctc cgcgtccacg    4620
aaggtgattg gcttgtaagt gtaggtcacg tgatctgcac cccccaaagg ggtataaaag    4680
ggggcgtgcc caccctctcc gtcactttct tccgcatcgc tgtggaccag agccagctgt    4740
tcgggtgagt aggccctctc aaaagccggc atgatctcgg cgctcaagtt gtcagtttct    4800
acaaacgagg tggatttgat attcacgtgc cccgcggcga tgcttttgat ggtggagggg    4860
tccatctgat cagaaaacac gatctttttg ttgtcaagtt tggtggcgaa agacccgtag    4920
agggcgttga aaagcaactt ggcgatggag cgcagggtct gatttttctc ccgatcggcc    4980
ctctccttgg cggcgatgtt gagttgcacg tactcccggg ccgcgcaccg ccactcgggg    5040
aacacggcgc tgcgctcgtc gggcaggatg cgcacgcgcc agccgcgatt gtgcagggtg    5100
atgaggtcca cgctggtagc cacctccccg cggaggggct cgttggtcca acacaatcgc    5160
```

```
ccccctttc tggagcagaa cggaggcagg ggatctagca agttggcggg cggggggtcg     5220
gcgtcgatgg tgaagatacc gggtagcagg atcttattaa aataatcgat ttcggtgtcc     5280
gtgtcttgca acgcgtcttc ccacttcttc accgccaggg ccctttcgta gggattcagg     5340
ggcggtcccc agggcatggg gtgggtcagg gccgaggcgt acatgccgca gatgtcatac     5400
acgtacaggg gttccctcaa cacccccgatg taagtggggt aacagcgccc cccgcggatg     5460
ctggctcgca cgtagtcgta catctcgcgc gagggagcca tgaggccgtc tcccaagtgg     5520
gtcttgtggg gttttccggc ccggtagagg atctgtctga agatggcgtg ggagttggaa     5580
gagatggtgg ggcgttggaa gacgttaaag ttggccccgg gtagtcccac ggagtcttgg     5640
atgaactggg cgtaggattc ccggagtttg tccaccaggg cggcggtcac cagcacgtcg     5700
agagcgcagt agtccaacgt ctcgcggacc aggttgtagg ccgtctcttg tttttctcc     5760
cacagttcgc ggttgaggag gtattcctcg cggtctttcc agtactcttc ggcgggaaat     5820
cctttttcgt ccgctcggta agaacctaac atgtaaaatt cgttcaccgc tttgtatgga     5880
caacagcctt tttctaccgg cagggcgtac gcttgagcgg cctttctgag agaggtgtgg     5940
gtgagggcga aggtgtcccg caccatcact ttcaggtact gatgtttgaa gtccgtgtcg     6000
tcgcaggcgc cctgttccca cagcgtgaag tcggtgcgct ttttctgcct gggattgggg     6060
agggcgaagg tgacatcgtt aaagagtatt ttccggcgc ggggcatgaa gttgcgagag     6120
atcctgaagg gccgggcac gtccgagcgg ttgttgatga cctgcgccgc caggacgatc     6180
tcgtcgaagc cgttgatgtt gtgacccacg atgtaaagtt cgatgaagcg cggctgtccc     6240
ttgagggccg gcgcttttt caactcctcg taggtgagac agtccggcga ggagagaccc     6300
agctcagccc gggcccagtc ggagagttga ggattagccg caaggaagga gctccataga     6360
tccaaggcca ggagagtttg caagcggtcg cggaactcgc ggaacttttt ccccacggcc     6420
attttctccg gtgtcactac gtaaaaggtg ttggggcggt tgttccacac gtcccatcgg     6480
agctctaggg ccagctcgca ggcttggcga acgagggtct cctcgccaga gacgtgcatg     6540
accagcataa agggtaccaa ctgttcccg aacgagccca tccatgtgta ggtttctacg     6600
tcgtaggtga caaagagccg ctgggtgcgc gcgtgggagc cgatcggaaa gaagctgatc     6660
tcctgccacc agctggagga atgggtgtta atgtggtgga agtagaagtc ccgccggcgc     6720
acagagcatt cgtgctgatg tttgtaaaag cgaccgcagt agtcgcagcg ctgcacgctc     6780
tgtatctcct gaacgagatg cgcttttcgc ccgcgcacca gaaaccggag ggggaagttg     6840
agacgggggg ctggtggggc gacatcccct tcgccttggc ggtgggagtc tgcgtctgcg     6900
tcctccttct ctgggtggac gacgtgggg acgacgacgc cccgggtgcc gcaagtccag     6960
atctccgcca cggaggggtg caggcgctgc aggaggggac gcagctgccc gctgtccagg     7020
gagtcgaggg aagtcgcgct gaggtcggcg ggaagcgttt gcaagttcac tttcagaaga     7080
ccggtaagag cgtgagccag gtgcagatgg tacttgattt ccaggggggt gttggatgaa     7140
gcgtccacgg cgtagaggag tccgtgtccg cgcggggcca ccaccgtgcc ccgaggaggt     7200
tttatctcac tcgtcgaggg cgagcgccgg ggggtagagg cggctctgcg ccgggggggca     7260
gcggaggcag aggcacgttt tcgtgaggat tcggcagcgg ttgatgacga gcccggagac     7320
tgctggcgtg ggcgacgacg cggcggttga ggtcctggat gtgccgtctc tgcgtgaaga     7380
ccaccggccc ccgggtcctg aacctaaaga gagttccaca gaatcaatgt ctgcatcgtt     7440
aacgcggcc tgcctgagga tctcctgcac gtcgcccgag ttgtcctgat aggcgatctc     7500
```

```
ggccatgaac tgttccactt cttcctcgcg gaggtcaccg tggcccgctc gctccacggt   7560
ggcggccagg tcgttggaga tgcggcgcat gagttgagag aaggcgttga ggccgttctc   7620
gttccacacg cggctgtaca ccacgtttcc gaaggagtcg cgcgctcgca tgaccacctg   7680
ggccacgttg agttccacgt ggcgggcgaa gacggcgtag tttctgaggc gctggaagag   7740
gtagttgagc gtggtggcga tgtgctcgca gacgaagaag tacataatcc agcgccgcag   7800
ggtcatctcg ttgatgtctc cgatggcttc gagacgctcc atggcctcgt agaagtcgac   7860
ggcgaagttg aaaaattggg agttgcgggc ggccaccgtg agttcttctt gcaggaggcg   7920
gatgagatcg cgaccgtgt cgcgcacctc ctgttcgaaa cgccccgag cgcctctgc   7980 ttcttcctcc ggctcctcct cttccagggg ctcgggttcc tccggcagct ctgcgacggg   8040
gacggggcgg cgacgtcgtc gtctgaccgg caggcggtcc acgaagcgct cgatcatttc   8100
gccgcgccgg cgacgcatgg tctcggtgac ggcgcgtccg ttttcgcgag gtcgcagttc   8160
gaagacgccg ccgcgcagag cgcccccgtg caggagggt aagtggttag ggccgtcggg   8220
cagggacacg gcgctgacga tgcattttat caattgctgc gtaggcactc cgtgcaggga   8280
tctgagaacg tcgaggtcga cgggatccga gaacttctct aggaaagcgt ctatccaatc   8340
gcaatcgcaa ggtaagctga gaacggtggg tcgctggggg gcgttcgcgg gcagttggga   8400
ggtgatgctg ctgatgatgt aattaaagta ggcggtcttc aggcggcgga tggtggcgag   8460
gaggaccacg tctttgggcc cggcctgttg aatgcgcagg cgctcggcca tgccccaggc   8520
ctcgctctga cagcgacgca ggtctttgta gaagtcttgc atcagtctct ccaccggaac   8580
ctctgcttct ccctgtctg ccatgcgagt cgagccgaac ccccgcaggg gctgcagcaa   8640
cgctaggtcg gccacgaccc tttcggccag cacggcctgt tgaatctgcg tgagggtggc   8700
ctggaagtcg tccaggtcca cgaagcggtg ataggccccc gtgttgatgg tgtaggtgca   8760
gttggccatg acggaccagt tgacgacttg catgccgggt tgggtgatct ccgtgtactt   8820
gaggcgcgag taggccctgg actcgaacac gtagtcgttg catgtgcgca ccagatactg   8880
gtagccgacc aggaagtgag gaggcggctc tcggtacagg ggccagccaa cggtggcggg   8940
ggcgccgggg gacaggtcgt ccagcatgag gcggtggtag tggtagatgt agcgggagag   9000
ccaggtgatg ccggccgagg tggttgcggc cctggtgaat tcgcggacgc ggttccagat   9060
gttgcgcagg ggaccaaagc gctccatggt gggcacgctc tgccccgtga ggcgggcgca   9120
atcttgtacg ctctagatgg aaaaaagaca gggcggtcat cgactccttt ccgtagcttg   9180
gggggtaaag tcgcaagggt gcggcggcgg ggaaccccgg ttcgagaccg gccggatccg   9240
ccgctcccga tgcgcctggc cccgcatcca cgacgtccgc gccgagaccc agccgcgacg   9300
ctccgcccca atacggaggg gagtcttttg gtgttttttc gtagatgcat ccggtgctgc   9360
ggcagatgcg acccagacg cccactacca ccgccgtggc ggcagtaaac ctgagcggag   9420
gcggtgacag ggaggaggaa gagctggctt tagacctgga agaggggagag gggctggccc   9480 ggctgggagc gccatcccca gagagacacc ctagggttca gctcgtgagg gacgccaggc   9540
aggcttttgt gccgaagcag aacctgttta gggaccgcag cggtcaggag gcggaggaga   9600
tgcgcgattg caggtttcgg gcgggcagag agctcagggc gggcttcgat cgggagcggc   9660
tcctgagggc ggaggatttc gagcccgacg agcgttctgg ggtgagcccg gccgcgctc   9720 acgtatcggc ggccaacctg gtgagcgcgt acgagcagac ggtgaacgag gagcgcaact   9780
tccaaaagag ctttaacaat cacgtgagga ccctgatcgc gagggaggag gtgaccatcg   9840
ggctgatgca tctgtgggac ttcgtggagg cctacgtgca gaacccggct agcaaacccc   9900
```

-continued

```
tgacggccca gctgttcctg atcgtgcagc acagccgcga caacgagacg ttccgcgacg    9960
ccatgttgaa catcgcggag cccgagggtc gctggctctt ggatctgatt aacatcctgc   10020
agagcatcgt ggtgcaggag aggggcctga gtttagcgga caaggtggcg gccattaact   10080
attcgatgca gagcctgggg aagttctacg ctcgcaagat ctacaagagc ccttacgtgc   10140
ccatagacaa ggaggtgaag atagacagct tttacatgcg catggcgctg aaggtgctga   10200
cgctgagcga cgacctcggc gtgtaccgta acgacaagat ccacaaggcg gtgagcgcca   10260
gccgccggcg ggagctgagc gacagggagc tgatgcacag cctgcagagg gcgctggcgg   10320
gcgccgggga cgaggagcgc gaggcttact tcgacatggg agccgatctg cagtggcgtc   10380
ccagcgcgcg cgccttggag gcggcgggtt atcccgacga ggaggatcgg gacgatttgg   10440
aggaggcagg cgagtacgag gacgaagcct gaccgggcag gtgttgtttt agatgcagcg   10500
gccggcggac gggaccaccg cggatcccgc acttttggca tccatgcaga gtcaaccttc   10560
gggcgtgacc gcctccgatg actgggcggc ggccatggac cgcatcatgg cgctgaccac   10620
ccgcaacccc gaggctttta ggcagcaacc ccaggccaac cgttttcgg ccatcttgga    10680
agcggtggtg ccgtcgcgca ccaacccgac gcacgagaaa gtcctgacta tcgtgaacgc   10740
cctggtagac agcaaggcca tccgccgtga cgaggcgggc ttgatttaca acgctctttt   10800
ggaacgcgtg gcgcgctaca acagcactaa cgtgcagacc aatctggacc gcctcaccac   10860
cgacgtgaag gaggcgctgg cgcagaagga gcggtttctg agggacagta atctgggctc   10920
tctggtggca ctgaacgcct tcctgagctc acagccggcc aacgtgcccc gcgggcagga   10980
ggattacgtg agcttcatca gcgctctgag actgctggtg tccgaggtgc cccagagcga   11040
ggtgtaccag tctgggccgg attactttt ccagacgtcc cgacagggct tgcaaacggt    11100
gaacctgact caggccttta aaaacttgca aggcatgtgg ggggtcaagg ccccggtggg   11160
cgatcgcgcc actatctcca gtctgctgac ccccaacact cgcctgctgc tgctcttgat   11220
cgcaccgttt accaacagta gcactatcag ccgtgactcg tacctgggtc atctcatcac   11280
tctgtaccgc gaggccatcg gccaggctca gatcgacgag catacgtatc aggagattac   11340
taacgtgagc cgtgccctgg gtcaggaaga taccggcagc ctggaagcca cgttgaactt   11400
tttgctaacc aaccggaggc aaaaaatacc ctcccagttc acgttaagcg ccgaggagga   11460
gaggattctg cgatacgtgc agcagtccgt gagcctgtac ttgatgcgcg agggcgccac   11520
cgcttccacg gctttagaca tgacggctcg gaacatggaa ccgtccttt actccgccca    11580
ccggccgttc attaaccgtc tgatggacta cttccatcgc gcggccgcca tgaacgggga   11640
gtacttcacc aatgccatcc tgaatccgca ttggatgccc ccgtccggct tctacaccgg   11700
ggagtttgac ctgcccgaag ccgacgacgg cttttctgtgg gacgacgtgt ccgatagcat   11760
tttcacgccg gctaatcgcc gattccagaa gaaggagggc ggagacgagc tcccctctc    11820
cagcgtggaa gcggcctcaa ggggagagag tccctttcca gtctgtctt ccgccagtag    11880
cggtcgggta acgcgtccac ggttgccggg ggagagcgac tacctgaacg accccttgct   11940
gcgaccggct agaaagaaaa attttcccaa taacggggtg gaaagcttgg tggataaaat   12000
gaatcgttgg aagacgtacg cccaggagca gcggagtgg gaggacagtc agccgcggcc    12060
gctggtaccg ccgcattggc gtcgccagag agaagacccg gacgactccg cagacgatag   12120
tagcgtgttg gacctgggag ggagcggagc caacccctt gctcacttgc aacccaaggg    12180
gcgctcgagt cgcctgtatt aataaaaaag acgcggaaac ttaccagagc catggccaca   12240
```

```
gcgtgtgtgc tttcttcctc tctttcttcc tcggcgcggc agaatgagaa gagcggtgag   12300
agtcacgccg gcggcgtatg agggcccgcc cccttcttac gaaagcgtga tgggatcagc   12360
gaacgtgccg gccacgctgg aggcgcctta cgttcctccc agatacctgg gacctacgga   12420
gggcagaaac agcatccgtt actccgagct ggcgcccctg tacgatacca ccaaggtgta   12480
cctggtggac aacaagtcgg cggacatcgc ctccctgaat taccaaaacg atcacagtaa   12540
ctttctgact accgtggtgc agaacaatga cttcaccccg acggaggcgg gcacgcagac   12600
cattaacttt gacgagcgtt cccgctgggg cggtcagctg aaaaccatcc tgcacaccaa   12660
catgcccaac atcaacgagt tcatgtccac caacaagttc agggctaagc tgatggtaga   12720
aaaaagtaat gcggaaactc ggcagccccg atacgagtgg ttcgagttta ccattccaga   12780
gggcaactat tccgaaacta tgactatcga tctcatgaat aacgcgatcg tggacaatta   12840
cctgcaagtg gggagacaga acggggtgct ggaaagcgat atcggcgtga aattcgatac   12900
cagaaacttc cgactggggt gggatcccgt gaccaagctg gtgatgccag gcgtgtacac   12960
caacgaggct tttcacccgg acatcgtgct gctgccgggg tgcggtgtgg acttcactca   13020
gagccgtttg agtaacctgt taggaattag aaagcgccgc cccttccaag agggctttca   13080
aatcatgtat gaggacctgg agggaggtaa tatacccgcc ttactggacg tgtcgaagta   13140
cgaagctagc atacaacgcg ccaaagcgga gggtagagag attcggggag acacctttgc   13200
ggtagctccc caggacctgg aaatagtgcc tttaactaaa gacagcaaag acagaagcta   13260
caatattata aacaacacga cggacaccct gtatcggagc tggtttctgg cttacaacta   13320
cggagacccc gagaaaggag tgagatcatg gaccatactc accaccacgg acgtgacctg   13380
tggctcgcag caagtgtact ggtccctgcc ggatatgatg caagacccgg tcaccttccg   13440
cccctccacc caagtcagca acttcccggt ggtgggcacc gagctgctgc ccgtccatgc   13500
caagagcttc tacaacgagc aggccgtcta ctcgcaactt attcgccagt ccaccgcgct   13560
tacccacgtg ttcaatcgct ttcccgagaa ccagattctg gtgcgccctc ccgctcctac   13620
cattaccacc gtcagtgaaa acgttcccgc cctcacagat cacggaaccc tgccgctgcg   13680
cagcagtatc agtggagttc agcgcgtgac catcaccgac gccagacgtc gaacctgccc   13740
ctacgtttac aaagcgcttg gcgtggtggc tcctaaagtt cttttctagtc gcaccttcta   13800 aaaacatgtc catcctcatc tctcccgata caacaccggc tggggactg ggctccggca   13860 agatgtacgg cggagccaaa aggcgctcca gtcagcaccc agttcgagtt cggggccact   13920
tccgcgctcc ttggggagct tacaagcgag gactctcggg tcgaacggct gtagacgata   13980
ccatagatgc cgtgattgcc gacgcccgcc ggtacaaccc cggaccggtc gctagcgccg   14040
cctccaccgt ggattccgtg atcgacagcg tggtagccgg cgctcgggcc tatgctcgcc   14100
gcaagaggcg gctgcatcgg agacgtcgcc ccaccgccgc catgctggca gccagggccg   14160
tgctgaggcg ggcccggagg gcaggcagaa gggctatgcg ccgcgctgcc gccaacgccg   14220
ccgccgggag ggcccgccga caggctgccc gccaggctgc cgctgccatc gctagcatgg   14280
ccagacccag gagagggaac gtgtactggg tgcgtgattc tgtgacggga gtccgagtgc   14340
cggtgcgcag ccgacctccc cgaagttaga agatccaagc tgcgaagacg gcggtactga   14400
gtctccctgt tgttatcagc ccaacatgag caagcgcaag tttaaagaag aactgctgca   14460
gacgctggtg cctgagatct atggccctcc ggacgtgaag ccagacatta agccccgcga   14520
tatcaagcgt gttaaaaagc gggaaaagaa agaggaactc gcggtggtag acgatggcgg   14580
agtggaattt attaggagtt cgccccgcg acgcagggtt caatggaaag ggcggcgggt   14640
```

```
acaacgcgtt ttgaggccgg gcaccgcggt agtttttacc ccgggagagc ggtcggccgt   14700 tagggggtttc aaaaggcagt acgacgaggt gtacggcgac gaggacatat tggaacaggc   14760
ggctcaacag atcggagaat ttgcctacgg aaagcgttcg cgtcgcgaag acctggccat   14820
cgccttagac agcggcaacc ccacgcccag cctcaaaccc gtgacgctgc agcaggtgct   14880
tcccgtgagc gccagcacgg acagcaagag ggggattaag agagaaatgg aagatctgca   14940
tcccaccatc caactcatgg tccctaaacg gcagaggctg gaagaggtcc tggagaagat   15000
gaaagtggac cccagcatag agccggatgt aaaagtcaga cctattaagg aagtgggccc   15060
cggtcttggg gtgcaaacgg tggacattca atccccgtc accaccgctt caaccgccgt   15120
ggaagctatg gaaacgcaaa cggagacccc tgccgcgatc ggtaccaggg aagtggcgtt   15180
gcaaacggag ccttggtacg aatacgcagc ccctcggcgt cagaggcgtt ccgctcgtta   15240
cggccccgcc aacgccatca tgccagaata tgcgctgcat ccgtctattc tgcccactcc   15300
cggataccgg ggtgtgacgt atcgcccgtc tggaacccgc cgccgaaccc gtcgccgccg   15360
ccgctcccgt cgcgctctgg cccccgtgtc ggtgcggcgt gtgacccgcc ggggaaagac   15420
agtcgtcatt cccaacccgc gttaccaccc tagcatcctt taataactct gccgttttgc   15480
agatggctct gacttgccgc gtgcgccttc ccgttccgca ctatcgagga agatctcgtc   15540
gtaggagagg catgacgggc agtggtcgcc ggcgggcttt gcgcaggcgc atgaaaggcg   15600
gaattttacc cgccctgata cccataattg ccgccgccat cggtgccata cccggcgttg   15660
cttcagtggc gttgcaagca gctcgtaata aataaacaaa ggcttttgca cttatgacct   15720
ggtcctgact attttatgca gaaagagcat ggaagacatc aattttacgt cgctggctcc   15780
gcggcacggc tcgcggccgc tcatgggcac ctggaacgac atcggcacca gtcagctcaa   15840
cgggggcgct ttcaattggg ggagccttg gagcggcatt aaaaactttg gctccacgat   15900
taaatcctac ggcagcaaag cctggaacag tagtgctggt cagatgctcc gagataaact   15960
gaaggacacc aacttccaag aaaaagtggt caatggggtg gtgaccggca tccacggcgc   16020
ggtagatctc gccaaccaag cggtgcagaa agagattgac aggcgtttgg aaagctcgcg   16080
ggtgccgccg cagagagggg atgaggtgga ggtcgaggaa gtagaagtag aggaaaagct   16140
gcccccgctg gagaaagttc ccggtgcgcc tccgagaccg cagaagcggc ccaggccaga   16200
actagaagag actctggtga cggagagcaa ggagcctccc tcgtacgagc aagccttgaa   16260
agagggcgcc tctccacccct cctacccgat gactaagccg atcgcaccca tggctcgacc   16320
ggtgtacggc aaggattaca agcccgtcac gctagagctg ccccccaccgc ccccacgcg   16380 cccgaccgtc ccccccctgc cgactccgtc ggcggccgcg gcgggacccg tgtccgcacc   16440
atccgctgtg cctctgccag ccgcccgtcc agtggccgtg gccactgcca gaaacccccag   16500 aggccagaga ggagccaact ggcaaagcac gctgaacagc atcgtgggcc tgggagtgaa   16560
aagcctgaaa cgccgccgtt gctattatta aaaaagtgta gctaaaaagt ctcccgttgt   16620
atacgcctcc tatgttaccg ccagagacga gtgactgtcg ccgcgagcgc cgcttttcaag   16680 atggccaccc catcgatgat gccgcagtgg tcttacatgc acatcgccgg ccaggacgcc   16740
tcggagtacc tgagtccgg cctcgtgcag tttgcccgcg ccaccgacac ctacttcagc   16800
ttgggaaaca agtttagaaa ccccaccgtg gcccccaccc acgatgtgac cacggaccgc   16860
tcgcagaggc tgacccctgcg cttttgtgccc gtagaccggg aggacaccgc gtactcttac   16920
aaagtgcgct acacgttggc cgtaggggac aaccgagtgc tggacatggc cagcacctac   16980
```

```
tttgacatcc ggggggtgct ggatcggggt cccagcttca agccctattc cggcaccgct    17040
tacaactccc tggcccccaa gggagctccc aaccccctcgg aatggacgga cacttccgac   17100
aacaaactta aagcatatgc tcaggctccc taccagagtc aaggacttac aaaggatggt    17160
attcaggttg ggctagttgt gacagagtca ggacaaacac cccaatatgc aaacaaagtg   17220
taccaacccg agccacaaat tggggaaaac caatggaatt tagaacaaga agataaagcg   17280
gcgggaagag tcctaaagaa agataccccct atgtttccct gctatgggtc atatgccagg   17340
cccacaaacg aacaaggagg gcaggcaaaa aaccaagaag tagatttaca gttttttgcc    17400
actccgggcg acacccagaa cacggctaaa gtggtacttt atgctgaaaa tgtcaacctg    17460
gaaactccag atactcactt agtgtttaaa cccgatgacg acagcaccag ttcaaaactt    17520
cttcttgggc agcaggctgc acctaacaga cccaactaca taggttttag agataatttt   17580
attggtttaa tgtactacaa tagcactgga aacatgggcg tgctggccgg acaggcttct   17640
caattgaatg ccgtagtcga cttgcaggac agaaacaccg agttgtccta ccagctgatg    17700
ctggacgcac tgggggatcg cagccgatat ttttcaatgt ggaatcaggc agtagacagc    17760
tatgacccag acgttagaat tatagaaaac cacggagtgg aagacgaact gccaaactat    17820
tgttttcctc tgggaggaat ggtggtgact gacaattaca actctgtgac gcctcaaaat    17880
ggaggcagtg gaaatacatg gcaggcagac aatactacat ttagtcaaag aggagcgcag    17940
attggctccg gaaacatgtt tgccctggaa attaacctac aggccaacct ctggcgcggc   18000
ttcttgtatt ccaatattgg gttgtatctt ccagactctc tgaaaatcac ccccgacaac    18060
atcacgctgc cagaaaacaa aaacacttat cagtacatga acggtcgcgt aacgccaccc    18120
gggctcatag acacctatgt aaacgtgggc gcgcgctggt cccccgatgt catggacagc    18180
attaacccct tcaaccacca ccgtaacgcg ggcttgcgct accgctccat gctcttgggc    18240
aacggccgtt atgtgccttt tcacattcag gtgccccaaa aattctttgc cattaaaaac    18300
ctgctgcttc tccccggttc ctatacctat gagtggaact tccgcaagga tgtcaacatg    18360
atcctgcaga gctcgctggg taatgacctg cgagtggacg gggccagcat acgctttgac    18420
agcattaacc tgtatgccaa cttttttccc atggcccaca acacggcctc taccctggaa    18480
gccatgctgc gcaacgacac caatgaccag tccttcaacg actacctgtg cgcggctaac    18540
atgctgtacc ccatccccgc caacgccacc agcgtgccca tttctattcc ttctcggaac    18600
tgggctgcct tcaggggctg gagttttact cgcctcaaaa ccaaggagac tccctcgctg    18660
ggctccggtt tgaccccta ctttgtttac tccggctcca ttccctacct agatggcacc    18720
ttttacctca accacactt caaaaaggtg tctattatgt ttgactcctc ggttagctgg    18780
cccggcaacg accgcctgct aacgcccaac gagttcgaaa ttaagcgttc cgtggacggt    18840
gaagggtaca acgtggccca gagcaacatg accaaggact ggtttctaat tcaaatgctc    18900
agtcactata ataggtta ccagggcttc tatgtgcccg agaactacaa ggaccgcatg    18960
tactccttct tccgcaactt ccaaccaatg agccggcagg tggtagatac cgtgacttat   19020
acagactaca aagatgtcaa gctcccctac caacacaaca actcagggtt cgtgggctac   19080
atgggaccca ccatgcgaga gggacaggcc tacccggcca actatcccta cccctgatc    19140 ggagagactg ccgtacccag cctcacgcag aaaaagttcc tctgcgaccg ggtgatgtgg   19200 aggatacccct tctctagcaa ctttatgtcg atgggctccc tcaccgacct ggggcagaac   19260
atgctgtacg ccaactccgc tcacgccttg gacatgactt ttgaggtgga tcccatggat    19320
gagcccacgc ttctctatgt tctgtttgaa gtcttcgacg tggtgcgcat ccaccagccg    19380
```

```
caccgcggcg tcatcgaggc cgtctacctg cgcacacctt tctctgccgg taacgccacc   19440
acctaaagaa gctgatgggt tccagcgaac aggagttgca ggccattgtt cgcgacctgg   19500
gctgcgggcc ctgcttttg gcaccttcg acaagcgttt tcccggattc atgtcccccc    19560
acaagccggc ctgcgccatc gttaacacgg ccggacggga gacaggggg gtgcactggc   19620 tcgccttcgc ctggaacccg cgcaaccgca cctgctacct gttcgaccct tttggtttct   19680
ccgacgaaag gctgaagcag atctaccaat tcgagtacga ggggctcctc aagcgcagcg   19740
ctctggcctc cacgcccgac cactgcgtca ccctggaaaa gtccacccag acggtccagg   19800
ggcccctctc ggccgcctgc gggcttttct gttgcatgtt tttgcacgcc ttcgtgcact   19860
ggcctcacac ccccatggag cgcaacccca ccatggatct gctcaccgga gtcccaaca   19920 gcatgcttca cagtccccag gtcgccccca ccctgcgtcg caatcaggac cacctgtatc   19980
gctttctggg gaaacactct gcctatttcc gccgccaccg gcagcgcatc gaacaggcca   20040
cggccttcga aagcatgagc caaagagtgt aatcaataaa aaccgttttt atttgacatg   20100
atacgcgctt ctggcgtttt tattaaaaat cgaagggttc gagggagggg tcctcgtgcc   20160
cgctggggag ggacacgttg cggtactgga atcggcgct ccaacgaaac tcggggatca   20220
ccagccgcgg cagggccacg tcttccatgt tctgcttcca aaactgtcgc accagctgca   20280
gggctcccat cacgtcgggc gctgagatct tgaagtcgga gttagggccg gagcccccgc   20340
ggctgttgcg gaacacgggg ttggcacact ggaacaccaa cacgctgggg ttgtggatac   20400
tagccagggc cgtcgggtcg gtcacctccg atgcatccag atcctcggca ttgctcaggg   20460
cgaacggggt cagcttgcac atctgccgcc cgatctgggg taccaggtcg cgcttgttga   20520
ggcagtcgca gcgcagaggg atgaggatgc gacgctgccc gcgttgcatg atggggtaac   20580
tcgccgccag gaactcctct atctgacgga aggccatctg ggccttgacg ccctcggtga   20640
aaaatagccc acaggacttg ctggaaaaca cgttattgcc acagttgatg tcttccgcgc   20700
agcagcgcgc atcttcgttc ttcagctgaa ccacgttgcg accccagcgg ttctgaacca   20760
ccttggcttt cgtgggatgc tccttcagcg cccgctgtcc gttctcgctg gtcacatcca   20820
tttccaccac gtgctccttg cagaccatct ccactccgtg gaaacagaac agaatgccct   20880
cctgttgggt attgcgatgc tcccacacgg cgcaccggt ggactccag ctcttgtgtt    20940 tcaccccgc gtaggcttcc atgtaagcca ttagaaatct gcccatcagc tcagtgaagg    21000
tcttctggtt ggtgaaggtt agcggcaggc gcggtgttc ctcgttcaac caagtttgac    21060
agatcttgcg gtacacggct ccctggtcgg gcagaaactt aaaagtcgtt ctgctctcgt   21120
tgtccacgtg gaacttctcc atcaacatcg tcatgacttc catgcccttc tcccaggcag   21180
tcaccagcgg cgcgctctcg gggttcttca ccaacacggc ggtggagggg ccctcgccgg   21240
ccccgacgtc cttcatggac atttttgaa actccacggt gccgtccgcg cggcgtactc    21300
tgcgcatcgg agggtagctg aagcccacct ccatgacggt gctttcgccc tcgctgtcgg   21360
agacgatctc cggggagggc ggcggaacgg gggcagactt gcgagccttc ttcttgggag   21420
ggagcggagg cacctcctgc tcgcgctcgg gactcatctc ccgcaagtag ggggtgatgg   21480
agcttcctgg ttggttctga cggttggcca ttgtatccta ggcagaaaga catggagctt   21540
atgcgcgagg aaactttaac cgccccgtcc ccgtcagcg acgaagaggt catcgtcgaa    21600
caggacccgg gctacgttac gccgcccgag gatctggagg ggcccttaga cgaccggcgc   21660
gacgctagtg agcggcagga aaatgagaaa gaggaggagg agggctgcta cctcctggaa   21720
```

```
ggcgacgttt tgctaaagca tttcgccagg cagagcacca tactcaagga ggccttgcaa   21780
gaccgctccg aggtgccctt ggacgtcgcc gcgctctccc aggcctacga ggcgaacctt   21840
ttctcgcccc gagtgcctcc gaagagacag cccaacggca cctgcgagcc caacccgcga   21900
ctcaacttct accccgtgtt cgccgtgccc gaggcgctgg ccacctacca catcttttc    21960 aaaaaccagc gcattcccct ttcctgccgg gccaaccgca ccgcggccga taggaagcta   22020
acactcagaa acggagtcag catacctgat atcacgtcac tggaggaagt gcctaagatc   22080
ttcgagggtc tgggtcgaga tgagaagcgg gcggcgaacg ctctgcagaa agaacagaaa   22140
gagagtcaga acgtgctggt ggagctggag ggggacaacg cgcgtctgac cgtcctcaaa   22200
cgttgcatag aagtttccca cttcgcctac ccggccctca acctgccgcc caaagttatg   22260
aaatcggtca tggaccagct actcatcaag agagctgagc ccctgaatcc cgaccaccct   22320
gaggcggaaa actcagagga cggaaagccc gtcgtcagcg acgaggagct cgagcggtgg   22380
ctggaaacca gggacccca gcagttgcaa gagaggcgca agatgatgat ggcggccgtg   22440
ctggtcacgg tggagctaga atgcctgcaa cggttttca gcgacgtgga gacgctacgc    22500
aaaatcgggg agtccctgca ctacaccttc cgccagggct acgttcgcca ggcctgcaaa   22560
atctccaacg tagagctcag caacctggtt tcctacatgg gcatcctcca cgagaaccgg   22620
ctggggcaga gcgtgctgca ctgcaccttg caaggcgagg cgcgaaggga ctacgtccga   22680
gactgcgtct acctcttcct caccctcacc tggcagaccg ccatgggcgt gtggcagcag   22740
tgcttggaag agagaaacct caaagagctg acaaactcc tctgccgcca gcggcgggcc    22800
ctctggaccg gcttcagcga gcgcacggtc gcctgcgccc tggcagacat cattttccca   22860
gaacgcctga tgaaaacctt gcagaacggc ctgccggatt tcatcagtca gagcatcttg   22920
caaaacttcc gctccttcgt cctggagcgc tccgggatct tgcccgccat gagctgcgcg   22980
ctgccttctg actttgtccc cctttcctac cgcgagtgcc ctcccccact gtggagccac   23040
tgctacctct tccaactggc caactttctg gcctaccact ccgacctcat ggaagacgtg   23100
agcggagagg ggctgctcga gtgccactgc cgctgcaacc tctgcacccc ccacagatcg   23160
ctggcctgca acaccgagct gctcagcgaa acccaggtca taggtacctt cgagatccag   23220
gggccccagc agcaagaggg tgcttccggc ttgaagctca ctccggcgct gtggacctcg   23280
gcttacttac gcaaatttgt agccgaggac taccacgccc acaaaattca gttttacgaa   23340
gaccaatctc gaccaccgaa agccccctc acggcctgcg tcatcaccca gagcaaaatc    23400
ctggcccaat tgcaatccat caaccaagcg cgccgagatt tccttttgaa aaagggtcgg   23460
ggggtgtacc tggaccccca gaccggcgag gaactcaacc cgtccacact ttccgtcgaa   23520 gcagccccc cgagacatgc cacccaaggg aaccgccaag cagctgatcg ctcggcgag     23580 agcgaagaag caagagctgc tccagcagca ggtggaggac gaggaagagc tgtgggacag   23640
ccaggcagag gaggtgtcag aggacgagga ggagatggaa agctgggaca gcctagacga   23700
ggaggacgag ctttcagagg aagaggcgac cgaagaaaaa ccacctgcat ccagcgcgcc   23760
ttctctgagc cgacagccga agccccgcc cccgacgccc ccggccggct cactcaaagc    23820
cagccgtagg tgggacgcca ccggatctcc agcggcagcg caacggcag cgggtaaggc    23880 caaacgcgag cggcggggt attgctcctg gcggacccac aaaagcagta tcgtgaactg    23940
cttgcaacac tgcgggggaa acatctcctt tgcccgacgc tacctcctct tccatcacgg   24000
tgtggccttc cctcgcaacg ttctctatta ttaccgtcat ctctacagcc cctacgaaac   24060
gctcggagaa aaaagctaag gcctcctctg ccgcgaggaa aaactccgcc gccgctgccg   24120
```

```
ccaaggatcc gccggccacc gaggagctga gaaagcgcat ctttcccact ctgtatgcta  24180
tctttcagca aagccgcggg cagcaccctc agcgcgaact gaaaataaaa aaccgctcct  24240
tccgctcact cacccgcagc tgtctgtacc acaagagaga agaccagctg cagcgcaccc  24300
tggacgacgc cgaagcactg ttcagcaaat actgctcagc gtctcttaaa gactaaaaga  24360
cccgcgcttt ttccccctcg ggcgccaaaa cccacgtcat cgccagcatg agcaaggaga  24420
ttcccacccc ttacatgtgg agctatcagc cccagatggg cctggccgcg ggggccgccc  24480
aggactactc cagcaaaatg aactggctca gcgccggccc ccacatgatc tcacgagtta  24540
acggcatccg agcccaccga aaccagatcc tcttagaaca ggcggcaatc accgccacac  24600
cccggcgcca actcaacccg cccagttggc ccgccgccca ggtgtatcag gaaactcccc  24660
gcccgaccac agtcctcctg ccacgcgacg cggaggccga agtcctcatg actaactctg  24720
gggtacaatt agcgggcggg tccaggtacg ccaggtacag aggtcgggcc gctccttact  24780
ctcccgggag tataaagagg gtgatcattc gaggccgagg tatccagctc aacgacgagg  24840
cggtgagctc ctcaaccggt ctcagacctg acggagtctt ccagctcgga ggagcgggcc  24900
gctcttcctt caccactcgc caggcctacc tgaccctgca gagctcttcc tcgcagccgc  24960
gctccggggg aatcggcact ctccagttcg tggaagagtt cgtcccctcc gtctacttca  25020
acccgttttc cggctcacct ggacgctacc cggacgcctt cattcccaac tttgacgcag  25080
tgagtgaatc cgtggacggc tacgactgat gacagatggt gcggccgtga gagctcggct  25140
gcgacatctg catcactgcc gccagcctcg ctgctacgct cgggaggcga tcgtgttcag  25200
ctactttgag ctgccggacg agcaccctca gggaccggct cacggggttga aactcgagat  25260
tgagaacgcg cttgagtctc acctcatcga cgccttcacc gcccggcctc tcctggtaga  25320
aaccgaacgc gggatcacta ccatcaccct gttctgcatc tgccccacgc ccggattaca  25380
tgaagatctg tgttgtcatc tttgcgctca gtttaataaa aactgaactt tttgccgtac  25440
cttcaacgcc acgcgttgtt tctccttgtg aaaaaacccc aggagtcctt aacttacaca  25500
tagcaaaacc cttgtatttt accatagaaa acaactagc cctttcaatt ggaaaagggt  25560
taacaatttc tgctacagga cagttggaaa gcacagcaag cgtacaggac agcgctacac  25620
cacccctacg tggtatttcc cctttaaagc tgacagacaa cggttaaaca ttaagctatt  25680
cagatcccct gcgtgtggta ggtgaccaac ttacgtttaa ttttacttct ccactacgtt  25740
acgaaaatgg cagtcttaca ttcaactaca cttctcccat gacactaata acaacagtc  25800
ttgctattaa cgtcaatacc tccaaaggcc tcagtagtga caacggcaca ctcgctgtaa  25860
atgttactcc agattttaga tttaacagct ctggtgcctt aacttttggc atacaaagtc  25920
tatggacttt tccaaccaaa actcctaact gtaccgtgtt taccgaaagt gactccctgc  25980
tgagtctttg cttgactaaa tgcggagctc acgtacttgg aagcgtgagt ttaagcggag  26040
tggcaggaac catgctaaaa atgacccaca cttctgttac cgttcagttt tcgtttgatg  26100
acagtggtaa actaatattc tctccacttg cgaacaacac ttggggtgtt cgacaaagcg  26160
agagtccgtt gcccaaccca tccttcaacg ctctcacgtt tatgccaaac agtaccattt  26220
attctagagg agcaagtaac gaacctcaaa acaattatta tgtccagacg tatcttagag  26280
gcaacgtgcg aaagccaatt ctactaactg ttacctacaa ctcagttaat tcaggatatt  26340
ccttaacttt taaatgggat gctgtcgcca atgaaaaatt tgccactcct acatcttcgt  26400
tttgctatgt tgcagagcaa taaaaccctg ttaccccacc gtctcgtttt tttcagatga  26460
```

```
aacgagcgag agttgatgaa gacttcaacc cagtgtaccc ttatgacccc ccatacgctc  26520
ccgtcatgcc cttcattact ccgccttttc cctcctcgga tggttgcag gaaaaaccac   26580 ttggagtgtt aagtttaaac tacagggatc ccattactac acaaaatggg tctctcacgt   26640
taaaactagg aaacggcctc actctaaaca accagggaca gttaacatca actgctggcg   26700
aagtggagcc tccgctcact aatgctaaca acaaacttgc actagcctat agcgaaccat   26760
tagcagtaaa aagcaaccgc ctaactctat cacacaccgc tccccttgtc atcgctaata   26820
attctttagc gttgcaagtt tcagagccta ttttttgtaaa tgacgatgac aagctagccc   26880
tgcagacagc cgccccccctt gtaaccaacg ctggcaccct tcgcttacag agcgctgccc   26940
ctttaggatt ggttgaaaat actcttaaac tgctgttttc taaacccttg tatttgcaaa   27000
atgattttct tgcattagcc attgaacgcc cctggctgt agcagccgca ggtactctga   27060
ccctacaact tactcctcca ttaaagacta acgatgacgg gctaacacta tccacagtcg   27120
agccattaac tgtaaaaaac ggaaacctag gcttgcaaat atcgcgccct ttagttgttc   27180
aaaacaacgg cctttcgctt gctattaccc ccccgctgcg tttgtttaac agcgaccccg   27240
ttcttggttt gggcttcact tttcccctag ctgtcacaaa caacctcctc tccttaaaca   27300
tgggagacgg agttaaactt acctataata aactaacagc caatttgggt agggatttac   27360
aatttgaaaa cggtgcgatt gccgtaacgc ttactgccga attaccctttg caatacacta   27420 acaaacttca actgaatatt ggagctggcc ttcgttacaa tggagccagc agaaaactag   27480
atgtaaacat taaccaaaat aaaggcttaa cttgggacaa cgatgcagtt attcccaaac   27540
taggatcggg cttacaattt gaccctaatg gcaacatcgc tgttatccct gaaaccgtga   27600
agccgcaaac gttatggacg actgcagatc cctcgcctaa ctgctcagtg taccaggact   27660
tggatgccag gctgtggctc gctcttgtta aaagtggcga catggtgcat ggaagcattg   27720
ccctaaaagc cctaaagggg acgttgctaa atcctacagc cagctacatt tccattgtga   27780
tatattttta cagcaacgga gtcaggcgta ccaactatcc aacgtttgac aacgaaggca   27840
ccttagctaa cagcgccact tggggatacc gacaggggca atctgctaac actaatgtga   27900
ccaatgccac tgaatttatg cccagctcaa gcaggtaccc cgtgaataaa ggagacaaca   27960
ttcaaaatca atcttttttca tacacctgta ttaaaggaga ttttgctatg cctgtcccgt   28020
tccgtgtaac atataatcac gccctggaag ggtattccct taagttcacc tggcgcgttg   28080
tagccaatca ggccttttgat attccttgct gttcattttc atacatcaca gaataaaaaa   28140
ccactttttc atttttaattt ctttttatttt tacacgaaca gtgagacttc ctccaccctt   28200
ccatttgaca gcatacacca gcctctcccc cttcatagca gtaaactgtt gtgaatcagt   28260
ccggtatttg ggagttaaaa tccaaacagt ctctttggtg atgaaacgtc gatcagtaat   28320
ggacacaaat ccctgggaca ggttttccaa cgtttcggtg aaaaactgca caccgcccta   28380
caaaacaaac aggttcaggc tctccacggg ttatctcccc gatcaaactc agacagggta   28440
aaggtgcggt ggtgttccac taaaccacgc aggtggcgct gtctgaacct tcggtgcga   28500 ctcctgtgag gctggtaaga agttagattg tccagtagcc tcacagcatg tatcatcagt   28560
ctacgagtgc gtctggcgca gcagcgcatc tgaatctcac tgagattccg gcaagaatcg   28620
cacaccatca caatcaggtt gttcatgatc ccatagctga acacgctcca gccaaagctc   28680
attcgctcca acagcgccac cgcgtgtccg tccaaccttta ctttaacata aatcaggtgt   28740
ctgccgcgta caaacatgct acccacatac agaacttccc ggggcaggcc cctgttcacc   28800
acctgtctgt accagggaaa cctcacattt atcagggagc catagatggc cattttaaac   28860
```

```
caattagcta ataccgcccc accagctcta cactgaagag aaccgggaga gttacaatga    28920
cagtgaataa tccatctctc ataacccctg atggtctgat gaaaatctag atctaacgtg    28980
gcacaacaaa tacacacttt catatacatt ttcataacat gttttccca ggccgttaaa    29040
atacaatccc aatacacggg ccactcctgc agtacaataa agctaataca agatggtata    29100
ctcctcacct cactgacact gtgcatgttc atattttcac attctaagta ccgagagttc    29160
tcctctacag cagcactgct gcggtcctca caaggtggta gctggtgatg attgtagggg    29220
gccagtctgc agcgataccg tctgtcgcgt tgcatcgtag accaggaacc gacgcacctc    29280
ctcgtacttg tggtagcaga accacgtccg ctgccagcac gtctccacgt aacgccggtc    29340
cctgcgtcgc tcacgctccc tcctcaatgc aaagtgcaac cactcttgta atccacacag    29400
atccctctcg gcctccgggg tgatgcacac ctcaaaccta cagatgtctc ggtacagttc    29460
caaacacgta gtgagggcga gttccaacca agacagacag cctgatctat cccgacacac    29520
tggaggtgga ggaagacacg gaagaggcat gttattccaa gcgattcacc aacgggtcga    29580
aatgaagatc ccgaagatga caacggtcgc ctccggagcc ctgatggaat ttaacagcca    29640
gatcaaacgt tatgcgattc tccaagctat cgatcgccgc ttccaaaaga gcctggaccc    29700
gcacttccac aaacaccagc aaagcaaaag cactattatc aaactcttca atcatcaagc    29760
tgcaggactg tacaatgcct aagtaatttt cgtttctcca ctcgcgaatg atgtcgcggc    29820
agatagtctg aaggttcatc ccgtgcaggg taaaaagctc cgaaagggcg ccctctacag    29880
ccatgcgtag acacaccatc atgactgcaa gatatcgggc tcctgagaca cctgcagcag    29940
atttaacaga tcaaggtcag gttgctctcc gcgatcacga atctccatcc gcaaggtcat    30000
ttgcaaaaaa ttaaataaat ctatgccgac tagatctgtc aactccgcat taggaaccaa    30060
atcaggtgtg gctacgcagc acaaaagttc cagggatggt gccaaactca ctagaaccgc    30120
tcccgagtaa caaaactgat gaatgggagt aacacagtgt aaaatgtgca accaaaaatc    30180
actaaggtgc tcctttaaaa agtccagtac ttctatattc agtccgtgca agtactgaag    30240
caactgtgcg ggaatatgca caacaaaaaa aatagggcgg ctcagataca tgttgaccta    30300
aaataaaaag aatcattaaa ctaaagaagc ttggcgaacg gtgggataaa tgacacgctc    30360
cagcagcaga caggcaaccg gctgtccccg ggaaccgcgg taaaattcat ccgaatgatt    30420
aaaaagaaca acagaaactt cccaccatgt actcggttgg atctcctgag cacacagcaa    30480
tacccccctc acattcatgt ccgccacaga aaaaaacgt cccagatacc cagcggggat    30540
atccaacgac agctgcaaag acagcaaaac aatccctctg ggagcgatca caaaatcctc    30600
cggtgaaaaa agcacataca tattagaata accctgttgc tggggcaaaa aggcccggcg    30660
tcccagcaaa tgcacataaa tatgttcatc agccattgcc ccgtcttacc gcgtaatcag    30720
ccacgaaaaa atcgagctaa aattcaccca acagcctata gctatatata cactccgccc    30780
aatgacgcta ataccgcacc acccacgacc aaagttcacc cacacccaca aaacccgcga    30840
aaatccagcg ccgtcagcac ttccgcaatt tcagtctcac aacgtcactt ccgcgcgcct    30900
tttcacattc ccacacacac ccgcgccctt cgccccgccc tcgcgccacc ccgcgtcacc    30960
gcacgtcacc ccggccccgc ctcgctcctc cccgctcatt atcatattgg cacgtttcca    31020
gaataaggta tattattgat gatg                                          31044
```

<210> SEQ ID NO 6
<211> LENGTH: 34115
<212> TYPE: DNA

<213> ORGANISM: simian adenovirus SV-39

<400> SEQUENCE: 6

```
catcatcaat ataacaccgc aagatggcga ccgagttaac atgcaaatga ggtgggcgga      60
gttacgcgac ctttgtcttg ggaacgcgga agtgggcgcg gcgggtttcg gggaggagcg     120
cggggcgggg cggcgtgtc gcgcggcggt gacgcgccgg ggacccggaa attgagtagt     180
ttttattcat tttgcaagtt tttctgtaca ttttggcgca aaaactgaaa cgaggaagtg     240
aaaagtgaaa aatgccgagg tagtcaccgg gtggagatct gacctttgcc gtgtggagtt     300
tacccgctga cgtgtgggtt tcggtctcta tttttcact gtggttttcc gggtacggtc     360
aaaggtcccc attttatgac tccacgtcag ctgatcgcta gggtatttaa tgcgcctcag     420
accgtcaaga ggccactctt gagtgccggc gagaagagtt ttctcctccg cgttccgcca     480
actgtgaaaa atgaggaac ttcttgctat ctccggggct gccagcgacc gtagccgccg      540
agctgttgga ggacattgtt accggagctc tgggagacga tcctcaggtg atttctcact     600
tttgtgaaga ttttagtctt catgatctct atgatattga tccgggtgtt gagggggcaag    660
aggatgaatg gctggagtct gtggatgggt ttttccgga cgctatgctg ctagaggctg     720
atttgccacc acctcacaac tctcacactg agcccgagtc agctgctatt cctgaattgt     780
catcaggtga acttgacttg gcttgttacg agactatgcc tccggagtcg gatgaggagg     840
acagcgggat cagcgatccc acggctttta tggtctctaa ggcgattgct atactaaaag     900
aagatgatga tggcgatgat ggatttcgac tggacgctcc ggcggtgccg gggagagact     960
gtaagtcctg tgaataccac cgggatcgta ccggagaccc gtctatgttg tgttctctgt    1020
gttatctccg tcttaacgct gcttttgtct acagtaagtg ttttgtgctt ttttaccctg    1080
tggctttgtt gagtttattt ttttctgtgt ctcatagggt gttgtttatt ataggtcctg    1140
tttcagatgt ggaggaacct gatagtacta ctggaaatga ggaggaaaag ccctccccgc    1200
cgaaactaac tcagcgctgc agacctaata ttttgagacc ctcggcccag cgtgtgtcat    1260
cccggaaacg tgctgctgtt aattgcatag aagatttatt ggaagagccc actgaaccttt   1320
tggacttgtc cttaaagcga ccccgcccgc agtagggcgc ggtgccagtt ttttctctct    1380
agcttccggg tgactcagtg caataaaat tttcttggca acaggtgtat gtgtttactt     1440
tacgggcggg aagggattag gggagtataa agctggaggg gaaaaatctg aggctgtcag    1500
atcgagtgag aagttccatg gacttgtacg agagcctaga gaatctaagt tctttgcgac    1560
gtttgctgga ggaggcctcc gacagaacct cttacatttg gaggtttctg ttcggttccc    1620
ctctgagtcg cttttttgcac cgggtgaagc gagagcacct gacggaattt gatgggcttt    1680
tagagcagct gcctggactg tttgattctt tgaatctcgg ccaccggacg ctgctagagg    1740
agaggctttt tccacaattg gactttcct ctccaggccg tctgtgttca gcgcttgctt     1800
ttgctgtaca tctgttggac agatggaacg agcagacgca gctcagcccg ggttacactc    1860
tggacttcct gacgctatgc ctatggaagt tcggaatcag gagggggagg aagctgtacg    1920
ggcgcttggt ggagaggcat ccgtctctgc gccagcagcg tctgcaagct caagtgctgc    1980
tgaggcggga ggatctggaa gccatttcgg aggaggagag cggcatggaa gagaagaatc    2040
cgagagcggg gctggaccct ccggcggagg agtaggggga ataccggacc cttttcctga    2100
gttggctttg ggggcggtgg ggggcgcttc tgtggtacgt gaggatgaag aggggcgcca    2160
acgcggtcag aagagggagc attttgagtc ctcgactttc ttggctgatg taaccgtggc    2220
cctgatggcg aaaaacaggc tggaggtggt gtggtacccg gaagtatggg aggactttga    2280
```

-continued

```
gaaggggac ttgcacctgc tggaaaaata aactttgag caggtgaaaa catactggat    2340
gaacccggat gaggactggg aggtggtttt gaaccgatac ggcaaggtag ctctgcgtcc    2400
cgactgtcgc taccaggttc gcgacaaggt ggtcctgcga cgcaacgtgt acctgttggg    2460
caacggcgcc accgtggaga tggtggaccc cagaaggggt ggttttgtgg ccaatatgca    2520
agaaatgtgc cctggggtgg tgggcttgtc tggggtgact tttcatagtg tgaggtttag    2580
cggtagcaat tttgggggtg tggttattac cgcgaacact cctgtggtcc tgcataattg    2640
ctactttttt ggcttcagca acacctgtgt ggaaatgagg gtgggaggca aagtgcgcgg    2700
gtgttccttt tacgcttgct ggaaggggt ggtgagccag ggtaaggcta aagtgtctgt    2760
tcacaagtgt atgttggaga gatgcacctt gggcatttcc agtgagggct tcctccacgc    2820
cagcgacaac gtggcttctg acaacggctg cgcctttctt atcaagggag ggggtcgcat    2880
ctgtcacaac atgatatgcg gccctgggga tgtcccccca aagccttacc agatggttac    2940
ctgcacagat ggcaaggtgc gcatgctcaa gcctgtgcac attgtgggcc accggcgcca    3000
ccgctggcca gagtttgaac acaatgtgat gacccgctgt agcttgtacc tgggaggcag    3060
gcgaggagtt ttcttgccca gacagtgtaa cctggcccac tgcaacgtga tcatggaaca    3120
atccgccgct acccaggttt gctttggagg aatatttgat ataagcatgg tggtgtataa    3180
gatcctgcgc tacgacgact gtcgggctcg tactcgaacc tgcgactgcg gagcctctca    3240
cctgtgtaac ctgactgtga tgggatggt gactgaggag gtgcgactgg accactgtca    3300
gcactcttgc ctgcgggagg agttttcttc ctcggacgag gaggactagg taggtggttg    3360
gggcgtggcc agcgagaggg tgggctataa aggggaggtg tcggctgacg ctgtcttctg    3420
tttttcaggt accatgagcg gatcaagcag ccagaccgcg ctgagcttcg acggggccgt    3480
gtacagcccc tttctgacgg ggcgcttgcc tgcctgggcc ggagtgcgtc agaatgttac    3540
cggttcgacc gtggacggac gtcccgtgga tccatctaac gctgcttcta tgcgctacgc    3600
tactatcagc acatctactc tggacagcgc cgctgccgcc gcagccgcca cctcagccgc    3660
tctctccgcc gccaagatca tggctattaa cccaagcctt tacagccctg tatccgtgga    3720
cacctcagcc ctggagcttt accggcgaga tctagctcaa gtggtggacc aactcgcagc    3780
cgtgagccaa cagttgcagc tggtgtcgac ccgagtggag caactttccc gccctcccca    3840
gtaaccgcaa aaattcaata aacagaattt aataaacagc acttgagaaa gtttaaaact    3900
tgtggttgac tttattcctg gatagctggg gggagggaac ggcgggaacg gtaagacctg    3960
gtccatcgtt cccggtcgtt gagaacacgg tggattttt ccaagacccg atagaggtgg    4020
gtctgaacgt tgagatacat gggcatgagc ccgtctcggg ggtggaggta ggcccactgc    4080
agggcctcgt tttcaggggt ggtgttgtaa atgatccagt cgtaggcccc ccgctgggcg    4140
tggtgctgga agatgtcctt cagcagcaag ctgatggcaa cgggaagacc cttggtgtag    4200
gtgttgacaa agcggttgag ttgggagggg tgcatgcggg gactgatgag gtgcattttg    4260
gcctggatct tgaggttggc tatgttgccg cccagatcgc gcctgggatt catgttatgc    4320
aagaccacca gcaccgagta accggtgcag cgggggaatt tgtcgtgcag cttggaaggg    4380
aaagcgtgga agaatttgga gacccctcgg tgcccgccta ggttttccat gcactcatcc    4440
atgatgatgg cgatgggccc ccgggaggca gcctgggcaa aaacgttgcg ggggtccgtg    4500
acatcgtagt tgtggtcctg ggtgagttca tcataggaca tttttgacaaa gcgcgggcag    4560 agggtcccag actggggaat gatggttcca tccggtccgg gggcgtagtt gccctcgcag    4620
```

```
atttgcattt cccaggcttt gatttcagag ggagggatca tgtcaacctg ggggcgatg      4680 aaaaaaatgg tctctggggc gggggtgatg agctgggtgg aaagcaggtt gcgcaagagc      4740
tgtgacttgc cgcagccggt gggcccgtag atgacagcta tgacgggttg cagggtgtag      4800
tttagagagc tacaactgcc atcatccttc aaaagcgggg ccacactgtt taaaagttct      4860
ctaacatgta agttttcccg cactaagtcc tgcaggagac gtgaccctcc tagggagaga      4920
agttcaggaa gcgaagcaaa gttttttaagt ggcttgaggc catcggccaa gggcaagttc      4980
ctgagagttt gactgagcag ttccagccgg tcccagagct cggttacgtg ctctacggca      5040
tctcgatcca gcagacctcc tcgtttcggg ggttggggcg gctctggctg tagggaatga      5100
ggcggtgggc gtccagctgg gccatggtgc ggtccctcca tgggcgcagg gttctcttca      5160
gggtggtctc ggtcacggtg aatgggtggg ccccgggctg ggcgctggcc agggtgcgct      5220
tgaggctgag gcggctggtg gcgaaccgtt gcttttcgtc tccctgcaag tcagccaaat      5280
agcaacggac catgagctca tagtccaggc tctctgcggc atgtcctttg gcgcgaagct      5340
tgcctttgga aacgtgcccg cagtttgagc agagcaagca ttttagcgcg tagagttttg      5400
gcgccaagaa cacggattcc ggggaataag catccccacc gcagttggag caaacggttt      5460
cgcattccac cagccaggtc agctgaggat cttttgggtc aaaaaccaag cgcccgccgt      5520 ttttttgat gcgcttccta cctcgggtct ccatgaggcg gtgcccgcgt tcggtgacga      5580
agaggctgtc ggtgtctccg tagacggagg tcagggcgcg ctcctccagg ggggtcccgc      5640
ggtcctcggc gtagagaaac tcgcaccact ctgacataaa cgcccgggtc caggctagga      5700
cgaatgaggc gatgtgggaa gggtaccggt cgttatcgat gaggggggtcg gttttttcca      5760 aggtgtgcag gcacatgtcc ccctcgtccg cttccaaaaa tgtgattggc ttgtaggtgt      5820
aagtcacgtg atcctgtcct tccgcggggg tataaaaggg ggcgtttccc ccctcctcgt      5880
cactctcttc cggttcgctg tcgccaaagg ccagctgttg gggtacgtaa acgcgggtga      5940
aggcgggcat gacctgtgcg ctgaggttgt cagtttctat atacgaggaa gatttgatgg      6000
cgagcgcccc cgtggagatg cccttgaggt gctcggggcc catttggtca gaaaacacaa      6060
tctgtcggtt atcaagcttg gtggcaaaag acccgtagag ggcgttggag agcaacttgg      6120
cgatggagcg ctgggtttgg ttttttttccc ggtcggcttt ttccttggcc gcgatgttga      6180
gctggacgta ctccctggcc acgcacttcc agccgggaaa aacggccgtg cgctcgtccg      6240
gcaccagcct cacgctccat ccgcggttgt gcagggtgat gacgtcgatg ctggtggcca      6300
cctctccgcg caggggctcg ttggtccagc agaggcgacc gcccttgcga gagcagaagg      6360
ggggcagggg gtcaagcagg cgctcgtccg gggggtcggc gtcgatggta aagatggcgg      6420
gcagcaggtg tttgtcaaag taatcgatct gatgcccggg gcaacgcagg gcggtttccc      6480
agtcccgcac cgccaaggcg cgctcgtatg gactgagggg ggcgcccag ggcatgggat      6540 gcgtcagggc cgaggcgtac atgccgcaga tgtcatagac gtaaagggc tcctccagga      6600 cgccgaggta ggtggggtag cagcgccccc gcggatgct ggcccgtacg tagtcgtaga      6660
gctcgtgcga gggggccaga aggtggcggc tgaggtgagc gcgctggggc ttttcatctc      6720
ggaagaggat ctgcctgaag atggcgtggg agttggagga tggtgggc cgctgaaaaa      6780 tgttgaagcg ggcgtcgggc agacccacgg cctcgccgat aaagtgggcg taggactctt      6840
gcagcttttc caccagggag gcggtgacca gcacgtccag agcgcagtag tccagggttt      6900
cccgcacgat gtcataatgc tcttccttt tttccttcca gaggtctcgg ttgaagagat      6960
actcttcgcg gtctttccag tactcttgga gaggaaaccc gttttcgtct ccacggtaag      7020
```

```
agcccaacat gtaaaactgg ttgacggcct gatagggaca gcatcccttc tccacgggca   7080
gcgagtaggc cagggcggcc ttgcgcaggg aggtgtgagt cagggcaaag gtgtcgcgga   7140
ccataacttt tacaaactgg tacttaaagt cccggtcgtc gcacatgcct cgctcccagt   7200
ctgagtagtc tgtgcgcttt ttgtgcttgg ggttaggcag ggagtaggtg acgtcgttaa   7260
agaggatttt gccacatctg gcataaagt tgcgagagat tctgaagggg ccgggcacct    7320
ccgagcggtt gttgatgact tgggcagcca ggagaatttc gtcgaagccg ttgatgttgt   7380
gccccacgac gtagaactct atgaaacgcg gagcgccgcg cagcagggg cacttttcaa    7440 gttgctggaa agtaagttcc cgcggctcga cgccgtgttc cgtgcggctc cagtcctcca   7500
ccgggtttcg ctccacaaaa tcctgccaga tgtggtcgac tagcaagagc tgcagtcggt   7560
cgcgaaattc gcggaatttt ctgccgatgg cttgcttctg ggggttcaag caaaaaagg    7620 tgtctgcgtg gtcgcgccag gcgtcccagc cgagctcgcg agccagattc agggccagca   7680
gcaccagagc cggctcaccg gtgattttca tgacgaggag aaagggcacc agctgttttc   7740
cgaacgcgcc catccaggtg taggtctcca cgtcgtaggt gagaaacaga cgttcggtcc   7800
gcgggtgcga tcccaggggg aaaaacttga tgggctgcca ccattgggag ctctgggcgt   7860
ggatgtgatg gaagtaaaag tcccggcggc gcgtggaaca ttcgtgctgg tttttgtaaa   7920
agcggccgca gtggtcgcag cgcgagacgg agtgaaggct gtgaatcagg tgaatcttgc   7980
gtcgctgagg gggccccaga gccaaaaagc ggagcgggaa cgaccgcgcg gccacttcgg   8040
cgtccgcagg caagatggat gagggttcca ccgttccccg cccgcggacc gaccagactt   8100
ccgccagctg cggcttcagt tcttgcacca gctctcgcag cgtttcgtcg ctgggcgaat   8160
cgtgaatacg gaagttgtcg ggtagaggcg ggaggcggtg gacttccagg aggtgtgtga   8220
gggccggcag gagatgcagg tggtacttga tttcccacgg atgacggtcg cgggcgtcca   8280
aggcgaagag atgaccgtgg ggccgcgcg ccaccagcgt tccgcgggg gtctttatcg     8340 gcggcgggga cgggctcccg gcggcagcgg cggctcggga cccgcgggca agtcgggcag   8400
cggcacgtcg gcgtggagct cgggcagggg ctggtgctgc gcgcggagct gactggcaaa   8460
ggctatcacc cggcgattga cgtcctggat ccggcggcgc tgcgtgaaga ccaccggacc   8520
cgtggtcttg aacctgaaag agagttcgac agaatcaatc tcggcatcgt taaccgcggc   8580
ctggcgcagg atttcggcca cgtccccgga gttgtcttga tacgcgattt ctgccatgaa   8640
ctggtcgatt tcctcttcct gcaagtctcc gtgaccggcg cgttcgacgg tggccgcgag   8700
atcgttggag atgcggccca tgagctggga aaaggcattg atgccgacct cgttccacac   8760
tcggctgtac accacctctc cgtgaacgtc gcgggcgcgc atcaccacct gggcgagatt   8820
gagttccacg tggcgggcga aaaccggata gtttcggagg cgctgataca gatagttgag   8880
ggtggtggcg gcgtgctcgg ccacaaaaaa atacatgatc cagcggcgga gggtcagctc   8940
gttgatgtcg cccagcgcct ccaggcgttc catggcctcg taaaagtcca cggcaaagtt   9000
gaaaaattgg ctgttcctgg ccgagaccgt gagctcttct tccaagagcc gaatgagatc   9060
cgccacggtg gccctgactt cgcgttcgaa agccccgggt gcctcctcca cctcttcctc   9120
ctcgacttct tcgaccgctt cgggcacctc ctcttcctcg accaccacct caggcggggc   9180
tcggcggcgc cggcggcgga cgggcaggcg gtcgacgaaa cgctcgatca tttcccccct   9240
ccgtcgacgc atggtctcgg tgacggcgcg accctgttcg cgaggacgca gggtgaaggc   9300
gccgccgccg agcggaggta acagggagat cgggggggcgg tcgtggggga gactgacggc   9360
```

```
gctaactatg catctgatca atgtttgcgt agtgacctcg ggtcggagcg agctcagcgc    9420
ttgaaaatcc acgggatcgg aaaaccgttc caggaacgcg tctagccaat cacagtcgca    9480
aggtaagctg aggaccgtct cgggggcttg tctgttctgt cttcccgcgg tggtgctgct    9540
gatgaggtag ttgaagtagg cgctcttgag gcggcggatg tggacagga gaaccacgtc     9600
tttgcgccca gcttgctgta tccgcaggcg gtcggccatg ccccacactt ctccttgaca    9660
gcggcggagg tccttgtagt attcttgcat cagccttttcc acgggcacct cgtcttcttc    9720
ttccgctcgg ccggacgaga gccgcgtcag gccgtacccg cgctgcccct gtggttggag    9780
cagggccagg tcgccacga cgcgctcggc cagcacggcc tgctggatgc gggtgagggt    9840
gtcctgaaag tcgtcgagat ccacaaagcg gtggtacgcg ccagtgttga tggtgtaggt    9900
gcagttgctc atgacggacc agtttacggt ctgggtgcca tggcccacgg tttccaggta    9960
gcggagacgc gagtaggccc gcgtctcgaa gatgtagtcg ttgcaggtcc gcagcaggta    10020
ctggtagccc accagcagat gcggcggcgg ctggcggtag aggggccacc gctgggtggc    10080
gggggcgttg ggggcgagat cttccaacat gaggcggtga tagccgtaga tgtagcgcga    10140
catccaagtg atgccgctgg ccgtggtgct ggcgcgggcg tagtcgcgaa cgcggttcca    10200
gatgtttcgc agcggctgga agtactcgat ggtggggcga ctctgccccg tgaggcgggc    10260
gcagtcggcg atgctctacg gggaaaaaga agggccagtg aacaaccgcc ttccgtagcc    10320
ggaggagaac gcaagggggt caaagaccac cgaggctcgg gttcgaaacc cgggtggcgg    10380
cccgaatacg gagggcggtt ttttgctttt ttctcagatg catcccgtgc tgcggcagat    10440
gcgtccgaac gcggggtccc agtccccggc ggtgcctgcg gccgtgacgg cggcttctac    10500
ggccacgtcg cgctccaccc cgcctaccac ggcccaggcg gcggtggctc tgcgcggcgc    10560
aggggaaccc gaagcagagg cggtgttgga cgtggaggag ggccaggggt tggctcggct    10620
gggggccctg agtcccgagc ggcacccgcg cgtggctctg aagcgcgacg cggcggaggc    10680
gtacgtgccg cggagcaatc tgtttcgcga ccgcagcggc gaggaggccg aggagatgcg    10740
agacttgcgt tttcgggcgg ggagggagtt gcgtcacggg ctggaccggc agagggttct    10800
gagagaggag gactttgagg cggacgagcg cacggggtg agtcccgcgc gggctcacgt     10860
ggcggccgcc aacctggtga gcgcgtacga gcagacggtc aaggaggaga tgaacttcca    10920
gaagagcttc aatcatcacg tgcgcacgct gattgcgcgc gaagaggtgg ccatcggcct    10980
catgcatctg tgggattttg tggaggcgta cgttcagaac cccagcagca agccgctgac    11040
ggctcagctg ttcctcatcg tgcaacatag tcgagacaac gaaacgttca gggaggccat    11100
gctgaacatt gcagagcctg aggggcgctg gctcttggat ctcattaaca tcttgcagag    11160
tatcgtagtg caggagcgct cgctgagcct ggccgacaag gtggctgcca tcaactacag    11220
catgctgtcg ctgggcaaat tttacgcccg caagatctac aagtctccgt tcgtccccat    11280
agacaaggag gtgaagatag acagctttta catgcgcatg gcgctcaagg tgctgactct    11340
aagcgacgac ctgggggtgt accgcaacga ccgcatacac aaggcggtga gcgccagccg    11400
ccggcgcgag ctgagcgacc gcgagctttt gcacagcctg catcgggcgt tgactggtgc    11460
cggcagcgcc gaggcggccg agtactttga cgccggagcg gacttgcgct ggcagccatc    11520
ccgacgcgcg ctgaggcgg ctggcgtcgg ggagtacggg gtcgaggacg acgatgaagc    11580
ggacgacgag ttgggcattg acttgtagcc gttttttcgtt agatatgtcg gcgaacgagc    11640
cgtctgcggc cgccatggtg acggcggcgg gcgcgcccca ggaccggcc acgcgcgcgg    11700
cgctgcagag tcagccttcc ggagtgacgc ccgcggacga ctggtccgag gccatgcgtc    11760
```

```
gcatcctggc gctgacggcg cgcaacccg  aggcttttcg gcagcagccg caggcaaacc   11820
ggtttgcggc cattttggaa gcggtggtgc cctccagacc caaccccacc cacgaaaagg   11880
tgctggccat cgtcaacgcc ctggcggaga ccaaggccat ccgcccagac gaggccgggc   11940
aggtttacaa cgcgctgcta gaaagggtgg gacgctacaa cagctccaac gtgcagacca   12000
atctggaccg cttggtgacg gacgtgaagg aggccgtagc ccagcgagag cggttttttca  12060
aggaagccaa tctgggctcg ctggtggccc tcaacgcctt cctgagcacg ctgccggcga   12120
acgtgccccg cggtcaggag gactacgtga actttctgag cgccctccgc ctgatggtgg   12180
ccgaggtgcc gcagagcgag gtgtaccagt ctggcccaa  ctactacttc cagacctccc   12240
ggcagggcct gcagacggta aacctgacgc aggcctttca gaacctgcag ggcctttggg   12300
gggtgcgcgc tccgctgggc gaccgcagca cggtgtccag cctgctgacc cccaatgccc   12360
ggctgctctt gcttctcatt gctccgttca ccgacagcgg ttccatcagc cgcgactctt   12420
acctgggaca cctgctcacc ctgtaccggg aggccatcgg gcaggcgcgg gtggacgagc   12480
agacgtacca ggaaatcacc agcgtgagcc gcgcgctggg gcaggaggac acgggcagct   12540
tggaggcgac tctgaacttc ctgctgacca accggcggca gcgcctacct ccccagtacg   12600
cgctgaacgc ggaggaggag cgcatcctgc gtttcgtgca gcagagcacc gcgctgtact   12660
tgatgcggga aggcgcctct cccagcgctt cgctggacat gacggcggcc aacatggagc   12720
catcgttcta cgccgccaac cgtcccttcg tcaaccggct aatggactat ttgcatcggg   12780
cggcggcccct gaacccggaa tactttacta cgtcatcct  gaacgaccgt tggctgccac   12840
ctcccggctt ctacacgggg gagttcgacc tcccggaggc caacgacggt tcatgtggg    12900
acgacgtgga cagcgtgttc ctgcccggca agaaggaggc gggtgactct cagagccacc   12960
gcgcgagcct cgcagacctg ggggcgaccg ggcccgcgtc tccgctgcct cgcctgccga   13020
gcgccagcag cgccagcgtg gggcgggtga gccgtccgcg cctcagcggt gaggaggact   13080
ggtggaacga tccgctgctc cgtccggccc gcaacaaaaa cttccccaac aacgggatag   13140
aggatttggt agacaaaatg aaccgttgga agacgtatgc ccaggagcat cgggagtggc   13200
aggcgaggca acccatgggc cctgttctgc cgccctctcg gcgcccgcgc agggacgaag   13260
acgccgacga ttcagccgat gacagcagcg tgttggatct gggcgggagc gggaacccct   13320
ttgcccacct gcaacctcgc ggcgtgggtc ggcggtggcg ctaggaaaaa aaattattaa   13380
aagcacttac cagagccatg gtaagaagag caacaaaggt gtgtcctgct ttcttcccgg   13440
tagcaaaatg cgtcgggcgg tggcagttcc ctccgcggca atggcgttag gcccgccccc   13500
ttcttacgaa agcgtgatgg cagcggccac cctgcaagcg ccgttggaga atccttacgt   13560
gccgccgcga tacctggagc ctacgggcgg gagaaacagc attcgttact cggagctgac   13620
gcccctgtac gacaccaccc gcctgtacct ggtggacaac aagtcagcag atatcgccac   13680
cttgaactac cagaacgacc acagcaactt tctcacgtcc gtggtgcaga acagcgacta   13740
cacgcccgcc gaagcgagca cgcagaccat taacttggac gaccgctcgc gctggggcgg   13800
ggacttgaaa accattctgc acactaacat gcccaacgtg aacgagttca tgtttaccaa   13860
ctcgttcagg gctaaactta tggtggcgca cgaggccgac aaggacccgg tttatgagtg   13920
ggtgcagctg acgctgccgg aggggaactt ttcagagatt atgaccatag acctgatgaa   13980
caacgccatt atcgaccact acctggcggt agcagacag  caggggtgaa aagaaagcga   14040
gatcggcgtc aagtttgaca cgcgcaactt tcgtctgggc tgggacccgg agacggggct   14100
```

```
tgtgatgccg ggggtgtaca cgaacgaagc tttccatccc gacgtggtcc tcttgccggg    14160
ctgcggggtg gactttacct acagccggtt aaacaacctg ctaggcatac gcaagagaat    14220 gcccttcag  gaagggtttc agatcctgta cgaggacctg gagggcggta acatcccggc    14280
cctgctggac gtgccggcgt acgaggagag catcgccaac gcaagggagg cggcgatcag    14340
gggcgataat ttcgcggcgc agccccaggc ggctccaacc ataaaacccg ttttggaaga    14400
ctccaaaggg cggagctaca acgtaatagc caacaccaac aacacggctt acaggagctg    14460
gtatctggct tataactacg gcgacccgga aaggggggtt agggcctgga ccctgctcac    14520
cactccggac gtgacgtgcg gttcagagca ggtctactgg tcgctgcctg acatgtacgt    14580
ggaccctgtg acgtttcgct ccacgcagca agttagcaac tacccagtgg tgggagcgga    14640
gcttatgccg attcacagca agagcttta  caacgagcag gccgtctact cacagctcat    14700
tcgtcagacc accgccctaa cgcacgtttt caaccgcttc cccgagaacc aaatcctagt    14760
gcgacctcca gcgcccacca tcaccaccgt cagcgagaac gtgcccgctc taaccgatca    14820
cgggacgctg cctttgcaga acagcatccg cggagttcag cgagttacca tcacggacgc    14880
ccgtcgtcgg acctgtccct acgtctacaa agccttggga atcgtggccc cgcgcgtcct    14940
gtcgagtcgc actttctaga tgtccatcct catctctccc agcaacaata ccggttgggg    15000
tctgggcgtg accaaaatgt acggaggcgc caaacgacgg tccccacaac atcccgtgcg    15060
agtgcgcggg cactttagag ccccatgggg gtcgcacacg cgcgggcgca ccggccgaac    15120
caccgtcgac gacgtgatcg atagcgtggt ggccgacgcc cgcaactacc agcccgctcg    15180
atccacggtg gacgaagtca tcgacggcgt ggtggccgac gccagggcct acgcccgcag    15240
aaagtctcgt ctgcgccgcc gccgttcgct aaagcgcccc acggccgcca tgaaagccgc    15300
tcgctctctg ctgcgtcgcg cacgtatcgt gggtcgccgc gccgccagac gcgcagccgc    15360
caacgccgcc gccggccgag tgcgccgccg ggccgcccag caggccgccg ccgccatctc    15420
cagtctatcc gccccccgac gcgggaatgt gtactgggtc agggactcgg ccaccggcgt    15480
gcgagttccc gtgagaaccc gtcctcctcg tccctgaata aaaagttcta agcccaatcg    15540
gtgttccgtt gtgtgttcag ctcgtcatga ccaaacgcaa gtttaaagag gagctgctgc    15600
aagcgctggt ccccgaaatc tatgcgccgg cgccggacgt gaaaccgcgt cgcgtgaaac    15660
gcgtgaagaa gcaggaaaag ctagagacaa aagaggaggc ggtggcgttg ggagacgggg    15720
aggtggagtt tgtgcgctcg ttcgcgccgc gtcggcgagt gaattggaag gggcgcaagg    15780
tgcaacgggt gctgcgtccc ggcacggtgg tgtcttcac  cccgggtgaa aaatccgcct    15840
ggaagggcat aaagcgcgtg tacgatgagg tgtacgggga cgaagacatt ctggagcagg    15900
cgctggatag aagcggggag tttgcttacg gcaagagggc gaggacgggc gagatcgcca    15960
tcccgctgga cacttccaac cccacccca  gtctgaaacc cgtgacgctg caacaggtgt    16020
tgccggtgag cgccccctcg cgacgcggca taaaacgcga gggcggcgag ctgcagccca    16080
ccatgcagct cctggttccc aagaggcaga aactagagga cgtactggac atgataaaaa    16140
tggagcccga cgtgcagccc gatattaaaa tccgtcccat caaagaagtg gcgccgggaa    16200
tgggcgtgca gaccgtggac atccagattc ccatgaccag cgccgcacag cggtagagg    16260 ccatgcagac cgacgtgggg atgatgacgg acctgccgc  agctgctgcc gccgtggcca    16320
gcgccgcgac gcaaacggaa gccggcatgc agaccgaccc gtggacggag gcgcccgtgc    16380
agccggccag aagacgcgtc agacggacgt acggccccgt ttctggcata atgcggagt    16440 acgcgctgca tccttccatc atccccaccc ccggctaccg ggggcgcacc taccgtccgc    16500
```

```
gacgcagcac cactcgccgc cgtcgccgca cggcacgagt cgccaccgcc agagtgagac  16560
gcgtaacgac acgtcgcggc cgccgcttga ccctgcccgt ggtgcgctac catcccagca  16620
ttctttaaaa aaccgctcct acgttgcaga tgggcaagct tacttgtcga ctccgtatgg  16680
ccgtgcccgg ctaccgagga agatcccgcc gacgacggac tttgggaggc agcggtttgc  16740
gccgccgtcg ggcggttcac cggcgcctca agggaggcat tctgccggcc ctgatcccca  16800
taatcgccgc agccatcggg gccattcccg gaatcgccag cgtagcggtg caggctagcc  16860
agcgccactg attttactaa ccctgtcggt cgcgccgtct ctttcggcag actcaacgcc  16920
cagcatggaa gacatcaatt tctcctctct ggccccgcgg cacggcacgc ggccgtatat  16980
ggggacgtgg agcgagatcg gcacgaacca gatgaacggg ggcgctttca attggagcgg  17040
tgtgtggagc ggcttgaaaa atttcggttc cactctgaaa acttacggca accgggtgtg  17100
gaactccagc acggggcaga tgctgaggga caagctaaag acacgcagt ttcagcaaaa  17160 ggtggtggac ggcatcgctt cgggcctcaa cggcgccgtc gacctggcca accaggccat  17220
tcaaaaggaa attaacagcc gcctggagcc gcggccgcag gtggaggaga acctgccccc  17280
tctggaggcg ctgccccca agggagagaa gcgcccgcgg cccgacatgg aggagacgct  17340
agttactaag agcgaggagc cgccatcata cgaggaggcg gtgggtagct cgcagctgcc  17400
gtccctcacg ctgaagccca ccacctatcc catgaccaag cccatcgcct ccatggcgcg  17460
ccccgtggga gtcgacccgc ccatcgacgc ggtggccact ttggacctgc cgcgccccga  17520
acccggcaac cgcgtgcctc ccgtcccat cgctccgccg gtttctcgcc ccgccatccg  17580
ccccgtcgcc gtggccactc cccgctatcc gagccgcaac gccaactggc agaccaccct  17640
caacagtatt gtcggactgg gggtgaagtc tctgaagcgc cgtcgctgtt tttaaagcac  17700 aattttattaa acgagtagcc ctgtcttaat ccatcgttgt atgtgtgcct atatcacgcg  17760
ttcagagcct gaccgtccgt caagatggcc actccgtcga tgatgccgca gtggtcgtac  17820
atgcacatcg ccgggcagga cgcctcggag tacctgagcc cgggtctggt gcagtttgcc  17880
cgtgcgacgg aaacctactt ctcactgggc aacaagttca ggaaccccac cgtggcgccc  17940
acccacgacg tcaccaccga tcggtcccag cgactgacaa tccgcttcgt ccccgtggac  18000
aaggaagaca ccgcttactc ctacaaaacc cgcttcacgc tggccgtggg cgacaaccgg  18060
gtgctagaca tggccagtac ctactttgac atccgcggcg tgatcgaccg cggacctagc  18120
ttcaagcctt actccggcac ggcttacaac tcactggctc ccaaaggggc gcccaacaac  18180
agccaatgga acgccacaga taacgggaac aagccagtgt gttttgctca ggcagctttt  18240
ataggtcaaa gcattacaaa agacggagtg caaatacaga actcagaaaa tcaacaggct  18300
gctgccgaca aaacttacca accagagcct caaattggag tttccacctg ggataccaac  18360
gttaccagta acgctgccgg acgagtgtta aaagccacca ctcccatgct gccatgttac  18420
ggttcatatg ccaatcccac taatccaaac gggggtcagg caaaaacaga aggagacatt  18480
tcgctaaact ttttcacaac aactgcggca gcagacaata atcccaaagt ggttctttac  18540
agcgaagatg taaaccttca agcccccgat actcacttag tatataagcc aacggtggga  18600
gaaaacgtta tcgccgcaga agccctgcta acgcagcagg cgtgtcccaa cagagcaaac  18660
tacataggtt tccgagataa ctttatcggt ttaatgtatt ataacagcac agggaacatg  18720
ggagttctgg caggtcaggc ctcgcagtta aacgcagttg tagacctgca agatcgaaac  18780
acggaactgt cctatcagct aatgctagat gctctgggtg acagaactcg atatttctca  18840
```

```
atgtggaatc aggccgtgga cagctacgat ccagacgtta ggattatcga gaaccatggg   18900
gtggaagacg agctgcccaa ttactgtttt ccactcccag gcatgggtat ttttaactcc   18960
tacaagggg taaaaccaca aaatggcggt aatggtaact gggaagcaaa cggggaccta    19020
tcaaatgcca atgagatcgc tttaggaaac atttttgcca tggaaattaa cctccacgca   19080
aacctgtggc gcagcttctt gtacagcaat gtggcgctgt acctgccaga cagctataaa   19140
ttcactcccg ctaacatcac tctgcccgcc aaccaaaaca cctacgagta tatcaacggg   19200
cgcgtcactt ctccaaccct ggtggacacc tttgttaaca ttggagcccg atggtcgccg   19260
gatcccatgg acaacgtcaa ccccttaac catcaccgga acgcgggcct ccgttaccgc    19320
tccatgctgc tgggaaatgg acgcgtggtg ccttccaca tacaagtgcc gcaaaatt     19380
ttcgcgatta agaacctcct gcttttgccc ggctcctaca cttacgagtg gagcttcaga   19440
aaagacgtga acatgattct gcagagcacc ctgggcaatg atcttcgagt ggacggggcc   19500
agcgtccgca ttgacagcgt caacttgtac gccaactttt tccccatggc gcacaacacc   19560
gcttctacct tggaagccat gctgcgaaac gacaccaacg accagtcgtt taacgactac   19620
ctcagcgcgg ccaacatgct ttatcccatt ccggccaacg ccaccaacgt tcccatttcc   19680
attccctccc gcaactgggc ggccttccgg ggatggagct tcacccgcct taaagccaag   19740
gaaacgcctt ccttgggctc cggctttgac ccctactttg tgtactcagg caccattcct   19800
tacctggacg gcagcttta cctcaaccac actttcaaac gtctgtccat catgttcgat    19860
tcttccgtaa gttggccggg caacgaccgc tccctgacgc cgaacgagtt cgaaattaag   19920
cgcattgtgg acggggaagg ctacaacgtg gctcaaagta acatgaccaa agactggttt   19980
ttaattcaaa tgctcagcca ctacaacatc ggctaccaag gcttctatgt tcccgagggc   20040
tacaaggatc ggatgtattc tttcttccga aactttcagc ccatgagccg ccaggtgccg   20100
gatcccaccg ctgccggcta tcaagccgtt ccctgccca gacaacacaa caactcgggc    20160
tttgtgggt acatgggccc gaccatgcgc gaaggacagc catacccggc caactacccc   20220
tatccctga tcggcgctac cgccgtcccc gccattaccc agaaaaagtt ttgtgcgac    20280
cgcgtcatgt ggcgcatacc tttttccagc aactttatgt caatgggggc cctgaccgac   20340
ctcggacaga acatgcttta cgctaactcc gcccatgccc tggatatgac ttttgaggtg   20400
gaccccatga acgagcccac gttgctgtac atgcttttg aggtgttcga cgtggtcaga    20460
gtgcaccagc cgcaccgcgg tattatcgag gccgtgtacc tgcgcacccc cttctctgcg   20520
ggcaatgcca ccacataagc cgctgaacta gctggttttt accccagatc ccatgggctc   20580
cacggaagac gaactgcggg ccattgtgcg agacctgggc tgcggaccct acttcctggg   20640
cacctttgac aagcggtttc ccgggttcgt gtctcctcgc aaactcgcgt gcgcgatcgt   20700
gaataccgcc ggccgagaga ccggaggaga gcattggcta gctctgggct ggaaccccg    20760
ctcgtccacg ttttcctgt tcgaccccct tggcttttca gaccaacgct tgaagcagat    20820
ctatgcattt gaatatgagg gtctactcaa gcgaagcgcg ctggcctcct ccgccgatca   20880
ctgtctaacc ctggtaaaga gcactcagac ggttcagggc cctcacagcg ccgcctgtgg   20940
ccttttttgt tgcatgtttt tgcacgcctt tgtgaactgg ccggacaccc ccatggaaaa   21000
caaccccacc atgacctcc tgactggcgt tcccaactcc atgctccaaa gcccagcgt    21060
gcagaccacc ctcctccaaa accagaaaaa tctgtacgcc tttctgcaca agcactctcc   21120
ctactttcgc cgccatcggg aacaaataga aaatgcaacc gcgttaaca aaaactctgta   21180
acgtttaata aatgaacttt ttattgaact ggaaaacggg tttgtgattt ttaaaaatca   21240
```

```
aaggggttga gctggacatc catgtgggag gccggaaggg tggtgttctt gtactggtac   21300
ttgggcagcc acttaaactc tggaatcaca aacttgggca gcggtatttc tgggaagttg   21360
tcgtgccaca gctggcgggt cagctgaagt gcctgcagaa catcggggc ggagatcttg    21420 aagtcgcagt ttatctggtt cacggcacgc gcgttgcggt acatgggatt ggcacactga   21480
aacaccagca ggctgggatt cttgatgcta gccaggcca cggcgtcggt cacgtcaccg    21540
gtgtcttcta tgttggacag cgaaaaaggc gtgactttgc aaagctggcg tcccgcgcga   21600
ggcacgcaat ctcccaggta gttgcactca cagcggatgg gcagaagaag atgcttgtgg   21660
ccgcgggtca tgtagggata ggccgctgcc ataaaagctt cgatctgcct gaaagcctgc   21720
ttggccttgt gcccttcggt ataaaaaaca ccgcaggact tgttggaaaa ggtattactg   21780
gcgcaagcgg catcgtgaaa gcaagcgcgt gcgtcttcgt ttcgtaactg caccacgctg   21840
cggccccacc ggttctgaat caccttggcc ctgccggggt tttccttgag agcgcgctgg   21900
ccggcttcgc tgcccacatc catttccacg acatgctcct tgttaatcat ggccagaccg   21960
tggaggcagc gcagctcctc gtcatcgtcg gtgcagtgat gctcccacac gacgcagcca   22020
gtgggctccc acttgggctt ggaggcctcg gcaatgccag aatacaggag aacgtagtgg   22080
tgcagaaaac gtcccatcat ggtgccaaag gttttctggc tgctgaaggt catcgggcag   22140
tacctccagt cctcgttaag ccaagtgttg cagatcttcc tgaagaccgt gtactgatcg   22200
ggcataaagt ggaactcatt gcgctcggtc ttgtcgatct tatactttc catcagacta    22260 tgcataatct ccatgccctt ttcccaggcg caaacaatct tggtgctaca cgggttaggt   22320
atggccaaag tggttggcct ctgaggcggc gcttgttctt cctcttgagc cctctcccga   22380
ctgacggggg ttgaaagagg gtgcccttg gggaacggct tgaacacggt ctggcccgag    22440
gcgtcccgaa gaatctgcat cggggattg ctggccgtca tggcgatgat ctgaccccgg    22500
ggctcctcca cttcgtcctc ctcgggactt tcctcgtgct tttcgggga cggtacggga    22560 gtagggggaa gagcgcggcg cgccttcttc ttgggcggca gttccggagc ctgctcttga   22620
cgactggcca ttgtcttctc ctaggcaaga aaaacaagat ggaagactct ttctcctcct   22680
cctcgtcaac gtcagaaagc gagtcttcca ccttaagcgc cgagaactcc cagcgcatag   22740
aatccgatgt gggctacgag actcccccg cgaactttc gccgccccc ataaacacta     22800 acgggtggac ggactacctg gccctaggag acgtactgct gaagcacatc aggcggcaga   22860
gcgttatcgt gcaagatgct ctcaccgagc gactcgcgt tccgctggaa gtggcggaac    22920
ttagcgccgc ctacgagcga accctcttct ccccaaagac tcccccaag aggcaggcta    22980 acggcacctg cgagcctaac cctcgactca acttctaccc tgcctttgcc gtgccagagg   23040
tactggctac gtaccacatt tttttccaaa accacaaaat ccctctctcg tgccgcgcca   23100
accgcaccaa agccgatcgc gtgctgcgac tggaggaagg ggctcgcata cctgagattg   23160
cgtgtctgga ggaagtccca aaaatctttg aaggtctggg ccgcgacgaa aagcgagcag   23220
caaacgctct ggaagagaac gcagagagtc acaacagcgc cttggtagaa ctcgagggcg   23280
acaacgccag actggccgtc ctcaaacggt ccatagaagt cacgcacttc gcctacccccg  23340 ccgttaaccct ccctccaaaa gttatgacag cggtcatgga ctcgctgctc ataaagcgcg   23400 ctcagcccctt agacccagag cacgaaaaca acagtgacga aggaaaaccg gtggtttctg   23460
atgaggagtt gagcaagtgg ctgtcctcca acgaccccgc cacgttggag gaacgaagaa   23520
aaaccatgat ggccgtggtg ctagttaccg tgcaattaga atgtctgcag aggttctttt    23580
```

```
cccacccaga gaccctgaga aaagtggagg aaacgctgca ctacacattt aggcacggct   23640
acgtgaagca agcctgcaag atttccaacg tagaacttag caacctcatc tcctacctgg   23700
ggatcttgca cgaaaaccgc ctcggacaaa acgtgctgca cagcacactg aaaggagaag   23760
cccgccgaga ctatgtgcga gactgcgtgt tcctagcgct agtgtacacc tggcagagcg   23820
gaatgggagt ctggcagcag tgcctggagg acgaaaacct caaagagctt gaaaagctgc   23880
tggtgcgctc cagaagggca ctgtggacca gttttgacga gcgcaccgcc gcgcgagacc   23940
tagctgatat tattttcct cccaagctgg tgcagactct ccgggaagga ctgccagatt    24000
ttatgagtca aagcatcttg caaaacttcc gctctttcat cttggaacgc tcgggaatct   24060
tgcccgccac tagctgcgcc ctacccacag attttgtgcc tctccactac cgcgaatgcc   24120
caccgccgct gtggccgtac acttacttgc ttaaactggc caactttcta atgttccact   24180
ctgacctggc agaagacgtt agcggcgagg ggctgctaga atgccactgc cgctgcaacc   24240
tgtgcacccc ccaccgctct ctagtatgca acactcccct gctcaatgag acccagatca   24300
tcggtacctt tgaaatccag ggaccctccg acgcggaaaa cggcaagcag gggtctgggc   24360
taaaactcac agccggactg tggacctccg cctacttgcg caaatttgta ccagaagact   24420
atcacgccca ccaaattaaa ttttacgaaa accaatcaaa accacccaaa agcgagttaa   24480
cggcttgcgt cattacgcag agcagctag ttgggcagtt gcaagccatt aacaaagcgc    24540
ggcaagagtt tctcctaaaa aaaggaaaag gggtctactt ggaccccag accggcgagg    24600 aactcaacgg accctcctca gtcgcaggtt gtgtgcccca tgccgcccaa aaagaacacc   24660
tcgcagtgga acatgccaga gacggaggaa gaggagtgga gcagtgtgag caacagcgaa   24720
acggaggaag agccgtggcc cgagggggtgc aacggggaag aggacacgga gggacggcga   24780
agtcttcgcc gaagaactct cgccgctgcc cccgaagtcc cagccggccg cctcggccca   24840
agatcccgca cacacccgta gatgggatag caagaccaaa aagccgggta agagaaacgc   24900
tcgcccccgc cagggctacc gctcgtggag aaagcacaaa aactgcatct tatcgtgctt   24960
gctccagtgc ggcggagacg tttcgttcac ccgtagatac ttgcttttta acaaaggggt   25020
ggccgtcccc cgtaacgtcc tccactacta ccgtcactct tacagctccg aagcggacgg   25080
ctaagaaaac gcagcagttg ccggcgggag gactgcgtct cagcgcccga gaaccccag    25140 ccaccaggga gctccgaaac cgcatatttc ccaccctcta cgctatcttt cagcaaagcc   25200
gggggcagca gcaagaactg aaaataaaaa accgcacgct gaggtcgctt acccgaagct   25260
gcctctatca caagagcgaa gagcagctgc agcgaaccct ggaggacgca gaagcgctgt   25320
tccagaagta ctgcgcgacc accctaaata actaaaaaag cccgcgcgcg ggacttcaaa   25380
ccgtctgacg tcaccagccg cgcgccaaaa tgagcaaaga gattcccacg ccttacatgt   25440
ggagttacca gccgcagatg ggattagccg ccggcgccgc ccaggattac tccacgaaaa   25500
tgaactggct cagcgccggg ccccacatga tttcccgcgt aaacgacatt cgcgccacc    25560 gcaatcagct attgttagaa caggctgctc tgaccgccac gccccgtaat aacctgaacc   25620
ctcccagctg gccagctgcc ctggtgtacc aggaaacgcc tccacccacc agcgtactt    25680 tgccccgtga cgcccaggcg gaagtccaga tgactaacgc gggcgcgcaa ttagcgggcg   25740
gatcccggtt tcggtacaga gttcacgcg ccgcaccta tagcccaggt ataaagaggc     25800
tgatcattcg aggcagaggt gtccagctca acgacgagac agtgagctct tcgcttggtc   25860
tacgaccaga cggagtgttc cagctcgcgg gctcgggccg ctcttcgttc acgcctcgcc   25920
aggcatacct gactctgcag agctctgcct ctcagcctcg ctcgggagga atcggacccc   25980
```

```
ttcagtttgt ggaggagttt gtgccctcgg tctactttca gcctttctcc ggatcgcccg    26040
gccagtaccc ggacgagttc atccccaact tcgacgcggt gagtgactct gtggacggtt    26100
atgactgatg tcgagcccgc ttcagtgcta gtggaacaag cgcggctcaa tcacctggtt    26160
cgttgccgcc gccgctgctg cgtggctcgc gacttgagct tagctctcaa gtttgtaaaa    26220
aacccgtccg aaaccgggag cgctgtgcac gggttggagc tagtgggtcc tgagaaggcc    26280
accatccacg ttctcagaaa ctttgtggaa aaacccattt tggttaaacg agatcagggg    26340
ccttttgtaa tcagcttact ctgcacctgt aaccatgttg accttcacga ctattttatg    26400
gatcatttgt gcgctgaatt caataagtaa agcgaattct taccaagatt atgatgtcca    26460
tgactgttcc tcgccactat acgatgttgt gccagtaaac tctcttgtcg acatctatct    26520
gaactgttcc ttttggtccg cacagcttac ttggtactac ggtgacaccg tcctttctgg    26580
ctcactgggc agctcacacg gaataacact tcacctcttt tcgccgtttc gatacggaaa    26640
ctacagctgt cgtgccggta cctgcctcca cgttttcaat cttcagccct gtccaccgac    26700
caaacttgta tttgtcgact ctaagcactt acagctcaac tgcagcattc taggccccag    26760
tatcttgtgg acatacaata aaatcaggtt ggtggaattt gtctactacc cacccagcgc    26820
ccgcggtttt ggggaaattc cttttccagat ctactacaac tatcttgcca cacattatgc    26880
aagtcaacag caactaaact tgcaagcacc cttcacgcca ggagagtact cctgtcacgt    26940
aggctcctgc acagaaactt ttattctctt caacagatct tctgccattg aacgcttcac    27000
tactaactac tttagaaacc aagttgtgct tttcactgac gaaaccccta acgtcaccct    27060
ggactgtgca tgttttctc atgacaccgt aacttggact cttaacaata ctctctggct    27120
cgcgttcgat aaccaaagct tgattgttaa aaattttgat ttaaccttta ctaaaccctc    27180
tcctcgcgaa atagttatct ttgctccttt taatccaaaa actacccttag cctgtcaggt    27240 tttgtttaag ccttgccaaa caaactttaa gtttgtttat ttgcctccgc aatctgtcaa    27300
actcatagaa aaatacaaca aagcgcccgt cttggctcct aaaaaccttct accactggct    27360 aacctacacg gggctgtttg cactaattgt ttttttccta attaacattt ttatatgttt    27420
cttgccttcc tccttctttt cgcgaacacc gttgccgcag aaagacctct ccttattact    27480
gtagcgcttg ctatacaaaa ccaagagtgg tcaaccgtgc tctcaatcta ttttcaattt    27540
ttcattttgt ccttaatact ttctcttatt gtcgttaaca atgatctgga gcattggtct    27600 cgccttttt tggctgctta gtgcaaaagc cactattttt cacaggtatg tggaagaagg    27660
aactagcacc ctctttacga tacctgaaac aattaaggcg gctgatgaag tttcttggta    27720
caaaggctcg ctctcagacg gcaaccactc attctcagga cagaccctt gcatccaaga    27780 aacttatttt aaatcagaac tacaatacag ctgcataaaa aacttttcc atctctacaa    27840 catctcaaaa ccctatgagg gtatttacaa tgccaaggtt tcagacaact ccagcacacg    27900
gaacttttac tttaatctga cagttattaa agcaatttcc attcctatct gtgagtttag    27960
ctcccagttt cttcctgaaa cctactgttt aattactata aactgcacta aaaatcgcct    28020
tcacaccacc ataatctaca atcacacaca atcaccttgg gttttaaacc taaaattttc    28080
tccacacatg ccttcgcaat ttctcacgca agttaccgtc tctaacataa gcaagcagtt    28140
tggcttttac tatcctttcc acgaactgtg cgaaataatt gaagccgaat atgaaccaga    28200 ctacttact tacattgcca ttggtgtaat cgttgtttgc ctttgctttg ttattggggg    28260
gtgtgtttat ttgtacattc agagaaaaat attgctctcg ctgtgctcct gcggttacaa    28320
```

```
agcagaagaa agaattaaaa tctctacact ttattaatgt tttccagaaa tggcaaaact   28380
aacgctccta cttttgcttc tcacgccggt gacgcttttt accatcactt tttctgccgc   28440
cgccacactc gaacctcaat gtttgccacc ggttgaagtc tactttgtct acgtgttgct   28500
gtgctgcgtt agcgtttgca gtataacatg ttttaccttt gttttttcttc agtgcattga   28560
ctacttctgg gtcagactct actaccgcag acacgcgcct cagtatcaaa atcaacaaat   28620
tgccagacta ctcggtctgc catgattgtc ttgtatttta ccctgatttt ttttcacctt   28680
acttgcgctt gtgattttca cttcactcaa ttttggaaaa cgcaatgctt cgacccgcgc   28740
ctctccaacg actggatgat ggctcttgca attgccacgc ttggggcgtt tggacttttt   28800
agtggttttg ctttgcatta caaatttaag actccatgga cacatggctt tctttcagat   28860
tttccagtta cacctactcc gccgcctccc ccggccatcg acgtgcctca ggttccctca   28920
ccttctccat ctgtctgcag ctactttcat ctgtaatggc cgacctagaa tttgacggag   28980
tgcaatctga gcaagggct atacacttcc aacgccagtc ggaccgcgaa cgcaaaaaca   29040
gagagctgca aaccatacaa acacccacc aatgtaaacg cgggatattt tgtattgtaa   29100
aacaagctaa gctccactac gagcttctat ctggcaacga ccacgagctc caatacgtgg   29160
tcgatcagca gcgtcaaacc tgtgtattct taattggagt ttcccccatt aaagttactc   29220
aaaccaaggg tgaaaccaag ggaaccataa ggtgctcatg tcacctgtca gaatgccttt   29280
acactctagt taaaaccccta tgtggcttac atgattctat cccctttaat taaataaact   29340
tactttaaat ctgcaatcac ttcttcgtcc ttgtttttgt cgccatccag cagcaccacc   29400
ttcccctctt cccaactttc atagcatatt ttccgaaaag aggcgtactt tcgccacacc   29460
ttaaagggaa cgtttacttc gctttcaagc tctcccacga ttttcattgc agatatgaaa   29520
cgcgccaaag tggaagaagg atttaacccc gtttatccct atggatattc tactccgact   29580
gacgtggctc ctccctttgt agcctctgac ggtcttcaag aaaacccacc tggggtcttg   29640
tccctaaaaa tatccaaacc tttaactttt aatgcctcca aggctctaag cctggctatt   29700
ggtccaggat taaaaattca agatggtaaa ctagtggggg agggacaagc aattcttgca   29760
aacctgccgc ttcaaatcac caacaacaca atttcactac gttttgggaa cacacttgcc   29820
ttgaatgaca ataatgaact ccaaaccaca ctaaaatctt catcgcccct taaaatcaca   29880
gaccagactc tgtcccttaa cataggggac agccttgcaa ttaaagatga caaactagaa   29940
agcgctcttc aagcgaccct cccactctcc attagcaaca acaccatcag cctcaacgtg   30000
ggcaccggac tcaccataaa tggaaacgtt ttacaagctg ttcccttaaa tgctctaagt   30060
cccctaacta tttccaacaa taacatcagc ctgcgctatg gcagttccct gacggtgctt   30120
aacaatgaac tgcaaagcaa cctcacagtt cactccccctt taaaactcaa ctccaacaac   30180
tcaatttctc tcaacactct atctccgttt agaatcgaga atggtttcct cacgctctat   30240
ttgggaacaa aatctggctt gctagttcaa aacagtggct taaagttca agcgggctac   30300
ggcctgcaag taacagacac caatgctctc acattaagat atctcgctcc actgaccatt   30360
ccagactcgg gctcagaaca aggcattctt aaagtaaaca ctggacaggg cctaagtgtg   30420
aaccaagctg gagcgcttga acatcccta ggaggtggat taaatatgc tgataacaaa   30480
ataacctttg atacaggaaa cggactgaca ttatctgaaa ataaacttgc agtagctgca   30540
ggtagtggtc taactttta gatggtgcc ttggtagcca cgggaaccgc atttacgcaa   30600
acactgtgga ctacgctga tccgtctccc aactgcacaa ttatacagga ccgcgacaca   30660
aaatttactt tggcgcttac cattagtggg agccaagtgc tggggacggt ttccattatt   30720
```

```
ggagtaaaag gcccccttc  aagtagcata  ccgtcagcta  ccgttacagt  acaacttaac  30780
tttgattcca  acggagccct  attgagctcc  tcttcactta  aaggttactg  ggggtatcgc  30840
caaggtccct  caattgaccc  ttaccccata  attaatgcct  taaactttat  gccaaactca  30900
ctggcttatc  ccccgggaca  agaaatccaa  gcaaaatgta  acatgtacgt  ttctactttt  30960
ttacgaggaa  atccacaaag  accaatagtt  ttaaacatca  cttttaataa  tcaaccagc   31020
gggttttcca  ttagatttac  atggacaaat  ttaaccacag  gagaagcatt  tgcaatgccc  31080
ccatgcactt  tttcctacat  tgctgaacaa  caataaacta  tgtaaccctc  accgttaacc  31140
cgcctccgcc  cttccatttt  attttataaa  ccacccgatc  cacctttca   gcagtaaaca  31200
attgcatgtc  agtaggggca  gtaaaacttt  tgggagttaa  aatccacaca  ggttcttcac  31260
aagctaagcg  aaaatcagtt  acacttataa  aaccatcgct  aacatcggac  aaagacaagc  31320
atgagtccaa  agcttccggt  tctggatcag  atttttgttc  attaacagcg  ggagaaacag  31380
cttctggagg  atttccatc   tccatctcct  tcatcagttc  caccatgtcc  accgtggtca  31440
tctgggacga  gaacgacagt  tgtcatacac  ctcataagtc  accggtcgat  gacgaacgta  31500
cagatctcga  agaatgtcct  gtcgccgcct  ttcggcagca  ctgggccgaa  ggcgaaagcg  31560
cccatgttta  acaatggcca  gcaccgcccg  cttcatcagg  cgcctagttc  ttttagcgca  31620
acagcgcatg  cgcagctcgc  taagactggc  gcaagaaaca  cagcacagaa  ccaccagatt  31680
gttcatgatc  ccataagcgt  gctgacacca  gcccatacta  acaaattgtt  tcactattct  31740
agcatgaatg  tcatatctga  tgttcaagta  aattaaatgg  cgcccccta   tgtaaacact  31800
tcccacgtac  aacacctcct  ttggcatctg  ataattaacc  acctcccgat  accaaataca  31860
tctctgatta  atagtcgccc  cgtacactac  ccgattaaac  caagttgcca  acataatccc  31920
ccctgccata  cactgcaaag  aacctggacg  gctacaatga  cagtgcaaag  tccacacctc  31980
gttgccatgg  ataactgagg  aacgccttaa  gtcaatagtg  gcacaactaa  tacaaacatg  32040
taaatagtgt  ttcaacaagt  gccactcgta  tgaggtgagt  atcatgtccc  agggaacggg  32100
ccactccata  aacactgcaa  aaccaacaca  tcctaccatc  ccccgcacgg  cactcacatc  32160
gtgcatggtg  ttcatatcac  agtccggaag  ctgaggacaa  ggaaaagtct  cgggagcatt  32220
ttcatagggc  ggtagtgggt  actccttgta  ggggttcagt  cggcaccggt  atctcctcac  32280
cttctgggcc  ataacacaca  agttgagatc  tgatttcaag  gtactttctg  aatgaaaacc  32340
aagtgctttc  ccaacaatgt  atccgatgtc  ttcggtcccc  gcgtcggtag  cgctccttgc  32400
agtacacacg  gaacaaccac  tcacgcaggc  ccagaagaca  gttttccgcg  gacggtgaca  32460
agttaatccc  cctcagtctc  agagccaata  tagtttcttc  cacagtagca  taggccaaac  32520
ccaaccagga  aacacaagct  ggcacgtccc  gttcaacggg  aggacaagga  agcagaggca  32580
gaggcatagg  caaagcaaca  gaatttttat  tccaactggt  cacgtagcac  ttcaaacacc  32640
aggtcacgta  aatggcagcg  atcttgggtt  tcctgatgga  acataacagc  aagatcaaac  32700
atgagacgat  tctcaaggtg  attaaccaca  gctggaatta  aatcctccac  gcgcacattt  32760
agaaacacca  gcaatacaaa  agcccggttt  tctccgggat  ctatcatagc  agcacagtca  32820
tcaattagtc  ccaagtaatt  ttcccgtttc  caatctgtta  taatttgcag  aataatgccc  32880
tgtaaatcca  agccggccat  ggcgaaaagc  tcagataatg  cactttccac  gtgcattcgt  32940
aaacacaccc  tcatcttgtc  aatccaaaaa  gtcttcttct  tgagaaacct  gtagtaaatt  33000
aagaatcgcc  aggttaggct  cgatgcctac  atcccggagc  ttcattctca  gcatgcactg  33060
```

```
caaatgatcc agcagatcag aacagcaatt agcagccagc tcatccccgg tttccagttc    33120
cggagttccc acggcaatta tcactcgaaa cgtgggacaa atcgaaataa catgagctcc    33180
cacgtgagca aaagccgtag ggccagtgca ataatcacag aaccagcgga aaaaagattg    33240
cagctcatgt ttcaaaaagc tctgcagatc aaaattcagc tcatgcaaat aacacagtaa    33300
agtttgcggt atagtaaccg aaaaccacac gggtcgacgt tcaaacatct cggcttacct    33360 aaaaagaag cacatttta aaccacagtc gcttcctgaa caggaggaaa tatggtgcgg      33420
cgtaaaacca gacgcgccac cggatctccg gcagagccct gataatacag ccagctgtgg    33480
ttaaacagca aaacctttaa ttcggcaacg gttgaggtct ccacataatc agcgcccaca    33540
aaaatcccat ctcgaacttg ctcgcgtagg gagctaaaat ggccagtata gccccatggc    33600
acccgaacgc taatctgcaa gtatatgaga gccacccat tcggcgggat cacaaaatca     33660
gtcggagaaa acaacgtata caccccggac tgcaaaagct gttcaggcaa acgcccctgc    33720
ggtccctctc ggtacaccag caaagcctcg ggtaaagcag ccatgccaag cgcttaccgt    33780
gccaagagcg actcagacga aaagtgtac tgaggcgctc agagcagcgg ctatatactc      33840
tacctgtgac gtcaagaacc gaaagtcaaa agttcacccg gcgcgcccga aaaaacccgc    33900
gaaaatccac ccaaaaagcc cgcgaaaaac acttccgtat aaaatttccg ggttaccggc    33960
gcgtcaccgc cgcgcgacac gcccgccccg cccgcgctc ctcccgaaa cccgccgcgc      34020 ccacttccgc gttcccaaga caaaggtcgc gtaactccgc ccacctcatt tgcatgttaa    34080
ctcggtcgcc atcttgcggt gttatattga tgatg                              34115
```

<210> SEQ ID NO 7
<211> LENGTH: 44
<212> TYPE: DNA
<213> ORGANISM: Artificial
<220> FEATURE:
<223> OTHER INFORMATION: primer P5L

<400> SEQUENCE: 7
gcgcacgcgt ctctatcgat gaattccatt ggtgatggac atgc          44

<210> SEQ ID NO 8
<211> LENGTH: 36
<212> TYPE: DNA
<213> ORGANISM: Artificial
<220> FEATURE:
<223> OTHER INFORMATION: primer P5ITR

<400> SEQUENCE: 8
gcgcatttaa atcatcatca ataatatacc tcaaac          36

<210> SEQ ID NO 9
<211> LENGTH: 31
<212> TYPE: DNA
<213> ORGANISM: Artificial
<220> FEATURE:
<223> OTHER INFORMATION: primer P5XTOP

<400> SEQUENCE: 9
gatacctagg aacgaggagg atttgatatt g          31

<210> SEQ ID NO 10
<211> LENGTH: 20
<212> TYPE: DNA
<213> ORGANISM: Artificial
<220> FEATURE:
<223> OTHER INFORMATION: primer P5XBOT

<400> SEQUENCE: 10
atgtacgcct ccgcgctcac                                                    20

<210> SEQ ID NO 11
<211> LENGTH: 31
<212> TYPE: DNA
<213> ORGANISM: Artificial
<220> FEATURE:
<223> OTHER INFORMATION: primer P5E4

<400> SEQUENCE: 11
gatcgaattc ccactctgta ccccatctct g                                       31

<210> SEQ ID NO 12
<211> LENGTH: 31967
<212> TYPE: DNA
<213> ORGANISM: Simian adenovirus
<220> FEATURE:
<221> NAME/KEY: CDS
<222> LOCATION: (13796)..(15322)
<220> FEATURE:
<221> NAME/KEY: CDS
<222> LOCATION: (18257)..(21010)
<220> FEATURE:
<221> NAME/KEY: CDS
<222> LOCATION: (27192)..(29015)

<400> SEQUENCE: 12

| | | | | |
|---|---|---|---|---|
| catcatcata | atatacctta | tttgggaacg | gtgccaatat | gataatgagg   aggcggggtt | 60 |
| aggggtggag | tgagggtggg | gtgcggatga | cgcgggcgcg | gggcggggtg   ggagtctgac | 120 |
| gtggggcgcg | gggtggagcg | cgagggtgag | ggcggggcga | gggcggcggg   cgcggcggaa | 180 |
| ttgacgtaca | cggtagtaag | tttgagcgga | aattaagtga | attgggcgtg   ttttttgtaa | 240 |
| cttttttgacg | tacacggtag | taagtttgag | cggaaattaa | gtgaattggg   cgtgtttttt | 300 |
| gtaactttttt | gacgtacacg | gtagtaagtt | tgagcggaaa | ttaagtgaat   tgggcgtgtt | 360 |
| ttttgtaact | ttttgacgta | cacggtagta | agtttgagcg | gaaattaagt   gaattgggcg | 420 |
| tgttttttgt | aactttttga | cgtacacggt | agtaagtttg | agcggaaatt   aagtgaattg | 480 |
| ggcgtgtttt | ttgtaacttt | ttgacgtaca | cggtagtaag | tttgagcgga   aattaagtga | 540 |
| attgggcgtg | ttttttgtaa | cttttttgacg | tacacggtag | taagtttgag   cggaaattaa | 600 |
| gtgaattggg | cgtgtttttt | gtaacttttt | ggtcatttttg | gcgcgaaaac   tgagtaatga | 660 |
| ggaagtgaga | cggactctgc | ccttttttac | ggttgggagg | gaaaactgct   gatcagcgct | 720 |
| gaactttggg | ctctgacgcg | gtggtttccc | tacgtggcag | tgccacgaga   aggctcaaag | 780 |
| tcctcgtttt | attgtgtgct | cagccttttt | gagggtattt | aaacaccgtc   agaccgtcaa | 840 |
| gaggccactc | ttgagtgcga | gcgagtagag | ttttctcctc | cgtcgctgcc   gcggctgctc | 900 |
| agtcttaccg | ccaggatgcg | aatgctgccg | gagatcttca | ccgggtcctg   ggaagatgtt | 960 |
| ttccagggac | ttttagaatc | tgaagacaac | tttccccaac | ctcctgagcc   ggaggagcta | 1020 |
| cctgaggttt | cgcttcacga | tctgtttgac | gtggaggtgg | agagccccga   cggagatccg | 1080 |
| aacgaggaag | ctgttgatgg | tatgttcccc | gactggatga | tatctcagag   cgagagtgct | 1140 |
| gaaggcagtg | cggactcggg | cgtttctggg | gttggaaacc | tggtgagggt   ggatctggac | 1200 |
| ttgaagtgtt | acgaggaagg | ttttcctcct | agcgactcag | agactgatga   agcctcagaa | 1260 |
| gcggaaggtc | aagaggagtc | tgtgtgtggt | tatgtgaaga | ttaatgaggg   ggagaacctg | 1320 |
| ctggtgttgg | actgtccgga | ccaacctgga | catggctgtc | gagcctgtga   ctttcaccgg | 1380 |

```
gggaccagcg gaaacccgga agctatctgt gctttgtgct acatgcgtct gaacgagcac   1440
tgcatataca gtgagtgtta ttcatgggtt atttatgggg aaagttgggg gaaagtcttg   1500
agaaggggaa aagtttaaca tgtcattttt gtacttgata ggtccagttt cggacgctga   1560
gggggattct gagtcccctg ctggtccttc ccagccctca ccctgctctt tgaccgccac   1620
gcccgcacct gacctagtta gaccaacgcc ctgccgagtg tcctgtagac gacgtgcagc   1680
tgttaattgc atagaagatt tattggcccc tgatgacgag aacgcacctt tgaacctgtg   1740
cctgaaacgc cctaagacat cttgagtgtt tatgctgtta ataaaagtgt tgacccttag   1800
atcctgtgtt tattccttgg gcgtgtgcgc gggtatataa agcagctgcg ggctggagtg   1860
ttagtttatt ctgatggagt actggagtga gctgcagaat taccagagcc tccggcgcct   1920
gctggagttg gcctctgcca gaacatccac ctgctggagg ttctgttttg gctcgactct   1980
cagtaacgtg gtgtatcggg tgaagcaaga gtacagctcg cgcttttctg agctgttggc   2040
ccgctacccg gctgttttg tttctctgga tctaggccat cacgtttatt ccaagaagc    2100 tgtagtcaga tatttggatt tttctactcc cgggcgtgcg gtttctgcga ttgccttcat   2160
ctgctttgtg ctagatcgat ggagcgccca aacccgcctg agcccgggt acaccctgga    2220 ctacctgacc atgtccctgt ggagggccat gctgcggaag aggagggtct caggcttctc   2280
gccggcgcgg cctccgcacg gactggatcc ggtgctggga gagtcggagc tggaggagga   2340
ggagaacccg agggccggcc tggaccctcc ggcggaatag tgacggaacc ggaggatccc   2400
caagagggta ctagtcaggg gggaggggg ccgaagagaa agcgggatga agaggaggcg    2460
atggaccccg acaggtttct aaaagaactg actttaagct taatgtctaa gagaagaccc   2520
gagacggtgt ggtggtctga tttggagaag gagttccacc aggggagat gaatctgttg     2580 tacaagtatg ggtttgagca ggtgaagact cactggctgg aagcctggga ggactgggag   2640
atggctttta acatgtttgc caaggtggcg ctgcgcccgg acactattta caccgtgact   2700
aagacggtgg aaatccgcaa gcctgtgtat gtgattggca acgggccgt ggttcggttc    2760 cagaccaccg accgggtggc ctttaattgc tgtatgcaga acctgggccc gggggtgatt   2820
aatcttaatg gagtgacctt tgcaatgtc agattcgcgg gggatggatt caacgggacg    2880
gtgtttgccg ccaccaccca gataaaccta cacgggtgt tcttccagca tgtaggcggg    2940
gcttgtgtag atacctgggc gagggcctct gtgaggggct gcacctttgt gggctgttgg   3000
aaagcggtgt tgggtcgacc caagagtgtg ctgtctgtga agaaatgtgt gtttgagaga   3060
tgtctgatgg ccatggtggt ggagggccag ggtaggatcc gccataacgc gggctccgag   3120
aatacctgtt tgccctgct gaagggtacg gcgaccgtga agcataacat gatctgcggg    3180
gtgggtcact cgcagctgct gacctgtgcg gatggcaact gccaggccct gcgcacggtg   3240
catgtggtgt cccaccggcg ccgccctgg ccggtgtttg aacataacat gctgatgcgc    3300
tgtaccatgc acctgggcta ccgccgcggc gtgtttgtgc cccatcagtg taacctgacc   3360
cacaccaagg tgttgctgga gacgatgct ttttcgcgag tgaatctgaa tggggtgttc    3420
gatctgacta tggagatgta caagatagtg agatttgatg aatcaaagac ccgttgtcgc   3480
ccctgcgagt gcggtgccaa tcacctgagg atgtatcccg tgaccctgaa cgtgacggag   3540
gagctgcgcc cggaccacca gatgctgtcc tgtctgcgca ccgattacga aagcagcgat   3600
gaggattaag aggtgagggg cggggcttgc atggggtata aggtgggggg aggaggtggg   3660 gaggggggaaa acccaaaatg agcggatcga tggaagggag cgctgtgagt tttgagggcg   3720
```

```
gggtgttcag cccatatctg acaacccgtc tccccgcctg ggcaggagtg cgtcagaatg    3780
tggtgggctc caacgtggac ggacgtccgg tggcccctgc caactccgcc actctcacct    3840
acgccaccgt cggatcgtcg ctggacaccg ccgctgccgc cgccgcttca gccgccgctt    3900
ctactgctcg cggtatggca gctgatttcg gactgtatca gcaactggct gcgcctcgct    3960
cgtcgctgag agaagatgat gccctgtccg tggtgctgac ccgcctggag gagctgtccc    4020
agcagctgca agagctgtct gccaaagtgg atgcacagaa cgtccccgct acccaatgaa    4080
taaataaacg agacaccgag tgtgtttgga aatcaaaatg tgttttatt tgttttttct     4140 ggcgcggtag gcccttgacc acctgtcgcg gtcgttaagg accttgtgga tgttttccag    4200
cacccggtag aggtgggctt ggatgttgag gtacatgggc atgagcccgt ctcggggtg     4260 gaggtagcac cactgagggg cgtcgtgctc ggggtggtg ttgtagataa tccagtcgta     4320
gcagggtttt tgggcatgga agcggaagat gtctttgaga agcaggctga tggccagggg    4380
gaggcccttg gtgtaggtgt tcacaaagcg gttgagctgg gagggatgca tgcggggga    4440 gatgagatgc atcttggcct gaatcttgag gttggcgatg ttgccgccca gatcccgccg    4500
ggggctcatg ttgtgcagga ccaccaggac ggtgtagccg gtgcacttgg ggaatttgtc    4560
atgcaacttg gaagggaagg cgtggaagaa cttggagacc cccttgtggc cgccgaggtt    4620
ctccatgcat tcgtccatga tgatggcgat gggaccctg gcggccgccc tggcgaagac     4680
gttgtcgggg tgggagacgt cgtagttctg ttccagggtg agctcgtcgt aggccatttt    4740
gacgaagcgg gggagcaggg tgcccgactg ggggacgatg gtaccttcgg gacccgggc    4800 gtagttgccc tcgcagattt gcatctccca ggccttgatc tccgaggggg ggatcatgtc    4860
cacctggggc gcgatgaaga agacggtctc cggggcgggg ttgatgagct gggaggagag    4920
gaggttgcgg agcagctgcg acttgccgca cccggtgggc ccgtagatga ccccgatgac    4980
gggttgcagc tggtagttta aggagctgca gctgccgtcc tcgcgcagga acggggcgac    5040
ctcgttcatc atgcttctga cgtgatggtt ttccctgacg aggtcttgca agagccgctc    5100
gccgcccagg gagagaagct cttccaggct gcggaaatgc ttgagggggtt tgaggccgtc   5160 ggccatggtc atcttttcca gggactggcg gagcaggtac aggcggtccc agagctcggt    5220
gacgtgttct acggcatctc gatccagcag acttcttggt tgcgggggtt ggggcggctt    5280
tggctgtagg ggaccagccg gtgcgcgtcc agggaggcga gggtgacgtc tttccagggc    5340
cgcagcgttc gcgtgagggt ggtctcggtg acgtgaagg gatgcgctcc cggttgggcg    5400
ctggccaggg tcctcttgag actcatcctg ctggtgtgga agcgggcgtc ttctccctgg    5460
gagtcggcca ggtagcattt gagcatgagg tcgtagctga gggcctcggc cgcgtggccc    5520
ttggcgcgca gcttgccttt ggagacgtgt ccgcaggcgg acagtgcag gcacttgagg     5580 gcgtagagct tgggggccag gaagacggac tcggggagt aggcgtcggc gccgcactga     5640 gcgcacgtg tctcgcactc gacgagccag gtgagctccg ggtgttgggg atcaaaaacc     5700
agctggcccc cgtgtttttt gatgcgcttc ttacctcggg tctccatgag gcggcgtccg    5760
gcttcggtga cgaagaggct gtcggtgtcg ccgtagacgg atttgagcgc gcgctgctcc    5820
aggggaatcc cgcgatcctc cgcgtgcagg aactcggacc actctgagac gaaggcccgg    5880
gtccacgcga ggacaaagga ggcgatctgg gacgggtagc ggtcgttctc caccagggga    5940
tccaccttct ccagggtgtg caggcagagg tcgtcctcct ccgcgtccat gaaggtgatt    6000
ggcttgtaag tgtatgtcac gtgaccgtcg ggtcgcgcg tggcttata aaagggggcg      6060 tgcccggcct ccccgtcact tcttccgca tcgctgtgga cgagatccag ctgctcgggt     6120
```

```
gagtaggcgc gctggaaggc gggcatgacc tcggcgctga gggtgtcagt ttccacgaac   6180
gaggtggatt tgatattgac ctgtccggcg gcgatgcttt tgacggtggc ggggtccatc   6240
tggtcagaaa agacgatctt tttgttgtcc agcttggtgg cgaacgaccc gtagagggcg   6300
ttggagagca gcttggcgat ggagcgcagg gtctggttct tctcgcggtc ggcgcgctcc   6360
ttggcggcga tgttgagctg gacgtactcg cgggccacgc agcgccattc ggggaagacg   6420
gtggcgcgct cgtccggcag gaggcgcacg cgccagccgc ggttgtgcag ggtgatgagg   6480
tccacgctgg tggccacctc gccgcgcagt ggctcgttgg tccagcagag gcgcccgccc   6540
ttgcgcgagc agaaggggggg caggacgtcg agctggtcct ccgcgggggg gtcggcgtcg   6600
atggtgaaga tgcccggtag caggtggcgg tcgaagtagt cgatggcgac cgcggggtcg   6660
gcgagggcgc gttcccagtc cctgaccgcc agggcgcgct cgtaggggtt gaggggcgcc   6720
ccccagggca tgggatgggt gagggccgag gcgtacatgc cgcagatgtc gtagacgtag   6780
aggggctcgc ggagcacgcc gaggtaggtg ggatagcagc gtccgccgcg gatgctggcg   6840
cgcacgtagt cgtacatctc gtgcgagggg gcgaggaggc cgcctccgag gtcgccgcgc   6900
tgcggtctga cggcccggta ggtgacctgg cggaagatgg cgtgcgagtt ggaggagatg   6960
gtgggccgct ggaagatgtt gaagctggcc tcggggagtc cgacggcgtc gtggacgaac   7020
tgggcgtagg agtcgcgcag cttctgcacg agcgcggcgg tgacgagcac gtccagggcg   7080
cagtagtcga gggtctcgcg gacgaggtcg taacggggct cttgcttctt ttcccagagt   7140
tcgcggttga ggaggtactc ctcgcgatcc ttccagtact cttcggccgg aaagccgcgt   7200
tcgtccgcca ggtaagaacc cagcatgtag aagcggttga cggctcggta gggacagcag   7260
cccttctcga cgggcaggga gtaggcctgc gcggccttcc tgagcgaggt gtgggtgagg   7320
gcgaaggtgt cgcgcaccat gaccttgagg aactggaacc tgaagtcggt gtcgtcgcag   7380 gcgcccccgct cccagagccc gtagtcggtg cgtttctggc tgcgggggtt gggcagggcg   7440
aaggtgacgt cgttgaagag gatcttgccg gcgcgcggca tgaagttgcg ggtgatcctg   7500
aagggccccg gcacgtccga gcggttgtta atgacctggg ccgcgaggac gatctcgtcg   7560
aagccgttga tgttgtggcc gacgatgtag agctcgacga agcgcgggcg cccctgcagc   7620
ttgggggcct tcttgagctc ctcgtaggta aggcagtcgg gcgagtagag gcccagctcc   7680
tgtcgggccc attcggccac ctgggggttg gcttgcaaga agccccgcca gagctgcagg   7740
gcgagctggg tctggaggcg gtcgcggtag tcgcggaact ttttgcccac cgccatcttc   7800 tcggggggtga ccacgtagaa ggtgcggccg tcctggcccc aggcgtccca gttctgctcg   7860
cgggcgagac ggcaggcctc ctcgacgagg gcctcctccc cggagagatg catgactagc   7920
atgaagggga cgagttgctt gccgaaggca cccatccacg tgtaggtctc tacgtcgtag   7980
gtgacgaaga gacgttcggt gcgaggatgc gagccgagag gaaagaagtt gatctcctgc   8040
caccagccgg aggagtgggc gttgacgtgg tggaagtaga agtcacgccg gcggaccgtg   8100
cattcgtgct gatatttgta aaagcggcg cagtactcgc agcgctgcac gctctgcact   8160
tcctgaacga gatgcacccg gcgcccgcgc accaggaggc ggaggggca gtccagtgga   8220 gcttcggcgc gctgtccttc agcctcgtca tgctcttctg cacctgcacg ctcctgctgt   8280
gggtggagga cggagggagt gacgacgccg cgcgagccgc aggtccagat gtcgacgcgc   8340
ggcggcctga ggctcagcgc cagggtgcgg atctgagcgg cgtccaggga gtcgaggaag   8400
gcctcgctga ggtcgacggg cagcgtccgc cggtggactt gcaggagacg ggtaagggcc   8460
```

```
ggcgccaggc gctgatggta cttgatctcg agcggttcgt tggtggaggt gtcgatggcg    8520
tagagcaggg cctgaccgcg ggcggcgacg atggtgccgc ggtgccggcg gtaggtggcg    8580
tattcggggg ggctcgttac atcacccgcc tgggcctggc gccgggcggc agcgggggtt    8640
ctggtcccgc cggcatgggc ggcagcggca cgtcggcgcg gggctccggc agcggctggt    8700
gctgagctcg cagctgactg gcgtgcgcga cgacgcggcg gttgaggtcc tggatgtgcc    8760
tccgctgcgt gaagaccacc ggtccccgga ctcggaacct gaaagagagt tcgacagaat    8820
caatctcggc atcgttgacg gccgcctgac gcaggatctc ctgcacgtcg cccgagttgt    8880
cctggtaggc gatctcggac atgaactggt cgatctcttc ctcctggagt cgccgcgtc    8940
cggcgcgttc gacggtggcc gcgaggtcgt tggagatgcg agccatgagc tgggagaagg    9000
cgttgaggcc gttctcgttc cacacgcgac tgtagacgac gttgccgacg gcgtcccggg    9060
cgcgcatgac cacctgcgcg acgttgagct ccacgtgtcg cgcgaagacg gcgtagttgc    9120
gcaggcgctg gaagaggtag ttgagggtgg tggcgatgtg ctcgcagacg aagaagtaca    9180
tgacccagcg gcgcagcgtc atctcgttga tgtctccgag ggcttccaag cgctccatgg    9240
cctcgtagaa gtcgacggcg aagttgaaga actgggagtt gcgcgccgcg accgtcagct    9300
cgtcttgcaa gagccggatc agctgggcca cggtctcccg cacctcgcgt tcgaaggccc    9360
ccggcgcttc ttcctcctct ggttcctcgg cggcctcttc ttccatgacg gcttcctctt    9420
cctccggttc ctcgggcacg ggcctccggc ggcgacggcg cctgatgggc aggcggtcca    9480
cgaagcgttc gatgatctct ccgcggcggc ggcgcatggt ttcggtgacg gcgcggccgt    9540
tctctcgggg ccgcagttcg aagacgcccc cgcgcaggcc gccggcgccg ccgagagggg    9600
gcaggaggtg ggggccttcg ggcagcgaga gggcgctgac gatgcaccgt atcatctgtt    9660
gcgtaggtac agctctccag gagtcgttga gcgagtccag ttggacggga tccgagaact    9720
tttcgaggaa agcttcgatc caatcgcagt cgcaaggtaa gctgaggacg gtgggatgag    9780
gggcttggcg ggaggcggag gcggcagaag aggaggagga gggcaggctg gaggtgatgc    9840
tgctgatgat gtaattgaag taggcggttt tcaaacggcg gatggtggcg aggaggacga    9900
cgtctttggg cccggcctgc tggatgcgca ggcggtcggc catgccccag gcgtggctct    9960
ggcatcggcg caggtccttg tagtagtctt gcatgagtct ctcgacgggg acgtcgtctt   10020
cgtcggcccg gtcggccatg cgggtggagc cgaacccgcg caggggctgc agcagggcca   10080
ggtcggcgac cacgcgttcg gccagcacgg cctgctggat ctgggtgagc gtggtctgga   10140
agtcgtccag gtccacgaag cggtggtagg agcccgtgtt gatggtgtag gtgcagttgg   10200
ccatgacgga ccagttgacg acttgcatgc cgggctgggt gatctcggtg tagcggaggc   10260
gcgagtaggc ccgcgactcg aagacgtagt cgttgcaggt gcgcacgagg tactggtagc   10320
cgacgaggaa gtgcggcggc ggctcgcggt agaggggcca gcgcacggtg gcggggcgc    10380
cggggccag gtcctccagc atgaggcggt ggtagtggta gacgtagcgc gagagccagg   10440
tgatgccggc ggcggaggtg gcggcgcggg cgaagtcgcg gacgcggttc cagatgttgc   10500
gcaaggggc gaagcgctcc atggtgggca cgctctggcc ggtgaggcgg gcgcagtcct   10560
gcacgctcta gacgggacag agagcgggag gttagcggct ccgctccgtg gcctggggga   10620
cagaccgcca gggtgcgacg gcggggaacc ccggttcgag accggctgga tccgtccgtc   10680
cccgacgcgc cggcccccgc tccacgaccc caccagaggc cgagacccag ccgcggtgcc   10740
cggacccag atacgaggg gagccttttt gtggttttt cccgtagatg catccggtgt   10800
tgcgacagat gcgtccgtcg ccagcgccgc cgacgcagcc gccgctcccg ccccccacta   10860
```

```
gcgccgcgga ggctctgtcc ggcggccgcg gcgacccgga ggaggaggcc atcctcgact    10920
tggaagaagg cgagggcctg gcccggctgg gagcgccctc ccccgagcgc catccccgcg    10980
tgcagctggc gagagactcg cgccaggcct acgtgccgcc gcagaatctg ttcagggacc    11040
gcagcggcca ggagcccgag gagatgaggg accgcaggtt tcacgcgggg cgggagctgc    11100
gcgcgggctt cgaccgtcgg cgggtgttgc gcgccgaaga cttcgagccc gacgagcgca    11160
gcggagtaag tccggcacgg gcgcacgtgt cggcggccaa cctggtgacc gcgtacgagc    11220
agacggtgaa cgaggagcgg agctttcaga aaagcttcaa caaccacgtg cgcaccctga    11280
tcgcgcgcga ggaggtggcc atcggcctga tgcatctgtg ggactttgtg gaggcgtacg    11340
tgcagaaccc gtcgagcaag ccgctgacgg cgcagttgtt cctgatcgtg cagcacagtc    11400
gggacaacga gacgttccgc gaggcgatgc tgaacatcgc ggagcccgag ggccgctggc    11460
tcttggacct gattaacatc ctgcagagca tcgtggtgca ggagcgcagc ctgagcctgg    11520
ccgacaaggt ggcggccatc aactacagca tgttgagcct gggcaagttt tacgcccgca    11580
agatctacaa gagcccctac gtgcccatag acaaggaggt gaagatcgac agcttttaca    11640
tgcggatggc gctgaaagtg ctgacgctga gcgacgatct gggggtgtac cgcaacgacc    11700
gcatccacaa ggccgtgagc gccagccgcc ggcgcgagct gagcgaccgc gagctgatgc    11760
acagcctgcg gagggcgctg gcgggcgccg gcggcggcga ggaggccgag tcctacttcg    11820
acatgggggc ggacttgcag tggcagccca gcgcgcgggc cctggaggcg gcgggctacc    11880
gcggcggcg cggcgtggtc gaggcggagg acgaggacga ggtggagtac gaggaggagg    11940
actgatcggc gaggtgtttt cgtagatgca gcgcgcgacg gcggcggcga gcgggccgca    12000
gggggacccc gccgtgctgg cggccctgca gagccaacct tcgggcgtga acgcctccga    12060
tgactgggcg gcggccatgg accgcatttt ggccttgacc acccgcaacc ccgaggcctt    12120
tagacagcag ccgcaggcca accgcttttc ggccatcttg gaagccgtgg tgccctcgcg    12180
caccaacccc acgcacgaga aggtcctggc ggtggtgaac gcgctgctgg agagcaaggc    12240
gatccgcaag gacgaggcgg ggctgattta caacgcccctg ctggagcggg tggcgcgcta    12300
caacagcacc aacgtgcagg ccaacctgga ccgtctgacg acggacgtgc gggaggcggt    12360
ggcgcagcgg gagcgcttca tgcgcgacac gaacctgggc tcgcaggtgg ccctgaacgc    12420
cttcctgagc acgcagccgg ccaacgtgcc gcgcgggcag gaggactacg tcagtttcat    12480
cagcgcgctg cgcctcctgg tggccgaggt gccgcagagc gaggtgtacc agtcgggtcc    12540
ggactacttc ttccagacct cgcggcaggg cctgcagacg gtgaacctga cgcaggcctt    12600
caagaacctg gaaggcatgt ggggcgtgcg ggccccgtg ggcgacgggg cgacgatctc    12660
cagcttgctg acgccgaaca cgcggctgct gctgctgctg atcgcgccct tcaccaatag    12720
cagtaccatc agccgcgact cgtacctggg ccacctgatc acgctgtacc gcgaggccat    12780
cgggcaggcg caggtggacg agcagaccct tccaggagatt acgagcgtga gccgggccct    12840
gggcagcag gacacgggta gcctggaggc gacgctgaat tttctgctga ccaaccggcg    12900
gcagaagatc ccctcccagt acacgctgag cacggaggag gagcgcatct tgcgctacgt    12960
gcagcagtcc gtgagcctgt atctgatgcg cgaggggcg agcccctcgt cggcgctgga    13020
catgacggcc cgtaacatgg agccgtcgct gtacgcggcc accggccgt tcgtgaaccg    13080
cctgatggac tacctgcacc gcgccgccgc catgaacggc gagtacttta cgaacgccat    13140
cctgaacccg cactggatgc cgccgtccgg tttctacacg ggggactttg acatgcccga    13200
```

```
                                                      -continued gggcgacgac gggttcctgt gggacgacgt gtcggacagc gtgttcgcgc cggtgcgtcc       13260
gggcaagaag gagggcggcg acgagctgcc gctgtccgtg gtgaggcgg cgtcgcgcgg        13320 ccagagcccg ttccccagcc tcccgtcgtt gtcggcgagc agcagcagcg gccgggtctc       13380
gcgcccgcgg ctggagggcg actacctgaa cgacccgctg ctgcgccccg cccggcccaa       13440
gaactttccc aacaacgggg tggagagcct agtggataag atgaatcgct ggaagaccta       13500
cgcccaggag cagcggagt gggaggagag tcagccccgc cccctgcctc cgccgcgctc       13560
caggtggcgc cggcgggaag aagacccgga agactcggcg gacgatagca gcgtgttgga      13620
cttggggggg accggtgccg cctcgacaaa cccgttcgcc cacctgcgcc cgcagggccg      13680
gctgggtcgg ctgtattgag gaaagaaact aataaaagaa aaagagctt gcttaccaga       13740 gccatggtcg cagcgtcggt ccctttgtgt gtgttttctc ctccccggta gcgaa atg       13798
                                                                   Met
                                                                     1 agg cgc gcg gtg gga gtg ccg ccg gtg atg gcg tac gcc gag ggt cct        13846
Arg Arg Ala Val Gly Val Pro Pro Val Met Ala Tyr Ala Glu Gly Pro
        5                  10                  15 cct cct tct tac gaa acg gtg atg ggc gcc gcg gat tcg ccg gcc acg        13894
Pro Pro Ser Tyr Glu Thr Val Met Gly Ala Ala Asp Ser Pro Ala Thr
 20                  25                  30 ctg gag gcg ctc tac gtc cct ccc cgc tac ctg ggg cct acg gag ggg        13942
Leu Glu Ala Leu Tyr Val Pro Pro Arg Tyr Leu Gly Pro Thr Glu Gly
 35                  40                  45 agg aac agc atc cgt tac tca gag ctg gcg ccg ctg tac gac acc acc        13990
Arg Asn Ser Ile Arg Tyr Ser Glu Leu Ala Pro Leu Tyr Asp Thr Thr
50                  55                  60                  65 cgc gtg tac ctg gtg gat aac aag tcg gcg gac atc gcg tcg ctg aac        14038
Arg Val Tyr Leu Val Asp Asn Lys Ser Ala Asp Ile Ala Ser Leu Asn
         70                  75                  80 tac cag aac gac cat agc aac ttt ctg acc acg gtg gtg cag aac aat        14086
Tyr Gln Asn Asp His Ser Asn Phe Leu Thr Thr Val Val Gln Asn Asn
         85                  90                  95 gac ttt acc ccg gtg gag gcg ggc acg cag acc ata aat ttc gac gag        14134
Asp Phe Thr Pro Val Glu Ala Gly Thr Gln Thr Ile Asn Phe Asp Glu
        100                 105                 110 cgc tcg cgg tgg ggc ggc gac ctg aaa acc atc ctg cgc acc aac atg        14182
Arg Ser Arg Trp Gly Gly Asp Leu Lys Thr Ile Leu Arg Thr Asn Met
115                 120                 125 ccc aac atc aac gag ttc atg tcc acc aac aag ttc agg gcc cgg ttg        14230
Pro Asn Ile Asn Glu Phe Met Ser Thr Asn Lys Phe Arg Ala Arg Leu
130                 135                 140                 145 atg gta gag aaa gtg aac aag gaa acc aat gcc cct cga tac gag tgg        14278
Met Val Glu Lys Val Asn Lys Glu Thr Asn Ala Pro Arg Tyr Glu Trp
            150                 155                 160 ttt gag ttc acc ctg ccc gag ggc aac tac tcg gag acc atg acc ata        14326
Phe Glu Phe Thr Leu Pro Glu Gly Asn Tyr Ser Glu Thr Met Thr Ile
            165                 170                 175 gac ctg atg aat aac gcg atc gtg gac aac tac ttg gaa gtg ggg cgg        14374
Asp Leu Met Asn Asn Ala Ile Val Asp Asn Tyr Leu Glu Val Gly Arg
            180                 185                 190 cag aac ggg gtg ctg gag agc gac atc ggg gtg aag ttt gac acg cgc        14422
Gln Asn Gly Val Leu Glu Ser Asp Ile Gly Val Lys Phe Asp Thr Arg
        195                 200                 205 aac ttc cgg ctg ggc tgg gac ccg gtc acc aag ctg gtc atg ccc ggc        14470
Asn Phe Arg Leu Gly Trp Asp Pro Val Thr Lys Leu Val Met Pro Gly
210                 215                 220                 225 gtg tac acc aac gag gcc ttc cac ccc gac atc gtc ctg ctg ccc ggc        14518
```

```
Val Tyr Thr Asn Glu Ala Phe His Pro Asp Ile Val Leu Leu Pro Gly
            230                 235                 240 tgc ggc gtg gac ttc acg cag agc cgg ctg agc aac ctg ctg ggg atc    14566
Cys Gly Val Asp Phe Thr Gln Ser Arg Leu Ser Asn Leu Leu Gly Ile
            245                 250                 255 cgc aag cgg atg ccc ttc cag gcg ggt ttt cag atc atg tac gag gac    14614
Arg Lys Arg Met Pro Phe Gln Ala Gly Phe Gln Ile Met Tyr Glu Asp
            260                 265                 270 ctg gag ggc ggc aac atc ccc gcc ttg cta gac gtg gcg aaa tac gag    14662
Leu Glu Gly Gly Asn Ile Pro Ala Leu Leu Asp Val Ala Lys Tyr Glu
        275                 280                 285 gcc agc att cag aag gcg cgg gag cag ggc cag gag atc cgc ggc gac    14710
Ala Ser Ile Gln Lys Ala Arg Glu Gln Gly Gln Glu Ile Arg Gly Asp
290                 295                 300                 305 aac ttt acc gtc atc ccc cgg gac gtg gag atc gtg ccc gtg gag aag    14758
Asn Phe Thr Val Ile Pro Arg Asp Val Glu Ile Val Pro Val Glu Lys
                310                 315                 320 gat agc aag gac cgc agt tac aac cta ctc ccc ggc gac cag acc aac    14806
Asp Ser Lys Asp Arg Ser Tyr Asn Leu Leu Pro Gly Asp Gln Thr Asn
            325                 330                 335 acg gcc tac cgc agc tgg ttc ctg gcc tac aac tac ggc gac ccc gag    14854
Thr Ala Tyr Arg Ser Trp Phe Leu Ala Tyr Asn Tyr Gly Asp Pro Glu
            340                 345                 350 aag ggc gtc agg tcc tgg acg ctg ctg acc acc acg gac gtc acc tgc    14902
Lys Gly Val Arg Ser Trp Thr Leu Leu Thr Thr Thr Asp Val Thr Cys
        355                 360                 365 ggc tcg cag cag gtg tac tgg tcg ctc ccg gac atg atg caa gac ccc    14950
Gly Ser Gln Gln Val Tyr Trp Ser Leu Pro Asp Met Met Gln Asp Pro
370                 375                 380                 385 gtg acc ttc cgg ccc tcc agc caa gtc agc aac tac ccc gtg gtg gga    14998
Val Thr Phe Arg Pro Ser Ser Gln Val Ser Asn Tyr Pro Val Val Gly
                390                 395                 400 gtc gag ctc ctg ccg gtg cac gcc aag agc ttt tac aac gag cag gcc    15046
Val Glu Leu Leu Pro Val His Ala Lys Ser Phe Tyr Asn Glu Gln Ala
            405                 410                 415 gtc tac tcg cag ctc atc cgc cag tcc acc gcg ctc acg cac gtc ttc    15094
Val Tyr Ser Gln Leu Ile Arg Gln Ser Thr Ala Leu Thr His Val Phe
            420                 425                 430 aac cgc ttc ccc gag aac cag atc ctg gtg cgc ccg ccc gct ccg acc    15142
Asn Arg Phe Pro Glu Asn Gln Ile Leu Val Arg Pro Pro Ala Pro Thr
            435                 440                 445 att acc acc gtc agt gaa aac gtt ccc gcc ctc aca gat cac gga acc    15190
Ile Thr Thr Val Ser Glu Asn Val Pro Ala Leu Thr Asp His Gly Thr
450                 455                 460                 465 ctg ccg ctg cgc agc agt atc agt gga gtc cag cgc gtg acc atc act    15238
Leu Pro Leu Arg Ser Ser Ile Ser Gly Val Gln Arg Val Thr Ile Thr
                470                 475                 480 gac gcc cgg cga agg acc tgc ccc tac gtg cac aag gcc ctg ggc ata    15286
Asp Ala Arg Arg Arg Thr Cys Pro Tyr Val His Lys Ala Leu Gly Ile
            485                 490                 495 gtc gct ccc aaa gtg ctc tct agc cgc acc ttt taa caagcatgtc         15332
Val Ala Pro Lys Val Leu Ser Ser Arg Thr Phe
            500                 505 cattctcatc tcgcccgaca acaacaccgg ctggggcctg cgctcggccg gcatgtacgg    15392
cggcgccaag cggcgctcca gcgagcaccc cgtccgcgtc cgcggccact accgggcccc    15452
ctggggcgcc cacaagcgcg gcgtctccac gcgcaccacc gtcgacgacg ccatcgacgc    15512
cgtcgtggcc caggccagac gctaccgccg gcccaagtcg acggtggacg ccgtcatcga    15572
```

```
cagcgtggtg gccgacgcgc ggcgatacgc tcgacgcaag cggcgtctgc accgccgtcg    15632
ccgtcccacc gccgccatgc tggccgccag agcggtcctg agacgcgcgc gccgcgtggg    15692
ccgccgagcc atgcgccgag ccgcggccaa cgccagcgcg ggtcgcgccc gtcgtcaggc    15752
cgcccggcag gccgccgccg ccatcgccaa cctggcccaa ccccgccggg gaaacgtgta    15812
ctgggtgcga gacgcgtcgg gcgtgcgcgt gccggtgcgc acccgccccc ctcggagtta    15872
gaagacaaaa agacggacga agactgagtt tccctgtcgt tgccagcatg agcaagcgca    15932
agttcaaaga agagctgctg gaggccctcg tgcccgagat ctacggcccg gccgccgctg    15992
ccgccgcggt ggcggacgtc aagcccgaag ttaagccccg cgcgctgaag cgggttaaaa    16052
agcgggaaaa gaaagaggag aagcaggaag cagggttgct agacgtcgac gacggcgtgg    16112
agttcgtgcg gtccttcgcg ccccgtcgcc gggtgcagtg gcggggtcgc cgcgtcaagc    16172
tcgtcccgcg gccgggcacc gtggtgtctt tcaccccgg cctgcgttcg gccacgcgcg    16232
gcctgaagcg cgagtacgac gaggtctatg gcgacgaaga catcctggag caggccgccc    16292
agcagctcgg ggagtttgct tacggcaagc gcggccgcta cggggaggtg gcgctggcgc    16352
tggaccaggg caatcccacg cccagcctca agcccgtcac gctgcagcag gtgctgcccg    16412
tgagcgcgtc gaccgagagc aagcggggca tcaagaggga gatgggcgac ctgcagccca    16472
ccatgcaact catggtgccc aaacggcaga agctggagga cgtgctggag aacatgaaag    16532
tggatcccag catcgagccc gaagtgaaag tgcgacccat caaggaagtg ggcccgggcc    16592
taggcgtgca gacggtggac attcagatcc ccgtgcgcgc ctccccgtt tctgccacca    16652 ctacgacggc cgtggaggcc atggaaacgc agacggagct gcccgcggcc ttggcggcag    16712
ccgccaccgc cgccgcggct acccgagaga tgggcatgca gaccgacccc tggtacgagt    16772
tcgccggccc cgcccgtcgt ccacgagccc gtcggtacgc ggcgaccacc tcccggctcc    16832
ctgactacgt cttgcatcct tcatcacgc cgacgcccgg ctaccgcgga acgaccttcc    16892
gccccggtcg cgcgcgcacc accacccgcc gtcgtcgcac caccgccgc cgtcgcagcc    16952 gtcgcgcact ggctcccatc gcggttcgcc gcgtcgtccg ccggggtcgc acgctgaccc    17012
tgcccaccgc gcgttaccac cccagcatcg tcatttaacc tgcgctgccg ttttgcagat    17072
ggctctgacg tgccgctttc gcttccccgt tcggcactac cgaggaagat ctcgccgtag    17132
gactggtcta gcgggcagcg gtctccgacg ccgccgccgc gcggtgcacc ggcgcatgaa    17192
gggcggcatt ctgcccgcgc tgatccccat tatcgccgcc gccatcgggg cgatccccgg    17252
cgtggcctcg gtggccttgc aagcagctcg caaaaattaa ataaagaagg cttgacactc    17312
actgcctggt cctgactgtt tcatgcagac aagacatgga agacatcaat tttgcgtcgt    17372
tggccccgcg gcacggctcg cggccgttca tgggcacctg gaacgagatc ggcaccagcc    17432
agctcaacgg gggcgctttc agttggagca gcctgtggag cggcattaaa aactttgggt    17492
ccacgattaa gacctatggc aacaaggcgt ggaacagtag cactggtcag atgctccgcg    17552
ataagctgaa ggaccagaac ttccagcaga aagtggtaga cggtctggcc tcgggcatca    17612
acggggtggt ggacctggcc aaccaggcgg tgcagaacca gatcaaccag cgtctggaga    17672
acagccgcca gccgccgcg gccctgcagc agcgtccgca ggtggaggag gtggaagtgg    17732
aggagaagct gccgccctg gagacggtgt cgccggtggg cgtgcctagc aaggggagga    17792
agcggccgcg gcccgagctc gaggagaccc tagtgaccga gaccctggag ccgccctcgt    17852
acgagcaggc cttgaaagag ggggccacgc ccctgcccat gacccggccc atcggaccca    17912
tggcccgacc ggtctacggc aaggaacaca aagccgtgac gctagagctg cctccgccgg    17972
```

```
                                                          -continued cgcccaccgt accccgatg cccggtccca ccctgggcac cgccgtgcct cgtcccgccg    18032
ccccgccggt cgccgtggcc acgcccgcgc gcccgagtcg cggagccaac tggcagagca    18092
ctctgaacag catcgtgggc ctgggagtga aaagcctgaa acgccgccgg tgttactatt    18152
aaagccagct aaatacccat gtgttgtatg cgcctcctgt gtcacgccag aaaaagccag    18212
ccgagtgacg ggtcaccgcc gccgccaaga gcgccgcttt caag atg gcc acc ccc    18268
                                                  Met Ala Thr Pro
                                                      510 tcg atg atg ccg cag tgg tct tac atg cac atc gcc ggg cag gac gcc    18316
Ser Met Met Pro Gln Trp Ser Tyr Met His Ile Ala Gly Gln Asp Ala
    515                 520                 525 tcg gag tac ctg agc ccg ggc ctg gtg cag ttc gcc cgc gcc acc gac    18364
Ser Glu Tyr Leu Ser Pro Gly Leu Val Gln Phe Ala Arg Ala Thr Asp
530                 535                 540 acg tac ttc agc ctg ggc aac aag ttt agg aac ccc acg gtg gcc ccc    18412
Thr Tyr Phe Ser Leu Gly Asn Lys Phe Arg Asn Pro Thr Val Ala Pro
545                 550                 555                 560 acc cac gac gtg acg acg gac cgg tcc cag cgg ctg acg ctg cgg ttc    18460
Thr His Asp Val Thr Thr Asp Arg Ser Gln Arg Leu Thr Leu Arg Phe
                565                 570                 575 gtg ccc gtc gac cgc gag gac acc gcg tac tcg tac aaa gtg cgc ttc    18508
Val Pro Val Asp Arg Glu Asp Thr Ala Tyr Ser Tyr Lys Val Arg Phe
            580                 585                 590 acg ctg gcc gtg ggc gac aac cgc gtg ctg gac atg gcc agc acg tac    18556
Thr Leu Ala Val Gly Asp Asn Arg Val Leu Asp Met Ala Ser Thr Tyr
        595                 600                 605 ttt gac atc cgc ggc gtg ttg gac cgc ggt ccc agc ttc aaa ccc tac    18604
Phe Asp Ile Arg Gly Val Leu Asp Arg Gly Pro Ser Phe Lys Pro Tyr
    610                 615                 620 tcc ggc acc gcc tac aac tcc ctg gcc ccc aag ggc gcc ccc aac ccg    18652
Ser Gly Thr Ala Tyr Asn Ser Leu Ala Pro Lys Gly Ala Pro Asn Pro
625                 630                 635                 640 tca gaa tgg aag ggc tca gac aac aaa att agt gta aga ggt cag gct    18700
Ser Glu Trp Lys Gly Ser Asp Asn Lys Ile Ser Val Arg Gly Gln Ala
                645                 650                 655 ccg ttt ttt agt aca tcc att aca aag gat ggt att caa gtg gcc act    18748
Pro Phe Phe Ser Thr Ser Ile Thr Lys Asp Gly Ile Gln Val Ala Thr
            660                 665                 670 gat act tct agc gga gct gtg tat gct aaa aag gaa tat cag cct gaa    18796
Asp Thr Ser Ser Gly Ala Val Tyr Ala Lys Lys Glu Tyr Gln Pro Glu
        675                 680                 685 cca caa gta ggg caa gaa caa tgg aac agc gaa gcc agt gat agt gat    18844
Pro Gln Val Gly Gln Glu Gln Trp Asn Ser Glu Ala Ser Asp Ser Asp
    690                 695                 700 aaa gta gct ggt agg att cta aaa gac aca aca ccc atg ttc cct tgt    18892
Lys Val Ala Gly Arg Ile Leu Lys Asp Thr Thr Pro Met Phe Pro Cys
705                 710                 715                 720 tac ggt tcc tac gcc aag ccc aca aat gaa cag ggg ggg caa ggc act    18940
Tyr Gly Ser Tyr Ala Lys Pro Thr Asn Glu Gln Gly Gly Gln Gly Thr
                725                 730                 735 aat act gta gat ctg cag ttc ttt gcc tct tca tcg gct acc tct acg    18988
Asn Thr Val Asp Leu Gln Phe Phe Ala Ser Ser Ser Ala Thr Ser Thr
            740                 745                 750 cct aaa gcc gta ctc tat gcc gag gac gtg gca ata gaa gca cca gac    19036
Pro Lys Ala Val Leu Tyr Ala Glu Asp Val Ala Ile Glu Ala Pro Asp
        755                 760                 765 acc cat ttg gtg tac aaa ccg gca gtt aca acc acg acc act agt tcc    19084
Thr His Leu Val Tyr Lys Pro Ala Val Thr Thr Thr Thr Thr Ser Ser
```

-continued

| | | |
|---|---|---|
| 770 | 775 | 780 |

| | | |
|---|---|---|
| caa gac ctg cta act cag cag gct gct ccc aac cga ccc aac tac att<br>Gln Asp Leu Leu Thr Gln Gln Ala Ala Pro Asn Arg Pro Asn Tyr Ile<br>785                    790                    795                    800 | 19132 |
| ggc ttc agg gat aat ttt atc ggt ctc atg tat tac aac tcc act ggc<br>Gly Phe Arg Asp Asn Phe Ile Gly Leu Met Tyr Tyr Asn Ser Thr Gly<br>                    805                    810                    815 | 19180 |
| aat atg ggt gtt ttg gca ggg caa gct tct cag cta aac gcg gtg gtt<br>Asn Met Gly Val Leu Ala Gly Gln Ala Ser Gln Leu Asn Ala Val Val<br>        820                    825                    830 | 19228 |
| gac ttg caa gac aga aac acc gag ctg tcc tac cag ctc atg ctt gat<br>Asp Leu Gln Asp Arg Asn Thr Glu Leu Ser Tyr Gln Leu Met Leu Asp<br>835                    840                    845 | 19276 |
| gct ttg ggc gac cgc agt cgt tac ttc tcc atg tgg aac cag gcc gta<br>Ala Leu Gly Asp Arg Ser Arg Tyr Phe Ser Met Trp Asn Gln Ala Val<br>        850                    855                    860 | 19324 |
| gac agc tat gac cct gat gtc aga att att gaa aat cat ggt gtg gag<br>Asp Ser Tyr Asp Pro Asp Val Arg Ile Ile Glu Asn His Gly Val Glu<br>865                    870                    875                    880 | 19372 |
| gat gag ctg cca aac tac tgt ttc ccg cta gga ggg tcg cta gta act<br>Asp Glu Leu Pro Asn Tyr Cys Phe Pro Leu Gly Gly Ser Leu Val Thr<br>                    885                    890                    895 | 19420 |
| gaa act tat aca ggc cta tca ccc caa aac gga agt aac acg tgg aca<br>Glu Thr Tyr Thr Gly Leu Ser Pro Gln Asn Gly Ser Asn Thr Trp Thr<br>900                    905                    910 | 19468 |
| acc gac agc acc acc tat gca act aga ggg gtg gaa atc ggc tct ggc<br>Thr Asp Ser Thr Thr Tyr Ala Thr Arg Gly Val Glu Ile Gly Ser Gly<br>        915                    920                    925 | 19516 |
| aac atg ttc gcc atg gaa att aat ttg gcg gcc aat cta tgg agg agt<br>Asn Met Phe Ala Met Glu Ile Asn Leu Ala Ala Asn Leu Trp Arg Ser<br>930                    935                    940 | 19564 |
| ttc ctg tac tcc aac gtg gcc ctg tac ctg ccc gac gag tac aag ctc<br>Phe Leu Tyr Ser Asn Val Ala Leu Tyr Leu Pro Asp Glu Tyr Lys Leu<br>945                    950                    955                    960 | 19612 |
| acc ccc gac aac atc acc ctc ccc gac aac aaa aac act tac gac tac<br>Thr Pro Asp Asn Ile Thr Leu Pro Asp Asn Lys Asn Thr Tyr Asp Tyr<br>                    965                    970                    975 | 19660 |
| atg aac ggc cgc gtg gcc gcc ccc agc tcc ctc gac acc tac gtc aac<br>Met Asn Gly Arg Val Ala Ala Pro Ser Ser Leu Asp Thr Tyr Val Asn<br>980                    985                    990 | 19708 |
| atc ggg gcg cgc tgg tcc ccc gac ccc atg gac aac gtc aac ccc ttc<br>Ile Gly Ala Arg Trp Ser Pro Asp Pro Met Asp Asn Val Asn Pro Phe<br>        995                    1000                  1005 | 19756 |
| aac cac cac cgc aac gcg gga ctg cgc tac cgc tcc atg ctg ctg<br>Asn His His Arg Asn Ala Gly Leu Arg Tyr Arg Ser Met Leu Leu<br>        1010                    1015                  1020 | 19801 |
| ggc aac ggc cgc tac gta ccc ttc cac atc caa gtg ccc cag aaa<br>Gly Asn Gly Arg Tyr Val Pro Phe His Ile Gln Val Pro Gln Lys<br>1025                    1030                  1035 | 19846 |
| ttc ttc gcc atc aaa aac ctc ctg ctc ctc ccc ggg tcc tac acc<br>Phe Phe Ala Ile Lys Asn Leu Leu Leu Leu Pro Gly Ser Tyr Thr<br>        1040                    1045                  1050 | 19891 |
| tac gag tgg aac ttc cgc aag gac gtc aac atg atc ctc cag agc<br>Tyr Glu Trp Asn Phe Arg Lys Asp Val Asn Met Ile Leu Gln Ser<br>1055                    1060                  1065 | 19936 |
| agc ctg ggt aac gac ctc cgc gtc gac ggg gcc agc gtc agg ttc<br>Ser Leu Gly Asn Asp Leu Arg Val Asp Gly Ala Ser Val Arg Phe<br>        1070                    1075                  1080 | 19981 |
| gac agc atc aac ctg tac gcc aac ttc ttc ccc atg gcc cac aac<br> Asp Ser Ile Asn Leu Tyr Ala Asn Phe Phe Pro Met Ala His Asn | 20026 |

```
                Asp Ser Ile Asn Leu Tyr Ala Asn Phe Phe Pro Met Ala His Asn
                1085                1090                1095 acc gcc tcc acg ctc gag gcc atg ctg cgc aac gac acc aac gac             20071
Thr Ala Ser Thr Leu Glu Ala Met Leu Arg Asn Asp Thr Asn Asp
1100                1105                1110 cag tcg ttc aac gac tac ctc tgc gct gcc aac atg ctc tac ccc             20116
Gln Ser Phe Asn Asp Tyr Leu Cys Ala Ala Asn Met Leu Tyr Pro
1115                1120                1125 atc ccc gcc aac gcc acc agc gtg ccc atc tcc att ccc tcg cgg             20161
Ile Pro Ala Asn Ala Thr Ser Val Pro Ile Ser Ile Pro Ser Arg
1130                1135                1140 aac tgg gcc gcc ttc cgg ggc tgg agc ttc acc cgg ctc aag acc             20206
Asn Trp Ala Ala Phe Arg Gly Trp Ser Phe Thr Arg Leu Lys Thr
1145                1150                1155 aag gag acc ccc tct ctg ggc tcc ggc ttc gat ccc tac ttc acc             20251
Lys Glu Thr Pro Ser Leu Gly Ser Gly Phe Asp Pro Tyr Phe Thr
1160                1165                1170 tac tcg ggc tcc atc ccc tac ctg gac ggc acc ttc tac ctc aac             20296
Tyr Ser Gly Ser Ile Pro Tyr Leu Asp Gly Thr Phe Tyr Leu Asn
1175                1180                1185 cac act ttc aag aag gtc tcc atc atg ttc gac tcc tcc gtc agc             20341
His Thr Phe Lys Lys Val Ser Ile Met Phe Asp Ser Ser Val Ser
1190                1195                1200 tgg ccc ggc aac gac cgc ctg ctg acc ccc aac gag ttc gag atc             20386
Trp Pro Gly Asn Asp Arg Leu Leu Thr Pro Asn Glu Phe Glu Ile
1205                1210                1215 aag cgc acc gtg gac ggg gaa ggg tac aac gtg gcc cag tgc aac             20431
Lys Arg Thr Val Asp Gly Glu Gly Tyr Asn Val Ala Gln Cys Asn
1220                1225                1230 atg acc aag gac tgg ttc ctc atc cag atg ctc agc cac tac aac             20476
Met Thr Lys Asp Trp Phe Leu Ile Gln Met Leu Ser His Tyr Asn
1235                1240                1245 atc ggc tac cag ggc ttc tac gtg ccc gag ggc tac aag gac agg             20521
Ile Gly Tyr Gln Gly Phe Tyr Val Pro Glu Gly Tyr Lys Asp Arg
1250                1255                1260 atg tac tct ttc ttc cgc aac ttc caa ccc atg agc cgc cag gtg             20566
Met Tyr Ser Phe Phe Arg Asn Phe Gln Pro Met Ser Arg Gln Val
1265                1270                1275 gtc gac acc acc acc tac acc gac tac aaa aac gtc acc ctc ccc             20611
Val Asp Thr Thr Thr Tyr Thr Asp Tyr Lys Asn Val Thr Leu Pro
1280                1285                1290 ttc cag cac aac aac tcg ggg ttc gtg gga tac atg ggc ccc acc             20656
Phe Gln His Asn Asn Ser Gly Phe Val Gly Tyr Met Gly Pro Thr
1295                1300                1305 atg cgc gag ggg cag gcc tac ccc gcc aac tac ccc tac ccc ctg             20701
Met Arg Glu Gly Gln Ala Tyr Pro Ala Asn Tyr Pro Tyr Pro Leu
1310                1315                1320 atc ggc aag acc gcc gtg ccc agc ctc acg cag aaa aag ttc ctc             20746
Ile Gly Lys Thr Ala Val Pro Ser Leu Thr Gln Lys Lys Phe Leu
1325                1330                1335 tgc gac cgc acc atg tgg cgc atc ccc ttc tcc agt aac ttc atg             20791
Cys Asp Arg Thr Met Trp Arg Ile Pro Phe Ser Ser Asn Phe Met
1340                1345                1350 tcc atg ggg gcg ctc acc gac ctg ggg cag aac atg ctg tac gcc             20836
Ser Met Gly Ala Leu Thr Asp Leu Gly Gln Asn Met Leu Tyr Ala
1355                1360                1365 aac tcc gcc cac gcc ctc gac atg acc ttc gag gtg gac ccc atg             20881
Asn Ser Ala His Ala Leu Asp Met Thr Phe Glu Val Asp Pro Met
1370                1375                1380
```

| | | | | | | | | | | | | |
|---|---|---|---|---|---|---|---|---|---|---|---|---|
| gat | gag | ccc | acg | ctt | ctc | tat | gtt | ctg | ttc | gaa | gtg | ttc gac gtc | 20926 |
| Asp | Glu | Pro | Thr | Leu | Leu | Tyr | Val | Leu | Phe | Glu | Val | Phe Asp Val | |
| | | 1385 | | | | 1390 | | | | 1395 | | | |
| gtg | cgc | atc | cac | cag | ccg | cac | cgc | ggc | gtc | atc | gag | gcc gtc tac | 20971 |
| Val | Arg | Ile | His | Gln | Pro | His | Arg | Gly | Val | Ile | Glu | Ala Val Tyr | |
| | 1400 | | | | 1405 | | | | 1410 | | | | |
| ctg | cgc | acg | ccg | ttc | tcg | gcc | ggt | aac | gcc | acc | acc | taa ggagggggcc | 21020 |
| Leu | Arg | Thr | Pro | Phe | Ser | Ala | Gly | Asn | Ala | Thr | Thr | | |
| | 1415 | | | | 1420 | | | | 1425 | | | | |

```
gccgacggat gggctccagc gagccggagc tggtcgccat cgcgcgcgac ctgggctgcg   21080
ggccctactt cctgggcacc tttgacaaac gcttcccggg cttcgtggcg ccgcacaagc   21140
tggcctgcgc catcgtcaac accgccggac gcgagaccgg cggcgtccac tggctggccc   21200
tggcctggaa cccccgcagc cgaacctgct acctcttcga ccccttcggc ttctcggacg   21260
acaggctcag gcagatctac cagttcgagt acgaaggcct gctccggcgc agcgccctcg   21320
cctccacccc cgaccactgc gtcaccctcg tcaagtccac ccagaccgtc caggggcccc   21380
gctcggccgc ctgcggcctc ttctgctgca tgttcctgca cgccttcgtg cgctggcccg   21440
cctcccccat ggacggcaac cccaccatgg acctccttac gggcgttccc aacagcatgc   21500
ttcagagtcc ccaggtcgag cccaccctcc accgcaacca ggaggaactc tacgccttcc   21560
tggctcggca ctcccctac tttcgccgcc accgcgagcg catagaaaag gccaccgcgt   21620
ttgacaaaat gaacgactag attttctgtg aaaaacactc aataaagcct ttattggttc   21680
accacacgtg cacgcatgca gacttttat ttaaaagggc tccgcctcct cgtcgccgtg   21740
gctggtgggg agggagacgt tgcgatactg caggcgggag ctccatctga actcgggaat   21800
cagcagcttg ggcaggggc cctcgacgtt tcgctccac agcttgcgca ccagctgcag   21860
ggcgcccagc aggtcgggcg cggagatctt gaagtcgcag ttggggccct ggttgccgcg   21920
ggagttgcgg tacaccgggt tggcgcactg gaacaccagc acgctgggt gctcgatgct   21980
ggccagcgcc gtcttgtcgg tcacctcgtc gccgcgcagg gactccgcgt tgctcagcgc   22040
gaaggcggtc agcttgcaca gctgccgacc cagcacgggc accccgctcg gctggttcag   22100
gcagtcgcag cgcatagcca tcagcagccg cttctgcccg tgctgcatct tcggatagtc   22160
ggctcgcatg aaggcctcca tctgccggaa ggcgtctgc gccttgctgc cctccgagaa   22220
gaacagcccg caggacttgc cggagaacac gttgttgccg cagctcacgt cttccacgca   22280
gcagcgcgcg tcgtcgttct tcagctgcac cacgctgcgg ccccagcggt tctgcaccac   22340
cttggtcttg ccgggatgtt ccttcagggc ccgctggccg ttctcgctgg tcacgtccat   22400
ctccaccacc tgctccttct ggatcatctc cagcccgtgg tagcagcgca gcacgccctc   22460
ctgctcggtg cacccgtgca gccagacggc gcagccggtc ggctccagct gttgaggttt   22520
caccccggcg taggtctcca cgtacgcccg caggaagcgg cccatcatct ccacaaaggt   22580
cttctgaccg gtgaaggtca gctgcagccc gcgatgctcc tcgttgagcc acgtctgaca   22640
gatcttgcgg tacaccttgc cctgctcggg cagaaacttg aaagcggcct tctcctcggg   22700
ctccacgtgt tacttctcca tcagcgccga catcagctcc atgcccttct cccaggccga   22760
caccagcggc tccgcgcggg ggttcaccac cgccatgcct cgggaagtgc cggggcgctc   22820
atcttcctcc tcctcctcgt cttcttcttg aggcggcggt ggcggcagtt gtctcacgaa   22880
tctcttgccg ttggccttct ggacgatctc cacgccgggg tgggtgaacc cgtgggccac   22940
caccacttcg tcctccttcct cttcgctgtc gggcacgact tcgggagagg gaggcggcgg   23000
aggaaccggt gcggccactg cggccatcgc ggcgttcttg cgcgccttct tggggggcag   23060
```

```
aggcggcgtc tcgcgctccg ggctggtctc ttgcaggtag ggcgtgatgg tgtgggaggt   23120
ggggcgctct ggctgacggc cggccatgct gatgcttgac tcctaggcga aaagatggag   23180
gaggatctta gacagccgca gcccgtctcc gaaaccttaa ccaccccgc ctctgaggtc    23240 ggcgccggcg agctagacat gcaacgggag gaggaggagg acgtgcgagt ggagcaagac   23300
ccgggctacg tgacgccgcc cgaggacggc gaggagccgc aggcaccggc gccaacgctc   23360
agcgaagccg actacctggg aggggaggac gacgtgctgc tgaagcacct ggcgcggcag   23420
agcaccatcg tgcaggaggc cctcaaggag cgcgaggagg tcccgctgac ggtggaggag   23480
ctcagccggg cctacgaagc caacctcttc tcgccgcggg tgcccccaa gaagcaggcc    23540 aacggcacct gcgagcccaa ccccgcctc aacttctacc ccgtctttgc ggtgcccgag    23600
gcgctggcca cctatcacat cttcttcaag aaccagcgca tccccctctc gtgccgcgcc   23660
aaccgcaccc gcgccgaccg cctcctgcat ctccgagccg gcgccgccat acctgagatc   23720
gcctccctgg aggaagtccc caagatcttc gaaggtctcg gcaaggacga gaagcgcgcg   23780
gcaaacgctc tggaaaagaa cgagagcgag ggtcagaacg tgctggtcga gctgaaggc    23840 gacaacgcgc gtctggccgt gctcaaacgc accatcgaag tctcccactt cgcctacccc   23900
gcgctcaacc ttccccccaa ggtcatgcgc tcggtcatgg atcagctgct catcaagcgc   23960
gccgagcccc tcgagaacga ctccgaggtg gattccgagg acggaaaacc cgtggtctcg   24020
gacgaggagc tcgcgcgctg gctgggcacg caggaccccg ccgagttgca agagcggcgc   24080
aagatgatga tggcggccgt gctggtcacc gccgagctcg agtgcctgca gcgcttcttc   24140
gccgaccccc agaccctgcg caaggtcgag gagtccctgc actacgcctt ccgccacggc   24200
tacgtgcgcc aggcctgcaa gatctccaac gtggagctta gcaacctggt ctcctacatg   24260
ggcatcctgc acgagaaccg cctcgggcag aacgtcctcc actgcaccct gaccggggag   24320
gcccgccgcg actacgtccg cgactgcatc tacctctttc tcaccctcac ctggcagacc   24380
gccatggggg tctggcagca gtgtctggag gagcgcaacc ttcgcgagct cgacaagcta   24440
ctgagccgcg agcgccgcga gctctggacg gctttcagcg agcgcaccgc cgcctgccgt   24500
ctggccgacc tcatcttccc cgagcgactc aggcaaaccc tccagaacgg cctgcccgac   24560
tttgtcagcc agagcatgct gcaaaacttt cgctccttca tcctgagcg atccggcatc    24620 ttgcccgcca tgagctgcgc cctgccctcc gatttcgtcc ccctctatta tcgcgagtgc   24680
cccccgccgc tctggagcca ctgctacctg ctgcgtctgg ccaactacct cgcccaccac   24740
tccgacctca tggaagactc cagcggcgag gggctgctgg agtgccactg ccgctgcaac   24800
ctctgcaccc ccaccgctc gctggtctgc aacaccgagc tgctcagcga gacgcaagtg     24860
atcggtacct ttgagatcca gggaccagag gggccggagg gtgcttccaa cctcaagctc   24920
agcccggcgc tctggacttc cgcctacctg cgcaaattta tccccgagga ctatcacgcc   24980
caccagatcc aattctacga agaccaatcg cgaccccca aagcccccct cacggcctgt    25040
gtcatcaccc agagccagat tctgcccaa ttgcaagcca tccagcaggc ccgcaagag     25100 ttcctcctga aaagggtca cgggggtctat ctggacccc agaccggcga ggaactcaac    25160
accccgtcac cctccgccgc cgcttcgtgc cgcccgcaga accatgccgc ccaaagggaa   25220
caagcaggcc atcgcccagc ggcgggccaa gaagcagcaa gagctccagg agcagtggga   25280
cgaggagtcc tgggacagcc aggcggagga agtctcagac gaggaggagg acatggagag   25340
ctgggacagc ctagacgagg aggaggaggc cgaggagcta gaggacgagc ctctcgagga   25400
```

-continued

```
ggaagagccc agcagcgccg cggcaccatc ggcttccaaa gaagcggctc ggagccggcc    25460
ggccccgaag cagcagaagc agcaacagcc gccaccgtcg cccccgacgc caccaccagg    25520
ctcactcaaa gccagccgta ggtgggacgc ggtgtccatc gcgggatcgc ccaaagcccc    25580
agtcggtaag ccaccgggc ggtcgcggcg ggggtactgt tcctggcgcc cccacaagag    25640
caagatcgtc gcctgcctcc agcactgccg gggcaacatc tccttcgcgc ggcgctactt    25700
gctcttccac gacggggtgg cggtgccgcg caacgtcctc tactattacc gtcatctcta    25760
cagcccctac gagacagaag gcccggcctc cgcgtaagac cagccgccag acggtctcct    25820
ccgccatcgc gacccgccag gactcggccg ccacgcagga gctcagaaaa cgcatctttc    25880
ccaccctgta tgctatcttc cagcagagcc gcggccagca gctggaactg aaagtaaaaa    25940
accgctccct gcgttcgctc acccgcagct gtctgtacca caggagggaa gaccaactgc    26000
agcgcacgct cgaggacgcc gaggcactgt tcaataaata ctgctcggtg tctcttaagg    26060
actgaaagcc cgcgcttttt cagaggctca ttacgtcatc atcatcatga gcaaggacat    26120
tcccacgcct tacatgtgga gctaccagcc gcagatggga ctggcggccg cgcctcccct    26180
ggattactcc agtcgcatga actggctgag tgccggcccc cacatgatcg ggcgggtcaa    26240
tgggattcgt gccacccgca atcagatact gctggaacag gccgccctca cctccacccc    26300
gcgacgtcag ctgaacccgc cgcttggcc cgccgcccag gtgtaccagg aaaaccccgc    26360
cccgaccaca gtcctcctgc cacgcgacgc ggaggccgaa gtccagatga ctaactccgg    26420
ggcgcaatta gcgggcggcg cccgccacgt cgtcgctccc gggtacagag gtcggccgc    26480 accctacccc tccggcccta taagaggct gatcattcga ggccgaggta tccagctcaa    26540
cgacgaggtg gtgagctcct cgaccggtct tcggcccgac ggagtcttcc agcttggagg    26600
cgccggccgc tcttccttca ccactcgcca ggcctacctg acgctccaga gctcttcctc    26660
ccagcctcgc tccggcggca tcggcaccct ccagttcgtg gaggagttcg tgccctcggt    26720
ctacttcaac ccgttctccg gctctcccgg ccgctacccg gacagcttca tccccaacta    26780
cgacgcggtg agcgaatccg tggacggcta cgattgatga ccgatggtgc ggccgtaact    26840
gcgcggcggc aacatctgca tcactgccat cgtcctcggt gcttcgcccg ggaggcctgt    26900
gagttcatct acttccagct cgcccccggac cagcttcagg gccttcgca cggcgttaag    26960 ctcgtgatag aggaagagct cgagagtagc tgcctgcgct gttttacctc cgcccccatc    27020
ctagtcgaga gggaacgcgg taggaccacc ctcaccctct actgcatctg tgactccccg    27080
gaattacatg aagatctgtg ttgccttcta tgtgccgaac aataacccct cttgtaacta    27140
cctacatcca caataaacca gaatttggaa actcctttcg tttgtttgca g atg aaa    27197
                                                            Met Lys
```

| | | | | | | | | | | | | |
|---|---|---|---|---|---|---|---|---|---|---|---|---|
| cgc | gcc | cgc | ctc | gac | gac | gac | ttc | aac | ccc | gtc | tac | ccc | tat | gac | 27242 |
| Arg | Ala | Arg | Leu | Asp | Asp | Asp | Phe | Asn | Pro | Val | Tyr | Pro | Tyr | Asp | |
| | 1430 | | | | | 1435 | | | | | 1440 | | | | |

| act | ccc | aac | gct | ccc | tct | gtt | ccc | ttc | atc | act | cct | ccc | ttc | gtc | 27287 |
|---|---|---|---|---|---|---|---|---|---|---|---|---|---|---|---|
| Thr | Pro | Asn | Ala | Pro | Ser | Val | Pro | Phe | Ile | Thr | Pro | Pro | Phe | Val | |
| | 1445 | | | | | 1450 | | | | | 1455 | | | | |

| tcc | tcg | gac | ggc | ttg | caa | gaa | aaa | cca | ccc | gga | atg | ctc | agt | ctc | 27332 |
|---|---|---|---|---|---|---|---|---|---|---|---|---|---|---|---|
| Ser | Ser | Asp | Gly | Leu | Gln | Glu | Lys | Pro | Pro | Gly | Met | Leu | Ser | Leu | |
| | 1460 | | | | | 1465 | | | | | 1470 | | | | |

| aac | tac | caa | gat | cct | att | acc | acc | caa | aac | ggg | gca | tta | act | cta | 27377 |
|---|---|---|---|---|---|---|---|---|---|---|---|---|---|---|---|
| Asn | Tyr | Gln | Asp | Pro | Ile | Thr | Thr | Gln | Asn | Gly | Ala | Leu | Thr | Leu | |
| | 1475 | | | | | 1480 | | | | | 1485 | | | | |

| aag | ctt | ggc | agc | gga | ctg | aac | ata | aac | caa | gat | ggg | gaa | ctt | acc | 27422 |
|---|---|---|---|---|---|---|---|---|---|---|---|---|---|---|---|
| Lys | Leu | Gly | Ser | Gly | Leu | Asn | Ile | Asn | Gln | Asp | Gly | Glu | Leu | Thr | |

```
                                     -continued
         1490                1495                1500
tca gac gcc agc gtt ctc gtc act ccc ccc att aca aaa gcc aac      27467
Ser Asp Ala Ser Val Leu Val Thr Pro Pro Ile Thr Lys Ala Asn
        1505                1510                1515 aac aca ata ggc cta gcc ttc aat gca cct ctt acc ttg caa agc      27512
Asn Thr Ile Gly Leu Ala Phe Asn Ala Pro Leu Thr Leu Gln Ser
        1520                1525                1530 gat act tta aat ctt gct tgt aac gcc cca ctt acc gtg caa gac      27557
Asp Thr Leu Asn Leu Ala Cys Asn Ala Pro Leu Thr Val Gln Asp
        1535                1540                1545 aat agg ttg gga ata aca tac aac tct ccc ctc acc ttg caa aac      27602
Asn Arg Leu Gly Ile Thr Tyr Asn Ser Pro Leu Thr Leu Gln Asn
        1550                1555                1560 agc gaa ctt gcc cta gcg gtc acc ccg cct ctt gac act gcc aat      27647
Ser Glu Leu Ala Leu Ala Val Thr Pro Pro Leu Asp Thr Ala Asn
        1565                1570                1575 aac aca ctt gcg ctt aaa acc gcc cgg cct ata att aca aac tct      27692
Asn Thr Leu Ala Leu Lys Thr Ala Arg Pro Ile Ile Thr Asn Ser
        1580                1585                1590 aat aac gag ctt aca ctc tcc gct gat gct ccc cta aac acc agc      27737
Asn Asn Glu Leu Thr Leu Ser Ala Asp Ala Pro Leu Asn Thr Ser
        1595                1600                1605 acg ggt acc ctc cgc cta caa agc gca gca cca ctg ggg cta gtt      27782
Thr Gly Thr Leu Arg Leu Gln Ser Ala Ala Pro Leu Gly Leu Val
        1610                1615                1620 gac caa acc ctg cga gtg ctt ttt tct aac cca ctc tac ttg caa      27827
Asp Gln Thr Leu Arg Val Leu Phe Ser Asn Pro Leu Tyr Leu Gln
        1625                1630                1635 aac aac ttt ctc tca cta gcc att gaa cgc cca ttg gct tta act      27872
Asn Asn Phe Leu Ser Leu Ala Ile Glu Arg Pro Leu Ala Leu Thr
        1640                1645                1650 acc act ggt tct atg gct atg cag att tcc caa cca tta aaa gtg      27917
Thr Thr Gly Ser Met Ala Met Gln Ile Ser Gln Pro Leu Lys Val
        1655                1660                1665 gaa gac gga agc tta agc ttg agc att gaa agc cct cta aat cta      27962
Glu Asp Gly Ser Leu Ser Leu Ser Ile Glu Ser Pro Leu Asn Leu
        1670                1675                1680 aaa aac gga aat ctt act tta gga acc caa agt ccc act gtc          28007
Lys Asn Gly Asn Leu Thr Leu Gly Thr Gln Ser Pro Leu Thr Val
        1685                1690                1695 act ggt aac aac ctc agc ctt aca aca aca gcc cca tta acg gtt      28052
Thr Gly Asn Asn Leu Ser Leu Thr Thr Thr Ala Pro Leu Thr Val
        1700                1705                1710 cag aac aac gct cta gcc ctc tca gtg tta ctg ccg ctt aga cta      28097
Gln Asn Asn Ala Leu Ala Leu Ser Val Leu Leu Pro Leu Arg Leu
        1715                1720                1725 ttt aat aac acc tca ctg gga gtg gca ttc aac cca ccc att tct      28142
Phe Asn Asn Thr Ser Leu Gly Val Ala Phe Asn Pro Pro Ile Ser
        1730                1735                1740 tca gca aac aac ggg ctg tct ctt gac att gga aat ggc ctt aca      28187
Ser Ala Asn Asn Gly Leu Ser Leu Asp Ile Gly Asn Gly Leu Thr
        1745                1750                1755 ctg caa tac aac agg ctc gta gtg aac att ggc ggc ggg cta cag      28232
Leu Gln Tyr Asn Arg Leu Val Val Asn Ile Gly Gly Gly Leu Gln
        1760                1765                1770 ttt aac aac ggt gct att acc gct tcc ata aat gca gct ctg ccg      28277
Phe Asn Asn Gly Ala Ile Thr Ala Ser Ile Asn Ala Ala Leu Pro
        1775                1780                1785 ttg cag tat tcc aat aac cag ctt tct ctt aat att gga ggc ggg      28322
```

```
                                                        -continued
Leu Gln Tyr Ser Asn Asn Gln Leu Ser Leu Asn Ile Gly Gly Gly
         1790                1795                1800 ctg cga tac aac ggc act tac aaa aat tta gcc gtc aaa acc gac         28367
Leu Arg Tyr Asn Gly Thr Tyr Lys Asn Leu Ala Val Lys Thr Asp
         1805                1810                1815 tct ttt agg ggt ctt gaa att gac agt aat cag ttc ctg gtg cca         28412
Ser Phe Arg Gly Leu Glu Ile Asp Ser Asn Gln Phe Leu Val Pro
         1820                1825                1830 aga ctg ggt tct ggt cta aag ttt gat caa tat ggg tac att agc         28457
Arg Leu Gly Ser Gly Leu Lys Phe Asp Gln Tyr Gly Tyr Ile Ser
         1835                1840                1845 gtc ata cct cca act gtt acg cca aca aca ctt tgg act aca gca         28502
Val Ile Pro Pro Thr Val Thr Pro Thr Thr Leu Trp Thr Thr Ala
         1850                1855                1860 gac cct tct ccc aac gct act ttt tac gac agc tta gat gct aag         28547
Asp Pro Ser Pro Asn Ala Thr Phe Tyr Asp Ser Leu Asp Ala Lys
         1865                1870                1875 gta tgg ctg gcc tta gta aaa tgc aac ggc atg gtt aat gga acc         28592
Val Trp Leu Ala Leu Val Lys Cys Asn Gly Met Val Asn Gly Thr
         1880                1885                1890 ata gcc ata aag gct tta aaa ggt act ctg ctc caa cct acg gct         28637
Ile Ala Ile Lys Ala Leu Lys Gly Thr Leu Leu Gln Pro Thr Ala
         1895                1900                1905 agt ttt att tct ttt gtt atg tat ttt tac agc aat ggc acc aga         28682
Ser Phe Ile Ser Phe Val Met Tyr Phe Tyr Ser Asn Gly Thr Arg
         1910                1915                1920 aga act aac tac ccc acg ttt gaa aat gaa ggc ata cta gct agt         28727
Arg Thr Asn Tyr Pro Thr Phe Glu Asn Glu Gly Ile Leu Ala Ser
         1925                1930                1935 agt gct aca tgg ggt tat cgt caa gga aac tcg gca aac acc aac         28772
Ser Ala Thr Trp Gly Tyr Arg Gln Gly Asn Ser Ala Asn Thr Asn
         1940                1945                1950 gtc acc agt gcc gtt gaa ttt atg cct agc tcc aca aga tat cct         28817
Val Thr Ser Ala Val Glu Phe Met Pro Ser Ser Thr Arg Tyr Pro
         1955                1960                1965 gtt aac aag ggt act gag gtt cag aac atg gaa ctc acc tac act         28862
Val Asn Lys Gly Thr Glu Val Gln Asn Met Glu Leu Thr Tyr Thr
         1970                1975                1980 ttc ttg cag gga gac ccc act atg gcc ata tca ttt caa gct att         28907
Phe Leu Gln Gly Asp Pro Thr Met Ala Ile Ser Phe Gln Ala Ile
         1985                1990                1995 tat aac cat gct ttg gaa ggt tac tct tta aaa ttt acc tgg cga         28952
Tyr Asn His Ala Leu Glu Gly Tyr Ser Leu Lys Phe Thr Trp Arg
         2000                2005                2010 gtt cgc aac agg gaa cgc ttt gat atc ccc tgc tgt tct ttt tct         28997
Val Arg Asn Arg Glu Arg Phe Asp Ile Pro Cys Cys Ser Phe Ser
         2015                2020                2025 tac ata acg gaa gaa taa acactgtttt tcttttcaat gttttattc             29045
Tyr Ile Thr Glu Glu
         2030 tgcttttta cacagttcga accgtcagac tccctccccc cttccacttc acccggtaca    29105
cctcccgctc cccctggatc gctgcgtaca actgcagttt ggtgttcaga cacgggttct   29165
taggtgacag tatccacacg gcctctttgc cggccaggcg ctggtccgta atgctcacaa   29225
atccctccga cacgtcctcc agacacacgg tggaatccaa ggcgcccgtc tacaaaacaa   29285
acacagtcat gctctccacg ggttctctcc tcggtcgtac tgcgccagcg tgaacgggcg   29345
atggtgctcc atcagggctc gcagcaaccg ctgtcggcgc ggctcaccca ggctccggcg   29405
```

```
aaaagcgccc cgtctgggag tgctattcaa aaaacgcacc gcctttatca acagtctcct   29465
cgtgcggcgg gcgcagcagc gcacctggat ctctgtcagg tctttacaat aggtacagcc   29525
catcaccacc atgttgttta aaatcccaaa gctaaacacg ctccacccaa atgacatgaa   29585
ttccagcacc gccgcggcgt ggccatcata caatatgcgg aggtaaatca ggtgccgccc   29645
cctaatacaa acgctcccca tatacatcac ctccttaggc agttgataat taaccacctc   29705
ccggtaccag ggaaacctca cgtttactaa agccccaaac accaacattt taaaccagtt   29765
agccagcacc accctcccg ccttacactg cagcgacccc ggctgtttac aatgacagtg   29825
aatcacccac ctctcatacc ccctaatgac ctggcgtggc tccacatcta tagtagcaca   29885
gcacacgcac accctcatgt aatgcttcat cacaaatctt tcccaagggg ttagtatcat   29945
gtcccagggt acgggccact cctgcagcac ggtgaaaggt acgcaggcgg gaacagtcct   30005
cacctcggac acataatgca tattcagatg ttcacactct aaaacccgg ggcttccctc   30065 caacgcagcc actggcaagt tctcagaggg tggtgtaagg cggtggtgct gatagggact   30125
caatctgtgt cgacaccgtc tgtcgcgttg catcgtagac caacgcttgg cgcaccgcct   30185
cgtacttcgc ccaaagaaaa cgggtgcgac gccaacacac ttccgcgtac cgtgggttcc   30245
gcactcgagc tcgctcagtt ctcaacgcat aatgcagcca ttcctgtaat ccacacaaca   30305
gtcgctcggc ttccaaagag atgtgcacct cgtatcttat aacgtcccga tatatatcca   30365
agcaggcagt cagggccact tgcaaccagt gcacgcaggc ggactgatcg cgacacactg   30425
gaggtggagg gagagacgga agaggcatgt tactccagac ggtcgaaaag cggatcaaag   30485
tgcagatcgc gaagatggca gcgatccccg ccgctacgct ggtgatagat cacagccagg   30545
tcaaacataa tgcggttttc caaatgacct attaccgcct ccaccagagc cgccacgcgc   30605
acttccagaa acaccagcac ggctacggca ttctcctcaa aatcttcaaa cattaagctg   30665
catgattgaa tcaccccaa ataattctcc tccttccatt ctcgcaaaat ttgagtaaaa   30725
acctctcgca gattagctcc gtggcgttca aaaaggtcac ttagagcgcc ctccaccgcc   30785
atgcgcaagc acaccctcat gattgaaaaa tgccagtctc ctgaaccacc tgcagttgat   30845
ttaaaagacc tatattagga tcaattccac tctcccgcag ctccacgcgt agcattagct   30905
gcaaaaagtc atttaaatct tcgcaaacta gcgcggtaag ctcgccgccg ggaattaggt   30965
ctgaagcagt caccacacac ataatttcca gtgaaggagt cagtctaagc agcaaaaagc   31025
cgcatgagca gtgttgaaaa ggaggggtca cgcaatgtaa catatgcagc caaaaatctc   31085
caaggtgtct gtgcataaac tccaccactg aaaagtccaa atcatgtaaa tatgccatca   31145
ccgcctcagg aaccaccacg gacacaaaaa cgggccgtag caaatacatg gtgtcctgca   31205
aagcaaaaac acatttatac catagaggcg cgaattactt ggggaaaaat cactcgctcc   31265
aaaactaaac aggccaccgt ctgaccgcgc cagccataaa aaaagcggtt cgaatgatta   31325
aaaagaataa tagacacctc ccaccaggta ctcggctgca actcgtgcgc ccctatcaaa   31385
accccgcgga cgttcatgtc ggccatagaa aaaatgcggc ccaaatatcc caccggaatc   31445
tccacggcca gctgcagtga tagcaaaaga acgccatgag gagcaatcac aaaattttca   31505
ggcgataaaa gcacataaag gttagaatag ccctgctgca caggtaataa agcccgcgag   31565
ctcagcaaat gcacataaac cgcttcagcc atccgtctt accgcgaaca aaaggctcac   31625
agtacacagt tactcaaccc acacgccaca cagtatttat acactcctca atcgccacgt   31685
cacccgcccc gaacaaactc caaaagtcca aaaagtccaa aacgcccgcg taaaagcccg   31745
ccaaaacagc acttcctcat ttactctccc acagtacgtc acttccgccg cgcccgccgc   31805
```

```
cctcgccccg ccctcaccct cgcgctccac cccgcgcccc acgtcagact cccacccgc    31865 cccgcgcccg cgtcatccgc accccaccct cactccaccc ctaacccgc ctcctcatta    31925 tcatattggc accgttccca aataaggtat attatgatga tg                      31967
```

<210> SEQ ID NO 13
<211> LENGTH: 508
<212> TYPE: PRT
<213> ORGANISM: Simian adenovirus

<400> SEQUENCE: 13

```
Met Arg Arg Ala Val Gly Val Pro Pro Val Met Ala Tyr Ala Glu Gly
1               5                   10                  15

Pro Pro Pro Ser Tyr Glu Thr Val Met Gly Ala Ala Asp Ser Pro Ala
            20                  25                  30

Thr Leu Glu Ala Leu Tyr Val Pro Pro Arg Tyr Leu Gly Pro Thr Glu
        35                  40                  45

Gly Arg Asn Ser Ile Arg Tyr Ser Glu Leu Ala Pro Leu Tyr Asp Thr
    50                  55                  60

Thr Arg Val Tyr Leu Val Asp Asn Lys Ser Ala Asp Ile Ala Ser Leu
65                  70                  75                  80

Asn Tyr Gln Asn Asp His Ser Asn Phe Leu Thr Thr Val Val Gln Asn
                85                  90                  95

Asn Asp Phe Thr Pro Val Glu Ala Gly Thr Gln Thr Ile Asn Phe Asp
            100                 105                 110

Glu Arg Ser Arg Trp Gly Gly Asp Leu Lys Thr Ile Leu Arg Thr Asn
        115                 120                 125

Met Pro Asn Ile Asn Glu Phe Met Ser Thr Asn Lys Phe Arg Ala Arg
    130                 135                 140

Leu Met Val Glu Lys Val Asn Lys Glu Thr Asn Ala Pro Arg Tyr Glu
145                 150                 155                 160

Trp Phe Glu Phe Thr Leu Pro Glu Gly Asn Tyr Ser Glu Thr Met Thr
                165                 170                 175

Ile Asp Leu Met Asn Asn Ala Ile Val Asp Asn Tyr Leu Glu Val Gly
            180                 185                 190

Arg Gln Asn Gly Val Leu Glu Ser Asp Ile Gly Val Lys Phe Asp Thr
        195                 200                 205

Arg Asn Phe Arg Leu Gly Trp Asp Pro Val Thr Lys Leu Val Met Pro
    210                 215                 220

Gly Val Tyr Thr Asn Glu Ala Phe His Pro Asp Ile Val Leu Leu Pro
225                 230                 235                 240

Gly Cys Gly Val Asp Phe Thr Gln Ser Arg Leu Ser Asn Leu Leu Gly
                245                 250                 255

Ile Arg Lys Arg Met Pro Phe Gln Ala Gly Phe Gln Ile Met Tyr Glu
            260                 265                 270

Asp Leu Glu Gly Gly Asn Ile Pro Ala Leu Leu Asp Val Ala Lys Tyr
        275                 280                 285

Glu Ala Ser Ile Gln Lys Ala Arg Glu Gln Gly Glu Ile Arg Gly
    290                 295                 300

Asp Asn Phe Thr Val Ile Pro Arg Asp Val Glu Ile Pro Val Glu
305                 310                 315                 320

Lys Asp Ser Lys Asp Arg Ser Tyr Asn Leu Leu Pro Gly Asp Gln Thr
                325                 330                 335

Asn Thr Ala Tyr Arg Ser Trp Phe Leu Ala Tyr Asn Tyr Gly Asp Pro
```

-continued

```
                340                 345                 350
Glu Lys Gly Val Arg Ser Trp Thr Leu Leu Thr Thr Asp Val Thr
            355                 360                 365

Cys Gly Ser Gln Gln Val Tyr Trp Ser Leu Pro Asp Met Met Gln Asp
            370                 375                 380

Pro Val Thr Phe Arg Pro Ser Ser Gln Val Ser Asn Tyr Pro Val Val
385                 390                 395                 400

Gly Val Glu Leu Leu Pro Val His Ala Lys Ser Phe Tyr Asn Glu Gln
                405                 410                 415

Ala Val Tyr Ser Gln Leu Ile Arg Gln Ser Thr Ala Leu Thr His Val
            420                 425                 430

Phe Asn Arg Phe Pro Glu Asn Gln Ile Leu Val Arg Pro Pro Ala Pro
            435                 440                 445

Thr Ile Thr Thr Val Ser Glu Asn Val Pro Ala Leu Thr Asp His Gly
            450                 455                 460

Thr Leu Pro Leu Arg Ser Ser Ile Ser Gly Val Gln Arg Val Thr Ile
465                 470                 475                 480

Thr Asp Ala Arg Arg Arg Thr Cys Pro Tyr Val His Lys Ala Leu Gly
                485                 490                 495

Ile Val Ala Pro Lys Val Leu Ser Ser Arg Thr Phe
                500                 505

<210> SEQ ID NO 14
<211> LENGTH: 917
<212> TYPE: PRT
<213> ORGANISM: Simian adenovirus

<400> SEQUENCE: 14

Met Ala Thr Pro Ser Met Met Pro Gln Trp Ser Tyr Met His Ile Ala
1               5                   10                  15

Gly Gln Asp Ala Ser Glu Tyr Leu Ser Pro Gly Leu Val Gln Phe Ala
            20                  25                  30

Arg Ala Thr Asp Thr Tyr Phe Ser Leu Gly Asn Lys Phe Arg Asn Pro
        35                  40                  45

Thr Val Ala Pro Thr His Asp Val Thr Thr Asp Arg Ser Gln Arg Leu
    50                  55                  60

Thr Leu Arg Phe Val Pro Val Asp Arg Glu Asp Thr Ala Tyr Ser Tyr
65                  70                  75                  80

Lys Val Arg Phe Thr Leu Ala Val Gly Asp Asn Arg Val Leu Asp Met
                85                  90                  95

Ala Ser Thr Tyr Phe Asp Ile Arg Gly Val Leu Asp Arg Gly Pro Ser
            100                 105                 110

Phe Lys Pro Tyr Ser Gly Thr Ala Tyr Asn Ser Leu Ala Pro Lys Gly
        115                 120                 125

Ala Pro Asn Pro Ser Glu Trp Lys Gly Ser Asp Asn Lys Ile Ser Val
    130                 135                 140

Arg Gly Gln Ala Pro Phe Phe Ser Thr Ser Ile Thr Lys Asp Gly Ile
145                 150                 155                 160

Gln Val Ala Thr Asp Thr Ser Ser Gly Ala Val Tyr Ala Lys Lys Glu
                165                 170                 175

Tyr Gln Pro Glu Pro Gln Val Gly Gln Glu Trp Asn Ser Glu Ala
            180                 185                 190

Ser Asp Ser Asp Lys Val Ala Gly Arg Ile Leu Lys Asp Thr Thr Pro
        195                 200                 205
```

```
Met Phe Pro Cys Tyr Gly Ser Tyr Ala Lys Pro Thr Asn Glu Gln Gly
    210                 215                 220
Gly Gln Gly Thr Asn Thr Val Asp Leu Gln Phe Phe Ala Ser Ser Ser
225                 230                 235                 240
Ala Thr Ser Thr Pro Lys Ala Val Leu Tyr Ala Glu Asp Val Ala Ile
                245                 250                 255
Glu Ala Pro Asp Thr His Leu Val Tyr Lys Pro Ala Val Thr Thr Thr
            260                 265                 270
Thr Thr Ser Ser Gln Asp Leu Leu Thr Gln Gln Ala Ala Pro Asn Arg
        275                 280                 285
Pro Asn Tyr Ile Gly Phe Arg Asp Asn Phe Ile Gly Leu Met Tyr Tyr
    290                 295                 300
Asn Ser Thr Gly Asn Met Gly Val Leu Ala Gly Gln Ala Ser Gln Leu
305                 310                 315                 320
Asn Ala Val Val Asp Leu Gln Asp Arg Asn Thr Glu Leu Ser Tyr Gln
                325                 330                 335
Leu Met Leu Asp Ala Leu Gly Asp Arg Ser Arg Tyr Phe Ser Met Trp
            340                 345                 350
Asn Gln Ala Val Asp Ser Tyr Asp Pro Asp Val Arg Ile Ile Glu Asn
        355                 360                 365
His Gly Val Glu Asp Glu Leu Pro Asn Tyr Cys Phe Pro Leu Gly Gly
    370                 375                 380
Ser Leu Val Thr Glu Thr Tyr Thr Gly Leu Ser Pro Gln Asn Gly Ser
385                 390                 395                 400
Asn Thr Trp Thr Thr Asp Ser Thr Thr Tyr Ala Thr Arg Gly Val Glu
                405                 410                 415
Ile Gly Ser Gly Asn Met Phe Ala Met Glu Ile Asn Leu Ala Ala Asn
            420                 425                 430
Leu Trp Arg Ser Phe Leu Tyr Ser Asn Val Ala Leu Tyr Leu Pro Asp
        435                 440                 445
Glu Tyr Lys Leu Thr Pro Asp Asn Ile Thr Leu Pro Asp Asn Lys Asn
    450                 455                 460
Thr Tyr Asp Tyr Met Asn Gly Arg Val Ala Ala Pro Ser Ser Leu Asp
465                 470                 475                 480
Thr Tyr Val Asn Ile Gly Ala Arg Trp Ser Pro Asp Pro Met Asp Asn
                485                 490                 495
Val Asn Pro Phe Asn His His Arg Asn Ala Gly Leu Arg Tyr Arg Ser
            500                 505                 510
Met Leu Leu Gly Asn Gly Arg Tyr Val Pro Phe His Ile Gln Val Pro
        515                 520                 525
Gln Lys Phe Phe Ala Ile Lys Asn Leu Leu Leu Pro Gly Ser Tyr
    530                 535                 540
Thr Tyr Glu Trp Asn Phe Arg Lys Asp Val Asn Met Ile Leu Gln Ser
545                 550                 555                 560
Ser Leu Gly Asn Asp Leu Arg Val Asp Gly Ala Ser Val Arg Phe Asp
                565                 570                 575
Ser Ile Asn Leu Tyr Ala Asn Phe Phe Pro Met Ala His Asn Thr Ala
            580                 585                 590
Ser Thr Leu Glu Ala Met Leu Arg Asn Asp Thr Asn Asp Gln Ser Phe
        595                 600                 605
Asn Asp Tyr Leu Cys Ala Ala Asn Met Leu Tyr Pro Ile Pro Ala Asn
    610                 615                 620
Ala Thr Ser Val Pro Ile Ser Ile Pro Ser Arg Asn Trp Ala Ala Phe
```

```
                  625                 630                 635                 640
Arg Gly Trp Ser Phe Thr Arg Leu Lys Thr Lys Glu Thr Pro Ser Leu
                    645                 650                 655
Gly Ser Gly Phe Asp Pro Tyr Phe Thr Tyr Ser Gly Ser Ile Pro Tyr
                660                 665                 670
Leu Asp Gly Thr Phe Tyr Leu Asn His Thr Phe Lys Lys Val Ser Ile
            675                 680                 685
Met Phe Asp Ser Ser Val Ser Trp Pro Gly Asn Asp Arg Leu Leu Thr
        690                 695                 700
Pro Asn Glu Phe Glu Ile Lys Arg Thr Val Asp Gly Glu Gly Tyr Asn
705                 710                 715                 720
Val Ala Gln Cys Asn Met Thr Lys Asp Trp Phe Leu Ile Gln Met Leu
                    725                 730                 735
Ser His Tyr Asn Ile Gly Tyr Gln Gly Phe Tyr Val Pro Glu Gly Tyr
                740                 745                 750
Lys Asp Arg Met Tyr Ser Phe Phe Arg Asn Phe Gln Pro Met Ser Arg
            755                 760                 765
Gln Val Val Asp Thr Thr Thr Tyr Thr Asp Tyr Lys Asn Val Thr Leu
        770                 775                 780
Pro Phe Gln His Asn Asn Ser Gly Phe Val Gly Tyr Met Gly Pro Thr
785                 790                 795                 800
Met Arg Glu Gly Gln Ala Tyr Pro Ala Asn Tyr Pro Tyr Pro Leu Ile
                    805                 810                 815
Gly Lys Thr Ala Val Pro Ser Leu Thr Gln Lys Lys Phe Leu Cys Asp
                820                 825                 830
Arg Thr Met Trp Arg Ile Pro Phe Ser Ser Asn Phe Met Ser Met Gly
            835                 840                 845
Ala Leu Thr Asp Leu Gly Gln Asn Met Leu Tyr Ala Asn Ser Ala His
        850                 855                 860
Ala Leu Asp Met Thr Phe Glu Val Asp Pro Met Asp Glu Pro Thr Leu
865                 870                 875                 880
Leu Tyr Val Leu Phe Glu Val Phe Asp Val Val Arg Ile His Gln Pro
                    885                 890                 895
His Arg Gly Val Ile Glu Ala Val Tyr Leu Arg Thr Pro Phe Ser Ala
                900                 905                 910
Gly Asn Ala Thr Thr
            915

<210> SEQ ID NO 15
<211> LENGTH: 607
<212> TYPE: PRT
<213> ORGANISM: Simian adenovirus

<400> SEQUENCE: 15

Met Lys Arg Ala Arg Leu Asp Asp Asp Phe Asn Pro Val Tyr Pro Tyr
1               5                   10                  15
Asp Thr Pro Asn Ala Pro Ser Val Pro Phe Ile Thr Pro Pro Phe Val
                20                  25                  30
Ser Ser Asp Gly Leu Gln Glu Lys Pro Pro Gly Met Leu Ser Leu Asn
            35                  40                  45
Tyr Gln Asp Pro Ile Thr Thr Gln Asn Gly Ala Leu Thr Leu Lys Leu
        50                  55                  60
Gly Ser Gly Leu Asn Ile Asn Gln Asp Gly Glu Leu Thr Ser Asp Ala
65                  70                  75                  80
```

```
Ser Val Leu Val Thr Pro Pro Ile Thr Lys Ala Asn Asn Thr Ile Gly
            85                  90                  95

Leu Ala Phe Asn Ala Pro Leu Thr Leu Gln Ser Asp Thr Leu Asn Leu
            100                 105                 110

Ala Cys Asn Ala Pro Leu Thr Val Gln Asp Asn Arg Leu Gly Ile Thr
            115                 120                 125

Tyr Asn Ser Pro Leu Thr Leu Gln Asn Ser Glu Leu Ala Leu Ala Val
            130                 135                 140

Thr Pro Pro Leu Asp Thr Ala Asn Asn Thr Leu Ala Leu Lys Thr Ala
145                 150                 155                 160

Arg Pro Ile Ile Thr Asn Ser Asn Asn Glu Leu Thr Leu Ser Ala Asp
                165                 170                 175

Ala Pro Leu Asn Thr Ser Thr Gly Thr Leu Arg Leu Gln Ser Ala Ala
            180                 185                 190

Pro Leu Gly Leu Val Asp Gln Thr Leu Arg Val Leu Phe Ser Asn Pro
            195                 200                 205

Leu Tyr Leu Gln Asn Asn Phe Leu Ser Leu Ala Ile Glu Arg Pro Leu
            210                 215                 220

Ala Leu Thr Thr Thr Gly Ser Met Ala Met Gln Ile Ser Gln Pro Leu
225                 230                 235                 240

Lys Val Glu Asp Gly Ser Leu Ser Leu Ser Ile Glu Ser Pro Leu Asn
                245                 250                 255

Leu Lys Asn Gly Asn Leu Thr Leu Gly Thr Gln Ser Pro Leu Thr Val
            260                 265                 270

Thr Gly Asn Asn Leu Ser Leu Thr Thr Thr Ala Pro Leu Thr Val Gln
            275                 280                 285

Asn Asn Ala Leu Ala Leu Ser Val Leu Leu Pro Leu Arg Leu Phe Asn
290                 295                 300

Asn Thr Ser Leu Gly Val Ala Phe Asn Pro Pro Ile Ser Ser Ala Asn
305                 310                 315                 320

Asn Gly Leu Ser Leu Asp Ile Gly Asn Gly Leu Thr Leu Gln Tyr Asn
                325                 330                 335

Arg Leu Val Val Asn Ile Gly Gly Gly Leu Gln Phe Asn Asn Gly Ala
            340                 345                 350

Ile Thr Ala Ser Ile Asn Ala Ala Leu Pro Leu Gln Tyr Ser Asn Asn
            355                 360                 365

Gln Leu Ser Leu Asn Ile Gly Gly Leu Arg Tyr Asn Gly Thr Tyr
370                 375                 380

Lys Asn Leu Ala Val Lys Thr Asp Ser Phe Arg Gly Leu Glu Ile Asp
385                 390                 395                 400

Ser Asn Gln Phe Leu Val Pro Arg Leu Gly Ser Gly Leu Lys Phe Asp
                405                 410                 415

Gln Tyr Gly Tyr Ile Ser Val Ile Pro Pro Thr Val Thr Pro Thr Thr
            420                 425                 430

Leu Trp Thr Thr Ala Asp Pro Ser Pro Asn Ala Thr Phe Tyr Asp Ser
            435                 440                 445

Leu Asp Ala Lys Val Trp Leu Ala Leu Val Lys Cys Asn Gly Met Val
            450                 455                 460

Asn Gly Thr Ile Ala Ile Lys Ala Leu Lys Gly Thr Leu Leu Gln Pro
465                 470                 475                 480

Thr Ala Ser Phe Ile Ser Phe Val Met Tyr Phe Tyr Ser Asn Gly Thr
                485                 490                 495

Arg Arg Thr Asn Tyr Pro Thr Phe Glu Asn Glu Gly Ile Leu Ala Ser
```

-continued

```
                  500             505             510
Ser Ala Thr Trp Gly Tyr Arg Gln Gly Asn Ser Ala Asn Thr Asn Val
            515                 520             525

Thr Ser Ala Val Glu Phe Met Pro Ser Ser Thr Arg Tyr Pro Val Asn
            530                 535             540

Lys Gly Thr Glu Val Gln Asn Met Glu Leu Thr Tyr Thr Phe Leu Gln
545                 550                 555                 560

Gly Asp Pro Thr Met Ala Ile Ser Phe Gln Ala Ile Tyr Asn His Ala
                565                 570                 575

Leu Glu Gly Tyr Ser Leu Lys Phe Thr Trp Arg Val Arg Asn Arg Glu
            580                 585                 590

Arg Phe Asp Ile Pro Cys Cys Ser Phe Ser Tyr Ile Thr Glu Glu
            595                 600                 605

<210> SEQ ID NO 16
<211> LENGTH: 24
<212> TYPE: DNA
<213> ORGANISM: Artificial
<220> FEATURE:
<223> OTHER INFORMATION: synthetic oligomer

<400> SEQUENCE: 16
gcgacgggcc gacgctgccc ggct                                    24

<210> SEQ ID NO 17
<211> LENGTH: 4
<212> TYPE: PRT
<213> ORGANISM: Artificial
<220> FEATURE:
<223> OTHER INFORMATION: artifical

<400> SEQUENCE: 17

Arg Arg Ala Ser
1

<210> SEQ ID NO 18
<211> LENGTH: 24
<212> TYPE: DNA
<213> ORGANISM: Artificial
<220> FEATURE:
<223> OTHER INFORMATION: synthetic oligomer

<400> SEQUENCE: 18
gcggcgcgcc gacgctgccc ggct                                    24
```